United States Patent
Cleve et al.

(10) Patent No.: US 6,861,432 B2
(45) Date of Patent: Mar. 1, 2005

(54) PIPERAZINE DERIVATIVES THAT DESTABILIZE ANDROGEN RECEPTORS

(75) Inventors: Arwed Cleve, Berlin (DE); Christoph Huwe, Berlin (DE); Volker Schulze, Berlin (DE); Helmut Morack, Blankenfelde (DE); Dieter Zopf, Berlin (DE); Jens Hoffmann, Muehlenbeck (DE); Andreas Reichel, Berlin (DE)

(73) Assignee: Schering Aktiengesellschaft, Berlin (DE)

(*) Notice: Subject to any disclaimer, the term of this patent is extended or adjusted under 35 U.S.C. 154(b) by 57 days.

(21) Appl. No.: 10/301,871

(22) Filed: Nov. 22, 2002

(65) Prior Publication Data

US 2004/0009969 A1 Jan. 15, 2004

Related U.S. Application Data

(60) Provisional application No. 60/406,650, filed on Aug. 29, 2002, and provisional application No. 60/383,785, filed on May 30, 2002.

(30) Foreign Application Priority Data

Nov. 23, 2001 (DE) .......................... 101 59 035
Aug. 19, 2002 (DE) .......................... 102 38 742

(51) Int. Cl.$^7$ .................. C07D 207/44; C07D 417/12; C07D 409/12; C07D 233/86; A61K 31/4015

(52) U.S. Cl. ................. 514/252.11; 514/214.14; 514/253.01; 514/253.06; 514/254.02; 514/254.03; 514/254.04; 514/254.05; 514/254.06; 514/254.07; 514/254.08; 514/254.1; 514/217.08; 514/217.09; 540/603; 544/63; 544/295; 544/357; 544/360; 544/363; 544/367; 544/370; 544/371; 544/372

(58) Field of Search .................. 544/372, 360, 544/367, 363, 371, 370, 357, 295, 63; 540/603; 514/252.11, 252.14, 253.01, 253.06, 254.02, 254.03, 254.04, 254.05, 254.06, 254.07, 254.08, 254.1, 217.08, 217.09

(56) References Cited

U.S. PATENT DOCUMENTS

| 5,627,201 A | 5/1997 | Gaillard-Kelly et al. .... 514/386 |
| 5,859,014 A | 1/1999 | Bantle et al. ................ 514/255 |

FOREIGN PATENT DOCUMENTS

| EP | 0 580 459 A | 1/1994 |
| EP | 1 122 242 A1 | 8/2001 |
| WO | WO 97/00071 A | 1/1997 |

*Primary Examiner*—Bruck Kifle
(74) *Attorney, Agent, or Firm*—Millen, White, Zelano & Branigan, P.C.

(57) ABSTRACT

This invention relates to new piperazine derivatives of general formula I, $$V-W-(CH_2)_n-N\underset{R'}{\overset{R}{\diagup\diagdown}}N-Y-Z \quad\quad I$$

Figure 1:
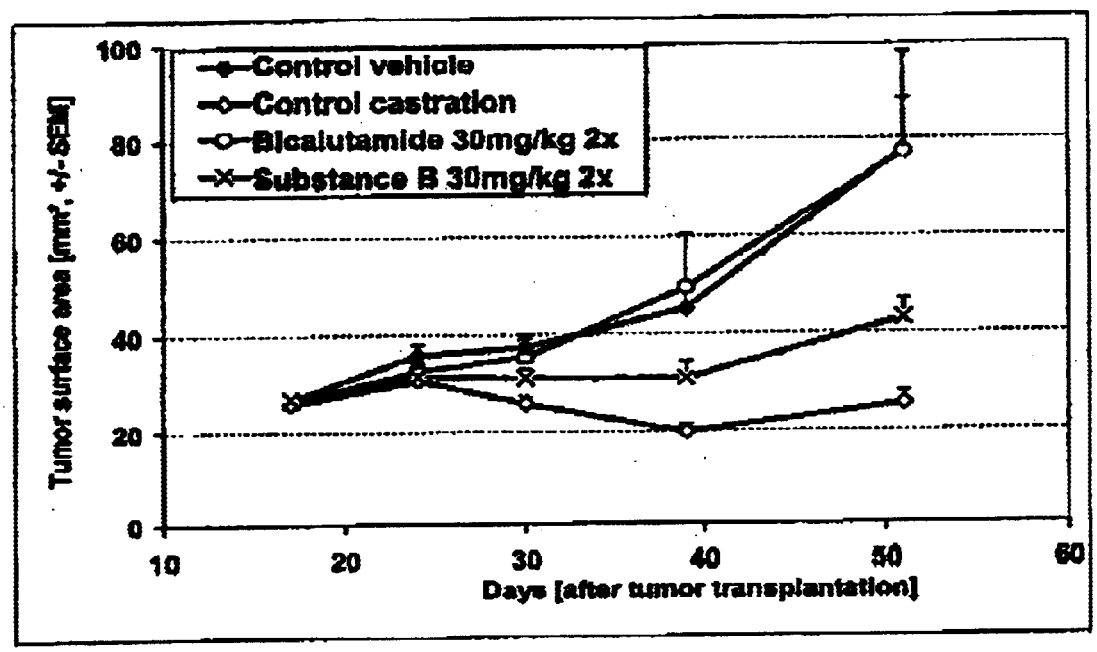

in which V, W, n, R, R', i, j, Y and Z have the meaning that is indicated in the description.

The compounds according to the invention are distinguished by a diazacycloalkane substituent. They have at their disposal a special action with respect to the action that destabilizes the androgen receptor and can be used, for example, for treating prostrate cancer.

20 Claims, 2 Drawing Sheets

PIPERAZINE DERIVATIVES THAT DESTABILIZE ANDROGEN RECEPTORS

This application claims the benefit of the filing date of U.S. Provisional Application Ser. No. 60/406,650 filed Aug. 29, 2002 and U.S. Provisional Application Ser. No. 60/383,785, filed May 30, 2002.

This invention relates to substituted piperazine derivatives that destabilize the androgen receptor (AR), and process for the production of these piperazine derivatives, their intermediate products as well as pharmaceutical preparations that contain the piperazine derivatives according to the invention and their use for the production of pharmaceutical agents.

In industrialized countries, prostate cancer, behind lung cancer, is the second main cause of death by cancer in men. In men over 55 years of age, 4% of deaths are attributed to a prostate tumor disease, and it is suggested that the proportion in men over 80 increases up to 80% of deaths. The mortality rate is still always relatively low, but it increases annually to about 14%. The number of men in whom a prostate tumor was diagnosed increased in recent years by 30%, which can be attributed, however, less to an increasing number of new diseases but rather to that the population is generally older, that the diagnostic processes have improved and that systematic screening programs were introduced (E. J. Small, D. M. Reese, Curr. Opi. Oncol. 2000, 12, 265–272).

The prostate tumor grows in an androgen-dependent manner in the early stages. As long as the tumor is limited locally to the prostate, it can be treated removed by surgical intervention or by radiation therapy, whereby these methods are associated with corresponding risks. In the cases in which the tumor is no longer locally limited, and has already formed metastases, the tumor is treated in a palliative manner by reduction of the testosterone level in the blood. This is carried out either surgically by castration or medicinally by treatment with antiandrogens (bicalutamide, cyproterone acetate, flutamide), LHRH agonists (buserelin, zoladex), LHRH antagonists (cetrorelix) or 5α-reductase inhibitors (finasteride). Since the adrenal androgen synthesis remains unaffected in surgical castration, more recently a combined surgical and medicinal treatment is frequently performed. This treatment, however, has only temporary success, since renewed growth of the tumor generally occurs after two years at the latest, and said renewed growth in most cases is then hormone-independent (L. J. Denis, K. Griffith, Semin. in Surg. Onc. 2000, 18, 52–74). Up until now despite intensive research in the last 50 years, there has been no effective treatment against these advanced stages. The 5-year survival rate in these patients is under 15%.

There are various indications that show that the androgen receptor plays an important role in the development and the growth of the prostate tumor not only in the early hormone-dependent stages but also in late hormone-independent stages of the tumor progression.

The androgen receptor belongs to the family of steroid hormone receptors that act as transcription factors. The androgen receptor binds androgens, by which it is stabilized and protected from a quick proteolytic degradation. After hormone binding, it is transported into the nucleus where it activates certain genes by binding to so-called androgen-responsive DNA elements that are in promoter regions (D. J. Lamb et al., Vitamn. Horm. 2001, 62, 199–230).

Studies on prostate tumors show that an amplification of the androgen receptor locus was detected in 30% of the advanced tumors. In other cases, a number of mutations were found in the androgen receptor gene that are located in various domains of the androgen receptor molecule and result in altered receptor properties. Mutated receptors can have either a higher affinity for androgens, can be constitutively active, can change their ligand specificity, such that they are activated by other steroid hormones or even antiandrogens, can be activated via interactions with molecules from other growth-promoting signal-transmission methods, which change interaction with co-factors, or can activate other target genes (J. P. Elo, T. Visakorpi, Ann. Med. 2001, 33, 130–41).

The identification of antiandrogens that inhibit not only the natural androgen receptor but also its mutated forms and in addition change the receptor molecule so that it is destabilized, would presumably be very helpful in treating prostate tumors in various stages. Such compounds could prevent a recurrence of tumor growth or at least considerably delay such recurrence. In the case of the estrogen receptor, ligands could be identified that destabilize the receptor and result in a reduction of the receptor content in vitro and in vivo (S. Dauvois et al. Proc. Natl. Acad. Sci. USA 1992, 89, 4037–41; R. A. McClelland et al. Eur. J. Cancer 1996, 32A, 413–6).

Nonsteroidal antiandrogens are described in U.S. Pat. No. 5,411,981 (phenylimidazolidine derivatives), in WO97/00071 (specifically substituted phenyldimethylhydantoins as well as imino or thione derivatives thereof), in WO00/37430 (phenylalanines, phenylhydantoins as well as phenylureas), in WO01/58855 (aminopropanilides) and in EP1122242 (substituted cyanophenylpiperazines).

The object of this invention consists in making available compounds with antiandrogenic action that destabilize the androgen receptor, inhibit the prostate tumor growth and simultaneously have a high, optionally oral bioavailability.

Studies with nonsteroidal antiandrogens have shown that they have advantages compared to the steroidal compounds and therefore are to be preferred. Thus with nonsteroidal compounds, a more selective action can be achieved with fewer adverse side effects. In contrast to the steroidal antiandrogens, e.g., the progestagenic activity is lacking in the known nonsteroids bicalutamide and flutamide, and in addition, their use results in an increase in the testosterone level in the serum, which clinically could result in preserving potency.

This object is achieved according to the invention by the new compounds of general formula I:

This invention relates to compounds of general formula I, whereby

I.

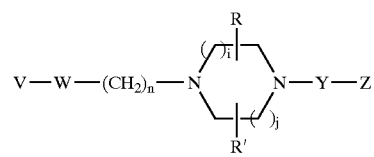

V stands for a substituted, aromatic radical of general formula II,

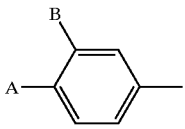

in which
A stands for an acetyl group, an acetylamino group, a cyano group, a nitro group, a trifluoromethyl group, or a halogen (fluorine, chlorine),
B stands for a hydrogen atom, a halogen (fluorine, chlorine) or a trifluoromethyl group, or
A and B together stand for a cyclic group of formula III or IV that is bonded to the aromatic ring, whereby E stands for a methylene group or an oxygen atom,

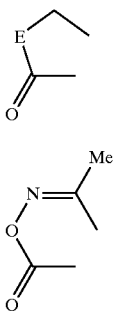

W stands for a heterocyclic compound of formula V,

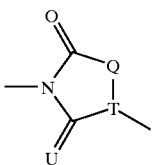

in which
T can represent carbon or nitrogen,
if T stands for carbon, a double bond is to be present between Q and T, and Q means a group =C(CH$_3$)— and U means oxygen, and n is to assume one of the integral values 1, 2, 3, 4, 5, 6, 7, or 8, or
if T stands for nitrogen, a single bond is to be present between Q and T, and Q means a group —C(CH$_3$)$_2$— and U means sulfur, and n is to assume one of the integral values 2, 3, 4, 5, 6, 7, or 8,
i and j, independently of one another, stand for the values 1 and 2, whereby i+j can assume the value 2 or 3,
R and R', independently of one another, can be a hydrogen atom or a methyl group,
Y stands for a bond between the heterocyclic nitrogen and Z, for a carbonyl group —C(O)—, for a sulfonyl group —S(O)$_2$—, for an iminocarbonyl group —C(O)N(Z')—, for an iminosulfonyl group —S(O)$_2$N(Z')—, for an imino(thioxomethyl) group —C(S)N(Z')—, for an oxycarbonylimino(thioxomethyl) group —C(S)N(Z')C(O)O—, for an oxycarbonyl group —C(O)O—, for a sulfanylcarbonyl group —C(O)S—, and
Z and Z', independently of one another, stand for an unbranched C$_1$–C$_8$-alkyl group or branched C$_3$–C$_8$-alkyl group, a C$_3$–C$_6$-cycloalkyl group that is optionally substituted with a phenyl radical, a (C$_3$–C$_6$-cycloalkyl)-C$_1$–C$_4$-alkylene group, a branched or unbranched C$_2$–C$_5$-alkenyl group, a branched or unbranched C$_2$–C$_5$-alkenyl group, a C$_3$–C$_5$-alkinyl group, a C$_1$–C$_4$-alkoxy group, cyano group, phenylsulfanyl group or hydroxy-C$_1$–C$_4$-alkylene group, a (2-methoxyethoxy)methyl group, a [2-(2-methoxyethoxy)ethoxy]methyl group, a 2-(2-methoxyethoxy)ethyl group, a 2-[2-(2-methoxyethoxy)ethoxy]ethyl group, a C$_1$–C$_4$-alkoxy-C$_1$–C$_4$-alkylene group, a C$_1$–C$_4$-alkyxycarbonyl-C$_1$–C$_4$-alkylene group, an adamantyl group, a trichloroacetyl group; an aryl, heteroaryl, heterocyclyl, aryl-C$_1$–C$_4$-alkylene, heteroaryl-C$_1$–C$_4$-alkylene, aryloxy-C$_1$–C$_4$-alkylene, heteroaryloxy-C$_1$–C$_4$-alkylene, aryl-C$_1$–C$_4$-alkylenoxy-C$_1$–C$_4$-alkylene group that is unsubstituted or that is substituted with up to three branched or unbranched C$_1$–C$_4$-alkyl, C$_2$–C$_6$-alkenyl, C$_3$–C$_6$-cycloalkyl, C$_3$–C$_6$-cycloalkyloxy, phenyl, cyano, halogen, methoxy, ethoxy, phenoxy, benzyloxy, methylsulfanyl, ethylsulfanyl, benzylsulfanyl, phenylsulfanyl, dimethylamino, acetylamino, trifluoromethyl, trifluoromethoxy, trifluoromethylsulfanyl, acetyl, (1-iminoethyl) or nitro groups, or a radical of formula C$_p$F$_q$H$_r$ with p=1, 2, 3, 4, q>1 and q+r=2p+1, and
Z' in addition to the above-mentioned definitions stands for a hydrogen atom.

The compounds according to the invention are distinguished in that in each case they contain a diazacycloalkane nucleus whose nitrogen atoms are presented in substituted form in each case.

The unbranched C$_1$–C$_8$-alkyl groups for radicals Z and Z' can be, for example, a methyl, ethyl, n-propyl, n-butyl, n-pentyl, n-hexyl, n-heptyl or n-octyl group; the branched C$_3$–C$_8$-alkyl groups are an iso-propyl, iso-butyl, sec-butyl, tert-butyl, iso-pentyl, neo-pentyl, 2-methylpentyl, 2,2-dimethylbutyl, 2,3-dimethylbutyl, 2-methylhexyl, 2,2-dimethylpentyl, 2,2,3-trimethylbutyl or 2,3,3-trimethylbutyl group.

The C$_3$–C$_6$-cycloalkyl groups that are optionally substituted with a phenyl radical for radicals Z and Z' can readily be a cyclopropyl, cyclobutyl, cyclopentyl, cyclohexyl or phenylcyclopropyl group, phenylcyclobutyl, phenylcyclopentyl, or phenylcyclohexyl group.

The (C$_3$–C$_6$-cycloalkyl)-C$_1$–C$_4$-alkylene groups for radicals Z and Z' can be, for example, a cyclopropylmethyl, cyclobutylmethyl, cyclopentylmethyl, cyclohexylmethyl, cyclopropylethyl, cyclobutylethyl, cyclopentylethyl, cyclohexylethyl, cyclopropylpropyl, cyclobutylpropyl, cyclopentylpropyl, cyclohexylpropyl, cyclopropylbutyl, cyclobutylbutyl, cyclopentylbutyl or cyclohexylbutyl group.

The branched or unbranched C$_2$–C$_5$-alkenyl groups for the radicals Z and Z' can be, for example, a vinyl, allyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, 2-methylvinyl, 3-methylbut-3-enyl, 2-methylbut-3-enyl, (E)-2-methylbut-2-enyl, (Z)-2-methylbut-2-enyl, or 3-methylbut-2-enyl group.

The C$_3$–C$_5$-alkinyl groups for radicals Z and Z' can be, for example, a prop-1-inyl, prop-2-inyl, but-1-inyl, but-2-inyl, but-3-inyl, pent-1-inyl, penty-2-inyl, pent-3-inyl, pent-4-inyl, 1-methylprop-2-inyl, 1-methylbut-3-inyl, or 1-ethylprop-2-inyl group.

The C$_1$–C$_4$-alkoxy groups for radicals Z and Z' can be, for example, a methoxy, ethoxy, n-propoxy, iso-propoxy, n-butoxy, sec-butoxy, iso-butoxy or tert-butoxy group.

The $C_1$–$C_4$-alkylene groups within radicals Z and Z' can be, for example, a methylene group (—$CH_2$—), ethylidene group [—$CH(CH_3)$—], ethylene group (—$CH_2CH_2$—), 1,3-propylene group (—$CH_2CH_2CH_2$—), 1,2-propylene group [—$CH_2CH(CH_3)$—], 1,4-butylene group (—$CH_2CH_2CH_2CH_2$—), 1,3-butylene group [—$CH_2CH_2CH(CH_3)$—], 1,2-butylene group [—$CH_2CH(CH_2CH_3)$—], 2-methyl-1,2-propylene group [—$CH_2C(CH_3)_2$—], or 2-methyl-1,3-propylene group [—$CH_2CH(CH_3)CH_2$—].

The hydroxy-$C_1$–$C_4$-alkylene groups for radicals Z and Z' can be a hydroxymethyl group ($HOCH_2$—), 2-hydroxyethyl group ($HOCH_2CH_2$—), 1-hydroxyethyl group [$CH_3CH(OH)$—], 3-hydroxypropyl group ($HOCH_2CH_2CH_2$—), 2-hydroxypropyl group [$CH_3CH(OH)CH_2CH_2$—], 1-hydroxypropyl group [$CH_3CH_2CH(OH)$—], 4-hydroxybutyl group ($HOCH_2CH_2CH_2CH_2$—), 3-hydroxybutyl group [$CH_3CH(OH)CH_2CH_2$—], 2-hydroxybutyl group [$CH_3CH_2CH(OH)CH_2$—], 1-hydroxybutyl group [$CH_3CH_2CH_2CH(OH)$—], 1-hydroxy-1-methylethyl group [$(CH_3)_2C(OH)$—], or 1-hydroxy-1-methylpropyl group [$CH_3CH_2C(CH_3)(OH)$—].

The $C_1$–$C_4$-alkoxycarbonyl-$C_1$–$C_4$-alkylene groups for radicals Z and Z' are, for example, a combination of the $C_1$–$C_4$-alkoxycarbonyl group and the $C_1$–$C_4$-alkylene group. A $C_1$–$C_4$-alkoxycarbonyl group is defined as methoxycarbonyl-[MeOC(O)—], ethoxycarbonyl [EtOC(O)—], n-propoxycarbonyl-[$CH_3CH_2CH_2OC(O)$—], iso-propoxycarbonyl-[$(CH_3)_2CHOC(O)$—], n-butoxycarbonyl-[$CH_3CH_2CH_2CH_2OC(O)$—], iso-butoxycarbonyl-[$(CH_3)_2CHCH_2OC(O)$—], sec-butoxycarbonyl-[$CH_3CH_2(CH_3)CHOC(O)$—], tert-butoxycarbonyl [$(CH_3)_3COC(O)$—]. A $C_1$–$C_4$-alkylene group is defined as the $C_1$–$C_4$-alkylene groups that are further mentioned above. For example, the following radicals can be produced from the combination of these groups to form the $C_1$–$C_4$-alkoxycarbonyl-$C_1$–$C_4$-alkylene groups: (methoxycarbonyl)methyl-[$CH_3OC(O)CH_2$—], (ethoxycarbonyl)methyl-[$CH_3CH_2OC(O)CH_2$—], (n-propoxycarbonyl)methyl-[$CH_3CH_2CH_2OC(O)CH_2$—], (iso-propoxycarbonyl)methyl-[$(CH_3)_2CHOC(O)CH_2$—], (n-butoxycarbonyl)methyl-[$CH_3CH_2CH_2CH_2OC(O)CH_2$—], (iso-butoxycarbonyl)methyl-[$(CH_3)_2CHCH_2OC(O)CH_2$—], (sec-butoxycarbonyl)methyl-[$CH_3CH_2(CH_3)CHOC(O)CH_2$—], (tert-butoxycarbonyl)methyl-[$(CH_3)_3COC(O)CH_2$—], 2-(methoxycarbonyl)ethyl-[$CH_3OC(O)CFH_2CH_2$—], 2-(ethoxycarbonyl)ethyl-[$CH_3CH_2OC(O)CH_2CH_2$—], 2-(n-propoxycarbonyl)ethyl-[$CH_3CH_2CH_2OC(O)CH_2CH_2$—, 2-(iso-propoxycarbonyl)ethyl-[$(CH_3)_2CHOC(O)CH_2CH_2$—], 2-(n-butoxycarbonyl)ethyl-[$CH_3CH_2CH_2CH_2OC(O)CH_2CH_2$—], 2-(iso-butoxycarbonyl)ethyl-[$(CH_3)_2CHCH_2OC(O)CH_2CH_2$—], 2-(sec-butoxycarbonyl)ethyl-[$CH_3CH_2(CH_3)CHOC(O)CH_2CH_2$—], 2-(tert-butoxycarbonyl)ethyl-[$(CH_3)_3COC(O)CH_2CH_2$—].

The aryl groups for radicals Z and Z' can be a phenyl, naphthalen-1-yl, naphthalen-2-yl, [1,1'-biphenyl]-2-yl, [1,1'-biphenyl]-3-yl or a [1,1'-biphenyl]-4-yl group.

The heteroaryl groups for radicals Z and Z' can be a pyridinyl, pyrimidinyl, quinolinyl, isoquinolinyl, benzofuranyl, benzothienyl, 1,3-benzodioxolyl, 2,1,3-benzothiadiazolyl, indolyl, furanyl, thienyl, oxazolyl, isoxazolyl, thiazolyl, pyrrolyl, pyrazolyl or an imidazolyl group that is linked via one of the sites that can be substituted.

The heterocyclyl groups for radicals Z and Z' can be piperidinyl, morpholinyl, thiomorpholinyl, piperazinyl, tetrahydrofuranyl, tetrahydrothienyl, imidazolidinyl or a pyrrolidinyl group that is linked via one of the sites that can be substituted.

The substituents of the aryl, heteroaryl and heterocyclyl radicals, also in each case within the aryl-$C_1$–$C_4$-alkylene, heteroaryl-$C_1$–$C_4$-alkylene, aryloxy-$C_1$–$C_4$-alkylene, heteroaryloxy-$C_1$–$C_4$-alkylene, aryl-$C_1$–$C_4$-alkylenoxy-$C_1$–$C_4$-alkylene units for radical Z, can be, i.a., Unbranched or branched $C_1$–$C_4$-alkyl groups (methyl, ethyl, n-propyl, iso-propyl, n-butyl, sec-butyl, iso-butyl, as well as tert-butyl-) and/or $C_2$–$C_6$-alkenyl groups (vinyl, allyl, homoallyl, (E)-but-2-enyl, (Z)-but-2-enyl, pent-4-enyl, (E)-pent-3-enyl, (Z)-pent-3-enyl, (E)-pent-2-enyl, (Z)-pent-2-enyl, 2-methylvinyl, 3-methylbut-3-enyl, 2-methylbut-3-enyl, (E)-2-methylbut-2-enyl, (Z)-2-methylbut-2-enyl, 2-ethylprop-2-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, 1-methylpent-4-enyl, (E)-1-methylpent-3-enyl, (Z)-1-methylpent-3-enyl, 1-ethylbut-3-enyl, (E)-1-methylpent-2-enyl, (Z)-1-methylpent-2-enyl) and/or $C_3$–$C_6$-cycloalkyl groups (cyclopropyl, cyclobutyl, cyclopentyl, cyclohexyl) and/or halogen (fluorine, chlorine, bromine, iodine).

The aryl-$C_1$–$C_4$-alkylene groups for radicals Z and Z' can be a combination of the above-defined aryl and $C_1$–$C_4$-alkyl groups, for example: a phenylmethyl, 1-phenylethyl, 2-phenylethyl, 1-methyl-1-phenylethyl, 3-phenylpropyl-4-phenylbutyl, (naphthalen-1-yl)methyl, 1-(naphthalen-1-yl)ethyl, 2-(naphthalen-1-yl)-ethyl, (naphthalen-2-yl)methyl, 1-(naphthalen-2-yl)ethyl, 2-(naphthalen-2-yl)ethyl, ([1,1'-biphenyl]-2-yl)methyl, ([1,1'-biphenyl]-3-yl)methyl or a ([1,1'-biphenyl]-4-yl)methyl group.

The heteroaryl-$C_1$–$C_4$-alkylene groups for radicals Z and Z' can be a combination of the above-defined heteroaryl and $C_1$–$C_4$-alkylene groups, for example a (pyridin-2-yl)methyl, (pyridin-3-yl)methyl, (pyridin-4-yl)methyl, (furan-2-yl)methyl, (furan-3-yl)methyl, (thien-2-yl)methyl, (thien-3-yl)methyl, 2-(thien-2-yl)ethyl or a 2-(thien-3-yl)ethyl group.

The aryloxy-$C_1$–$C_4$-alkylene groups for radicals Z and Z' can be a combined linkage of the above-defined aryl and $C_1$–$C_4$-alkylene groups via an ether group (—O—), for example: a phenoxymethyl, 1-phenoxyethyl, 2-phenoxyethyl, 1-methyl-1-phenoxyethyl, 3-phenoxypropyl, 4-phenoxybutyl, [(naphthalen-1-yl)oxy]methyl, 1-[(naphthalen-1-yl)oxy]ethyl, 2-[(naphthalen-1-yl)oxy]-ethyl, [(naphthalen-2-yl)oxy]methyl, 1-[(naphthalen-2-yl)oxy]ethyl, 2-[(naphthalen-2-yl)-oxy]ethyl, [([1,1'-biphenyl]-2-yl)oxy]methyl, [([1,1'-biphenyl]-3-yl)oxy]methyl or a [([1,1'-biphenyl]-4-yl)oxy]methyl group.

The heteroaryloxy-$C_1$–$C_4$-alkylene groups for radicals Z and Z' can be a combined linkage of the previously defined heteroaryl and $C_1$–$C_4$-alkylene groups via an ether group (—O—), for example: a [(pyridin-2-yl)oxy]methyl, [(pyridin-3-yl)oxy]methyl or a [(pyridin-4-yl)oxy]methyl group.

The aryl-$C_1$–$C_4$-alkylenoxy-$C_1$–$C_4$-alkylene groups for radicals Z and Z' can be a sequentially combined linkage of the above-defined aryl and $C_1$–$C_4$-alkylene groups via an ether group (—O—) to the alkylene group, for example: a (phenylmethoxy)methyl group or a 2-(phenylmethoxy)ethyl group.

The radical of formula $C_pF_qH_r$ with p=1,2,3,4, q>1 and q+r=2p+1 for the radical Z can be a trifluoromethyl, pentafluoroethyl, perfluoropropyl, perfluorobutyl or a 2,2,2-trifluoroethyl group.

Preferred according to this invention are those compounds of general formula I, in which:

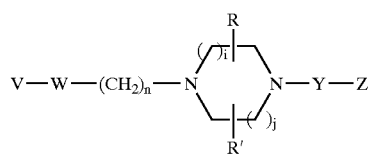

A stands for a cyano group,
B stands for a trifluoromethyl group, or
AB together stand for a cyclic group of formula IIIa that is bonded to the aromatic ring,

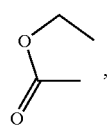

IIIa n stands for one of the integral values 1 (only for the case that T represents carbon), 2, 3, 4, 5, 6, 7 or 8,
i and j stand for the value 1,
R and R' stand f6r a hydrogen atom,
Y stands for a carbonyl group —C(O)—, for a sulfonyl group —S(O)$_2$—, for an iminocarbonyl group —C(O)N(Z')—, for an iminosulfonyl group —S(O)$_2$ N(Z'), for an imino(thioxomethyl) group —C(S)N(Z'), for an oxycarbonylimino(thioxomethyl) group —C(S)N(Z')C(O)O—, for an oxycarbonyl group —C(O)O—, for a sulfanylcarbonyl group —C(O)S—, and
Z and Z', independently of one another, stand for an unbranched $C_1$–$C_4$-alkyl group or branched $C_3$–$C_4$-alkyl group, a $C_3$–$C_6$-cycloalkyl group that is optionally substituted for one with a phenyl radical, a ($C_3$–$C_6$-cycloalkyl)-$C_1$–$C_4$-alkylene group, a branched or unbranched $C_2$–$C_3$-alkenyl group, a $C_1$–$C_4$-alkoxy, cyano, phenylsulfanyl, or hydroxy-$C_1$–$C_4$-alkylene group, a (2-methoxyethoxy)methyl group, a [2-(2-methoxyethoxy)-ethoxy]methyl group, a 2-(2-methoxyethoxy)ethyl group, a 2-[2-(2-methoxyethoxy)ethoxy]ethyl group, a $C_1$–$C_4$-alkoxy-$C_1$–$C_4$-alkylene group, a $C_1$–$C_4$-alkoxycarbonyl-$C_1$–$C_4$-alkylene group; an aryl, heteroaryl, heterocyclyl, aryl-$C_1$–$C_4$-alkylene, heteroaryl-$C_1$–$C_4$-alkylene, aryloxy-$C_1$–$C_4$-alkylene, heteroaryloxy-$C_1$–$C_4$-alkylene, aryl-$C_1$–$C_4$-alkylenoxy-$C_1$–$C_4$-alkylene group that is unsubstituted or that is substituted with up to three branched or unbranched $C_1$–$C_4$-alkyl, $C_2$–$C_4$-alkenyl, $C_3$–$C_6$-cylcoalkyl, $C_3$–$C_6$-cycloalkyloxy, phenyl, cyano, halogen, methoxy, ethoxy, phenoxy, benzyloxy, methylsulfanyl, ethylsulfanyl, benzyl, sulfanyl, phenylsulfanyl, dimethylamino, acetylamino, trifluoromethyl, trifluoromethoxy, trifluoromethylsulfanyl, or acetyl groups, or a radical of formula $C_pF_qH_r$ with p=1,2,3,4, q>and q+r=2p+1, and Z' in addition to the above-mentioned definitions stands for a hydrogen atom.

For the formation of pharmaceutically compatible salts of the compounds of general formula I according to the invention, according to the methods that are known to one skilled in the art, i.a., hydrochloric acid, hydrobromic acid, sulfuric acid and phosphoric acid, and nitric acid are considered as inorganic acids; i.a., acetic acid, propionic acid, hexanoic acid, octanoic acid, decanoic acid, olcic acid, stearic acid, maleic acid, fumaric acid, succinic acid, benzoic acid, ascorbic acid, oxalic acid, salicylic acid, tartaric acid, citric acid, lactic acid, glycolic acid, malic acid, mandelic acid, cinnamic acid, glutaminic acid, and aspartic acid are considered as carboxylic acids, and, i.a., methanesulfonic acid, ethanesulfonic acid, toluenesulfonic acid, benzenesulfonic acid as well as naphthalensulfonic acid are considered as sulfonic acids.

The compounds of Examples 1 to 745 that are mentioned below according to the invention are especially preferred.

Pharmacological Studies

The compounds according to the invention were tested in various models. The compounds of general formula I according to the invention are distinguished in that in this case, these are compounds with antiandrogenic action that destabilize the androgen receptor, inhibit the prostate tumor growth and simultaneously have a high, optionally oral bio-availability.

The in-vitro tests regarding the influences on the activities of the androgen receptor were performed as follows:

In the diagrams presented here, the following abbreviations were used:

Bicalutamide: N-[4-cyano-3-(trifluoromethyl)phenyl]-3-[(4-fluorophenyl)sulfonyl]-2-hydroxy-2-methylpropanamide R1881: Methyltrienolone, 17β-hydroxy-17α-methylestra-4,9,11-trien-3-one CPA: Cyproterone acetate, 17-(acetyloxy)-6-chloro-1β,2β-dihydro-3'H-cyclopropa[1,2]pregna-1,4,6-triene-3,20-dione Compound B: 4-[2,5-Dihydro-3-methyl-4-[4-[4-(methylsulfonyl)piperazin-1-yl]butyl]-2,5-dioxo-1H-pyrrol-1-yl]-2-(trifluoromethyl)benzonitrile (Example 117)

Model 1: Destabilization of the AR in LNCaP Cells by Test Substances

In a 25 cm$^2$ cell culture flask, 2*10$^6$ LNCaP cells in 6 ml of RPMI 1640 without phenol red are grown with 4 mmol of glutamine and 5% activated-carbon-treated serum (CCS) and are cultivated overnight at 37° C., 5% CO$_2$, in a moist atmosphere. On the next day, the cells are treated with the test substance at a concentration of 10 or 1 μm, whereby the final concentration of the solvent is 0.5% DMSO. As a control, cells are treated only with 0.5% DMSO. After an incubation time of 24 hours, the medium is changed with a renewed addition of substance and another 24 hours of incubation. After 48 hours, the cells are washed with PBS, dissolved with PBS/20 mmol of EDTA, washed again with PBS-CA$^{2+}$/Mg$^{2+}$ and then frozen for at least two hours as cell pellets at −80° C. Then, the cell pellet is resuspended in 200 μl of lysis buffer (50 mmol of tris/HCl, pH 7.5; 150 mmol of NaCl, 1.5 mmol of MgCl$_2$, 0.2% SDS, 10% glycerol, 1 mmol of DTT, 0.01×complete-EDTA protease inhibitors (Roche, Mannheim)) and treated with 10 U benzonase (Merck, Darnstadt) for 10 minutes at 4° C. After 5 mmol of EDTA is added, insoluble material is pelletized, and 25 μg of the cell extract is separated in a 4–12% SDS-polyacrylamide gel (Invitrogen). Then, the proteins are transferred to nitrocellulose (HyBondECL, Amersham) and incubated with monoclonal antibodies against the androgen receptor (AR441; Santa Cruz Biotechnologies; 1:400 dilution) and actin (ICN, 1:5000–1:20,000 dilution). After incubation with the secondary antibodies (anti-mouse IgG- HRP, Amersham or -AP, Invitrogen), the Western blot is developed by chemiluminescnce (ECL, Amersham; Western Breeze, Invitrogen), and the light signals are quantified with a Chemilmager™ (Kodak). The amount of androgen receptor is calculated in a ratio to actin as a percentage of the DMSO control.

Table 1 shows the action of selected test substances at concentrations of 10 or 1 μM on the content of androgen receptor protein in the human prostate cell line LNCaP. The data correspond to the proportion by percentage of the AR content of cells that were treated only with the solvent DMSO (=control). The treatment of the cells with the cited test substances results in a treatment concentration of 10 μM in a reduction of the AR content to one-fifth of the control (22% of Example 248: 4-[2,5-dihydro-3-[6-[4-(2-methoxybenzoyl)piperazin-1-yl]hexyl]-4-methyl-2,5-dioxo-1H-pyrrol-1-yl]-2-(trifluoromethyl)benzonitrile). The comparison substance bicalutamide does not influence the AR content, while the synthetic androgen R1881 stabilizes the AR protein. The latter is known from the literature (J. A. Kemppainen et al. J. Biol. Chem. 1992, 267, 968–974).

Example 248: 4-[2,5-Dihydro-3-[6-[4-(2-methoxybenzoyl)piperazin-1-yl]hexyl]-4-methyl-2,5-dioxo-1H-pyrrol-1-yl]-2-(trifluoromethyl)benzonitrile and Example 629: 4-[3-[5-[4-(ethyl-sulfonyl)piperazin-1-yl]pentyl]-4,4-dimethyl-5-oxo-2-thioxoimidazolidin-1-yl]-2-(trifluoromethyl)benzonitrile reduce the AR content also at a concentration of 1 μM to a value up to half of the control. By the reduction of the AR content, which presumably is carried out by a destabilization of the AR protein, the inhibitory action of the antihormones on the cell proliferation is to be further intensified.

TABLE 1

AR Content (%) in LNCaP Cells After Treatment with Selected Test Substances

| Example | Test Substance | AR Content [%] At 10 μM | At 1 μM |
|---|---|---|---|
| 248 | 4-[2,5-Dihydro-3-[6-[4-(2-methoxybenzoyl)-piperazin-1-yl]hexyl]-4-methyl-2,5-dioxo-1H-pyrrol-1-yl]-2-(trifluoromethyl)benzonitrile | 22 | 51 |
| 158 | 4-[3-[5-[4-(3,4-Dimethoxybenzoyl)piperazin-1-yl]pentyl]-2,5-dihydro-4-methyl-2,5-dioxo-1H-pyrrol-1-yl]-2-(trifluoromethyl)benzonitrile | 22 | |
| 117 | 4-[2,5-Dihydro-3-methyl-4-[4-[4-(methylsulfonyl)-piperazin-1-yl]butyl]-2,5-dioxo-1H-pyrrol-1-yl]-2-(trifluoromethyl)benzonitrile | 36 | 57 |
| 90 | 4-[3-[4-[4-(2-Chlorobenzoyl)piperazin-1-yl]butyl]-2,5-dihydro-4-methyl-2,5-dioxo-1H-pyrrol-1-yl]-2-(trifluoromethyl)benzonitrile | 34 | 50 |
| 300 | 4-[3-[6-[4-[(4-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile | 35 | |
| 365 | 4-[6-[1-[4-Cyano-3-(trifluoromethyl)phenyl]-2,5-dihydro-4-methyl-2,5-dioxo-1H-pyrrol-3-yl]hexyl]-N-(2,6-dichloropyridin-4-yl)piperazine-1-carboxamide | 36 | 82 |
| 264 | 4-[3-[6-[4-[(4-Chlorophenoxy)acetyl]piperazin-1-yl]hexyl]-2,5-dihydro-4-methyl-2,5-dioxo-1H-pyrrol-1-yl]-2-(trifluoromethyl)benzonitrile | 37 | |
| 340 | 4-[6-[1-[4-Cyano-3-(trifluoromethyl)phenyl]-2,5-dihydro-4-methyl-2,5-dioxo-1H-pyrrol-3-yl]hexyl]-N-[3-(methylsulfanyl)phenyl]piperazine-1-carboxamide | 41 | |
| 207 | 4-[3-[5-[4-[(2,1,3-Benzothiadiazol-4-yl)sulfonyl]piperazin-1-yl]pentyl]-2,5-dihydro-4-methyl-2,5-dioxo-1H-pyrrol-1-yl]-2-(trifluoromethyl)benzonitrile | 42 | |
| 326 | 4-[6-[1-[4-Cyano-3-(trifluoromethyl)phenyl]-2,5-dihydro-4-methyl-2,5-dioxo-1H-pyrrol-3-yl]hexyl]-N-(3-fluorophenyl)-piperazine-1-carboxamide | 45 | |
| 330 | 4-[6-[1-[4-Cyano-3-(trifluoromethyl)phenyl]-2,5-dihydro-4-methyl-2,5-dioxo-1H-pyrrol-3-yl]hexyl]-N-(4-fluorophenyl)-piperazine-1-carboxamide | 46 | |
| 295 | 4-[2,5-Dihydro-3-methyl-2,5-dioxo-4-[6-[4-(phenylsulfonyl)piperazin-1-yl]hexyl]-1H-pyrrol-1-yl]-2-(trifluoromethyl)benzonitrite | 48 | |
| 296 | 4-[2,5-Dihydro-3-methyl-4-[6-[4-(methyl-sulfonyl)piperazin-1-yl]hexyl]-2,5-dioxo-1H-pyrrol-1-yl]-2-(trifluoromethyl)benzonitrile | 48 | |
| 96 | 4-[3-[4-[4-(Dimethylamino)benzoyl]piperazin-1-yl]butyl]-2,5-dihydro-4-methyl-2,5-dioxo-1H-pyrrol-1-yl]-2-(trifluoromethyl)benzonitrile | 50 | |
| 315 | 4-[6-[1-[4-Cyano-3-(trifluoromethyl)phenyl]-2,5-dihydro-4-methyl-2,5-dioxo-1H-pyrrol-3-yl]hexyl]-N-phenylpiperazine-1-carboxamide | 52 | |
| 121 | 4-[3-[4-[4-[(4-Cyanophenyl)sulfonyl]piperazin-1-yl]butyl]-2,5-dihydro-4-methyl-2,5-dioxo-1H-pyrrol-1-yl]-2-(trifluoromethyl)benzonitrile | 53 | |
| 93 | 4-[3-[4-[4-(Cyclobutylcarbonyl)piperazin-1-yl]butyl]-2,5-dihydro-4-methyl-2,5-dioxo-1H-pyrrol-1-yl]-2-(trifluoromethyl)benzonitrile | 53 | |
| 297 | 4-[2,5-Dihydro-3-methyl-4-[6-[4-[(4-methylphenyl)sulfonyl]piperazin-1-yl]hexyl]-2,5-dioxo-1H-pyrrol-1-yl]-2-(trifluoromethyl)benzonitrile | 59 | |
| 351 | [4-[6-[1-[4-Cyano-3-(trifluoromethyl)phenyl]-2,5-dihydro-4-methyl-2,5-dioxo-1H-pyrrol-3-yl]hexyl]-N-(2,6-dichlorophenyl)piperazine-1-carboxamide | 61 | |
| 350 | 4-[6-[1-[4-Cyano-3-(trifluoromethyl)phenyl]-2,5-dihydro-4-methyl-2,5-dioxo-1H-pyrrol-3-yl]hexyl]-N-(2,6-difluorophenyl)piperazine-1-carboxamide | 61 | |
| 324 | 4-[6-[1-[4-Cyano-3-(trifluoromethyl)phenyl]-2,5-dihydro-4-methyl-2,5-dioxo-1H-pyrrol-3-yl]hexyl]-N-[2-(trifluoromethyl)phenyl]piperazine-1-carboxamide | 62 | |
| 270 | 4-[2,5-Dihydro-3-methyl-4-[6-[4-(3-methyl-1-oxobutyl)piperazin-1-yl]hexyl]-2,5-dioxo-1H-pyrrol-1-yl]-2-(trifluoromethyl)benzonitrile | 65 | |
| 99 | 4-[2,5-Dihydro-3-methyl-2,5-dioxo-4-[4-[4-[(thien-2-yl)carbonyl]piperazin-1-yl]butyl]-1H-pyrrol-1-yl]-2-(trifluoromethyl)benzonitrile | 66 | |
| 342 | 4-[6-[1-[4-Cyano-3-(trifluoromethyl)phenyl]-2,5-dihydro-4-methyl-2,5-dioxo-1H-pyrrol-3-yl]hexyl]-N-[4-(methylsulfanyl)phenyl]piperazine-1-carboxamide | 67 | |
| 268 | 4-[3-[6-[4-(4-Cyanobenzoyl)piperazin-1-yl]hexyl]-2,5-dihydro-4-methyl-2,5-dioxo-1H-pyrrol-1-yl]-2-(trifluoromethyl)benzonitrile | 73 | |
| 319 | 4-[6-[1-[4-Cyano-3-(trifluoromethyl)phenyl]-2,5-dihydro-4-methyl-2,5-dioxo-1H-pyrrol-3-yl]hexyl]-N-(1-methylethyl)-piperazine-1-carboxamide | 74 | |
| 629 | 4-[3-[5-[4-(Ethylsulfonyl)piperazin-1-yl]pentyl]-4,4-dimethyl-5-oxo-2-thioxoimidazolidin-1-yl]-2-(trifluoromethyl)benzonitrile | | 54 |
| 696 | S-Methyl 4-[6-[3-[4-cyano-3-(trifluoromethyl)phenyl]-5,5-dimethyl-4-oxo-2-thioxoimidazolidin-1-yl]hexyl]piperazine-1-carbothioate | 60 | |
| 524 | 4-[4,4-Dimethyl-5-oxo-3-[2-[4-[(thien-2-yl)carbonyl]-piperazin-1-yl]propyl]-2-thioxoimidazolidin-1-yl]-2-(trifluoromethyl)benzonitrile | 61 | |
| 546 | 4-[4,4-Dimethyl-3-[4-[4-(2-methyl-1-oxopropyl)piperazin-1-yl]butyl]-5-oxo-2- | 68 | |

TABLE 1-continued

AR Content (%) in LNCaP Cells After Treatment with Selected Test Substances

| Example | Test Substance | AR Content [%] At 10 μM | At 1 μM |
|---|---|---|---|
| | thioxoimidazolidin-1-yl]-2-(trifluoromethyl)benzonitrile | | |
| 653 | 4-[4,4-Dimethyl-3-[6-[4-(2-methyl-1-oxopropyl)piperazin-1-yl]hexyl]-5-oxo-2-thioxoimidazolidin-1-yl]-2-(trifluoromethyl)benzonitrile | | 71 |
| 632 | 4-[3-[5-[4-[(4-Cyanophenyl)sulfonyl]piperazin-1-yl]pentyl]-4,4-dimethyl-5-oxo-2-thioxoimidazolidin-1-yl]-2-(trifluoromethyl)benzonitrile | | 75 |
| Bicalutamide | N-[4-Cyano-3-(trifluoromethyl)phenyl]-3-[(4-fluorophenyl)sulfonyl]-2-hydroxy-2-methylpropanamide | 100 | |
| R-1881 (10 nM) | 17β-Hydroxy-17α-methylestra-4,9,11-trien-3-one | 250 | |

Model 2: Inhibition of the Proliferation of LNCaP Cells

For the proliferation assay, 6000 LNCaP cells/well are grown in a microtiter plate (96-well) in 50 μl of RPMI 1640 medium with 5% CCS and cultivated as in Model 1. After 24 hours, the cells receive 50 μl of twice-concentrated test substance that is diluted in culture medium. The solvent concentration is 0.5% DMSO. After 4 days, the cells receive another 100 μl of once-concentrated test substance that is diluted in culture medium. After 7–8 days, the proliferation rate of the cells is determined by means of crystal violet assay (Gillies et al. Anal. Biochem. 1986, 159, 109–113). For determining antagonism, the substance treatment is performed in the presence of 0.1 nM of R1881 (1:1000 dilution of ethanolic solution). Control cells receive only 0.5% DMSO. For the agonism, the cells are treated only with test substance (without R1881).

Table 2 shows the inhibitory action of test substances on the proliferation of human androgen-dependent prostate cell line LNCaP. The inhibition of the cell proliferation is an important requirement for the therapeutic use of substances in the treatment of prostate cancer. Seven AR-destabilizing test substances that are selected according to the invention inhibit the cell proliferation in the presence of 0.1 nM of synthetic androgen R1881 with a similar to considerably lower $IC_{50}$, such as the approved nonsteroidal antiandrogen bicalutamide. In a substance concentration of 1 μM, the proliferation is reduced by at least 80% compared to the cell growth in the presence of 0.1 nM of R1881. Example 696: S-Methyl 4-[6-[3-[4-cyano-3-(trifluoromethyl)phenyl]-5,5-dimethyl-4-oxo-2-thioxoimidazolidin-1-yl]hexyl]piperazine-1-carbothioate and Example 653: 4-[4,4-dimethyl-3-[6-[4-(2-methyl-1-oxopropyl)piperazin-1-yl]hexyl]-oxo-2-thioxoimidazolidin-1-yl]-2-(trifluoromethyl)benzonitrile completely block the growth at this concentration, while bicalutamide, under these conditions, achieves only an inhibition of 85%. Up to a tested concentration of 10 μM, a proliferation-stimulating action was not observed in any one of the seven test substances.

TABLE 2

Inhibition of the Proliferation of LNCaP Cells by Test Substances.

| Example | Test Substance | IC50 [$10^{-7}$ M] | % Inhibition at 1 μM |
|---|---|---|---|
| 248 | 4-[2,5-Dihydro-3-[6-[4-(2-methoxybenzoyl)-piperazin-1-yl]hexyl]-4-methyl-2,5-dioxo-1H-pyrrol-1-yl]-2-(trifluoromethyl)benzonitrile | 2.5 | 97.6 |
| 315 | 4-[6-[1-[4-Cyano-3-(trifluoromethyl)phenyl]-2,5-dihydro-4-methyl-2,5-dioxo-1H-pyrrol-3-yl]hexyl]-N-phenylpiperazine-1-carboxamide | 3.8 | 80.8 |
| 516 | 4-[3-[3-[4-(2-Methoxybenzoyl)piperazin-1-yl]propyl]-4,4-dimethyl-5-oxo-2-thioxoimidazolidin-1-yl]-2-(trifluoromethyl)-benzonitrile | 0.26 | 107 |
| 546 | 4-[4,4-Dimethyl-3-[4-[4-(2-methyl-1-oxopropyl)-piperazin-1-yl]butyl]-5-oxo-2-thioxoimidazolidin-1-yl]-2-(trifluoromethyl)benzonitrile | 0.8 | 97.5 |
| 602 | 4-[3-[5-[4-(2,2-Dimethyl-1-oxopropyl)-piperazin-1-yl]pentyl]-4,4-dimethyl-5-oxo-2-thioxoimidazolidin-1-yl]-2-(trifluoromethyl)-benzonitrile | 0.18 | 92 |
| 629 | 4-[3-[5-[4-(Ethylsulfonyl)piperazin-1-yl]pentyl]-4,4-dimethyl-5-oxo-2-thioxoimidazolidin-1-yl]-2-(trifluoromethyl)benzonitrile | 1.4 | 94.6 |
| 638 | 4-[5-[3-[4-Cyano-3-(trifluoromethyl)phenyl]-5,5-dimethyl-4-oxo-2-thioxoimidazolidin-1-yl]pentyl]-N-ethylpiperazine-1-carbothioamide | 0.33 | 95 |
| 645 | 4-[4,4-Dimethyl-3-[6-[4-methylpiperazin-1-yl)hexyl]-5-oxo-2-thioxoimidazolidin-1-yl]-2-(trifluoromethyl)benzonitrile | 0.26 | 92 |
| 648 | 4-[6-[3-[4-Cyano-3-(trifluoromethyl)phenyl]-5,5-dimethyl-4-oxo-2-thioxoimidazolidin-1-yl]hexyl]piperazine-1-carbonitrile | 0.11 | 99 |
| 653 | 4-[4,4-Dimethyl-3-[6-[4-(2-methyl-1-oxopropyl)piperazin-1-yl]hexyl]-5-oxo-2-thioxoimidazolidin-1-yl]-2-(trifluoromethyl)-benzonitrile | 0.9 | 108 |
| 656 | 4-8 3-[6-[4-(2-Hydroxy-2-methyl-1-oxopropyl)-piperazin-1-yl]hexyl]-4,4-dimethyl-5-oxo-2-thioxoimidazolidin-1-yl]-2-(trifluoromethyl)-benzonitrile | 0.26 | 99 |

TABLE 3

(Continuation) Inhibition of the Proliferation of LNCaP Cells by Test Substances.

| Example | Test Substance | IC50 [$10^{-7}$ M] | % Inhibition at 1 μM |
|---|---|---|---|
| 670 | 4-[4,4-Dimethyl-5-oxo-2-thioxo-3-[6-[4-(trifluoracetyl)piperazin-1-yl]hexyl]-imidazolidin-1-yl]-2-(trifluoromethyl)-benzonitrile | 0.24 | 96 |
| 672 | 4-[4,4-Dimethyl-5-oxo-3-[6-[4-[(thien-2-yl)acetyl]piperazin-1-yl]hexyl]-2-thioxoimidazolidin-1-yl]-2-(trifluoromethyl)-benzonitrile | 0.26 | 100 |
| 679 | rel-4-[3-[6-[(2R,5S)-2,5-Dimethyl-4-[(thien-2-yl)carbonyl]piperazin-1-yl]hexyl]-4,4-dimethyl-5-oxo-2-thioxoimidazolidin-1-yl]-2-(trifluoromethyl)benzonitrile | 0.55 | 97 |
| 696 | S-Methyl 4-[6-[3-[4-cyano-3-(trifluoromethyl)-phenyl]-5,5-dimethyl-4-oxo-2-thioxoimidazolidin-1-yl]hexyl]-piperazine-1-carbothioate | 0.2 | 110 |
| 706 | 4-[3-[7-[4-(Methoxyacetyl)piperazin-1-yl]heptyl]-4,4-dimethyl-5-oxo-2- | 0.19 | 101 |

TABLE 3-continued (Continuation) Inhibition of the Proliferation of LNCaP Cells by Test Substances.

| Example | Test Substance | IC50 [$10^{-7}$ M] | % Inhibition at 1 μM |
|---|---|---|---|
| 723 | thioxoimidazolidin-1-yl]-2-(trifluoromethyl)-benzonitrile 4-[4,4-Dimethyl-3-[8-[4-(methylsulfonyl)-piperazin-1-yl]octyl]-5-oxo-2-thioxoimidazolidin-1-yl]-2-(trifluoromethyl)-benzonitrile | 0.26 | 90 |
| Bicalutamide | N-[4-Cyano-3-(trifluoromethyl)phenyl]-3-[(4-fluorophenyl)sulfonyl]-2-hydroxy-2-methylpropanamide | 3.8 | 84.6 |

Model 3: Inhibition of the Proliferation of Other Cell Lines That do not Originate From the Prostate To examine the growth-inhibiting action of test substances in cells that are not of prostatic origin, MaTu cells, MaTu/Adr cells, HaCaT cells and A431 cells were treated with test substances, whereby

| | |
|---|---|
| MaTu: | means human breast cancer cell line |
| MaTu/Adr: | means adriamycin-resistant MaTu cell line |
| HaCaT: | means human fibroblast cell line |
| A-431: | means human epidermis cell line. |

Depending on the cell line, 1000–4000 cells/well were grown in RPMI 1640 medium (A431; MaTu and MaTu/Adr) or DMEM/HAM'SF12 medium (HaCaT) without phenol red with 2 mmol of L-glutamine and 10% CCS, and after a 24-hour incubation, they were treated with various concentrations of test substances diluted in culture medium. After a 3-day treatment period, the number of cells was determined by crystal violet assay, as in Model 2. The solvent control contained 0.1% ethanol.

Table 3 shows the effect of selective test substances on the proliferation of human cells that do not originate from the prostate. The substances were tested at a concentration of 10 μM, and the data correspond to the proportion, in percent, of the cell growth of the solvent control. It turns out that the test substances exerted no inhibitory action on the four different cell lines or, in individual cases, only a slight inhibitory action. Under the given test conditions, the comparison substance bicalutamide showed a slight inhibition in all cell lines except for MaTu. These results indicate that the antiproliferative action of the test substances is androgen receptor-dependent and that even at high substance concentrations in the micromolecular range, no secondary cytotoxic actions occur.

TABLE 4

Action of Selective Test Substances on the Proliferation of Non-Prostate Cells at a Concentration of 10 μM.

| | Proliferation in the Cell Line | | | |
|---|---|---|---|---|
| Test Substance (Example No.) | MaTu | MaTu/Adr | A431 | HaCaT |
| 4-[2,5-Dihydro-3-methyl-4-[4-[4-(methylsulfonyl)piperazin-1-yl]butyl]-2,5-dioxo-1H-pyrrol-1-yl]-2-(trifluoromethyl)-benzonitrile (117) | 103 ± 10% | 94 ± 4% | 100 ± 5% | 104 ± 6% |
| 4-[3-[4-[4-(2-Chlorobenzoyl)-piperazin-1-yl]butyl]-2,5-dihydro-4-methyl-2,5-dioxo-1H-pyrrol-1-yl]-2-(trifluoromethyl)-benzonitrile (90) | 96 +/− 3% | 80 +/− 2% | 98 +/− 7% | 102 +/− 12% |
| 4-[2,5-Dihydro-3-[6-[4-(2-methoxybenzoyl)piperazin-1-yl]hexyl]-4-methyl-2,5-dioxo-1H-pyrrol-1-yl]-2-(trifluoromethyl)-benzonitrile (248) | 98 +/− 4% | 88 +/− 4% | 102 +/− 5% | 104 +/− 7% |
| 4-[6-[1-[4-Cyano-3-(trifluoromethyl)phenyl]-2,5-dihydro-4-methyl-2,5-dioxo-1H-pyrrol-3-yl]hexyl]-N-phenylpiperazine-1-carboxamide (315) | 95 +/− 7% | 90 +/− 10% | 95 +/− 5% | 102 +/− 6% |
| Bicalutamide | 97 ± 3% | 84 ± 6% | 89 ± 7% | 92 ± 3% |

Model 4: Antiandrogenic Action of Selective Test Substances on the Growth of Accessory Sexual Glands of Mice The function and the size of accessory sexual glands (prostate and seminal vesicles) depend on androgens. In castrated animals, a growth of these (organs is induced by androgen administration. The simultaneous treatment with antiandrogens inhibits this growth, depending on the dose.

To examine the test substances, the mice were castrated. The treatment with testosterone propionate (0.03 mg/mouse) and the test substances (formulated 2×daily 30 mg/kg s.c. in benzyl benzoate-castor oil (10:90)) was on the same day. The treatment was carried out over 7 days and at the end of the test, the weights of the seminal vesicles and prostates were determined. The inhibition, in percent, of the seminal vesicle growth was calculated relative to the control groups (with and without testosterone). As a reference substance, cyproterone acetate (30 mg/kg s.c.) was used.

The results are shown in Table 4.

The treatment with the test substances of Example 629: 4-[3-[5-[4-(ethylsulfonyl)-piperazin-1-yl]pentyl]-4,4-dimethyl-5-oxo-2-thioxoimidazolidin-1-yl]-2-(trifluoromethyl)-benzonitrile and Example 546: 4-[4,4-dimethyl-3-[4-[4-(2-methyl-1-oxopropyl)piperazin-1-yl]butyl]-5-oxo-2-thioxoimidazolidin-1-yl]-2-(trifluoromethyl)-benzonitrile resulted in an almost 100% inhibition of the growth of the seminal vesicles, while the treatment with the reference substance cyproterone acetate resulted in an inhibition of only 85%. The inhibiting values for bicalutamide, determined in preceding tests, was also only at 86%.

TABLE 4

Action of Selective Test Substances on Testosterone-Stimulated Growth of the Seminal Vesicles at a Dose of 2 × 30 mg/kg.

| Example | Test Substance | % Inhibition of the MSB Growth |
|---|---|---|
| 629 | 4-[3-[5-[4-(Ethylsulfonyl)piperazin-1-yl]pentyl]-4,4-dimethyl-5-oxo-2-thioxoimidazolidin-1-yl]-2-(trifluoromethyl)benzonitrile | 98 |
| 546 | 4-[4,4-Dimethyl-3-[4-[4-(2-methyl-1-oxopropyl)-piperazin-1-yl]butyl]-5-oxo-2-thioxoimidazolidin-1-yl]-2-(trifluoromethyl)benzonitrile | 98 |
| 696 | S-Methyl 4-[6-[3-[4-cyano-3-(trifluoromethyl)phenyl]-5,5-dimethyl-4-oxo-2-thioxoimidazolidin-1-yl]hexyl]-piperazine-1-carbothioate | 87 |
| CPA | 17-(Acetyloxy)-6-chloro-1β,2β-dihydro-3'H-cyclopropa[1,2]pregna-1,4,6-triene-3,20-dione | 85 |
| Bicalutamide | N-[4-Cyano-3-(trifluoromethyl)phenyl]-3-[(4-fluorophenyl)-sulfonyl]-2-hydroxy-2-methylpropanamide | 86 |

Model 5: Antiandrogenic Action of a Selective Test Substance on the Growth of Human Prostate Cancer Xenografts In Vivo In this invention, the action of Example 117 according to the invention: 4-[2,5-dihydro-3-methyl-4-[4-[4-(methylsulfonyl)piperazin-1-yl]butyl]-2,5-dioxo-1H-pyrrol-1-yl]-2-(trifluoromethyl)benzonitrile on the tumor growth in vivo was studied by means of mouse-xenograft modules, in which the compound according to the invention was continuously administered subcutaneously.

The CWR22 tumor model [M. A. Wainstein, F. He, D. Robinson, H. J. Kung, S. Schwartz, J. M. Giaconia, N. L. Edgehouse, T. P. Pretlow, D. R. Bodner, E. D. Kursh, *Cancer Res.* 1994, 1; 54(23), 6049–52] is a hormone-dependent human prostate carcinoma model. The tumor model was established and further propagated by "scrial passaging" of prostate cancer tissue, which was removed during an OP in immunodeficient hairless mice. The androgen-dependent LNCaP prostate cancer model was also established from a patient tumor. This tumor model grows both in cell culture and as a xenotransplant on immunodeficient mice (Culig, Hoffman *Brit. J. Cancer*, 1999, 242–251). For therapy tests, 6-week-old male hairless mice (NMRI mice, M&B, Bornholdtgard, Denmark) were supplemented with testosterone pellets (12.5 mg, 90-day release; IRA, Sarasota, Fla.). Either LNCaP cells (1.5×10$^6$ cells) or small CWR22 tumor fragments (2×2 mm) were implanted subcutaneously in the left flank of the animals. After the tumors reached a size of 20–25 mm$^2$, the treatment with the invention substance was begun. [M. A. Wainstein, F. He, D. Robinson, H. J. Kung, S. Schwartz, J. M. Giaconia, N. L. Edgehouse, T. P. Pretlow, D. R. Bodner, E. D. Kursh, *Cancer Res.* 1994, 1; 54(23), 6049–52].

Figure 2:
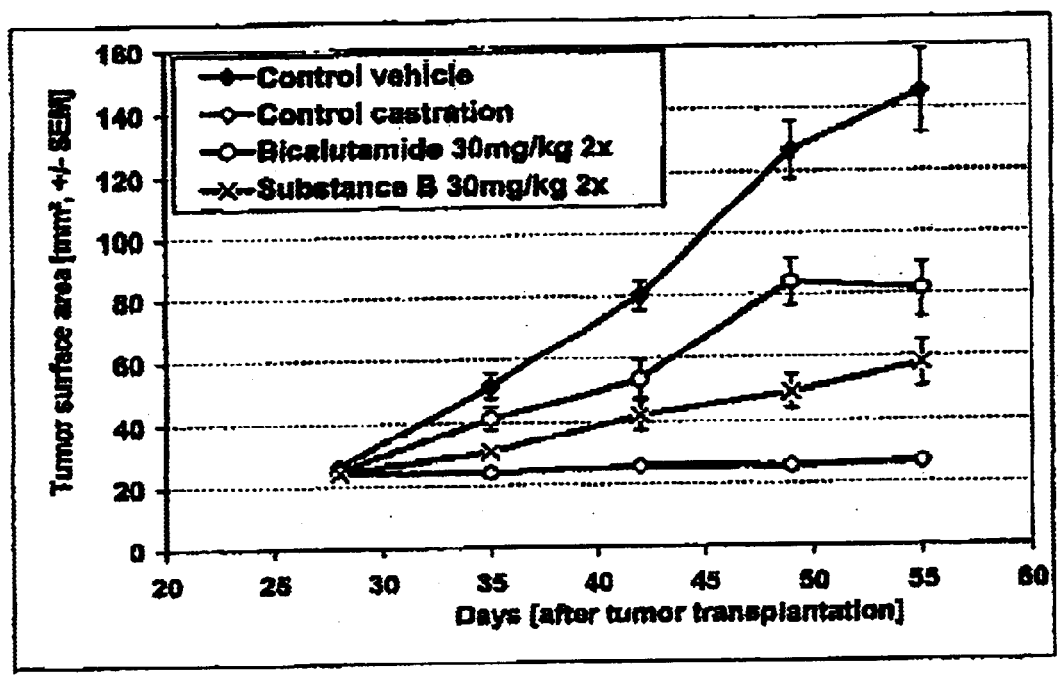

The results are shown in FIGS. 1 and 2.

FIGS. 1 and 2 show that, while the tumor grows quickly in the untreated control animals, the treatment with the invention substance results in a considerable growth inhibition of the prostate tumors. Both in the CWR22 tumor and in the LNCaP tumor, this growth inhibition is comparable to the effects of castration.

In both models, the inhibition of the tumor growth is superior in comparison to treatment with the antiandrogen bicalutamide. FIG. 1 shows growth inhibition of LNCaP prostate cancers by substance B of the invention and bicalutamide with administration 2 × daily s.c. with 30 mg/kg. FIG. 2 shows growth inhibition of CWR22 prostate cancers by substance B of the invention and bicalutamide with administration 2 × daily s.c. with 30 mg/kg.

In this invention, the action of a compound according to the invention on the tumor growth in vivo by means of a mouse-xenograft model was studied, in which the compound according to the invention was administered subcutaneously 2×daily over the entire treatment period. In comparison to the untreated control animals, an inhibition of tumor growth resulted. Retardation of the tumor growth was shown to be significant in castrated mice. The treatment was well-tolerated.

This invention shows that the compound according to the invention causes an inhibition of the prostate tumor growth that is superior to that of bicalutamide.

Dosage

In general, satisfactory results can be expected when the daily doses encompass a range of 5 μg to 50 mg of the compound according to the invention per kg of body weight. In larger mammals, for example humans, a recommended daily dose lies in the range of 10 μg to 30 mg per kg of body weight. Suitable dosages for the compounds according to the invention are from 0.005 to 50 mg per day per kg of body weight, depending on the age and constitution of the patient, whereby the necessary daily dose can be administered one or more times.

The formulation of the pharmaceutical preparations based on the new compounds is carried out in a way that is known in the art by the active ingredient being processed with the vehicles, fillers, substances that influence decomposition, binding agents, moisturizers, lubricants, absorbing agents, diluents, flavoring correctives, dyes, etc., that are commonly used in galenicals, and being converted into the desired form of administration. In this case, reference is made to Remington's Pharmaceutical Science, 15$^{th}$ Edition. Mack Publishing Company, East Pennsylvania (1980).

For oral administration, especially tablets, coated tablets, capsules, pills, powders, granulates, lozenges, suspensions, emulsions or solutions are suitable. For parenteral administration, injection and infusion preparations are possible. For intra-articular injection, correspondingly prepared crystal suspensions can be used. For intramuscular injection, aqueous and oily injection solutions or suspensions and corresponding depot preparations are used. For rectal administration, the new compounds can be used in the form of suppositories, capsules, solutions (e.g., in the form of enemas) and ointments both for systemic and for local therapy. For topical application, formulations in gels, ointments, fatty ointments, creams, pastes, powders, milks and tinctures are possible. The dosage of the compounds of general formula I should be 0.01%–20% in these preparations to achieve an adequate pharmacological action. The topical application can also be carried out by means of a transdermal system, for example a patch.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles. The invention also comprises a pharmaceutical composition that contains one of the pharmaceutically active compounds according to the invention or mixture thereof and a pharmaceutically compatible salt or pharmaceutically compatible adjuvants and vehicles.

Subjects of this invention are therefore also pharmaceutical compositions that contain at least one compound of general formula I, optionally together with pharmaceutically compatible adjuvants and/or vehicles.

These pharmaceutical compositions and pharmaceutical agents can be provided for oral, rectal, subcutaneous, transdermal, percutaneous, intravenous or intramuscular administration. In addition to commonly used vehicles and/or diluents, they contain at least one compound of general formula I.

The pharmaceutical agents of the invention are produced in a known way with commonly used solid or liquid vehicles or diluents and the commonly used pharmaceutical-technical adjuvants according to the desired type of administration with a suitable dosage. The preferred preparations consist of a form for dispensing that is suitable for oral administration. Such forms for dispensing are, for example, tablets, film tablets, coated tablets, capsules, pills, powders, solutions or suspensions or else depot forms.

The pharmaceutical compositions, which contain at least one of the compounds according to the invention, are preferably administered orally.

Parenteral preparations, such as injection solutions, are also considered.

In addition, for example, suppositories are also named as preparations.

Corresponding tablets can be obtained, for example, by mixing active ingredient with known adjuvants, for example inert diluents such as dextrose, sugar, sorbitol, mannitol, polyvinyl pyrrolidone, explosives such as corn starch or alginic acid, binding agents such as starches or gelatins, lubricants such as magnesium stearate or talc and/or agents for achieving a depot effect, such as carboxylpolymethylene, carboxymethyl cellulose, cellulose acetate phthalate, or polyvinyl acetate. The tablets can also consist of several layers.

Coated tablets can accordingly be produced by coating cores, which are produced analogously to the tablets, with agents that are commonly used in tablet coatings, for example polyvinyl pyrrolidone or shellac, gum arabic, talc, titanium oxide or sugar. In this case, the shell of the coated tablet can also consist of several layers, whereby the adjuvants that are mentioned above in the tablets can be used.

In addition, solutions or suspensions with the compounds of general formula I according to the invention can contain taste-improving agents such as saccharin, cyclamate or sugar, as well as, e.g., flavoring substances, such as vanilla or orange extract. In addition, they can contain suspending adjuvants such as sodium carboxymethyl cellulose or preservatives such as p-hydroxybenzoates.

The capsules that contain compounds of general formula I can be produced, for example, by the compound(s) of general formula I being mixed with an inert vehicle such as lactose or sorbitol and encapsulated in gelatin capsules.

Suitable suppositories can be produced, for example, by mixing with vehicles that are provided for this purpose, such as neutral fats or polyethylene glycol or derivatives thereof.

The compounds according to the invention can be administered combined with one or more of the following active ingredients for therapy of prostate cancers:
1) Gonadotropic-hormone (GnRH) agonists
2) 5α-Reductase inhibitor such as finasteride
3) Cytostatic agents
4) VEGF-kinase inhibitors
5) Antigestagens
6) Antiestrogens
7) Antisense oligonucleotides
8) EGF antibodies
9) Estrogens It is also possible, when treating prostate cancer with the compounds according to the invention, to combine their use with a clinical radiology method that is known in the art. (Laverdiere, J. et al., 1997, Intl. J. of Rad. One. Biol. Phys., 37, 247–252; Bolla, M. et al., 1997, New Engl. J. Med., 377, 95–300.)

Moreover, the compounds of general formula I according to the invention can be used for therapy and prophylaxis of other disease conditions that are not mentioned above.

The compounds of general formula I according to the invention can be produced as described below.

This invention also relates to the intermediate products of general formula VII

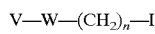

VII as well as of general formula VIII

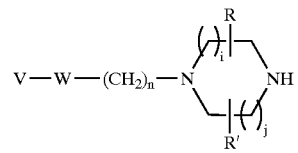

VIII in which

V stands for a substituted, aromatic radical of general formula II,

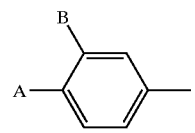

II in which

A stands for an acetyl group, an acetylamino group, a cyano group, a nitro group, a trifluoromethyl group, or a halogen (fluorine, chlorine), B stands for a hydrogen atom, a halogen (fluorine, chlorine) or a trifluoromethyl group, or A and B together stand for a cyclic group of formula III or IV that is bonded to the aromatic ring, whereby E stands for a methylene group or an oxygen atom,

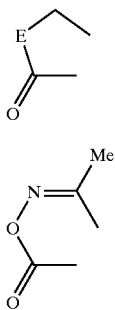

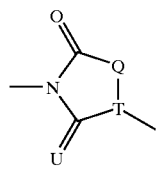

W stands for a heterocyclic compound of formula V,

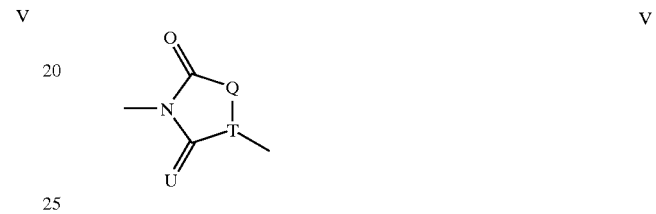

in which
   T stands for carbon, and a double bond is present between Q and T, and Q means a group $=C(CH_3)-$ and U means oxygen,
   n can assume one of the integral values 1, 2, 3, 4, 5, 6, 7, or 8,
   i and j, independently of one another, stand for the values 1 and 2, whereby i+j can assume the value 2 or 3,
   R and R', independently of one another, can be a hydrogen atom or a methyl group,
as well as the intermediate products of general formula VII and of general formula VIII,
in which
   A and B together stand for a cyclic group of formula III or IV that is bonded to the aromatic ring, whereby E stands for a methylene group or an oxygen atom, W stands for a heterocyclic compound of formula V, in which
   T stands for nitrogen, and a single bond is present between Q and T, and Q means a group $-C(CH_3)_2-$ and U means sulfur,
   n can assume one of the integral values 4, 5, 6, 7, or 8,
   i and j, independently of one another, stand for the values 1 and 2, whereby i+j can assume the value 2 or 3,
   R and R', independently of one another, can be a hydrogen atom or a methyl group.

This invention is explained in more detail based on the examples below without being limited thereto.

Synthesis Diagrams

According to the following diagram, maleimide derivatives of chain lengths n=4 to 8 can be produced:

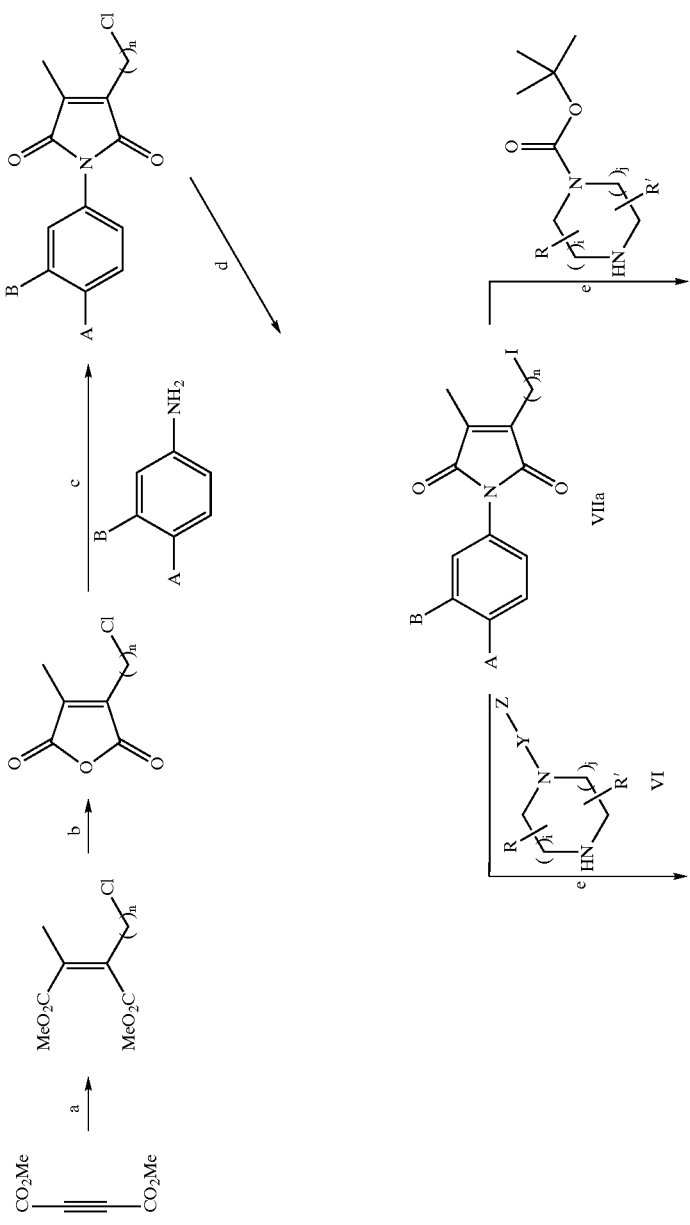

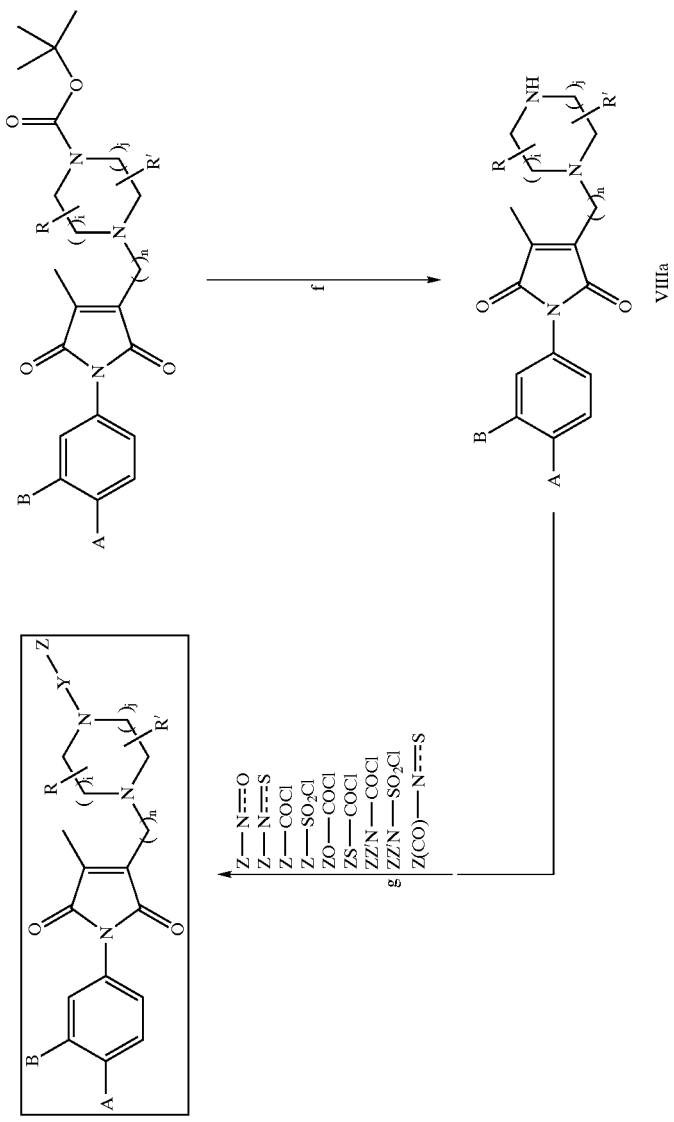
Reagents: (a) BrMg(CH$_2$)$_n$Cl, CuBrMe$_2$S, THF, then MeI, HMPT, THF; (b) LiOH, H$_2$O, THF, then HCl, extraction; (c) Aniline derivative, EtOH, MS 4Å; (d) NaI, ethylmethylketone; (e) THF; (f) trifluoroacetic acid, CH$_2$Cl$_2$; (g) NEt$_3$, THF.

According to the following diagram, maleimide derivatives of chain lengths n=1 to 8 can be produced:

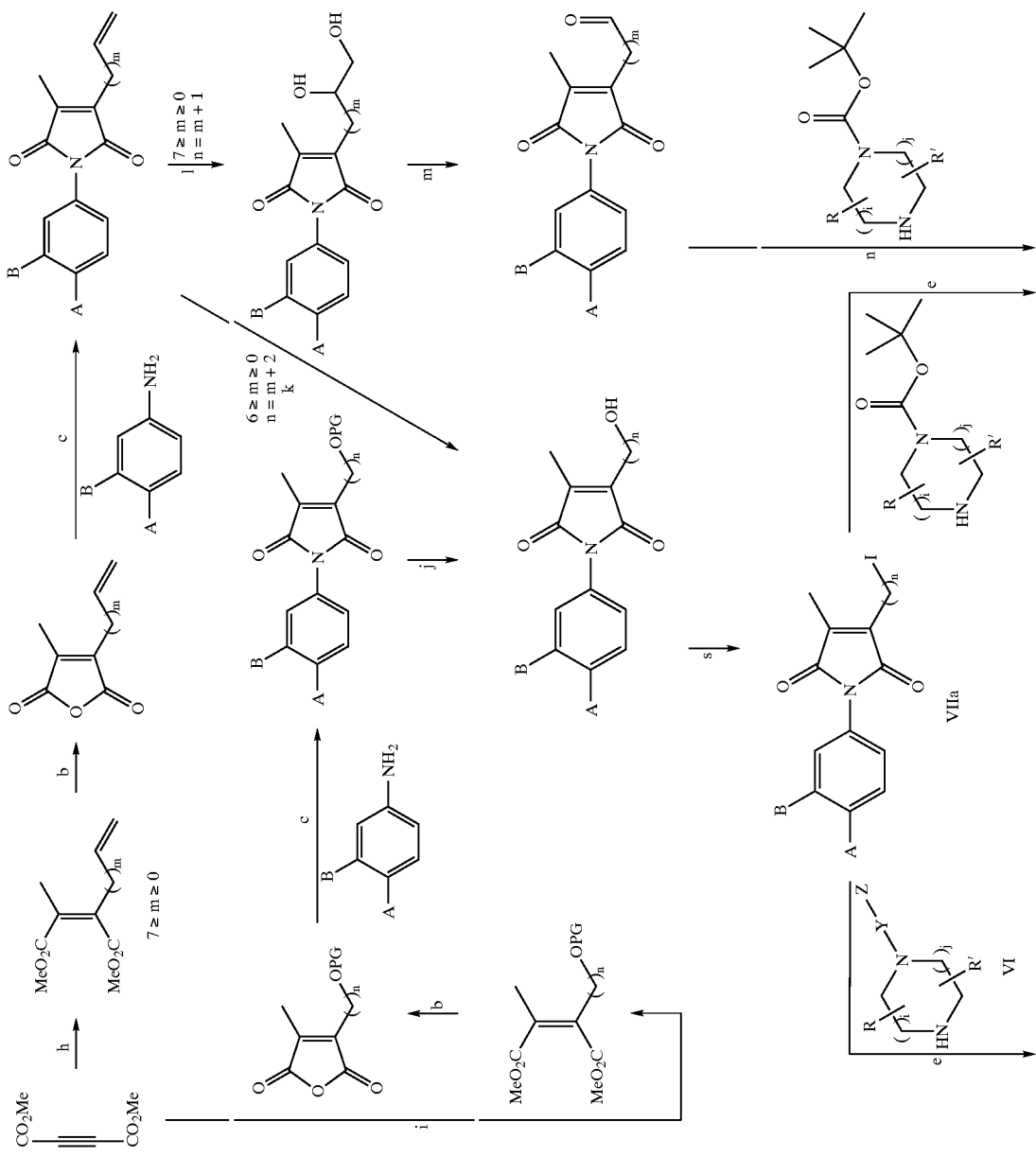

-continued
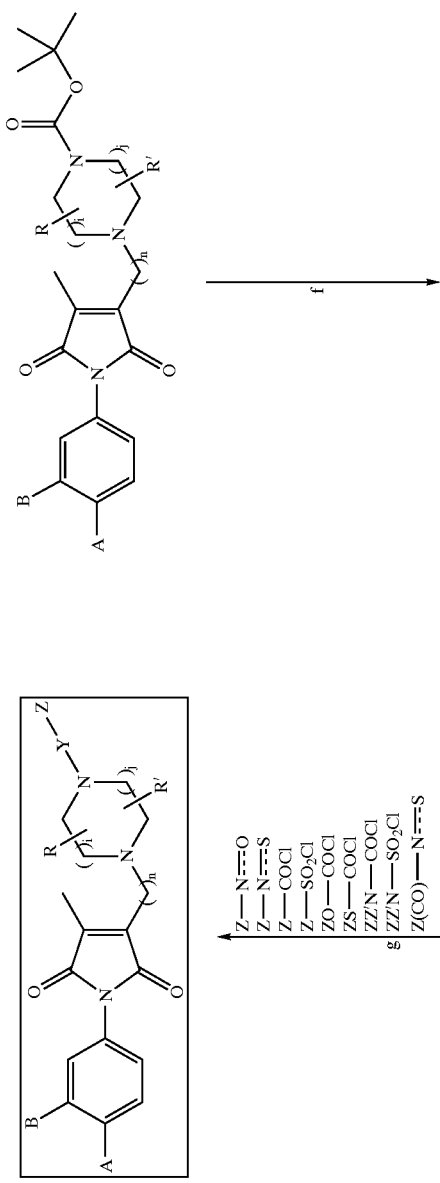
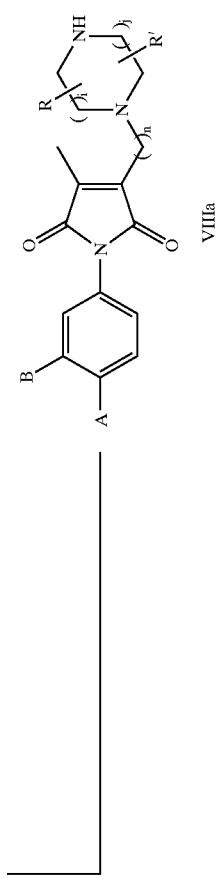
Reagents: (b) LiOH, H₂O, THF, then HCl, extraction; (c) aniline derivative, EtOH, MS 4A; (e) THF; (f) Trifluoroacetic acid, CH₂Cl₂; (g) NEt₃, THF; (h) BrMg(CH₂)m-CH=CH₂, CuBrMe₂S, THF, then MeI, HMPT, THF; (i) BrMg(CH₂)nOPG, CuBrMe₂S, THF, then MeI, HMPT, THF; (PG=protective group); (j) Protection removal; (k) 9-BBN, then NaOH, H₂O₂; (l) OsO₄; (m) NaIO₄; (n) Na(Oac)₃BH; (s) Imidazole, iodine, triphenylphosphine.

According to the following diagram, thiohydantoin derivatives of chain lengths n=4 to 8 can be produced:
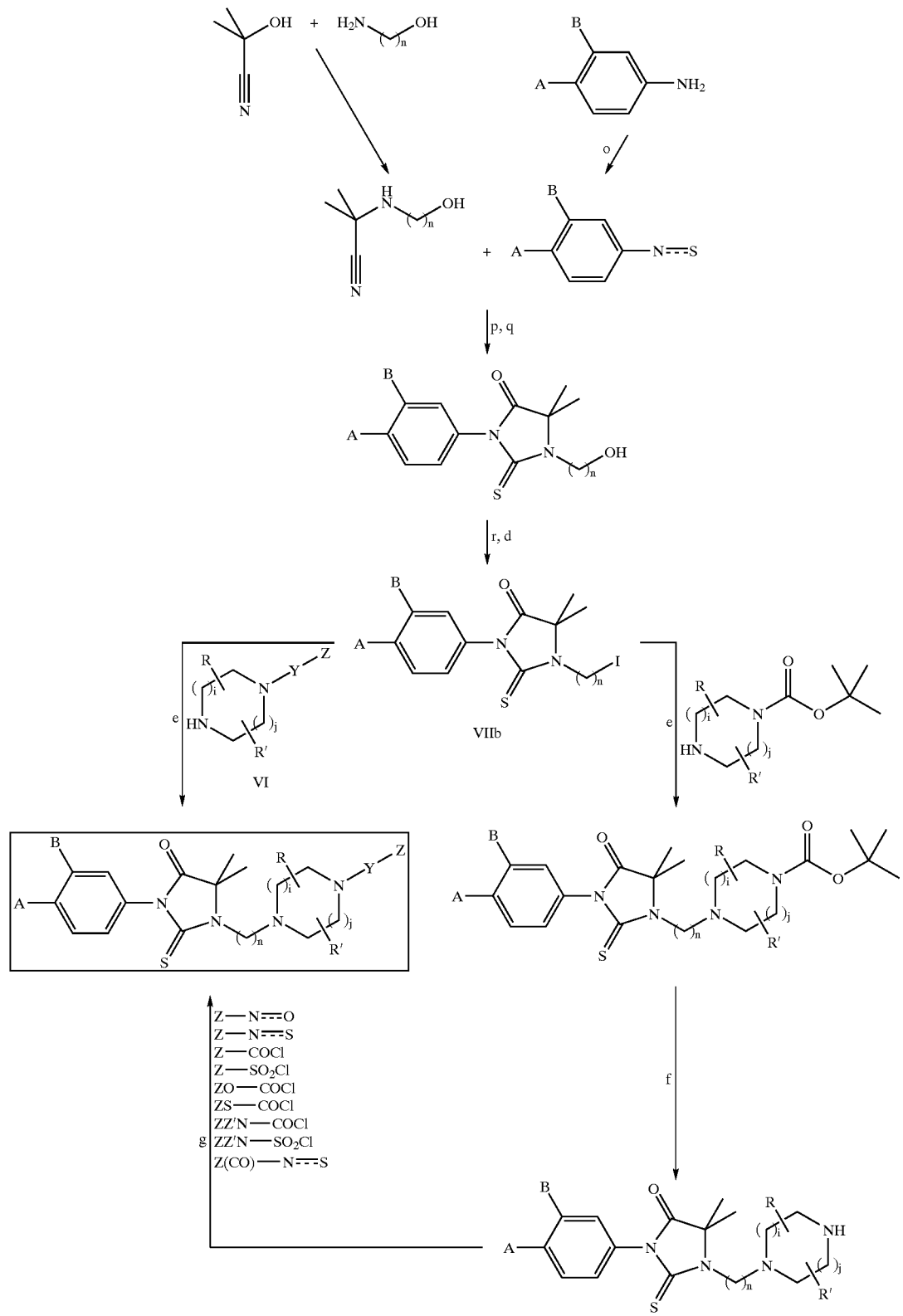
Reagents: (d) NaI, ethylmethylketone; (e) THF; (f) Trifluoroacetic acid, CH$_2$Cl$_2$; (g) NEt$_3$, THF; (o) CSCl$_2$, H$_2$O; (p) NEt$_3$, THF; (q) 4 M HCl; (r) RSO$_2$Cl, NEt$_3$, CH$_2$Cl$_2$.

According to the following diagram, thiohydantoin derivatives of chain lengths n=2 to 8 can be produced:

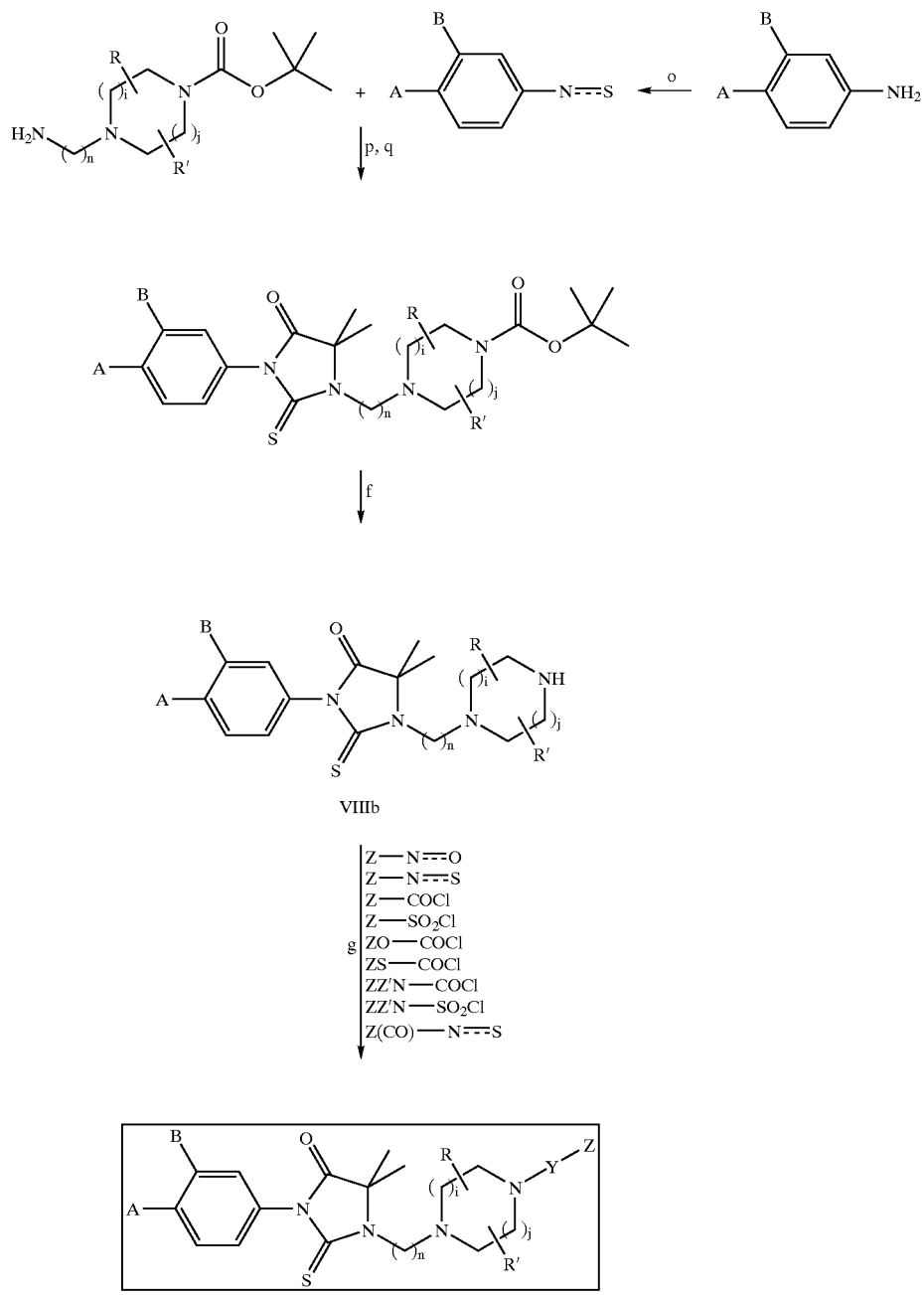

Reagents: (f) Trifluoroacetic acid, CH₂Cl₂; (g) NEt₃, THF; (o) CSCl₂, H₂O; (p) NEt₃, THF; (q) 4 M HCl.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Production Process

EXAMPLE 1

1,1-Dimethylethyl 4-[5-[1-[4-Cyano-3-(trifluoromethyl)phenyl]-2,5-dihydro-4-methyl-2,5-dioxo-1H-pyrrol-3-yl]pentyl]piperazine-1-carboxylate 1a) Dimethyl (Z)-2-(5-Chloropentyl)-3-methyl-2-butenedicarboxylate For the production of a Grignard reagent, 4.1 g of magnesium chips in 22 ml of tetrahydrofuran was introduced under nitrogen atmosphere, mixed with 31.3 g of 1-bromo-5-chloropentane in 200 ml of tetrahydrofuran, and it was stirred for 1 hour at room temperature. This mixture was then added in drops under nitrogen atmosphere and while being stirred at −35 to −40° C. to a suspension of 34.7 g of copper(I)-bromide-dimethyl sulfide complex in 700 ml of tetrahydrofuran, and it was stirred for another 2 hours at −40° C. Then, it was cooled to −65 to −70° C., and a solution of 20 g of dimethyl acetylenedicarboxylate and 48 ml of hexamethylphosphoric acid triamide in 290 ml of tetrahydrofuran were added in drops at this temperature while being stirred; after 5 minutes, a solution of 95 ml of hexamethylphosphoric acid triamide in 95 ml of tetrahydrofuran was added at −65 to −70° C., it was stirred for another 5 minutes at this temperature, 100 g of iodomethane in 280 ml of tetrahydrofuran was added in drops, and this mixture was heated overnight to room temperature. For working-up, it was cooled to −60° C. while being stirred, 410 ml of saturated ammonium chloride solution (with concentrated ammonia solution set at a pH of 8) was added in drops, heated to room temperature and stirred for 45 minutes at room temperature. This mixture was extracted four times with ethyl acetate, the combined organic phases were washed with saturated ammonium chloride solution (with concentrated ammonia solution set at a pH of 8) until the organic phase was light blue and then washed with water until the organic phase was colorless. After washing with saturated sodium chloride solution, drying on sodium sulfate and concentration by evaporation, it was chromatographed on silica gel with ethyl acetate/hexane, and thus in addition to 7.2 g of dimethyl (E)-2-(5-chloropentyl)-3-methyl-2-butenedicarboxylate, in each case 10.0 g of the title compound was obtained as a yellowish oil.

$^{1}$H-NMR (300 MHz, CDCl$_3$): δ [ppm]=3.76 s (3H, OCH$_3$); 3.75 s (3H, OCH$_3$); 3.53 t (J=6.5 Hz, 2H, CH$_2$Cl); 2.35 tbr (J=7 Hz, 2H, CH$_2$olefin); 1.95 s (3H, CH$_3$); 1.78 m (2H, CH$_2$); 1.47 m (4H, CH$_2$).

1b) 3-(5-Chloropentyl)-4-methyl-2,5-furandione 86 ml of water as well as 164 ml of a solution of lithium hydroxide in water (1 mol/l) were added to a solution of 7.16 g of (Z)-dimethyl 2-(5-chloropentyl)-3-methyl-2-butenedicarboxylate that was stirred under nitrogen atmosphere, and it was stirred for 2 days at room temperature. For working-up, it was concentrated by evaporation, the residue was dissolved in 290 ml of water, set at pH 2 with hydrochloric acid (2 mol/l) while being cooled in an ice bath and extracted three times with diethyl ether. The combined organic phases were washed with saturated sodium chloride solution, dried on sodium sulfate, concentrated by evaporation, and the title compound was thus obtained as a yellowish oil.

$^{1}$H-NMR (300 MHz, CDCl$_3$): δ [ppm]=3.54 t (J=6.5 Hz, 2H, CH$_2$Cl); 2.48 tbr (J=7.5 Hz, 2H, CH$_2$olefin); 2.08 sbr (3H, CH$_3$); 1.81 m (2H, CH$_2$); 1.63 m (2H, CH$_2$); 1.51 m (2H, CH$_2$).

1c) 4-[3-(5-Chloropentyl)-2,5-dihydro-4-methyl-2,5-dioxo-1H-pyrrol-1-yl]-2-(trifluoromethyl)benzonitrile A mixture of 9.46 g of 3-(5-chloropentyl)-4-methyl-2,5-furandione and 8.13 g of 4-amino-2-(trifluoromethyl)benzonitrile in 22 ml of ethanol was mixed under a nitrogen atmosphere with 2.5 g of an activated molecular sieve (0.3 nm), and it was stirred for 2 days at 90° C. For working-up, the molecular sieve was filtered off after cooling, washed with ethanol, and the combined ethanol solutions were concentrated by evaporation. The residue was taken up in ethyl acetate and washed with water as well as saturated sodium chloride solution. After drying on sodium sulfate and concentration by evaporation, it was chromatographed on silica gel with ethyl acetate/hexane/toluene, and 11.69 g of the title compound was thus obtained as a white solid.

$^{1}$H-NMR (300 MHz, CDCl$_3$): δ [ppm]=8.06 sbr (1H, aryl); 7.91 s (2H, aryl); 3.56 t (J=7 Hz, 2H, CH$_2$Cl); 2.53 t (J=7.5 Hz, 2H, CH$_2$olefin); 2.11 s (3H, CH$_3$); 1.83 m (2H, CH$_2$); 1.69–1.50 m (4H, CH$_2$).

1d) 4-[2,5-Dihydro-3-(5-iodopentyl)-4-methyl-2,5-dioxo-1H-pyrrol-1-yl]-2-(trifluoromethyl)benzonitrile A mixture of 11.68 g of 4-[3-(5-chloropentyl)-2,5-dihydro-4-methyl-2,5-dioxo-1H-pyrrol-1-yl]-2-(trifluoromethyl)benzonitrile and 18.2 g of sodium iodide in 180 ml of ethylmethylketone was stirred under a nitrogen atmosphere for 19 hours at 80° C. After cooling, it was diluted with ethyl acetate and washed with water as well as saturated sodium chloride solution. After drying on sodium sulfate and concentration by evaporation, 11.26 g of the title compound was obtained as a white solid.

$^{1}$H-NMR (300 MHz, CDCl$_3$): δ [ppm]=8.06 sbr (1H, aryl); 7.91 s (2H, aryl); 3.20 t (J=7 Hz, 2H, CH$_2$I); 2.52 t (J=7.5 Hz, 2H, CH$_2$olefin); 2.11 s (3H, CH$_3$); 1.86 m (2H, CH$_2$); 1.63 m (2H, CH$_2$); 1.50 m (2H, CH$_2$).

1e) 1,1-Dimethylethyl 4-[5-[1-[4-Cyano-3-(trifluoromethyl)phenyl]-2,5-dihydro-4-methyl-2,5-dioxo-1H-pyrrol-3-yl]pentyl]piperazine-1-carboxylate 1.56 g of 1,1-dimethylethyl piperazine-1-carboxylate was added under a nitrogen atmosphere to a solution of 2.0 g of 4-[2,5-dihydro-3-(5-iodopentyl)-4-methyl-2,5-dioxo-1H-pyrrol-1-yl]-2-(trifluoromethyl)benzonitrile in 53 ml of tetrahydrofuran, and this mixture was stirred for 7 days at room temperature. For working-up, it was diluted with ethyl acetate and washed with semi-saturated sodium bicarbonate solution. After drying on sodium sulfate and concentration by evaporation, it was chromatographed with methanol/dichloromethane on silica gel, and thus 2.2 g of the title compound was obtained as a yellowish oil.

$^{1}$H-NMR (300 MHz, CDCl$_3$): δ [ppm]=8.06 sbr (1H, aryl); 7.90 m (2H, aryl); 3.43 m (4H, piperazine); 2.50 tbr (J=7.5 Hz, 2H, CH$_2$olefin); 2.40–2.31 m (4H, piperazine); 2.40–2.31 m (2H, CH$_2$piperazine); 2.09 s (3H, CH$_3$); 1.66–1.36 m (6H, CH$_2$); 1.45 s (9H, CH$_3$).

EXAMPLE 2

4-[2,5-Dihydro-3-methyl-2,5-dioxo-4-[5-(piperazin-1-yl)pentyl]-1H-pyrrol-1-yl]-2-(trifluoromethyl)benzonitrile 60 ml of trifluoroacetic acid was added in drops to a solution of 4.5 g of 1,1-dimethylethyl 4-[5-[1-[4-cyano-3-(trifluoromethyl)phenyl]-2,5-dihydro-4-methyl-2,5-dioxo-1H-pyrrol-3-yl]pentyl]piperazine-1-carboxylate in 120 ml of dichloromethane under a nitrogen atmosphere and while being cooled in an ice bath, and it was stirred for 1 hour at room temperature. For working-up, the reaction solution was diluted with 250 ml of toluene, and the mixture was concentrated by evaporation. The residue was taken up in ethyl acetate and washed with saturated sodium bicarbonate solution. After drying on sodium sulfate and concentration by evaporation, it was chromatographed with methane/dichloromethane on silica gel, and 3.5 g of the title compound was thus obtained as a white solid.

$^{1}$H-NMR (300 MHz, CD$_3$OD): δ [ppm]=8.13 dbr (J=2 Hz, 1H, aryl); 8.08 dbr (J=8.5 Hz, 1H, aryl); 8.01 dd (J=8.5 Hz+2 Hz, 1H, aryl); 3.18 m (4H, piperazine); 2.69 m (4H, piperazine); 2.53 tbr (J=7.5 Hz, 2H, CH$_2$olefin); 2.47 tbr (J=7.5 Hz, 2H, CH$_2$piperazine); 2.07 s (3H, CH$_3$); 1.69–1.53 m (4H, CH$_2$); 1.44 m (2H, CH$_2$).

EXAMPLE 3

4-[2,5-Dihydro-3-methyl-4-[5-[4-[2-(methylsulfanyl)phenyl]piperazin-1-yl]pentyl]-2,5-dioxo-1H-pyrrol-1-yl]-2-(trifluoromethyl)benzonitrile 9 mg of 1-(2-thiomethylphenyl)piperazine in 0.5 ml of tetrahydrofuran was added to a solution of 10 mg of 4-[2,5-dihydro-3-(5-iodopentyl)-4-methyl-2,5-dioxo-1H-pyrrol-1-yl]-2-(trifluoromethyl)benzonitrile in 0.4 ml of tetrahydrofuran, and the mixture was stirred for 2 days at room temperature. For working-up, the reaction mixture was diluted with ethyl acetate and washed with semi-saturated sodium bicarbonate solution. After the organic phase was concentrated by evaporation, it was chromatographed with methanol/dichloromethane on silica gel, and 6 mg of the title compound was thus obtained as a yellowish oil.

ESI-MS: 557.

EXAMPLE 4

4-[3-[5-[4-(4-Cyanobenzoyl)piperazin-1-yl]pentyl]-2,5-dihydro-4-methyl-2,5-dioxo-1H-pyrrol-1-yl]-2-(trifluoromethyl)benzonitrile 0.2 ml of a solution of triethylamine in tetrahydrofuran (1.5 mol/l) and 7 mg of 4-cyanobenzoyl chloride in 0.4 ml of tetrahydrofuran were added to a solution of 9 mg of 4-[2,5-dihydro-3-methyl-2,5-dioxo-4-[5-(piperazin-1-yl)pentyl]-1H-pyrrol-1-yl]-2-(trifluoromethyl)benzonitrile in 0.4 ml of tetrahydrofuran, and the mixture was stirred for 8 hours at room temperature. For working-up, the reaction mixture was diluted with ethyl acetate and washed with semi-saturated sodium bicarbonate solution. After the organic phase was concentrated by evaporation, it was chromatographed with methanol/dichloromethane on silica gel, and 7 mg of the title compound was thus obtained as a yellowish oil.

ESI-MS: 564.

EXAMPLE 5

4-[3-[5-[4-[(3-Fluorophenyl)sulfonyl]piperazin-1-yl]pentyl]-2,5-dihydro-4-methyl-2,5-dioxo-1H-pyrrol-1-yl]-2-(trifluoromethyl)benzonitrile 0.2 ml of a solution of triethylamine in tetrahydrofuran (1.5 mol/l) and 8 mg of 3-fluorophenylsulfonyl chloride in 0.4 ml of tetrahydrofuran were added to a solution of 9 mg of 4-[2,5-dihydro-3-methyl-2,5-dioxo-4-[5-(piperazin-1-yl)pentyl]-1H-pyrrol-1-yl]-2-(trifluoromethyl)benzonitrile in 0.4 ml of tetrahydrofuran, and the mixture was stirred for 8 hours at room temperature. For working-up, the reaction mixture was diluted with ethyl acetate and washed with semi-saturated sodium bicarbonate solution. After the organic phase was concentrated by evaporation, it was chromatographed with methanol/dichloromethane on silica gel, and 6 mg of the title compound was thus obtained as a white solid.

ESI-MS: 593.

EXAMPLE 6

4-[5-[1-[4-Cyano-3-(trifluoromethyl)phenyl]-2,5-dihydro-4-methyl-2,5-dioxo-1H-pyrrol-3-yl]pentyl]-N-[4-(dimethylamino)phenyl]piperazine-1-carboxamide 0.2 ml of a solution of triethylamine in tetrahydrofuran (1.5 mol/l) and 7 mg of 4-(dimethylamino)phenylisocyanate in 0.4 ml of tetrahydrofuran were added to a solution of 9 mg of 4-[2,5-dihydro-3-methyl-2,5-dioxo-4-[5-(piperazin-1-yl)pentyl]-1H-pyrrol-1-yl]-2-(trifluoromethyl)benzonitrile in 0.4 ml of tetrahydrofuran, and the mixture was stirred for 8 hours at room temperature. For working-up, the reaction mixture was diluted with ethyl acetate and washed with semi-saturated sodium bicarbonate solution. After the organic phase was concentrated by evaporation, it was chromatographed with methanol/dichloromethane on silica gel, and 3 mg of the title compound was thus obtained as a yellowish oil.

ESI-MS: 597.

EXAMPLE 7

4-[2,5-Dihydro-3-methyl-4-[3-[4-(1-methylethylsulfonyl)piperazin-1-yl]propyl]-2,5-dioxo-1H-pyrrol-1-yl]-2-(trifluoromethyl)benzonitrile 7a) Dimethyl (Z)-2-Methyl-3-(prop-2-enyl)-2-butenedicarboxylate A solution of allylmagnesium chloride in tetrahydrofuran (8.5 ml, c=2.0 M) was added in drops under nitrogen atmosphere and while being stirred at −35 to −40° C. to a suspension of 3.47 g of copper(I)-bromide-dimethylsulfide complex in 70 ml of tetrahydrofuran, and it was stirred for 2 hours at −40° C. Then, it was cooled to −70° C., and a solution of 2.0 g of dimethyl acetylenedicarboxylate and 4.8 ml of hexamethylphosphoric acid triamide in 29 ml of tetrahydrofuran was added in drops at this temperature while being stirred. After 5 minutes, a solution of 9.5 ml of hexamethylphosphoric acid triamide in 9.5 ml of tetrahydrofuran was added at −70° C. It was stirred for 5 minutes at this temperature, then 4.2 ml of iodomethane in 28 ml of tetrahydrofuran was added in drops, and this mixture was heated overnight to room temperature. For working-up, it was cooled to −60° C. while being stirred, 200 ml of saturated ammonium chloride solution (with concentrated ammonia solution set at pH 8) was added in drops, it was heated to room temperature and stirred for 45 minutes at room temperature. This mixture was extracted four times with ethyl acetate, the combined organic phases were washed with saturated ammonium chloride solution (with concentrated ammonia solution set at pH 8) until the organic phase was light blue and was then washed with water until the organic phase was colorless. After washing with saturated sodium chloride solution, drying on sodium sulfate and concentration by evaporation, it was chromatographed on silica gel with ethyl acetate/hexane, and 980 mg of the title compound in addition to 950 mg of dimethyl (E)-2-methyl-3-(prop-2-enyl)-2-butenedicarboxylate in cache case were obtained as a yellowish oil.

$^1$H-NMR (300 MHz, CDCl$_3$): δ [ppm]=5.8 m (1H); 5.1 m (2H); 3.77 s (3H); 3.75 s (3H); 3.10 d (J=6.58 Hz, 2H); 1.96 s (3H). ESI-MS: 198

7b) 3-Methyl-4-(prop-2-enyl)-2,5-furandione 10 ml of water as well as 16 ml of a solution of lithium hydroxide in water (1 mol/l) were added to a solution, stirred under a nitrogen atmosphere, of 980 mg of the compound, produced under 7a, in 10 ml of tetrahydrofuran, and it was stirred for 2 days at room temperature. For working-up, it was concentrated by evaporation, the residue was dissolved in 30 ml of water, the pH was set at 2 with hydrochloric acid (2 mol/l) while being cooled in an ice bath, and it was extracted three times with diethyl ether. The combined organic phases were washed with saturated sodium chloride solution, dried on sodium sulfate, concentrated by evaporation, and 750 mg of the title compound was thus obtained as a yellowish oil.

ESI-MS: 152.

7c) 4-[2,5-Dihydro-3-methyl-2,5-dioxo-4-(prop-2-enyl)-1H-pyrrol-1-yl]-2-(trifluoromethyl)benzonitrile A mixture of 750 mg of the compound, produced under 7b, and 920 mg of 4-amino-2-(trifluoromethyl)benzonitrile in 10 ml of ethanol was mixed under a nitrogen atmosphere with 0.5 g of an activated molecular sieve (0.3 nm) and stirred for 2 days at 90° C. For working-up, the molecular sieve was filtered off after cooling, washed with ethanol, and the combined ethanol solutions were concentrated by evaporation. The residue was taken up in ethyl acetate and washed with water as well as saturated sodium chloride solution. After drying on sodium sulfate and concentration by evaporation, it was chromatographed on silica gel with ethyl acetate/hexane, and 731 mg of the title compound was thus obtained as a colorless oil.

ESI-MS: 320.

7d) 4-[2,5-Dihydro-3-(3-hydroxypropyl)-4-methyl-2,5-dioxo-1H-pyrrol-1-yl]-2-(trifluoromethyl)benzonitrile A solution of 720 mg of the compound, produced under 7c, in 15 ml of THF was mixed under a nitrogen atmosphere at −78° C. with 5.9 ml of a 0.5 molar solution of 9-borabicyclo(3.3.1)nonane. The solution was slowly heated to room temperature and stirred overnight at room temperature. The solution that was stirred vigorously was mixed at 0° C. with 3.1 ml of 10% sodium hydroxide solution and with 2.7 ml of 33% hydrogen peroxide solution, and it was stirred for 12 hours at room temperature. For working-up, it was mixed with water (20 ml) and extracted three times with ethyl acetate. The combined organic phases were washed with saturated sodium chloride solution, dried on sodium sulfate, concentrated by evaporation, chromatographed on silica gel with ethyl acetate/hexane, and 623 mg of the title compound was thus obtained as a yellowish oil.

ESI-MS: 338.

7e) 4-[2,5-Dihydro-3-(3-iodopropyl)-4-methyl-2,5-dioxo-1H-pyrrol-1-yl]-2-(trifluoromethyl)benzonitrile A solution of 610 mg of the compound, produced under 7d, of 565 mg of triphenylphosphine and 183 mg of 1H-imidazole in 50 ml of THF was mixed under a nitrogen atmosphere with 545 mg of iodine. The solution was stirred overnight at room temperature and then mixed with 20 ml of water and 10 ml of 20% sodium thiosulfate solution and extracted three times with ethyl acetate. The combined organic phases were washed with saturated sodium chloride solution, dried on sodium sulfate, concentrated by evaporation, chromatographed on silica gel with ethyl acetate/hexane, and 572 mg of the title compound was thus obtained as a yellowish oil.

ESI-MS: 448.

7f) 1,1-Dimethylethyl 4-[3-[1-[4-Cyano-3-(trifluoromethyl)phenyl]-2,5-dihydro-4-methyl-2,5-dioxo-1H-pyrrol-3-yl]propyl]piperazine-1-carboxylate The production of the title compound was carried-out analogously to the reaction described under 1e. Starting from 550 mg of the compound that was produced under 7e, 372 mg of the title compound was obtained.

ESI-MS: 506.

7g) 4-[2,5-Dihydro-3-methyl-2,5-dioxo-4-[3-(piperazin-1-yl)propyl]-1H-pyrrol-1-yl]-2-(trifluoromethyl)benzonitrile 350 mg of the compound that was produced under 7f was stirred with 3 ml of trifluoroacetic acid in 10 ml of dichloromethane for 6 hours at room temperature. The reaction mixture was concentrated by evaporation in a vacuum and concentrated by evaporation several times with toluene in a vacuum, taken up in methanol, set at a pH of 8 to 9 with anion exchanger (Bio-Rad AG 1-X8, OH form), filtered, and concentrated by evaporation in a vacuum. 227 mg of the title compound was obtained as a crude product, which was further reacted in this form.

ESI-MS: 406.

7h) 4-[2,5-Dihydro-3-methyl-4-[3-[4-(1-methylethylsulfonyl)piperazin-1-yl]propyl]-2,5-dioxo-1H-pyrrol-1-yl]-2-(trifluoromethyl)benzonitrile 25 mg of the compound that was produced under 7g was stirred with 11 µl of 1-methylethylsulfonyl chloride and 25 µl of triethylamine in 2 ml of tetrahydrofuran for 16 hours at room temperature. The reaction mixture was concentrated by evaporation in a vacuum. Column chromatography on silica gel with a mixture that consists of hexane/ethyl acetate yielded 23 mg of the title compound as a colorless oil.

ESI-MS: 512.

EXAMPLE 8

4-[2,5-Dihydro-3-methyl-4-[[4-(1-methylethylsulfonyl)piperazin-1-yl]methyl]-2,5-dioxo-1H-pyrrol-1-yl]-2-(trifluoromethyl)benzonitrile 8a) Dimethyl (Z)-2-Ethenyl-3-methyl-2-butenedicarboxylate The reaction of vinylmagnesium chloride with 5 g of dimethyl acetylenedicarboxylate analogously to the instructions described under 7a yielded 1.8 g of the title compound as a yellowish oil.

ESI-MS: 184.

8b) 4-[3-Ethenyl-2,5-dihydro-4-methyl-2,5-dioxo-1H-pyrrol-1-yl]-2-(trifluoromethyl)benzonitrile The reaction of 1.8 g of the compound, produced under 8a, analogously to the instructions described under 7b and 7c yielded 1.1 g of the title compound as a colorless oil.

ESI-MS: 306.

8c) 4-[3-(1,2-Dihydroxyethyl)-2,5-dihydro-4-methyl-2,5-dioxo-1H-pyrrol-1-yl]-2-(trifluoromethyl)benzonitrile A solution of 1.1 g of the compound, produced under 8b, in 50 ml of acetone was mixed at room temperature with a solution of 640 mg of N-methylmorpholine-N-oxide in 10 ml of water and 0.9 ml of a 10% solution of osmium tetraoxide. It was stirred for 30 hours at room temperature, then mixed with saturated sodium thiosulfate solution and extracted three times with ethyl acetate. The combined organic phases were washed with saturated sodium chloride solution, dried on sodium sulfate, concentrated by evaporation, chromatographed with dichloromethane/methanol on silica gel, and 770 mg of the title compound was thus obtained as a colorless oil.

ESI-MS: 340.

8d) 4-[3-Formyl-2,5-dihydro-4-methyl-2,5-dioxo-1H-pyrrol-1-yl]-2-(trifluoromethyl)benzonitrile A solution of 750 mg of the compound, produced under 8c, in 50 ml of dichloromethane was mixed at room temperature in succession with 619 mg of sodium periodate and with 5 ml of a 10% aqueous solution of sodium bicarbonate. It was stirred for 5 hours at room temperature, then mixed with sodium sulfate and diluted with 50 ml of dichloromethane. The mixture was filtered and concentrated by evaporation. 705 mg of the title compound was obtained as a crude product, which was further reacted in this form.

ESI-MS: 308.

8e) 4-[2,5-Dihydro-3-methyl-4-[[4-(1-methylethylsulfonyl)piperazin-1-yl]methyl]-2,5-dioxo-1H-pyrrol-1-yl]-2-(trifluoromethyl)benzonitrile 25 mg of the compound, produced under 8d, in 1 ml of 1,2-dichloroethane was mixed with 19 mg of 1-(1- methylethylsulfonyl)piperazine and stirred for 15 minutes at room temperature. 25 mg of sodium tris-acetoxy borohydride was added in portions, and it was stirred for 2 hours at room temperature. The reaction mixture was mixed with 10 ml of sodium bicarbonate solution, stirred for 15 minutes at room temperature, and extracted three times with ethyl acetate. The combined organic phases were washed with saturated sodium chloride solution, dried on sodium sulfate, concentrated by evaporation and chromatographed with dichloromethane/methanol on silica gel. 17 mg of the title compound was obtained as a colorless oil.

ESI-MS: 484.

EXAMPLE 9

4-[2,5-Dihydro-3-methyl-4-[7-[4-(1-methylethylsulfonyl)piperazin-1-yl]heptyl]-2,5-dioxo-1H-pyrrol-1-yl]-2-(trifluoromethyl)benzonitrile 9a) Dimethyl (Z)-2-[7-[(4-Methoxyphenyl)methoxy]heptyl]-3-methyl-2-butenedicarboxylate The reaction of 12.4 g of 1-[[(7-chloroheptyl)oxy]methyl]-4-methoxybenzene with 5.0 g of dimethyl acetylene dicarboxylate analogously to the instructions described under 1a yielded 4.18 g of the title compound as a yellowish oil.

ESI-MS: 378.

9b) 4-[2,5-Dihydro-3-[7-[(4-methoxyphenyl)methoxy]heptyl]-4-methyl-2,5-dioxo-1H-pyrrol-1-yl]-2-(trifluoromethyl)benzonitrile The reaction of 4.10 g of the compound, produced under 9a, analogously to the instructions described under 7b and 7c yielded 3.35 g of the title compound as a colorless oil.

ESI-MS: 514.

9c) 4-[2,5-Dihydro-3-(7-hydroxyheptyl)-4-methyl-2,5-dioxo-1H-pyrrol-1-yl]-2-(trifluoromethyl)benzonitrile 3.30 g of the compound, produced under 9b, in 100 ml of dichloromethane was mixed with 10 ml of water and 1.90 g of 4,5-dichloro-3,6-dioxocyclohexa-1,4-diene-1,2-dicarbonitrile, and it was stirred for 5 hours at room temperature. The reaction mixture was mixed with 20 ml of sodium bicarbonate solution and extracted three times with dichloromethane. The combined organic phases were washed with saturated sodium chloride solution, dried on sodium sulfate, concentrated by evaporation and chromatographed with dichloromethane/methanol on silica gel. 2.05 g of the title compound was obtained as a colorless oil.

ESI-MS: 394.

9d) 4-[3-(7-Iodoheptyl)-2,5-dihydro-4-methyl-2,5-dioxo-1H-pyrrol-1-yl]-2-(trifluoromethyl)benzonitrile The reaction of 2.0 g of the compound, produced under 9c, analogously to the instructions that are described under 7e, yielded 1.99 g of the title compound as a colorless oil.

ESI-MS: 504.

9e) 1,1-Dimethylethyl 4-[7-[1-[4-Cyano-3-(trifluoromethyl)phenyl]-2,5-dihydro-4-methyl-2,5-dioxo-1H-pyrrol-3-yl]heptyl]piperazine-1-carboxylate The production of the title compound was carried out analogously to the reaction that was described under 1e. Starting from 1.95 g of the compound that was produced under 9c, 1.01 g of the title compound was obtained.

ESI-MS: 562.

9f) 4-[2,5-Dihydro-3-methyl-2,5-dioxo-4-[7-(piperazin-1-yl)heptyl]-1H-pyrrol-1-yl]-2-(trifluoromethyl)benzonitrile The production of the title compound was carried out analogously to the reaction that was described under 7g. Starting from 1.0 g of the compound that was produced under 9e, 707 mg of the title compound was obtained.

ESI-MS: 462.

9g) 4-[2,5-Dihydro-3-methyl-4-[7-[4-(1-methylethylsulfonyl)piperazin-1-yl]heptyl]-2,5-dioxo-1H-pyrrol-1-yl]-2-(trifluoromethyl)benzonitrile The production of the title compound was carried out analogously to the reaction that was described under 7h. Starting from 25 mg of the compound that was produced under 9f, 20 mg of the title compound was obtained.

ESI-MS: 568.

EXAMPLE 10

1,1-Dimethylethyl 4-[5-[3-(1,3-Dihydro-1-oxoisobenzofuran-5-yl)-5,5-dimethyl-4-oxo-thioxoimidazolidin-1-yl]pentyl]piperazine-1-carboxylate 10a) 5-[3-(5-Hydroxypentyl)-5-imino-4,4-dimethyl-2-thioxoimidazolidin-1-yl]isobenzofuran-1(3H)-one 5 g of 5-aminoisobenzofuran-1-(3H)-one, whose production is described in R. N. Warrener, L. Liu, R. A. Russell, *Tetrahedron* 1998, 54, 7485–7496, with 2.8 ml of thiophosgene in 70 ml of water, was stirred for one hour at room temperature under nitrogen atmosphere. The reaction mixture was filtered. The residue was washed with water and then dried for 30 minutes at 60° C. in a vacuum. The thus-obtained crude isothiocyanate was combined with the cyanoamine that was produced by four hours of stirring of 520 µl of acetone cyanohydrin with 617 µl of 5-aminopentan-1-ol at room temperature, and it was heated to boiling with 4.7 ml of triethylamine in 100 ml of tetrahydrofuran for 30 minutes. After concentration by evaporation in a vacuum, the title compound was obtained as a crude product, which was immediately further reacted.

10b) 3-(1,3-Dihydro-1-oxoisobenzofuran-5-yl)-1-(5-hydroxypentyl)-5,5-dimethyl-2-thioxoimidazolidin-4-one The crude product that was produced under 10a was stirred with 17 ml of 4 molar aqueous hydrochloric acid in 150 ml of methanol overnight at room temperature. The reaction mixture was then poured onto saturated, aqueous sodium bicarbonate solution and extracted with ethyl acetate. The organic phase was washed with saturated aqueous sodium chloride solution, dried on sodium sulfate, filtered and concentrated by evaporation in a vacuum. Column chromatography on silica gel with a mixture that consists of hexane/ethyl acetate yields 4.0 g of the title compound as a colorless foam.

$^1$H-NMR (300 MHz, CDCl$_3$): δ [ppm]=8.03 d (J=8 Hz, 1H, aryl); 7.53 ddbr (J=8 Hz+1 Hz, 1H, aryl); 7.52 d (J=1 Hz, 1H, aryl); 5.37 s (1H, CH$_2$O); 3.71 m (2H, CH$_2$OH); 3.69 m (2H, CH$_2$N); 1.89 m (2H, CH$_2$); 1.66 m (2H, CH[$_2$); 1.58 s (6H, CH$_3$); 1.49 m (2H, CH$_2$).

10c) 3-(1,3-Dihydro-1-oxoisobenzofuran-5-yl)-5,5-dimethyl-1-[5-[[(4-methylphenyl)sulfonyl]oxy]pentyl]-2-thioxoimidazolidin-4-one 3.9 g of the compound that was produced under 10b was stirred with 12.3 g of p-toluenesulfonic acid chloride and 15 ml of triethylamine in 100 ml of dichloromethane for one hour at room temperature. The reaction mixture was poured into saturated aqueous sodium bicarbonate solution and extracted with dichloromethane. The organic phase was washed with saturated aqueous sodium chloride solution, dried on sodium sulfate, filtered and concentrated by evaporation in a vacuum. Column chromatography on silica gel with a mixture that consists of hexane/ethyl acetate yields 5.15 g of the title compound as a colorless foam.

Flash point 164.9° C. (methanol).

1H-NMR (300 MHz, CDCl$_3$): δ [ppm]=8.04 d (J=8 Hz, 1H, aryl); 7.81 d (J=9 Hz, 2H, tolyl); 7.54 dbr (J=8 Hz, 1H, aryl); 7.53 sbr (1H, aryl); 7.37 d (J=9 Hz, 2H, tolyl); 5.38 s (1H, CH$_2$O); 4.08 t (J=6 Hz, 2H, CH$_2$OTs); 3.68 m (2H, CH$_2$N); 1.86 m (2H, CH$_2$); 1.76 m (2H, CH$_2$); 1.58 s (6H, CH$_3$); 1.49 m (2H, CH$_2$).

10d) 3-(1,3-Dihydro-1-oxoisobenzofuran-5-yl)-5,5-dimethyl-1-(5-iodopentyl)-2-thioxo-imidazolidin-4-one 5.15 g of the compound that was produced under 10c was heated to boiling with 3 g of sodium iodide in 100 ml of acetone for one hour. The reaction mixture was filtered at room temperature and concentrated by evaporation in a vacuum. Column chromatography on silica gel with a mixture that consists of hexane/ethyl acetate yields 4.16 g of the title compound as a yellowish foam.

$^1$H-NMR (300 MHz, CDCl$_3$): δ [ppm]=8.03 d (J=8 Hz, 1H, aryl); 7.53 ddbr (J=8 Hz+2 Hz, 1H, aryl); 7.52 sbr (1H, aryl); 5.37 s (1H, CH$_2$O); 3.70 m (2H, CH$_2$N); 3.23 t (J=7 Hz, 2H, CH$_2$I); 1.89 m (4H, CH$_2$); 1.59 s (6H, CH$_3$); 1.53 m (2H, CH$_2$).

10c) 1,1-Dimethylethyl-4-[5-[3-(1,3-dihydro-1-oxoisobenzofuran-5-yl)-5,5-dimethyl-4-oxo-2-thioxoimidazolidin-1-yl]pentyl]piperazine-1-carboxylate 1 g of the compound that was produced under 10d was stirred with 790 mg of 1,1-dimethylethyl piperazine-1-carboxylate and 591 µl of triethylamine for three days at room temperature. The reaction mixture was concentrated by evaporation in a vacuum. Column chromatography on silica gel with a mixture that consists of hexane/ethyl acetate yields 903 mg of the title compound as a yellowish foam.

$^1$H-NMR (300 MHz, CDCl$_3$): δ [ppm]=8.04 d (J=8 Hz, 1H, aryl); 7.54 dbr (J=8 Hz, 1H, aryl); 7.52 sbr (1H, aryl); 5.37 s (1H, CH$_2$O); 3.69 m (2H, CH$_2$N); 3.44 m (4H, piperazine); 2.38 m (4H, piperazine); 2.36 m (2H, CH$_2$piperazine); 1.86 m (2H, CH$_2$); 1.58 s (6H, CH$_3$); 1.57 m (2H, CH$_2$); 1.46 s (9H, $^t$Bu); 1.42 m (2H, CH$_2$).

EXAMPLE 11

3-(1.3-Dihydro-1-oxoisobenzofuran-5-yl)-1-[5-(piperazin-1-yl)pentyl]-5,5-dimethyl-2-thioxoimidazolidin-4-one 450 mg of the compound that was produced under 10e was stirred with 653 µl of trifluoroacetic acid in 8.5 ml of dichloromethane for 24 hours at room temperature. The reaction mixture was concentrated by evaporation in a vacuum and concentrated by evaporation in a vacuum several times with toluene, taken up in methanol, set at a pH of 8 to 9 with anion exchanger (Bio-Rad AG 1-X8, OH form), filtered, and concentrated by evaporation in a vacuum. 313 mg of the title compound was obtained as a crude product, which was further reacted in this form.

$^1$H-NMR (300 MHz, CD$_3$OD): δ [ppm]=7.96 d (J=8 Hz, 1H, aryl); 7.57 dbr (J=8 Hz, 1H, aryl); 7.65 sbr (1H, aryl); 5.43 s (1H, CH$_2$O); 3.75 m (2H, CH$_2$N); 2.87 m (4H, piperazine); 2.48 m (4H, piperazine); 2.39 m (2H, CH$_2$piperazine); 1.88 m (2H, CH$_2$); 1.61 m (2H, CH$_2$); 1.58 s (6H, CH$_3$); 1.42 m (2H, CH$_2$).

EXAMPLE 12

4-[5-[3-(1,3-Dihydro-1-oxoisobenzofuran-5-yl)-5,5-dimethyl-4-oxo-2-thioxoimidazolidin-1-yl]pentyl]-N-ethylpiperazine-1-carbothioamide 20 mg of the compound that was produced under 11 was heated to 80° C. with 7.7 ml of isothiocyanatoethane and 12.4 µl of triethylamine in 3 ml of tetrahydrofuran for 6 hours. The reaction mixture was concentrated by evaporation in a vacuum. Column chromatography on silica gel with a mixture that consists of hexane/ethyl acetate yields 1.1 mg of the title compound as a colorless oil.

$^1$H-NMR (300 MHz, CDCl$_3$): δ [ppm]=8.02 d (J=8 Hz, 1H, aryl); 7.53 dbr (J=8 Hz, 1H, aryl); 7.51 sbr (1H, aryl); 5.47 tbr (J=5 Hz, 1H, NH); 5.37 s (1H, CH$_2$O); 3.81 m (4H, piperazine); 3.70 qd (J=7 Hz+5 Hz, 2H, CH$_2$N); 3.67 m (2H, CH$_2$N); 2.4 m (4H, piperazine); 2.38 m (2H, CH$_2$piperazine); 1.86 m (2H, CH$_2$); 1.57 s (6H, CH$_3$) 1.57 m (2H, CH$_2$); 1.41 m (2H, CH$_2$); 1.24 t (J=7 Hz, 3H, CH$_3$).

EXAMPLE 13

S-Methyl 4-[5-[3-(1,3-dihydro-1-oxoisobenzofuran-5-yl)-5,5-dimethyl-4-oxo-2-thioxoimidazolidin-1-yl]pentyl]piperazine-1-carbothioate 15.5 mg of the compound that was produced under 11 was refluxed for 4 hours with 6.2 ml of S-methyl chlorothioformate and 10 µl of triethylamine in 1 ml of tetrahydrofuran. The reaction mixture was concentrated by evaporation in a vacuum. Column chromatography on silica gel with a mixture that consists of hexane/ethyl acetate yields 8 mg of the title compound as a colorless oil.

$^1$H-NMR (300 MHz, CDCl$_3$): δ [ppm]=8.03 d (J=8 Hz, 1H, aryl); 7.53 dbr (J=8 Hz, 1H, aryl); 7.52 sbr (1H, aryl); 5.37 s (1H, CH$_2$O); 3.69 m (2H, CH$_2$N); 3.56 m (4H, piperazine); 2.43 m (4H, piperazine); 2.38 m (2H, CH$_2$piperazine); 2.33 s (3H, CH$_3$); 1.86 m (2H, CH$_2$); 1.57 s (6H, CH$_3$); 1.56 m (2H, CH$_2$); 1.42 m (2H, CH$_2$).

EXAMPLE 14

4-[5-[3-(1,3-Dihydro-1-oxoisobenzofuran-5-yl)-5,5-dimethyl-4-oxo-2-thioxoimidazolidin-1-yl]pentyl]-N,N-diethylpiperazine-1-carboxamide 15.5 mg of the compound that was produced under 11 was refluxed for 4 hours with 9.8 ml of diethylcarbamidoyl chloride and 10 µl of triethylamine in 1 ml of tetrahydrofuran. The reaction mixture was concentrated by evaporation in a vacuum. Column chromatography on silica gel with a mixture that consists of hexane/ethyl acetate yields 6 mg of the title compound as a colorless oil.

$^1$H-NMR (300 MHz, CDCl$_3$): δ [ppm]=8.03 d (J=8 Hz, 1H, aryl); 7.53 dbr (J=8 Hz, 1H, aryl); 7.52 sbr (1H, aryl); 5.37 s (1H, CH$_2$O); 3.69 m (2H, CH$_2$N); 3.23 m (4H, piperazine); 3.19 q (J=7 Hz, 4H, CH$_2$N); 2.43 m (4H, piperazine); 2.37 m (2H, CH$_2$piperazine); 1.86 m (2H, CH$_2$); 1.59 m (2H, CH$_2$); 1.58 s (6H, CH$_3$); 1.41 m (2H, CH$_2$); 1.11 t (J=7 Hz, 6H, CH$_3$).

EXAMPLE 15

4-[3-[2-[4-(2-Methoxybenzoyl)piperazin-1-yl]ethyl]-4,4-dimethyl-5-oxo-2-thioxoimidazolidin-1-yl]-2-(trifluoromethyl)benzonitrile 15a) 1,1-Dimethylethyl 4-[2-[3-[4-Cyano-3-(trifluoromethyl)phenyl]-4-imino-5,5-dimethyl-2-thioxoimidazolidin-1-yl]ethyl]piperazine-1-carboxylate 687 g of 4-amino-2-(trifluoromethyl)benzonitrile with 311 µl of thiophosgene in 4 ml of N,N-dimethylformamide was stirred for one hour at room temperature under nitrogen atmosphere. The reaction mixture was diluted with ethyl acetate, washed with water and then concentrated by evaporation in a vacuum. The thus obtained crude isothiocyanate was combined with the cyanoamine that was produced and filtered by two hours of stirring from 743 µl of acetone cyanohydrin with 930 mg of 1,1-dimethylethyl 4-(2-aminoethyl)piperazine-1-carboxylate and 406 mg of a molecular sieve 3 Å in 20 ml of tetrahydrofuran at room temperature, and it was heated to boiling for one hour with 0.57 ml of triethylamine in 40 ml of tetrahydrofuran. After concentration by evaporation in a vacuum, the title compound was obtained as a crude product, which was immediately further reacted.

15b) 1,1-Dimethylethyl 4-[2-[3-[4-Cyano-3-(trifluoromethyl)phenyl]-5,5-dimethyl-4-oxo-2-thioxoimidazolidin-1-yl]ethyl]piperazine-1-carboxylate The crude product that was produced under 15a was stirred with 3.7 ml of 4 molar aqueous hydrochloric acid in 40 ml of methanol overnight at room temperature. The reaction mixture was then poured onto saturated aqueous sodium bicarbonate solution and extracted with ethyl acetate. The organic phase was washed with saturated aqueous sodium chloride solution, dried on sodium sulfate, filtered and concentrated by evaporation in a vacuum. Column chromatography on silica gel with a mixture that consists of hexane/ethyl acetate yields 553 mg of the title compound as a colorless foam.

$^1$H-NMR (300 MHz, CDCl$_3$): δ [ppm]=7.95 d (J=8 Hz, 1H, aryl); 7.88 d (J=2 Hz, 1H, aryl); 7.77 ddbr (J=8 Hz+2 Hz, 1H, aryl); 3.85 m (2H, CH$_2$N); 3.44 m (4H, piperazine); 2.78 m (2H, CH$_2$N); 2.52 m (4H, piperazine); 1.59 s (6H, CH$_3$); 1.46 m (9H, $^t$Bu).

15c) 4-[4,4-Dimethyl-5-oxo-3-[2-(piperazin-1-yl)ethyl]-2-thioxoimidazolidin-1-yl]-2-(trifluoromethyl)benzonitrile 553 mg of the compound, produced under 15b, was stirred with 809 μl of trifluoroacetic acid in 10 ml of dichloromethane for 24 hours at room temperature. The reaction mixture was concentrated by evaporation in a vacuum and concentrated by evaporation in a vacuum several times with toluene, taken up in methanol, set at a pH of 8 to 9 with anion exchanger (Bio-Rad AG 1-X8, OH form), filtered and concentrated by evaporation in a vacuum. 426 mg of the title compound was obtained as a crude product, which was further reacted in this form.

$^1$H-NMR (300 MHz, CDCl$_3$): δ [ppm]=7.95 d (J=8 Hz, 1H, aryl); 7.89 d (J=2 Hz, 1H, aryl); 7.77 ddbr (J=8 Hz+2 Hz, 1H, aryl); 3.85 m (2H, CH$_2$N); 2.91 m (4H, piperazine); 2.76 m (2H, CH$_2$N); 2.55 m (4H, piperazine); 1.59 s (6H, CH$_3$).

15d) 4-[3-[2-[4-(2-Methoxybenzoyl)piperazin-1-yl]ethyl]-4,4-dimethyl-5-oxo-2-thioxoimidazolidin-1-yl]-2-(trifluoromethyl)benzonitrile 20 mg of the compound that was produced under 15c was refluxed with 14 ml of 2-methoxybenzoyl chloride and 13.1 μl of triethylamine in 1 ml of tetrahydrofuran for 4 hours. The reaction mixture was concentrated by evaporation in a vacuum. Column chromatography on silica gel with a mixture that consists of hexane/ethyl acetate yields 16 mg of the title compound as a colorless oil.

$^1$H-NMR (300 MHz, CDCl$_3$): δ [ppm]=7.95 d (J=8 Hz, 1H, aryl); 7.88 d (J=2 Hz, 1H, aryl); 7.76 ddbr (J=8 Hz+2 Hz, 1H, aryl); 7.35 ddd (J=8 Hz+7 Hz+2 Hz, 1H, aryl); 7.23 dd (J=7 Hz+2 Hz, 1H, aryl); 6.99 dd (J=7 Hz+7 Hz, 1H, aryl); 6.91 dbr (J=8 Hz, 1H, aryl); 3.85 m (2H, CH$_2$N); 3.84 m (1H, piperazine); 3.83 s (3H, OCH$_3$); 3.81 m (1H, piperazine); 3.28 m (2H, piperazine); 2.80 m (2H, CH$_2$N); 2.67 m (1H, piperazine); 2.55 m (1H, piperazine); 2.47 m (1H, piperazine); 1.59 (6H, CH$_3$).

The following compounds according to the invention were produced analogously to the previously described compounds.

TABLE 5

Compounds of General Formula I According to the Invention, in which V = Trifluoromethylbenzonitrile, W = Maleimide, n = 1

| Example | Name | Synthesis Analogous to Example | ESI-MS |
|---|---|---|---|
| 16 | 4-[3-[(4-Acetylpiperazin-1-yl)methyl]-2,5-dihydro-4-methyl-2,5-dioxo-1H-pyrrol-1-yl]-2-(trifluoromethyl)benzonitrile | 8 | 420 |
| 17 | 4-[2,5-Dihydro-3-[[4-(methoxyacetyl)piperazin-1-yl]methyl]-4-methyl-2,5-dioxo-1H-pyrrol-1-yl]-2-(trifluoromethyl)benzonitrile | 8 | 450 |
| 18 | 4-[2,5-Dihydro-3-[4-[[(2-methoxyethoxy)-acetyl]piperazin-1-yl]methyl]-4-methyl-2,5-dioxo-1H-pyrrol-1-yl]-2-(trifluoromethyl)benzonitrile | 8 | 494 |
| 19 | 4-[2,5-Dihydro-3-[[4-[[2-(2-methoxyethoxy)-ethoxy]acetyl]piperazin-1-yl]methyl]-4-methyl-2,5-dioxo-1H-pyrrol-1-yl]-2-(trifluoromethyl)-benzonitrile | 8 | 538 |
| 20 | 4-[2,5-Dihydro-3-[[4-2-(2-methoxybenzoyl)-piperazin-1-yl]methyl]-4-methyl-2,5-dioxo-1H-pyrrol-1-yl]-2-(trifluoromethyl)benzonitrile | 8 | 512 |
| 21 | 4-[2,5-Dihydro-3-methyl-4-[[4-(methylsulfonyl)-piperazin-1-yl]methyl]-2,5-dioxo-1H-pyrrol-1-yl]-2-(trifluoromethyl)benzonitrile | 8 | 456 |
| 22 | 4-[3-[[4-(Ethylsulfonyl)piperazin-1-yl]methyl]-2,5-dihydro-4-methyl-2,5-dioxo-1H-pyrrol-1-yl]-2-(trifluoromethyl)benzonitrile | 8 | 470 |
| 23 | 4-[2,5-Dihydro-3-[[4-(2-methoxyethyl)sulfonyl]-piperazin-1-yl]methyl]-4-methyl-2,5-dioxo-1H-pyrrol-1-yl]-2-(trifluoromethyl)benzonitrile | 8 | 500 |
| 24 | 4-[2,5-Dihydro-3-[[4-[[2-[2-(2-methoxy-ethoxy)-ethoxy]-ethyl]sulfonyl]piperazin-1-yl]methyl]-4-methyl-2,5-dioxo-1H-pyrrol-1-yl]-2-(trifluoromethyl)benzonitrile | 8 | 588 |
| 25 | 4-[2,5-Dihydro-3-methyl-2,5-dioxo-4-[[4-(phenylsulfonyl)piperazin-1-yl]methyl]-1H-pyrrol-1-yl]-2-(trifluoromethyl)benzonitrile | 8 | 518 |

TABLE 6

Compounds of General Formula I According to the Invention, in which V = Trifluoromethylbenzonitrile, W = Maleimide, n = 2

| Example | Name | Synthesis Analogous to Example | ESI-MS |
|---|---|---|---|
| 26 | 4-[3-[2-(4-Acetylpiperazin-1-yl)ethyl]-2,5-dihydro-4-methyl-2,5-dioxo-1H-pyrrol-1-yl]-2-(trifluoromethyl)benzonitrile | 7 (4) | 434 |
| 27 | 4-[2,5-Dihydro-3-methyl-2,5-dioxo-4-[2-(4-(1-oxopropyl)piperazin-1-yl)ethyl]-1H-pyrrol-1-yl]-2-(trifluoromethyl)benzonitrile | 7 (4) | 448 |
| 28 | 4-[3-[2-[4-(Cyclopropylcarbonyl)piperazin-1-yl]ethyl]-2,5-dihydro-4-methyl-2,5-dioxo-1H-pyrrol-1-yl]-2-(trifluoromethyl)benzonitrile | 7 (4) | 460 |
| 29 | 4-[2,5-Dihydro-3-[2-[4-(methoxyacetyl)piperazin-1-yl]ethyl]-4-methyl-2,5-dioxo-1H-pyrrol-1-yl]-2-(trifluoromethyl)benzonitrile | 7 (4) | 464 |
| 30 | 4-[2,5-Dihydro-3-[2-[4-(3-methoxy-1-oxopropyl)piperazin-1-yl]ethyl]-4-methyl-2,5-dioxo-1H-pyrrol-1-yl]-2-(trifluoromethyl)-benzonitrile | 7 (4) | 478 |
| 31 | 4-[2,5-Dihydro-3-[2-[4-[(2-methoxyethoxy)-acetyl]piperazin-1-yl]ethyl]-4-methyl-2,5-dioxo-1H-pyrrol-1-yl]-2-(trifluoromethyl)benzonitrile | 7 (4) | 508 |

TABLE 6-continued

Compounds of General Formula I According to the Invention, in which V = Trifluoromethylbenzonitrile, W = Maleimide, n = 2

| Example | Name | Synthesis Analogous to Example | ESI-MS |
|---|---|---|---|
| 32 | 4-[2,5-Dihydro-3-[2-[4-[[2-(2-methoxyethoxy)-ethoxy]acetyl]piperazin-1-yl]ethyl]-4-methyl-2,5-dioxo-1H-pyrrol-1-yl]-2-(trifluoromethyl)-benzonitrile | 7 (4) | 552 |
| 33 | 4-[2,5-Dihydro-3-[2-[4-(2-methoxybenzoyl)-piperazin-1-yl]ethyl]-4-methyl-2,5-dioxo-1H-pyrrol-1-yl]-2-(trifluoromethyl)benzonitrile | 7 (4) | 526 |
| 34 | 4-[2,5-Dihydro-3-methyl-4-[2-[4-(methylsulfonyl)-piperazin-1-yl]ethyl]-2,5-dioxo-1H-pyrrol-1-yl]-2-(trifluoromethyl)benzonitrile | 7 | 470 |
| 35 | 4-[3-[2-[4-(Ethylsulfonyl)piperazin-1-yl]ethyl]-2,5-dihydro-4-methyl-2,5-dioxo-1H-pyrrol-1-yl]-2-(trifluoromethyl)benzonitrile | 7 | 484 |
| 36 | 4-[3-[2-[4-(Cyclopropylsulfonyl)piperazin-1-yl]ethyl]-2,5-dihydro-4-methyl-2,5-dioxo-1H-pyrrol-1-yl]-2-(trifluoromethyl)benzonitrile | 7 | 496 |
| 37 | 4-[2,5-Dihydro-3-[2-[4-(2-methoxyethyl)-sulfonyl]piperazin-1-yl]ethyl]-4-methyl-2,5-dioxo-1H-pyrrol-1-yl]-2-(trifluoromethyl)benzonitrile | 7 | 514 |
| 38 | 4-[2,5-Dihydro-3-[2-[4-[[2-(2-methoxyethoxy)-ethyl]sulfonyl]piperazin-1-yl]ethyl]-4-methyl-2,5-dioxo-1H-pyrrol-1-yl]-2-(trifluoromethyl)-benzonitrile | 7 | 558 |
| 39 | 4-[2,5-Dihydro-3-[2-[4-[[2-[2-(2-methoxyethoxy)-ethoxy]ethyl]sulfonyl]piper-azin-1-yl]ethyl]-4-methyl-2,5-dioxo-1H-pyrrol-1-yl]-2-(trifluoromethyl)benzonitrile | 7 | 602 |
| 40 | 4-[2,5-Dihydro-3-methyl-2,5-dioxo-4-[2-[4-(phenylsulfonyl)piperazin-1-yl]ethyl]-1H-pyrrol-1-yl]-2-(trifluoromethyl)benzonitrile | 7 | 532 |
| 41 | 4-[2,5-Dihydro-3-methyl-2,5-dioxo-4-[2-[4-[(phenylmethyl)sulfonyl]piperazin-1-yl]ethyl]-1H-pyrrol-1-yl]-2-(trifluoromethyl)benzonitrile | 7 | 546 |
| 42 | 4-[2,5-Dihydro-3-methyl-4-[2-[4-[(1-methyl-1H-imidazol-4-yl)sulfonyl]piperazin-1-yl]ethyl]-2,5-dioxo-1H-pyrrol-1-yl]-2-(trifluoromethyl)benzonitrile | 7 | 536 |
| 43 | 4-[2-[1-[4-Cyano-3-(trifluoromethyl)phenyl]-2,5-dihydro-4-methyl-2,5-dioxo-1H-pyrrol-3-yl]ethyl]-N-(1-methylethyl)piperazine-1-carboxamide | 7 (6) | 477 |
| 44 | 4-[2-[1-[4-Cyano-3-(trifluoromethyl)phenyl]-2,5-dihydro-4-methyl-2,5-dioxo-1H-pyrrol-3-yl]ethyl]-N-ethylpiperazine-1-carbothioamide | 7 (12) | 479 |
| 45 | Methyl 4-[2-[1-[4-cyano-3-(trifluoromethyl)-phenyl]-2,5-dihydro-4-methyl-2,5-dioxo-1H-pyrrol-3-yl]ethyl]piperazine-1-carboxylate | 7 (13) | 450 |
| 46 | S-Methyl 4-[2-[1-[4-cyano-3-(trifluoromethyl)-phenyl]-2,5-dihydro-4-methyl-2,5-dioxo-1H-pyrrol-3-yl]ethyl]piperazine-1-carbothioate | 7 (13) | 466 |
| 47 | 4-[2-[1-[4-Cyano-3-(trifluoromethyl)phenyl]-2,5-dihydro-4-methyl-2,5-dioxo-1H-pyrrol-3-yl]ethyl]-N,N-dimethylpiperazine-1-sulfonamide | 7 | 499 |

TABLE 7

Compounds of General Formula I According to the Invention, in which V = Trifluoromethylbenzonitrile, W = Maleimide, n = 3

| Example | Name | Synthesis Analogous to Example | ESI-MS |
|---|---|---|---|
| 48 | 4-[3-[3-(4-Acetylpiperazin-1-yl)propyl]-2,5-dihydro-4-methyl-2,5-dioxo-1H-pyrrol-1-yl]-2-(trifluoromethyl)-benzonitrile | 7 (4) | 448 |
| 49 | 4-[2,5-Dihydro-3-methyl-2,5-dioxo-4-[3-[4-(1-oxopropyl)-piperazin-1-yl]propyl]-1H-pyrrol-1-yl]-2-(trifluoromethyl)-benzonitrile | 7 (4) | 462 |
| 50 | 4-[3-[3-[4-(Cyclopropylcarbonyl)piperazin-1-yl]-propyl]-2,5-dihydro-4-methyl-2,5-dioxo-1H-pyrrol-1-yl]-2-(trifluoromethyl)benzonitrile | 7 (4) | 474 |
| 51 | 4-[2,5-Dihydro-3-[3-[4-(methoxyacetyl)piperazin-1-yl]-propyl]-4-methyl-2,5-dioxo-1H-pyrrol-1-yl]-2-(trifluoromethyl)benzonitrile | 7 (4) | 478 |
| 52 | 4-[2,5-Dihydro-3-[3-[4-(3-methoxy-1-oxopropyl)-piperazin-1-yl]propyl]-4-methyl-2,5-dioxo-1H-pyrrol-1-yl]-2-(trifluoromethyl)benzonitrile | 7 (4) | 492 |
| 53 | 4-[2,5-Dihydro-3-[3-[4-[(2-methoxyethoxy)-acetyl]piperazin-1-yl]propyl]-4-methyl-2,5-dioxo-1H-pyrrol-1-yl]-2-(trifluoromethyl)benzonitrile | 7 (4) | 522 |
| 54 | 4-[2,5-Dihydro-3-[3-[4-[[2-(2-methoxyethoxy)-ethoxy]-acetyl]piperazin-1-yl]propyl]-4-methyl-2,5-dioxo-1H-pyrrol-1-yl]-2-(trifluoromethyl)-benzonitrile | 7 (4) | 566 |
| 55 | 4-[2,5-Dihydro-3-[3-[4-(2-methoxybenzoyl)-piperazin-1-yl]-propyl]-4-methyl-2,5-dioxo-1H-pyrrol-1-yl]-2-(trifluoromethyl)benzonitrile | 7 (4) | 540 |
| 56 | 4-[2,5-Dihydro-3-methyl-4-[3-[4-(methylsulfonyl)-piperazin-1-yl]propyl]-2,5-dioxo-1H-pyrrol-1-yl]-2-(trifluoromethyl)-benzonitrile | 7 | 484 |
| 57 | 4-[3-[3-[4-(Ethylsulfonyl)piperazin-1-yl]propyl]-2,5-dihydro-4-methyl-2,5-dioxo-1H-pyrrol-1-yl]-2-(trifluoromethyl)-benzonitrile | 7 | 498 |
| 58 | 4-[3-[3-[4-(Cyclopropylsulfonyl)piperazin-1-yl]propyl]-2,5-dihydro-4-methyl-2,5-dioxo-1H-pyrrol-1-yl]-2-(trifluoromethyl)benzonitrile | 7 | 510 |
| 59 | 4-[2,5-Dihydro-3-[3-[4-(2-methoxyethyl)-sulfonyl]piperazin-1-yl]propyl]-4-methyl-2,5-dioxo-1H-pyrrol-1-yl]-2-(trifluoromethyl)-benzonitrile | 7 | 528 |
| 60 | 4-[2,5-Dihydro-3-[3-[4-[[2-(2-methoxyethoxy)-ethoxy]ethyl]-sulfonyl]piperazin-1-yl]propyl]-4-methyl-2,5-dioxo-1H-pyrrol-1-yl]-2-(trifluoromethyl)-benzonitrile | 7 | 572 |
| 61 | 4-[2,5-Dihydro-3-[3-[4-[[2-[2-(2-methoxyethoxy)-ethoxy]-ethyl]sulfonyl]piperazin-1-yl]propyl]-4-methyl-2,5-dioxo-1H-pyrrol-1-yl]-2-(trifluoromethyl)benzonitrile | 7 | 616 |
| 62 | 4-[2,5-Dihydro-3-methyl-2,5-dioxo-4-[3-[4-(phenyl-sulfonyl)piperazin-1-yl]propyl]-1H-pyrrol-1-yl]-2-(trifluoromethyl)benzonitrile | 7 | 546 |
| 63 | 4-[2,5-Dihydro-3-methyl-2,5-dioxo-4-[3-[4-[(phenylmethyl)-sulfonyl]piperazin-1-yl]propyl]-1H-pyrrol-1-yl]-2-(trifluoromethyl)benzonitrile | 7 | 560 |
| 64 | 4-[2,5-Dihydro-3-methyl-4-[3-[4-[(1-methyl-1H-imidazol-4-yl)sulfonyl]piperazin-1-yl]propyl]-2,5-dioxo-1H-pyrrol-1-yl]-2-(trifluoromethyl)-benzonitrile | 7 | 550 |
| 65 | 4-[3-[1-[4-Cyano-3-(trifluoromethyl)phenyl]-2,5-dihydro-4-methyl-2,5-dioxo-1H-pyrrol-3-yl]propyl]-N-(1-methylethyl)-piperazine-1-carboxamide | 7 (6) | 491 |
| 66 | 4-[3-[1-[4-Cyano-3-(trifluoromethyl)phenyl]-2,5-dihydro-4-methyl-2,5-dioxo-1H-pyrrol-3-yl]propyl)-N-ethylpiperazine-1-carbothioamide | 7 (12) | 493 |

TABLE 7-continued

Compounds of General Formula I According to the Invention, in which V = Trifluoromethylbenzonitrile, W = Maleimide, n = 3

| Example | Name | Synthesis Analogous to Example | ESI-MS |
|---|---|---|---|
| 67 | Methyl 4-[3-[1-[4-cyano-3-(trifluoromethyl)-phenyl]-2,5-dihydro-4-methyl-2,5-dioxo-1H-pyrrol-3-yl]propyl]-piperazine-1-carboxylate | 7 (13) | 464 |
| 68 | S-Methyl 4-[3-[1-[4-cyano-3-(trifluoromethyl)-phenyl]-2,5-dihydro-4-methyl-2,5-dioxo-1H-pyrrol-3-yl]propyl]-piperazine-1-carbothioate | 7 (13) | 480 |
| 69 | 4-[3-[1-[4-Cyano-3-(trifluoromethyl)phenyl]-2,5-dihydro-4-methyl-2,5-dioxo-1H-pyrrol-3-yl]propyl]-N,N-dimethylpiperazine-1-sulfonamide | 7 | 513 |

TABLE 8

Compounds of General Formula I According to the Invention, in which V = Trifluoromethylbenzonitrile, W = Maleimide, n = 4

| Example | Name | Synthesis Analogous to Example | ESI-MS |
|---|---|---|---|
| 70 | 1,1-Dimethylethyl 4-[4-[1-[4-cyano-3-(trifluoromethyl)phenyl]-2,5-dihydro-4-methyl-2,5-dioxo-1H-pyrrol-3-yl]-butyl]piperazine-1-carboxylate | 1 | 521 |
| 71 | 4-[2,5-Dihydro-3-methyl-4-[4-[4-[2-(methylsulfanyl)-phenyl]piperazin-1-yl]butyl]-2,5-dioxo-1H-pyrrol-1-yl]-2-(trifluoromethyl)-benzonitrile | 3 | 543 |
| 72 | 4-[3-[4-[4-(3,5-Dichloropyridin-4-yl)piperazin-1-yl]butyl]-2,5-dihydro-4-methyl-2,5-dioxo-1H-pyrrol-1-yl]-2-(trifluoromethyl)benzonitrile | 3 | 566 |
| 73 | 4-[3-[4-[4-(Cyclopentylacetyl)piperazin-1-yl]butyl]-2,5-dihydro-4-methyl-2,5-dioxo-1H-pyrrol-1-yl]-2-(trifluoromethyl)benzonitrile | 4 | 531 |
| 74 | 4-[3-[4-[4-(2,6-Difluorobenzoyl)piperazin-1-yl]butyl]-2,5-dihydro-4-methyl-2,5-dioxo-1H-pyrrol-1-yl]-2-(trifluoromethyl)benzonitrile | 4 | 561 |
| 75 | 4-[3-[4-[4-(2,6-Dichlorobenzoyl)piperazin-1-yl]butyl]-2,5-dihydro-4-methyl-2,5-dioxo-1H-pyrrol-1-yl]-2-(trifluoromethyl)benzonitrile | 4 | 593 |
| 76 | 4-[3-[4-[4-(3-Fluorobenzoyl)piperazin-1-yl]butyl]-2,5-dihydro-4-methyl-2,5-dioxo-1H-pyrrol-1-yl]-2-(trifluoromethyl)benzonitrile | 4 | 543 |
| 77 | 4-[2,5-Dihydro-3-[4-[4-(3-methoxybenzoyl)-piperazin-1-yl]butyl]-4-methyl-2,5-dioxo-1H-pyrrol-1-yl]-2-(trifluoromethyl)benzonitrile | 4 | 555 |
| 78 | 4-[2,5-Dihydro-3-methyl-4-[4-[4-(3-methylbenzoyl)-piperazin-1-yl-]butyl]-2,5-dioxo-1H-pyrrol-1-yl]-2-(trifluoromethyl)benzonitrile | 4 | 539 |
| 79 | 4-[3-[4-[4-(4-Fluorobenzoyl)piperazin-1-yl]butyl]-2,5-dihydro-4-methyl-2,5-dioxo-1H-pyrrol-1-yl]-2-(trifluoromethyl)benzonitrile | 4 | 543 |
| 80 | 4-[2,5-Dihydro-3-methyl-4-[4-[4-[(naphthalen-1-yl)-carbonyl]piperazin-1-yl]butyl]-2,5-dioxo-1H-pyrrol-1-yl]-2-(trifluoromethyl)benzonitrile | 4 | 575 |
| 81 | 4-[2,5-Dihydro-3-methyl-4-[4-[4-[(naphthalen-2-yl)-carbonyl]piperazin-1-yl]butyl]-2,5-dioxo-1H-pyrrol-1-yl]-2-(trifluoromethyl)benzonitrile | 4 | 575 |
| 82 | 4-[3-[4-[4-(3-Cyanobenzoyl)piperazin-1-yl]butyl]-2,5-dihydro-4-methyl-2,5-dioxo-1H-pyrrol-1-yl]-2-(trifluoromethyl)benzonitrile | 4 | 550 |
| 83 | 4-[3-[4-[4-(Cyclohexylcarbonyl)piperazin-1-yl]butyl]-2,5-dihydro-4-methyl-2,5-dioxo-1H-pyrrol-1-yl]-2-(trifluoromethyl)benzonitrile | 4 | 531 |
| 84 | 4-[3-[4-[4-[(Furan-2-yl)carbonyl]piperazin-1-yl]butyl]-2,5-dihydro-4-methyl-2,5-dioxo-1H-pyrrol-1-yl]-2-(trifluoromethyl)benzonitrile | 4 | 515 |
| 85 | 4-[3-[4-[4-(Cyclopentylcarbonyl)piperazin-1-yl]butyl]-2,5-dihydro-4-methyl-2,5-dioxo-1H-pyrrol-1-yl]-2-(trifluoromethyl)benzonitrile | 4 | 517 |
| 86 | 4-[2,5-Dihydro-3-methyl-4-[4-[4-[(5-methylisoxazol-3-yl)carbonyl]piperazin-1-yl]butyl]-2,5-dioxo-1H-pyrrol-1-yl]-2-(trifluoromethyl)benzonitrile | 4 | 530 |
| 87 | 4-[2,5-Dihydro-3-methyl-2,5-dioxo-4-[4-[4-(phenyl-acetyl)piperazin-1-yl]butyl]-1H-pyrrol-1-yl]-2-(trifluoromethyl)benzonitrile | 4 | 539 |
| 88 | 4-[2,5-Dihydro-3-[4-[4-(2-methoxybenzoyl)-piperazin-1-yl]butyl]-4-methyl-2,5-dioxo-1H-pyrrol-1-yl]-2-(trifluoromethyl)benzonitrile | 4 | 555 |
| 89 | 4-[2,5-Dihydro-3-[4-[4-(methoxyacetyl)piper-azin-1-yl]-butyl]-4-methyl-2,5-dioxo-1H-pyrrol-1-yl]-2-(trifluoromethyl)benzonitrile | 4 | 492 |
| 90 | 4-[3-[4-[4-(2-Chlorobenzoyl)piperazin-1-yl]butyl]-2,5-dihydro-4-methyl-2,5-dioxo-1H-pyrrol-1-yl]-2-(trifluoromethyl)benzonitrile | 4 | 559 |
| 91 | 4-[3-[4-[4-(2-Fluorobenzoyl)piperazin-1-yl]butyl]-2,5-dihydro-4-methyl-2,5-dioxo-1H-pyrrol-1-yl]-2-(trifluoromethyl)benzonitrile | 4 | 543 |
| 92 | 4-[3-[4-(4-Benzoylpiperazin-1-yl)butyl]-2,5-dihydro-4-methyl-2,5-dioxo-1H-pyrrol-1-yl]-2-(trifluoromethyl)-benzonitrile | 4 | 525 |
| 93 | 4-[3-[4-[4-(Cyclobutylcarbonyl)piperazin-1-yl]butyl]-2,5-dihydro-4-methyl-2,5-dioxo-1H-pyrrol-1-yl]-2-(trifluoromethyl)benzonitrile | 4 | 503 |
| 94 | 4-[2,5-Dihydro-3-methyl-2,5-dioxo-4-[4-[4-[(pyridin-2-yl)carbonyl]piperazin-1-yl]butyl]-1H-pyrrol-1-yl]-2-(trifluoromethyl)benzonitrile | 4 | 526 |
| 95 | 4-[2,5-Dihydro-3-methyl-2,5-dioxo-4-[4-[4-[(pyridin-4-yl)carbonyl]piperazin-1-yl]butyl]-1H-pyrrol-1-yl]-2-(trifluoromethyl)benzonitrile | 4 | 526 |
| 96 | 4-[3-[4-[4-(Dimethylamino)benzoyl]piper-azin-1-yl]butyl-2,5-dihydro-4-methyl-2,5-dioxo-1H-pyrrol-1-yl]-2-(trifluoromethyl)benzonitrile | 4 | 568 |
| 97 | 4-[2,5-Dihydro-3-methyl-2,5-dioxo-4-[4-[4-[(phenyl-sulfanyl)acetyl]piperazin-1-yl]butyl]-1H-pyrrol-1-yl]-2-(trifluoromethyl)benzonitrile | 4 | 571 |
| 98 | 4-[2,5-Dihydro-3-methyl-2,5-dioxo-4-[4-[4-(phenoxy-acetyl)piperazin-1-yl]butyl]-1H-pyrrol-1-yl)-2-(trifluoromethyl)benzonitrile | 4 | 555 |
| 99 | 4-[2,5-Dihydro-3-methyl-2,5-dioxo-4-[4-[4-[(thien-2-yl)-carbonyl]piperazin-1-yl]butyl]-1H-pyrrol-1-yl]-2-(trifluoromethyl)benzonitrile | 4 | 531 |
| 100 | 4-[2,5-Dihydro-3-methyl-2,5-dioxo-4-[4-[4-(3-phenyl-1-oxopropyl)piperazin-1-yl]butyl]-1H-pyrrol-1-yl]-2-(trifluoromethyl)benzonitrile | 4 | 553 |
| 101 | 4-[3-[4-[4-[(1,3-Benzodioxol-5-yl)carbonyl]-piperazin-1-yl]-butyl]-2,5-dihydro-4-methyl-2,5-dioxo-1H-pyrrol-1-yl]-2-(trifluoromethyl)-benzonitrile | 4 | 569 |
| 102 | 4-[2,5-Dihydro-3-[4-[4-[(4-methoxyphenyl)-acetyl]piperazin-1-yl]butyl]-4-methyl-2,5-dioxo-1H-pyrrol-1-yl]-2-(trifluoromethyl)benzonitrile | 4 | 569 |
| 103 | 4-[2,5-Dihydro-3-methyl-4-[4-[4-(2-methylbenzoyl)-piperazin-1-yl]butyl]-2,5-dioxo-1H-pyrrol-1-yl]-2-(trifluoromethyl)benzonitrile | 4 | 539 |
| 104 | 4-[3-[4-[4-(4-Chlorobenzoyl)piperazin-1-yl]butyl]-2,5-dihydro-4-methyl-2,5-dioxo-1H-pyrrol-1-yl]-2-(trifluoromethyl)benzonitrile | 4 | 559 |
| 105 | 4-[2,5-Dihydro-3-methyl-2,5-dioxo-4-[4-[4-[(thien-2-yl)-acetyl]piperazin-1-yl]butyl]-1H-pyrrol-1-yl]-2-(trifluoromethyl)benzonitrile | 4 | 545 |

TABLE 8-continued

Compounds of General Formula I According to the Invention, in which V = Trifluoromethylbenzonitrile, W = Maleimide, n = 4

| Example | Name | Synthesis Analogous to Example | ESI-MS |
|---|---|---|---|
| 106 | 4-[3-[4-[4-(3-Chlorobenzoyl)piperazin-1-yl]butyl]-2,5-dihydro-4-methyl-2,5-dioxo-1H-pyrrol-1-yl]-2-(trifluoromethyl)benzonitrile | 4 | 559 |
| 107 | 4-[3-[4-[4-(4-Cyanobenzoyl)piperazin-1-yl]butyl]-2,5-dihydro-4-methyl-2,5-dioxo-1H-pyrrol-1-yl]-2-(trifluoromethyl)benzonitrile | 4 | 550 |
| 108 | 4-[2,5-Dihydro-3-[4-[4-(3-methoxy-1-oxopropyl)piperazin-1-yl]butyl]-4-methyl-2,5-dioxo-1H-pyrrol-1-yl]-2-(trifluoromethyl)benzonitrile | 4 | 506 |
| 109 | 4-[2,5-Dihydro-3-[4-[4-[(2-methoxyethoxy)-acetyl]piperazin-1-yl]butyl]-4-methyl-2,5-dioxo-1H-pyrrol-1-yl-2-(trifluoromethyl)benzonitrile | 4 | 536 |
| 110 | 4-[2,5-Dihydro-3-[4-[4-[[2-(2-methoxyethoxy)-ethoxy]-acetyl]piperazin-1-yl]butyl]-4-methyl-2,5-dioxo-1H-pyrrol-1-yl]-2-(trifluoromethyl)benzonitrile | 4 | 580 |
| 111 | 4-[4-[4-[4-(Cyclopropylsulfonyl)piperazin-1-yl]butyl]-2,5-dihydro-3-methyl-2,5-dioxo-1H-pyrrol-1-yl]-2-(trifluoromethyl)benzonitrile | 5 | 524 |
| 112 | 4-[2,5-Dihydro-3-[4-[4-(2-methoxyethyl)-sulfonyl]piperazin-1-yl]butyl]-4-methyl-2,5-dioxo-1H-pyrrol-1-yl]-2-(trifluoromethyl)benzonitrile | 5 | 542 |
| 113 | 4-[2,5-Dihydro-3-[4-[4-[[2-(2-methoxyethoxy)ethyl]-sulfonyl]piperazin-1-yl]butyl]-4-methyl-2,5-dioxo-1H-pyrrol-1-yl]-2-(trifluoromethyl)benzonitrile | 5 | 586 |
| 114 | 4-[2,5-Dihydro-3-[4-[4-[[2-[2-(2-methoxyethoxy)-ethoxy]-ethyl]sulfonyl]piperazin-1-yl]butyl]-4-methyl-2,5-dioxo-1H-pyrrol-1-yl]-2-(trifluoromethyl)benzonitrile | 5 | 630 |
| 115 | 4-[4-[1-[4-Cyano-3-(trifluoromethyl)phenyl]-2,5-dihydro-4-methyl-2,5-dioxo-1H-pyrrol-3-yl]butyl]-N,N-dimethylpiperazine-1-sulfonamide | 5 | 527 |
| 116 | 4-[2,5-Dihydro-3-methyl-2,5-dioxo-4-[4-[4-(phenyl-sulfonyl)piperazin-1-yl]butyl]-1H-pyrrol-1-yl]-2-(trifluoromethyl)benzonitrile | 5 | 561 |
| 117 | 4-[2,5-Dihydro-3-methyl-4-[4-[4-(methylsulfonyl)-piperazin-1-yl]butyl]-2,5-dioxo-1H-pyrrol-1-yl]-2-(trifluoromethyl)benzonitrile | 5 | 499 |
| 118 | 4-[2,5-Dihydro-3-methyl-4-[4-[4-[(4-methylphenyl)-sulfonyl]piperazin-1-yl]butyl]-2,5-dioxo-1H-pyrrol-1-yl]-2-(trifluoromethyl)-benzonitrile | 5 | 575 |
| 119 | N-[4-[[4-[4-[1-[4-Cyano-3-(trifluoromethyl)-phenyl]-2,5-dihydro-4-methyl-2,5-dioxo-1H-pyrrol-3-yl]butyl]piperazin-1-yl]sulfonyl]phenyl]acetamide | 5 | 618 |
| 120 | 4-[3-[4-[4-[(4-Chlorophenyl)sulfonyl]piperazin-1-yl]butyl]-2,5-dihydro-4-methyl-2,5-dioxo-1H-pyrrol-1-yl]-2-(trifluoromethyl)benzonitrile | 5 | 595 |
| 121 | 4-[3-[4-[4-[(4-Cyanophenyl)sulfonyl]piperazin-1-yl]butyl]-2,5-dihydro-4-methyl-2,5-dioxo-1H-pyrrol-1-yl]-2-(trifluoromethyl)benzonitrile | 5 | 586 |
| 122 | 4-[2,5-Dihydro-3-methyl-4-[4-[4-[(naphthalen-2-yl)-sulfonyl]piperazin-1-yl]butyl]-2,5-dioxo-1H-pyrrol-1-yl]-2-(trifluoromethyl)benzonitrile | 5 | 611 |
| 123 | 4-[3-[4-[4-[(Quinolin-8-yl)sulfonyl]piperazin-1-yl]butyl]-2,5-dihydro-4-methyl-2,5-dioxo-1H-pyrrol-1-yl]-2-(trifluoromethyl)benzonitrile | 5 | 612 |
| 124 | 4-[3-[4-[4-[(2-Cyanophenyl)sulfonyl]piperazin-1-yl]butyl]-2,5-dihydro-4-methyl-2,5-dioxo-1H-pyrrol-1-yl]-2-(trifluoromethyl)benzonitrile | 5 | 586 |
| 125 | 4-(3-[4-[4-[(3-Cyanophenyl)sulfonyl]piperazin-1-yl]butyl]-2,5-dihydro-4-methyl-2,5-dioxo-1H-pyrrol-1-yl]-2-(trifluoromethyl)benzonitrile | 5 | 586 |
| 126 | 4-[3-[4-[4-[(3,5-Dimethylisoxazol-4-yl)sulfonyl]-piperazin-1-yl]butyl]-2,5-dihydro-4-methyl-2,5-dioxo-1H-pyrrol-1-yl]-2-(trifluoromethyl)benzonitrile | 5 | 580 |
| 127 | 4-[3-[4-[4-[(5-Chloro-1,3-dimethyl-1H-pyrazol-4-yl)sulfonyl]piperazin-1-yl]butyl]-2,5-dihydro-4-methyl-2,5-dioxo-1H-pyrrol-1-yl]-2-(trifluoromethyl)benzonitrile | 5 | 613 |
| 128 | 4-[2,5-Dihydro-3-methyl-4-[4-[4-[(1-methyl-1H-imidazol-4-yl)sulfonyl]piperazin-1-yl]butyl]-2,5-dioxo-1H-pyrrol-1-yl]-2-(trifluoromethyl)benzonitrile | 5 | 565 |
| 129 | 4-[3-[4-[4-(Butylsulfonyl)piperazin-1-yl]butyl]-2,5-dihydro-4-methyl-2,5-dioxo-1H-pyrrol-1-yl]-2-(trifluoromethyl)-benzonitrile | 5 | 541 |
| 130 | 4-[4-Cyano-3-(trifluoromethyl)phenyl]-2,5-dihydro-4-methyl-2,5-dioxo-1H-pyrrol-3-yl]butyl]-N-phenylpiperazine-1-carboxamide | 6 | 540 |
| 131 | 4-[4-[1-[4-Cyano-3-(trifluoromethyl)phenyl]-2,5-dihydro-4-methyl-2,5-dioxo-1H-pyrrol-3-yl]butyl]-N-(naphthalen-1-yl)-piperazine-1-carboxamide | 6 | 590 |
| 132 | 4-[4-[1-[4-Cyano-3-(trifluoromethyl)phenyl]-2,5-dihydro-4-methyl-2,5-dioxo-1H-pyrrol-3-yl]butyl]-N-(naphthalen-2-yl)-piperazine-1-carboxamide | 6 | 590 |
| 133 | N-(2-Chlorophenyl)-4-[4-[1-[4-cyano-3-(trifluoromethyl)-phenyl]-2,5-dihydro-4-methyl-2,5-dioxo-1H-pyrrol-3-yl]-butyl)piperazine-1-carboxamide | 6 | 574 |
| 134 | 4-[4-[1-[4-Cyano-3-(trifluoromethyl)phenyl]-2,5-dihydro-4-methyl-2,5-dioxo-1H-pyrrol-3-yl]butyl]-N-[2-(trifluoromethyl)-phenyl]-piperazine-1-carboxamide | 6 | 608 |
| 135 | 4-[4-[1-[4-Cyano-3-(trifluoromethyl)phenyl]-2,5-dihydro-4-methyl-2,5-dioxo-1H-pyrrol-3-yl]butyl]-N-(3-methoxy-phenyl)piperazine-1-carboxamide | 6 | 570 |
| 136 | N-(4-Chlorophenyl)-4-[4-[1-[4-Cyano-3-(trifluoromethyl)-phenyl]-2,5-dihydro-4-methyl-2,5-dioxo-1H-pyrrol-3-yl]-butyl]piperazine-1-carboxamide | 6 | 574 |
| 137 | 4-[4-[1-[4-Cyano-3-(trifluoromethyl)phenyl]-2,5-dihydro-4-methyl-2,5-dioxo-1H-pyrrol-3-yl]butyl]N-(4-phenoxy-phenyl)piperazine-1-carboxamide | 6 | 632 |
| 138 | 4-[4-[1-[4-Cyano-3-(trifluoromethyl)phenyl]-2,5-dihydro-4-methyl-2,5-dioxo-1H-pyrrol-3-yl]butyl]-N-[4-(methylsulfanyl)phenyl]piperazine-1-carboxamide | 6 | 586 |
| 139 | N-([1,1'-Biphenyl]-2-yl)-4-[4-[1-[4-cyano-3-(trifluoromethyl)-phenyl]-2,5-dihydro-4-methyl-2,5-dioxo-1H-pyrrol-3-yl]-butyl]piperazine-1-carboxamide | 6 | 616 |
| 140 | 4-[4-[1-[4-Cyano-3-(trifluoromethyl)phenyl]-2,5-dihydro-4-methyl-2,5-dioxo-1H-pyrrol-3-yl]butyl]N-(2,5-dimethoxyphenyl)piperazine-1-carboxamide | 6 | 600 |
| 141 | 4-[4-[1-[4-Cyano-3-(trifluoromethyl)phenyl]-2,5-dihydro-4-methyl-2,5-dioxo-1H-pyrrol-3-yl]butyl]-N-[2-(1-methylethyl)phenyl]piperazine-1-carboxamide | 6 | 582 |
| 142 | 4-[4-[1-[4-Cyano-3-(trifluoromethyl)phenyl]-2,5-dihydro-4-methyl-2,5-dioxo-1H-pyrrol-3-yl]butyl]N-(2,4,6-trimethylphenyl)piperazine-1-carboxamide | 6 | 582 |
| 143 | (R)-4-[4-[1-[4-Cyano-3-(trifluoromethyl)phenyl]-2,5-dihydro-4-methyl-2,5-dioxo-1H-pyrrol-3-yl]butyl]-N-(1-phenylethyl)-piperazine-1-carboxamide | 6 | 568 |

TABLE 8-continued

Compounds of General Formula I According to the Invention, in which V = Trifluoromethylbenzonitrile, W = Maleimide, n = 4

| Example | Name | Synthesis Analogous to Example | ESI-MS |
|---|---|---|---|
| 144 | 4-[4-[1-[4-Cyano-3-(trifluoromethyl)phenyl]-2,5-dihydro-4-methyl-2,5-dioxo-1H-pyrrol-3-yl]butyl]N-[2-(1,1-dimethylethyl)phenyl]piperazine-1-carboxamide | 6 | 596 |
| 145 | 4-[4-[1-[4-Cyano-3-(trifluoromethyl)phenyl]-2,5-dihydro-4-methyl-2,5-dioxo-1H-pyrrol-3-yl]butyl]-N-hexylpiperazine-1-carboxamide | 6 | 548 |

TABLE 9

Compounds of General Formula I According to the Invention, in which V = Trifluoromethylbenzonitrile, W = Maleimide, n = 5

| Example | Name | Synthesis Analogous to Example | ESI-MS |
|---|---|---|---|
| 146 | 4-(2,5-Dihydro-3-methyl-2,5-dioxo-4-[5-[4-(pyrazin-2-yl)-piperazin-1-yl]pentyl]-1H-pyrrol-1-yl]-2-(trifluoromethyl)-benzonitrile | 3 | 513 |
| 147 | 4-[3-[5-[4-(2,4-Difluorophenyl)piperazin-1-yl]pentyl]-2,5-dihydro-4-methyl-2,5-dioxo-1H-pyrrol-1-yl]-2-(trifluoromethyl)benzonitrile | 3 | 547 |
| 148 | 4-[3-[5-[4-[(Furan-2-yl)carbonyl]piperazin-1-yl]pentyl]-2,5-dihydro-4-methyl-2,5-dioxo-1H-pyrrol-1-yl]-2-(trifluoromethyl)benzonitrile | 4 | 529 |
| 149 | 4-[2,5-Dihydro-3-methyl-4-[5-[4-[(5-methylisoxazol-3-yl)carbonyl]piperazin-1-yl]pentyl]-2,5-dioxo-1H-pyrrol-1-yl]-2-(trifluoromethyl)benzonitrile | 4 | 544 |
| 150 | 4-[2,5-Dihydro-3-methyl-2,5-dioxo-4-[5-[4-(phenylacetyl)-piperazin-1-yl]pentyl]-1H-pyrrol-1-yl]-2-(trifluoromethyl)-benzonitrile | 4 | 553 |
| 151 | 4-[2,5-Dihydro-3-[5-[4-(4-methoxybenzoyl)-piperazin-1-yl]-pentyl]-4-methyl-2,5-dioxo-1H-pyrrol-1-yl]-2-(trifluoromethyl)benzonitrile | 4 | 569 |
| 152 | 4-[2,5-Dihydro-3-[5-[4-(2-methoxybenzoyl)-piperazin-1-yl]-pentyl]-4-methyl-2,5-dioxo-1H-pyrrol-1-yl]-2-(trifluoromethyl)benzonitrile | 4 | 569 |
| 153 | 4-[2,5-Dihydro-3-[5-[4-(methoxyacetyl)piperazin-1-yl]pentyl]-4-methyl-2,5-dioxo-1H-pyrrol-1-yl]-2-(trifluoromethyl)benzonitrile | 4 | 507 |
| 154 | 4-[3-[5-[4-(2-Chlorobenzoyl)piperazin-1-yl]pentyl]-2,5-dihydro-4-methyl-2,5-dioxo-1H-pyrrol-1-yl]-2-(trifluoromethyl)benzonitrile | 4 | 573 |
| 155 | 4-[3-[5-[4-(2-Fluorobenzoyl)piperazin-1-yl]pentyl]-2,5-dihydro-4-methyl-2,5-dioxo-1H-pyrrol-1-yl]-2-(trifluoromethyl)benzonitrile | 4 | 557 |
| 156 | 4-[3-[5-(4-Benzoylpiperazin-1-yl)pentyl]-2,5-dihydro-4-methyl-2,5-dioxo-1H-pyrrol-1-yl]-2-(trifluoromethyl)benzonitrile | 4 | 539 |
| 157 | 4-[3-[5-[4-(Cyclobutylcarbonyl)piperazin-1-yl]pentyl]-2,5-dihydro-4-methyl-2,5-dioxo-1H-pyrrol-1-yl]-2-(trifluoromethyl)benzonitrile | 4 | 517 |
| 158 | 4-[3-[5-[4-(3,4-Dimethoxybenzoyl)piperazin-1-yl]pentyl]-2,5-dihydro-3-methyl-2,5-dioxo-1H-pyrrol-1-yl]-2-(trifluoromethyl)benzonitrile | 4 | 599 |
| 159 | 4-[2,5-Dihydro-3-methyl-2,5-dioxo-4-[5-[4-[(pyridin-3-yl)-carbonyl]piperazin-1-yl]pentyl]-1H-pyrrol-1-yl-2-(trifluoromethyl)benzonitrile | 4 | 540 |
| 160 | 4-[3-[5-[4-(Cyclopropylcarbonyl)piperazin-1-yl]pentyl]-2,5-dihydro-4-methyl-2,5-dioxo-1H-pyrrol-1-yl]-2-(trifluoromethyl)benzonitrile | 4 | 503 |
| 161 | 4-[2,5-Dihydro-3-methyl-2,5-dioxo-4-[5-[4-[(pyridin-4-yl)-carbonyl]piperazin-1-yl]pentyl]-1H-pyrrol-1-yl]-2-(trifluoromethyl)benzonitrile | 4 | 540 |
| 162 | 4-[3-[5-[4-[4-(Dimethylamino)benzoyl]piperazin-1-yl]-pentyl]-2,5-dihydro-4-methyl-2,5-dioxo-1H-pyrrol-1-yl]-2-(trifluoromethyl)benzonitrile | 4 | 582 |
| 163 | 4-[2,5-Dihydro-3-methyl-2,5-dioxo-4-[5-[4-[(phenylsulfanyl)acetyl]piperazin-1-yl]pentyl]-1H-pyrrol-1-yl]-2-(trifluoromethyl)benzonitrile | 4 | 585 |
| 164 | 4-[2,5-Dihydro-3-methyl-2,5-dioxo-4-[5-[4-(phenoxyacetyl)piperazin-1-yl]pentyl]-1H-pyrrol-1-yl]-2-(trifluoromethyl)benzonitrile | 4 | 569 |
| 165 | 4-[2,5-Dihydro-3-methyl-2,5-dioxo-4-[5-[4-[(thien-2-yl)-carbonyl]piperazin-1-yl]pentyl]-1H-pyrrol-1-yl]-2-(trifluoromethyl)benzonitrile | 4 | 545 |
| 166 | 4-[2,5-Dihydro-3-methyl-2,5-dioxo-4-[5-[4-[3-phenyl-1-oxopropyl)piperazin-1-yl]pentyl]-1H-pyrrol-1-yl]-2-(trifluoromethyl)benzonitrile | 4 | 567 |
| 167 | 4-[3-[5-[4-[(1,3-Benzodioxol-5-yl)carbonyl]-piperazin-1-yl]-pentyl]-2,5-dihydro-4-methyl-2,5-dioxo-1H-pyrrol-1-yl]-2-(trifluoromethyl)-benzonitrile | 4 | 583 |
| 168 | 4-[2,5-Dihydro-3-[5-[4-[(4-methoxyphenyl)-acetyl]piperazin-1-yl]pentyl]-4-methyl-2,5-dioxo-1H-pyrrol-1-yl]-2-(trifluoromethyl)benzonitrile | 4 | 583 |
| 169 | 4-[2,5-Dihydro-3-methyl-4-[5-[4-(2-methylbenzoyl)-piperazin-1-yl]pentyl]-2,5-dioxo-1H-pyrrol-1-yl]-2-(trifluoromethyl)benzonitrile | 4 | 553 |
| 170 | 4-[2,5-Dihydro-3-methyl-2,5-dioxo-4-[5-[4-[(thien-2-yl)-acetyl]piperazin-1-yl]pentyl]-1H-pyrrol-1-yl]-2-(trifluoromethyl)benzonitrile | 4 | 559 |
| 171 | 4-[3-[5-[4-[(4-Chlorophenoxy)acetyl]piperazin-1-yl]pentyl]-2,5-dihydro-4-methyl-2,5-dioxo-1H-pyrrol-1-yl]-2-(trifluoromethyl)benzonitrile | 4 | 603 |
| 172 | 4-[3-[5-[4-(3-Cyclopentyl-1-oxopropyl)piperazin-1-yl]-pentyl]-2,5-dihydro-4-methyl-2,5-dioxo-1H-pyrrol-1-yl-2-(trifluoromethyl)benzonitrile | 4 | 559 |
| 173 | 4-[3-[5-[4-(3-Chlorobenzoyl)piperazin-1-yl]pentyl]-2,5-dihydro-4-methyl-2,5-dioxo-1H-pyrrol-1-yl]-2-(trifluoromethyl)benzonitrile | 4 | 573 |
| 174 | 4-[3-[5-[4-(3,3-Dimethyl-1-oxobutyl)piperazin-1-yl]pentyl]-2,5-dihydro-4-methyl-2,5-dioxo-1H-pyrrol-1-yl]-2-(trifluoromethyl)benzonitrile | 4 | 533 |
| 175 | 4-[2,5-Dihydro-3-methyl-4-[5-[4-(3-methyl-1-oxobutyl)-piperazin-1-yl]pentyl]-2,5-dioxo-1H-pyrrol-1-yl)-2-(trifluoromethyl)benzonitrile | 4 | 519 |
| 176 | 4-[2,5-Dihydro-4-methyl-2,5-dioxo-3-[5-[4-[(phenyl-methoxy)acetyl]piperazin-1-yl]pentyl]-1H-pyrrol-1-yl]-2-(trifluoromethyl)benzonitrile | 4 | 583 |
| 177 | 4-[3-[5-[4-(Cyclopentylacetyl)piperazin-1-yl]pentyl]-2,5-dihydro-4-methyl-2,5-dioxo-1H-pyrrol-1-yl]-2-(trifluoromethyl)benzonitrile | 4 | 545 |
| 178 | 4-[3-[5-[4-(2,6-Difluorobenzoyl)piperazin-1-yl]pentyl]-2,5-dihydro-4-methyl-2,5-dioxo-1H-pyrrol-1-yl]-2-(trifluoromethyl)benzonitrile | 4 | 575 |
| 179 | 4-[3-[5-[4-(2,6-Dichlorobenzoyl)piperazin-1-yl]pentyl]-2,5-dihydro-4-methyl-2,5-dioxo-1H-pyrrol-1-yl]-2-(trifluoromethyl)benzonitrile | 4 | 607 |
| 180 | 4-[2,5-Dihydro-3-methyl-2,5-dioxo-4-[5-[4-[2-(trifluoromethyl)benzoyl]piperazin-1-yl]pentyl]-1H-pyrrol-1-yl]-2-(trifluoromethyl)benzonitrile | 4 | 607 |
| 181 | 4-[3-[5-[4-(3-Fluorobenzoyl)piperazin-1-yl]pentyl]-2,5-dihydro-4-methyl-2,5-dioxo-1H-pyrrol-1-yl]-2-(trifluoromethyl)benzonitrile | 4 | 557 |
| 182 | 4-[2,5-Dihydro-3-methyl-2,5-dioxo-4-[5-[4-[3-(trifluoromethyl)benzoyl]piperazin-1-yl]pentyl]-1H-pyrrol-1-yl]-2-(trifluoromethyl)benzonitrile | 4 | 607 |

TABLE 9-continued

Compounds of General Formula I According to the Invention, in which V = Trifluoromethylbenzonitrile, W = Maleimide, n = 5

| Example | Name | Synthesis Analogous to Example | ESI-MS |
|---|---|---|---|
| 183 | 4-[2,5-Dihydro-3-methyl-4-[5-[4-(4-methylbenzoyl)-piperazin-1-yl]pentyl]-2,5-dioxo-1H-pyrrol-1-yl]-2-(trifluoromethyl)benzonitrile | 4 | 553 |
| 184 | 4-[2,5-Dihydro-3-methyl-4-[5-[4-[(naphthalen-1-yl)-carbonyl]piperazin-1-yl]pentyl]-2,5-dioxo-1H-pyrrol-1-yl]-2-(trifluoromethyl)benzonitrile | 4 | 589 |
| 185 | 4-[2,5-Dihydro-3-methyl-4-[5-[4-[(naphthalen-2-yl)-carbonyl]piperazin-1-yl]pentyl]-2,5-dioxo-1H-pyrrol-1-yl]-2-(trifluoromethyl)benzonitrile | 4 | 589 |
| 186 | 4-[3-[5-[4-(3-Cyanobenzoyl)piperazin-1-yl]pentyl]-2,5-dihydro-4-methyl-2,5-dioxo-1H-pyrrol-1-yl]-2-(trifluoromethyl)benzonitrile | 4 | 564 |
| 187 | 4-[3-[5-[4-(Cyclohexylcarbonyl)piperazin-1-yl]pentyl]-2,5-dihydro-4-methyl-2,5-dioxo-1H-pyrrol-1-yl]-2-(trifluoromethyl)benzonitrile | 4 | 545 |
| 188 | 4-[3-[5-(4-Acetylpiperazin-1-yl)pentyl]-2,5-dihydro-4-methyl-2,5-dioxo-1H-pyrrol-1-yl]-2-(trifluoromethyl)-benzonitrile | 4 | 476 |
| 189 | 4-[2,5-Dihydro-3-[5-[4-(3-methoxy-1-oxopropyl)piperazin-1-yl]pentyl]-4-methyl-2,5-dioxo-1H-pyrrol-1-yl]-2-(trifluoromethyl)-benzonitrile | 4 | 520 |
| 190 | 4-[2,5-Dihydro-3-[5-[4-[(2-methoxyethoxy)-acetyl]piperazin-1-yl]pentyl]-4-methyl-2,5-dioxo-1H-pyrrol-1-yl]-2-(trifluoromethyl)benzonitrile | 4 | 550 |
| 191 | 4-[2,5-Dihydro-3-[5-[4-[[2-(2-methoxyethoxy)-ethoxy]-acetyl]piperazin-1-yl]pentyl]-4-methyl-2,5-dioxo-1H-pyrrol-1-yl]-2-(trifluoromethyl)benzonitrile | 4 | 594 |
| 192 | 4-[4-[5-[4-(Cyclopropylsulfonyl)piperazin-1-yl]pentyl]-2,5-dihydro-3-methyl-2,5-dioxo-1H-pyrrol-1-yl]-2-(trifluoromethyl)benzonitrile | 5 | 538 |
| 193 | 4-[2,5-Dihydro-3-[5-[4-[(2-methoxyethyl)-sulfonyl]piperazin-1-yl]pentyl]-4-methyl-2,5-dioxo-1H-pyrrol-1-yl]-2-(trifluoromethyl)-benzonitrile | 5 | 556 |
| 194 | 4-[2,5-Dihydro-3-[5-[4-[[2-(2-methoxyethoxy)-ethyl]-sulfonyl]piperazin-1-yl]pentyl]-4-methyl-2,5-dioxo-1H-pyrrol-1-yl]-2-(trifluoromethyl)-benzonitrile | 5 | 600 |
| 195 | 4-[2,5-Dihydro-3-[5-[4-[[2-[2-(2-methoxy-ethoxy)-ethoxy]-ethyl]sulfonyl]piperazin-1-yl]pentyl]-4-methyl-2,5-dioxo-1H-pyrrol-1-yl]-2-(trifluoromethyl)benzonitrile | 5 | 644 |
| 196 | 4-[5-[1-[4-Cyano-3-(trifluoromethyl)phenyl]-2,5-dihydro-4-methyl-2,5-dioxo-1H-pyrrol-3-yl]pentyl]-N,N-dimethylpiperazine-1-sulfonamide | 5 | 541 |
| 197 | 4-[2,5-Dihydro-3-methyl-2,5-dioxo-4-[5-[4-[(1-methylethyl)-sulfonyl]piperazin-1-yl]pentyl]-1H-pyrrol-1-yl]-2-(trifluoromethyl)benzonitrile | 5 | 541 |
| 198 | 4-[2,5-Dihydro-3-methyl-2,5-dioxo-4-[5-[4-(phenylsulfonyl)piperazin-1-yl]pentyl]-1H-pyrrol-1-yl]-2-(trifluoromethyl)benzonitrile | 5 | 575 |
| 199 | 4-[2,5-Dihydro-3-methyl-4-[5-[4-(methylsulfonyl)piperazin-1-yl]pentyl]-2,5-dioxo-1H-pyrrol-1-yl]-2-(trifluoromethyl)-benzonitrile | 5 | 513 |
| 200 | 4-[3-[5-[4-[(4-Chlorophenyl)sulfonyl]piperazin-1-yl]pentyl]-2,5-dihydro-4-methyl-2,5-dioxo-1H-pyrrol-1-yl]-2-(trifluoromethyl)benzonitrile | 5 | 609 |
| 201 | 4-[2,5-Dihydro-3-methyl-2,5-dioxo-4-[5-[4-[(phenylmethyl)-sulfonyl]piperazin-1-yl]pentyl]-1H-pyrrol-1-yl]-2-(trifluoromethyl)benzonitrile | 5 | 589 |
| 202 | 4-[3-[5-[4-[(4-Cyanophenyl)sulfonyl]piperazin-1-yl]pentyl]-2,5-dihydro-4-methyl-2,5-dioxo-1H-pyrrol-yl]-2-(trifluoromethyl)benzonitrile | 5 | 600 |
| 203 | 4-[4-[5-[4-[(Quinolin-8-yl)sulfonyl]piperazin-1-yl]pentyl]-2,5-dihydro-3-methyl-2,5-dioxo-1H-pyrrol-1-yl]-2-(trifluoromethyl)benzonitrile | 5 | 626 |
| 204 | 4-[3-[5-[4-[(2-Fluorophenyl)sulfonyl]piperazin-1-yl]pentyl]-2,5-dihydro-4-methyl-2,5-dioxo-1H-pyrrol-1-yl]-2-(trifluoromethyl)benzonitrile | 5 | 593 |
| 205 | 4-[3-[5-[4-[(2,5-Dimethoxyphenyl)sulfonyl]-piperazin-1-yl]pentyl]-2,5-dihydro-4-methyl-2,5-dioxo-1H-pyrrol-1-yl]-2-(trifluoromethyl)-benzonitrile | 5 | 635 |
| 206 | 4-[3-[5-[4-[(3-Cyanophenyl)sulfonyl]piperazin-1-yl]pentyl]-2,5-dihydro-4-methyl-2,5-dioxo-1H-pyrrol-1-yl]-2-(trifluoromethyl)benzonitrile | 5 | 600 |
| 207 | 4-[3-[5-[4-[(2,1,3-Benzothiadiazol-4-yl)sulfonyl]piperazin-1-yl]pentyl]-2,5-dihydro-4-methyl-2,5-dioxo-1H-pyrrol-1-yl]-2-(trifluoromethyl)benzonitrile | 5 | 633 |
| 208 | 4-[5-[1-[4-Cyano-3-(trifluoromethyl)phenyl]-2,5-dihydro-4-methyl-2,5-dioxo-1H-pyrrol-3-yl]pentyl]-N-(1,1-dimethyl-ethyl)piperazine-1-carboxamide | 6 | 534 |
| 209 | 4-[5-[1-[4-Cyano-3-(trifluoromethyl)phenyl]-2,5-dihydro-4-methyl-2,5-dioxo-1H-pyrrol-3-yl]pentyl]-N-(naphthalen-1-yl)piperazine-1-carboxamide | 6 | 604 |
| 210 | N-(4-Cyanophenyl)-4-[5-[1-[4-cyano-3-(trifluoromethyl)-phenyl]-2,5-dihydro-4-methyl-2,5-dioxo-1H-pyrrol-3-yl]-pentyl]piperazine-1-carboxamide | 6 | 579 |
| 211 | N-(2-Chlorophenyl)-4-[5-[1-[4-cyano-3-(trifluoromethyl)-phenyl]-2,5-dihydro-4-methyl-2,5-dioxo-1H-pyrrol-3-yl]-pentyl]piperazine-1-carboxamide | 6 | 588 |
| 212 | 4-[5-[1-[4-Cyano-3-(trifluoromethyl)phenyl]-2,5-dihydro-4-methyl-2,5-dioxo-1H-pyrrol-3-yl]pentyl]-N-[2-(trifluoromethyl)phenyl]piperazine-1-carboxamide | 6 | 622 |
| 213 | 4-[5-[1-[4-Cyano-3-(trifluoromethyl)phenyl]-2,5-dihydro-4-methyl-2,5-dioxo-1H-pyrrol-3-yl]pentyl]-N-(2-methyl-phenyl)piperazine-1-carboxamide | 6 | 568 |
| 214 | 4-[5-[1-[4-Cyano-3-(trifluoromethyl)phenyl]-2,5-dihydro-4-methyl-2,5-dioxo-1H-pyrrol-3-yl]pentyl]-N-(3-methyl-phenyl)piperazine-1-carboxamide | 6 | 568 |
| 215 | 4-[5-[1-[4-Cyano-3-(trifluoromethyl)phenyl]-2,5-dihydro-4-methyl-2,5-dioxo-1H-pyrrol-3-yl]pentyl]-N-(4-fluorophenyl)-piperazine-1-carboxamide | 6 | 572 |
| 216 | 4-[5-[1-[4-Cyano-3-(trifluoromethyl)phenyl]-2,5-dihydro-4-methyl-2,5-dioxo-1H-pyrrol-3-yl]pentyl]-N-(4-methoxy-phenyl)piperazine-1-carboxamide | 6 | 584 |
| 217 | N-(3-Cyanophenyl)-4-[5-[1-[4-cyano-3-(trifluoromethyl)-phenyl]-2,5-dihydro-4-methyl-2,5-dioxo-1H-pyrrol-3-yl]-pentyl]piperazine-1-carboxamide | 6 | 579 |
| 218 | 4-[5-[1-[4-Cyano-3-(trifluoromethyl)phenyl]-2,5-dihydro-4-methyl-2,5-dioxo-1H-pyrrol-3-yl]pentyl)-N-(3,5-dimethoxy-phenyl)piperazine-1-carboxamide | 6 | 614 |
| 219 | 4-[5-[1-[4-Cyano-3-(trifluoromethyl)phenyl]-2,5-dihydro-4-methyl-2,5-dioxo-1H-pyrrol-3-yl]pentyl]-N-(2-phenylethyl)-piperazine-1-carboxamide | 6 | 582 |
| 220 | N-([1,1'-Biphenyl]-2-yl)-4-[5-[1-[4-cyano-3-(trifluoromethyl)-phenyl]-2,5-dihydro-4-methyl-2,5-dioxo-1H-pyrrol-3-yl]-pentyl]piper- | 6 | 630 |

TABLE 9-continued

Compounds of General Formula I According to the Invention, in which V = Trifluoromethylbenzonitrile, W = Maleimide, n = 5

| Example | Name | Synthesis Analogous to Example | ESI-MS |
|---|---|---|---|
|  | azine-1-carboxamide |  |  |
| 221 | 4-[5-[1-[4-Cyano-3-(trifluoromethyl)phenyl]-2,5-dihydro-4-methyl-2,5-dioxo-1H-pyrrol-3-yl]pentyl]-N-[2-(1-methyl-ethyl)phenyl]piperazine-1-carboxamide | 6 | 596 |
| 222 | 4-[5-[1-[4-Cyano-3-(trifluoromethyl)phenyl]-2,5-dihydro-4-methyl-2,5-dioxo-1H-pyrrol-3-yl]pentyl]-N-(2,6-dichloropyridin-4-yl)piperazine-1-carboxamide | 6 | 623 |
| 223 | (R)-4-[5-[1-[4-Cyano-3-(trifluoromethyl)phenyl]-2,5-dihydro-4-methyl-2,5-dioxo-1H-pyrrol-3-yl]pentyl]-N-(1-phenyl-ethyl)piperazine-1-carboxamide | 6 | 582 |
| 224 | 4-[5-[1-[4-Cyano-3-(trifluoromethyl)phenyl]-2,5-dihydro-4-methyl-2,5-dioxo-1H-pyrrol-3-yl]pentyl]-N-[3-[(trifluoromethyl)sulfanyl]phenyl]piperazine-1-carboxamide | 6 | 654 |
| 225 | 4-[5-[1-[4-Cyano-3-(trifluoromethyl)phenyl]-2,5-dihydro-4-methyl-2,5-dioxo-1H-pyrrol-3-yl]pentyl]-N-[(3-methylphenyl)methyl]piperazine-1-carboxamide | 6 | 582 |
| 226 | 4-[5-[1-[4-Cyano-3-(trifluoromethyl)phenyl]-2,5-dihydro-4-methyl-2,5-dioxo-1H-pyrrol-3-yl]pentyl]-N-[(4-methoxy-phenyl)methyl]-piperazine-1-carboxamide | 6 | 598 |
| 227 | 1-[4-Cyano-3-(trifluoromethyl)phenyl]-2,5-dihydro-4-methyl-2,5-dioxo-1H-pyrrol-3-yl]pentyl]-N-(1,1,3,3-tetramethylbutyl)piperazine-1-carboxamide | 6 | 590 |

TABLE 10

Compounds of General Formula I According to the Invention, in which V = Trifluoromethylbenzonitrile, W = Maleimide, n = 6

| Example | Name | Synthesis Analogous to Example | ESI-MS |
|---|---|---|---|
| 228 | 1,1-Dimethylethyl 4-[6-[1-[4-cyano-3-(trifluoromethyl)phenyl]-2,5-dihydro-4-methyl-2,5-dioxo-1H-pyrrol-3-yl]hexyl]-piperazine-1-carboxylate | 1 | 549 |
| 229 | 4-[2,5-Dihydro-3-methyl-4-[6-(4-methylpiperazin-1-yl)hexyl]-2,5-dioxo-1H-pyrrol-1-yl]-2-(trifluoromethyl)-benzonitrile | 3 | 463 |
| 230 | Ethyl 4-[6-[1-[4-cyano-3-(trifluoromethyl)phenyl]-2,5-dihydro-4-methyl-2,5-dioxo-1H-pyrrol-3-yl]hexyl]piperazine-1-carboxylate | 3 | 521 |
| 231 | 4-[2,5-Dihydro-3-methyl-2,5-dioxo-4-[6-[4-(pyridin-2-yl)piperazin-1-yl]hexyl]-1H-pyrrol-1-yl]-2-(trifluoromethyl)-benzonitrile | 3 | 526 |
| 232 | (Phenylmethyl) 4-[6-[1-[4-cyano-3-(trifluoromethyl)phenyl]-2,5-dihydro-4-methyl-2,5-dioxo-1H-pyrrol-3-yl]hexyl]-piperazine-1-carboxylate | 3 | 583 |
| 233 | 4-[2,5-Dihydro-3-methyl-2,5-dioxo-4-[6-[4-(pyrimidin-2-yl)-piperazin-1-yl]hexyl]-1H-pyrrol-1-yl]-2-(trifluoromethyl)-benzonitrile | 3 | 527 |
| 234 | 4-[2,5-Dihydro-3-[6-[4-(2-methoxyphenyl)piperazin-1-yl]-hexyl]-4-methyl-2,5-dioxo-1H-pyrrol-1-yl]-2-(trifluoromethyl)benzonitrile | 3 | 555 |
| 235 | 4-[2,5-Dihydro-3-methyl-4-[6-[4-(2-nitrophenyl)piperazin-1-yl]hexyl]-2,5-dioxo-1H-pyrrol-1-yl]-2-(trifluoromethyl)-benzonitrile | 3 | 570 |

TABLE 10-continued

Compounds of General Formula I According to the Invention, in which V = Trifluoromethylbenzonitrile, W = Maleimide, n = 6

| Example | Name | Synthesis Analogous to Example | ESI-MS |
|---|---|---|---|
| 236 | 4-[2,5-Dihydro-3-methyl-2,5-dioxo-4-[6-[4-(pyrazin-2-yl)-piperazin-1-yl]hexyl]-1H-pyrrol-1-yl]-2-(trifluoromethyl)-benzonitrile | 3 | 527 |
| 237 | 4-[2,5-Dihydro-3-methyl-4-[6-[4-[2-(methylsulfanyl)-phenyl]piperazin-1-yl]hexyl]-2,5-dioxo-1H-pyrrol-1-yl]-2-(trifluoromethyl)-benzonitrile | 3 | 571 |
| 238 | 4-[2,5-Dihydro-3-methyl-2,5-dioxo-4-[6-[4-[3-(trifluoromethyl)pyridin-2-yl]piperazin-1-yl]hexyl]-1H-pyrrol-1-yl]-2-(trifluoromethyl)benzonitrile | 3 | 594 |
| 239 | 4-[2,5-Dihydro-3-[6-[4-(2-methoxy-ethyl)piperazin-1-yl]-hexyl)-4-methyl-2,5-dioxo-1H-pyrrol-1-yl]-2-(trifluoromethyl)benzonitrile | 3 | 507 |
| 240 | 4-[3-[6-[4-(3,5-Dichloropyridin-4-yl)piperazin-1-yl]hexyl]-2,5-dihydro-4-methyl-2,5-dioxo-1H-pyrrol-1-yl]-2-(trifluoromethyl)benzonitrile | 3 | 594 |
| 241 | 4-[3-[6-[4-(4-Acetylpiperazin-1-yl)hexyl]-2,5-dihydro-4-methyl-2,5-dioxo-1H-pyrrol-1-yl]-2-(trifluoromethyl)-benzonitrile | 4 | 491 |
| 242 | 4-[3-[6-[4-[(Furan-2-yl)carbonyl]piperazin-1-yl]hexyl]-2,5-dihydro-4-methyl-2,5-dioxo-1H-pyrrol-1-yl]-2-(trifluoromethyl)benzonitrile | 4 | 543 |
| 243 | 4-[2,5-Dihydro-3-methyl-2,5-dioxo-4-[6-[4-[(tetrahydrofuran-2-yl)carbonyl]piperazin-1-yl]hexyl]-1H-pyrrol-1-yl]-2-(trifluoromethyl)-benzonitrile | 4 | 547 |
| 244 | 4-[3-[6-[4-(Cyclopentylcarbonyl)piperazin-1-yl]hexyl]-2,5-dihydro-4-methyl-2,5-dioxo-1H-pyrrol-1-yl]-2-(trifluoromethyl)benzonitrile | 4 | 545 |
| 245 | 4-[2,5-Dihydro-3-methyl-4-[6-[4-[(5-methylisoxazol-3-yl)-carbonyl]piperazin-1-yl]hexyl]-2,5-dioxo-1H-pyrrol-1-yl]-2-(trifluoromethyl)benzonitrile | 4 | 558 |
| 246 | 4-[2,5-Dihydro-3-methyl-2,5-dioxo-4-[6-[4-(phenylacetyl)-piperazin-1-yl]hexyl]-1H-pyrrol-1-yl]-2-(trifluoromethyl)-benzonitrile | 4 | 567 |
| 247 | 4-[2,5-Dihydro-3-[6-[4-(4-methoxybenzoyl)-piperazin-1-yl]-hexyl]-4-methyl-2,5-dioxo-1H-pyrrol-1-yl]-2-(trifluoromethyl)benzonitrile | 4 | 583 |
| 248 | 4-[2,5-Dihydro-3-[6-[4-(2-methoxybenzoyl)-piperazin-1-yl]-hexyl]-4-methyl-2,5-dioxo-1H-pyrrol-1-yl]-2-(trifluoromethyl)benzonitrile | 4 | 583 |
| 249 | 4-[2,5-Dihydro-3-[6-[4-(methoxyacetyl)piperazin-1-yl]-hexyl]-4-methyl-2,5-dioxo-1H-pyrrol-1-yl]-2-(trifluoromethyl)benzonitrile | 4 | 521 |
| 250 | 4-[3-[6-[4-(2-Chlorobenzoyl)piperazin-1-yl]hexyl]-2,5-dihydro-4-methyl-2,5-dioxo-1H-pyrrol-1-yl]-2-(trifluoromethyl)benzonitrile | 4 | 587 |
| 251 | 4-[3-[6-[4-(2-Fluorobenzoyl)piperazin-1-yl]hexyl]-2,5-dihydro-4-methyl-2,5-dioxo-1H-pyrrol-1-yl]-2-(trifluoromethyl)benzonitrile | 4 | 571 |
| 252 | 4-[3-[6-[4-(4-Benzoylpiperazin-1-yl)hexyl]-2,5-dihydro-4-methyl-2,5-dioxo-1H-pyrrol-1-yl]-2-(trifluoromethyl)benzonitrile | 4 | 553 |
| 253 | 4-[3-[6-[4-(Cyclobutylcarbonyl)piperazin-1-yl]hexyl]-2,5-dihydro-4-methyl-2,5-dioxo-1H-pyrrol-1-yl]-2-(trifluoromethyl)benzonitrile | 4 | 531 |
| 254 | 4-[3-[6-[4-(3,4-Dimethoxybenzoyl)piperazin-1-yl]hexyl]-2,5-dihydro-4-methyl-2,5-dioxo-1H-pyrrol-1-yl]-2-(trifluoromethyl)benzonitrile | 4 | 613 |
| 255 | 4-[2,5-Dihydro-3-methyl-2,5-dioxo-4-[6-[4-[(phenylsulfanyl)acetyl]piperazin-1-yl]hexyl]-1H-pyrrol-1-yl]-2-(trifluoromethyl)benzonitrile | 4 | 599 |
| 256 | 4-[2,5-Dihydro-3-methyl-2,5-dioxo-4-[6-[4-(phenoxyacetyl)piperazin-1-yl]hexyl]-1H-pyrrol-1-yl]-2-(trifluoromethyl)benzonitrile | 4 | 583 |
| 257 | 4-[2,5-Dihydro-3-methyl-2,5-dioxo-4-[6-[4-[(thien-2-yl)carbonyl]piperazin-1-yl]hexyl]-1H-pyrrol-1-yl]-2-(trifluoromethyl)benzonitrile | 4 | 559 |

TABLE 10-continued

Compounds of General Formula I According to the Invention, in which V = Trifluoromethylbenzonitrile, W = Maleimide, n = 6

| Example | Name | Synthesis Analogous to Example | ESI-MS |
|---|---|---|---|
| 258 | 4-[2,5-Dihydro-3-methyl-2,5-dioxo-4-[6-[4-(3-phenyl-1-oxopropyl)piperazin-1-yl]hexyl]-1H-pyrrol-1-yl)-2-(trifluoromethyl)benzonitrile | 4 | 581 |
| 259 | 4-[3-[6-[4-[(1,3-Benzodioxol-5-yl)carbonyl]-piperazin-1-yl]-hexyl]-2,5-dihydro-4-methyl-2,5-dioxo-1H-pyrrol-1-yl]-2-(trifluoromethyl)benzonitrile | 4 | 597 |
| 260 | 4-[2,5-Dihydro-3-[6-[4-[(4-methoxyphenyl)-acetyl]piperazin-1-yl]hexyl]-4-methyl-2,5-dioxo-1H-pyrrol-1-yl]-2-(trifluoromethyl)benzonitrile | 4 | 597 |
| 261 | 4-[2,5-Dihydro-3-methyl-4-[6-[4-(2-methylbenzoyl)-piperazin-1-yl]hexyl]-2,5-dioxo-1H-pyrrol-1-yl]-2-(trifluoromethyl)benzonitrile | 4 | 567 |
| 262 | 4-[3-[6-[4-(4-Chlorobenzoyl)piperazin-1-yl]hexyl]-2,5-dihydro-4-methyl-2,5-dioxo-1H-pyrrol-1-yl]-2-(trifluoromethyl)benzonitrile | 4 | 587 |
| 263 | 4-[2,5-Dihydro-3-methyl-2,5-dioxo-4-[6-[4-[(thien-2-yl)-acetyl]piperazin-1-yl]hexyl]-1H-pyrrol-1-yl]-2-(trifluoromethyl)benzonitrile | 4 | 573 |
| 264 | 4-[3-[6-[4-[(4-Chlorophenoxy)acetyl]piperazin-1-yl]hexyl]-2,5-dihydro-4-methyl-2,5-dioxo-1H-pyrrol-1-yl]-2-(trifluoromethyl)benzonitrile | 4 | 617 |
| 265 | 4-[3-[6-[4-(3-Cyclopentyl-1-oxopropyl)piperazin-1-yl]-hexyl]-2,5-dihydro-4-methyl-2,5-dioxo-1H-pyrrol-1-yl]-2-(trifluoromethyl)benzonitrile | 4 | 573 |
| 266 | 4-[3-[6-[4-(3-Chlorobenzoyl)piperazin-1-yl]hexyl]-2,5-dihydro-4-methyl-2,5-dioxo-1H-pyrrol-1-yl]-2-(trifluoromethyl)benzonitrile | 4 | 587 |
| 267 | 4-[2,5-Dihydro-3-methyl-2,5-dioxo-4-[6-[4-[4-(trifluoromethyl)benzoyl]piperazin-1-yl]hexyl]-1H-pyrrol-1-yl]-2-(trifluoromethyl)benzonitrile | 4 | 621 |
| 268 | 4-[3-[6-[4-(4-cyanobenzoyl)piperazin-1-yl]hexyl]-2,5-dihydro-4-methyl-2,5-dioxo-1H-pyrrol-1-yl]-2-(trifluoromethyl)benzonitrile | 4 | 578 |
| 269 | 4-[3-[6-[4-(3,3-Dimethyl-1-oxobutyl)piperazin-1-yl]hexyl]-2,5-dihydro-4-methyl-2,5-dioxo-1H-pyrrol-1-yl]-2-(trifluoromethyl)benzonitrile | 4 | 547 |
| 270 | 4-[2,5-Dihydro-3-methyl-4-[6-[4-(3-methyl-1-oxobutyl)-piperazin-1-yl]hexyl]-2,5-dioxo-1H-pyrrol-1-yl]-2-(trifluoromethyl)benzonitrile | 4 | 533 |
| 271 | 4-[2,5-Dihydro-3-methyl-2,5-dioxo-4-[6-[4-[(phenyl-methoxy)acetyl]piperazin-1-yl]hexyl]-1H-pyrrol-1-yl]-2-(trifluoromethyl)benzonitrile | 4 | 597 |
| 272 | 4-[3-[6-[4-(Cyclopentylacetyl)piperazin-1-yl]hexyl]-2,5-dihydro-4-methyl-2,5-dioxo-1H-pyrrol-1-yl]-2-(trifluoromethyl)benzonitrile | 4 | 559 |
| 273 | 4-[3-[6-[4-(2,6-Difluorobenzoyl)piperazin-1-yl]hexyl]-2,5-dihydro-4-methyl-2,5-dioxo-1H-pyrrol-1-yl]-2-(trifluoromethyl)benzonitrile | 4 | 589 |
| 274 | 4-[3-[6-[4-(2,6-Dichlorobenzoyl)piperazin-1-yl]hexyl]-2,5-dihydro-4-methyl-2,5-dioxo-1H-pyrrol-1-yl]-2-(trifluoromethyl)benzonitrile | 4 | 621 |
| 275 | 4-[2,5-Dihydro-3-methyl-2,5-dioxo-4-[6-[4-[2-(trifluoromethyl)benzoyl]piperazin-1-yl]hexyl]-1H-pyrrol-1-yl]-2-(trifluoromethyl)benzonitrile | 4 | 621 |
| 276 | 4-[3-[6-[4-(3-Fluorobenzoyl)piperazin-1-yl]hexyl]2,5-dihydro-4-methyl-2,5-dioxo-1H-pyrrol-1-yl]-2-(trifluoromethyl)benzonitrile | 4 | 571 |
| 277 | 4-[2,5-Dihydro-3-[6-[4-(3-methoxybenzoyl)-piperazin-1-yl]-hexyl]-4-methyl-2,5-dioxo-1H-pyrrol-1-yl]-2-(trifluoromethyl)benzonitrile | 4 | 583 |
| 278 | 4-[2,5-Dihydro-3-methyl-2,5-dioxo-4-[6-[4-[3-(trifluoromethyl)benzoyl]piperazin-1-yl]hexyl]-1H-pyrrol-1-yl]-2-(trifluoromethyl)benzonitrile | 4 | 621 |
| 279 | 4-[2,5-Dihydro-3-methyl-4-[6-[4-(3-methylbenzoyl)-piperazin-1-yl]hexyl]-2,5-dioxo-1H-pyrrol-1-yl]-2-(trifluoromethyl)benzonitrile | 4 | 567 |
| 280 | 4-[3-[6-[4-(4-Fluorobenzoyl)piperazin-1-yl]hexyl]-2,5-dihydro-4-methyl-2,5-dioxo-1H-pyrrol-1-yl]-2-(trifluoromethyl)benzonitrile | 4 | 571 |
| 281 | 4-[2,5-Dihydro-3-methyl-4-[6-[4-(4-methylbenzoyl)-piperazin-1-yl]hexyl)-2,5-dioxo-1H-pyrrol-1-yl)-2-(trifluoromethyl)benzonitrile | 4 | 567 |
| 282 | 4-[2,5-Dihydro-3-methyl-4-[6-[4-[(naphthalen-1-yl)-carbonyl]piperazin-1-yl]hexyl]-2,5-dioxo-1H-pyrrol-1-yl]-2-(trifluoromethyl)benzonitrile | 4 | 603 |
| 283 | 4-[2,5-Dihydro-3-methyl-4-[6-[4-[(naphthalen-2-yl)-carbonyl]piperazin-1-yl]hexyl]-2,5-dioxo-1H-pyrrol-1-yl]-2-(trifluoromethyl)benzonitrile | 4 | 603 |
| 284 | 4-[3-[6-[4-(3-Cyanobenzoyl)piperazin-1-yl]hexyl]-2,5-dihydro-4-methyl-2,5-dioxo-1H-pyrrol-1-yl]-2-(trifluoromethyl)benzonitrile | 4 | 578 |
| 285 | 4-[3-[6-[4-(Cyclohexylcarbonyl)piperazin-1-yl]hexyl]-2,5-dihydro-4-methyl-2,5-dioxo-1H-pyrrol-1-yl]-2-(trifluoromethyl)benzonitrile | 4 | 559 |
| 286 | 4-[3-[6-[4-[[4-(1,1-Dimethylethyl)phenoxy]acetyl]-piperazin-1-yl]hexyl]-2,5-dihydro-4-methyl-2,5-dioxo-1H-pyrrol-1-yl]-2-(trifluoromethyl)-benzonitrile | 4 | 639 |
| 287 | 4-[2,5-Dihydro-3-[6-[4-(3-methoxy-1-oxopropyl)piperazin-1-yl]hexyl]-4-methyl-2,5-dioxo-1H-pyrrol-1-yl]-2-(trifluoromethyl)-benzonitrile | 4 | 534 |
| 288 | 4-[2,5-Dihydro-3-[6-[4-[(2-methoxyethoxy)-acetyl]piperazin-1-yl]hexyl]-4-methyl-2,5-dioxo-1H-pyrrol-1-yl]-2-(trifluoromethyl)benzonitrile | 4 | 564 |
| 289 | 4-[2,5-Dihydro-3-[6-[4-[[2-(2-methoxyethoxy)-ethoxy]-acetyl]piperazin-1-yl]hexyl]-4-methyl-2,5-dioxo-1H-pyrrol-1-yl]-2-(trifluoromethyl)-benzonitrile | 4 | 608 |
| 290 | 4-[4-[6-[4-(Cyclopropylsulfonyl)piperazin-1-yl]hexyl]-2,5-dihydro-3-methyl-2,5-dioxo-1H-pyrrol-1-yl]-2-(trifluoromethyl)benzonitrile | 5 | 552 |
| 291 | 4-[2,5-Dihydro-3-[6-[4-(2-methoxyethyl)-sulfonyl]piperazin-1-yl]hexyl]-4-methyl-2,5-dioxo-1H-pyrrol-1-yl]-2-(trifluoromethyl)benzonitrile | 5 | 570 |
| 292 | 4-[2,5-Dihydro-3-[6-[4-[[2-(2-methoxyethoxy)-ethyl]-sulfonyl]piperazin-1-yl]hexyl]-4-methyl-2,5-dioxo-1H-pyrrol-1-yl]-2-(trifluoromethyl)-benzonitrile | 5 | 614 |
| 293 | 4-[2,5-Dihydro-3-[6-[4-[[2-[2-(2-methoxy-ethoxy)-ethoxy]-ethyl]sulfonyl]piperazin-1-yl]hexyl]-4-methyl-2,5-dioxo-1H-pyrrol-1-yl]-2-(trifluoromethyl)]benzonitrile | 5 | 658 |
| 294 | 4-[6-[1-[4-Cyano-3-(trifluoromethyl)phenyl]-2,5-dihydro-4-methyl-2,5-dioxo-1H-pyrrol-3-yl]hexyl]-N, N-dimethyl]piperazine-1-sulfonamide | 5 | 555 |
| 295 | 4-[2,5-Dihydro-3-methyl-2,5-dioxo-4-[6-[4-(phenyl-sulfonyl)piperazin-1-yl]hexyl]-1H-pyrrol-1-yl]-2-(trifluoromethyl)benzonitrile | 5 | 589 |
| 296 | 4-[2,5-Dihydro-3-methyl-4-[6-[4-(methyl-sulfonyl)-piperazin-1-yl]hexyl]-2,5-dioxo-1H-pyrrol-1-yl]-2-(trifluoromethyl)benzonitrile | 5 | 527 |
| 297 | 4-[2,5-Dihydro-3-methyl-4-[6-[4-[(4-methylphenyl)-sulfonyl]piperazin-1-yl]hexyl]-2,5-dioxo-1H-pyrrol-1-yl]-2-(trifluoromethyl)-benzonitrile | 5 | 603 |
| 298 | N-[4-[[4-[6-[1-[4-Cyano-3-(trifluoromethyl)-phenyl]-2,5-dihydro-4-methyl-2,5-dioxo-1H- | 5 | 646 |

TABLE 10-continued

Compounds of General Formula I According to the Invention, in which V = Trifluoromethylbenzonitrile, W = Maleimide, n = 6

| Example | Name | Synthesis Analogous to Example | ESI-MS |
|---|---|---|---|
|  | pyrrol-3-yl]hexyl]piperazin-1-yl]sulfonyl]-phenyl]acetamide |  |  |
| 299 | 4-[2,5-Dihydro-3-methyl-2,5-dioxo-4-[6-[4-[(phenylmethyl)-sulfonyl]piperazin-1-yl]hexyl]-1H-pyrrol-1-yl]-2-(trifluoromethyl)benzonitrile | 5 | 603 |
| 300 | 4-[3-[6-[4-[(4-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile | 5 | 614 |
| 301 | 4-[2,5-Dihydro-3-methyl-4-[6-[4-[(naphthalen-2-yl)-sulfonyl]piperazin-1-yl]hexyl]-2,5-dioxo-1H-pyrrol-1-yl]-2-(trifluoromethyl)benzonitrile | 5 | 639 |
| 302 | 4-[3-[6-[4-[[5-(Dimethylamino)naphthalen-2-sulfonyl]piperazin-1-yl]hexyl]-2,5-dihydro-4-methyl-2,5-dioxo-1H-pyrrol-1-yl]-2-(trifluoromethyl)benzonitrile | 5 | 682 |
| 303 | 4-[2,5-Dihydro-3-methyl-2,5-dioxo-4-[6-[4-[(thien-2-yl)-sulfonyl]piperazin-1-yl]hexyl]-1H-pyrrol-1-yl]-2-(trifluoromethyl)benzonitrile | 5 | 595 |
| 304 | 4-[3-[6-[4-[(Quinolin-8-yl)sulfonyl]piperazin-1-yl]hexyl]-2,5-dihydro-4-methyl-2,5-dioxo-1H-pyrrol-1-yl]-2-(trifluoromethyl)benzonitrile | 5 | 640 |
| 305 | 4-[3-[6-[4-[(2-Fluorophenyl)sulfonyl]piperazin-1-yl]hexyl]-2,5-dihydro-4-methyl-2,5-dioxo-1H-pyrrol-1-yl]-2-(trifluoromethyl)benzonitrile | 5 | 607 |
| 306 | 4-[3-[6-[4-[(2-Chlorophenyl)sulfonyl]piperazin-1-yl]hexyl]-2,5-dihydro-4-methyl-2,5-dioxo-1H-pyrrol-1-yl]-2-(trifluoromethyl)benzonitrile | 5 | 623 |
| 307 | 4-[3-[6-[4-[(2-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile | 5 | 614 |
| 308 | 4-[3-[6-[4-[(3-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile | 5 | 614 |
| 309 | 4-[2,5-Dihydro-3-methyl-4-[6-[4-[[5-[2-methyl-5-(trifluoromethyl)-2H-pyrazol-3-yl]thien-2-yl]sulfonyl]-piperazin-1-yl]hexyl]-2,5-dioxo-1H-pyrrol-1-yl]-2-(trifluoromethyl)benzonitrile | 5 | 743 |
| 310 | 4-[2,5-Dihydro-3-methyl-2,5-dioxo-4-[6-[4-[[1,2,3,4-tetrahydro-2-(trifluoroacetyl)iso-quinolin-7-yl]sulfonyl]-piperazin-1-yl]hexyl]-1H-pyrrol-1-yl]-2-(trifluoromethyl)benzonitrile | 5 | 740 |
| 311 | 4-[3-[6-[4-[(3,5-Dimethylisoxazol-4-yl)sulfonyl]piperazin-1-yl]hexyl]-2,5-dihydro-4-methyl-2,5-dioxo-1H-pyrrol-1-yl]-2-(trifluoromethyl)benzonitrile | 5 | 608 |
| 312 | 4-[3-[6-[4-[(5-Chloro-1,3-dimethyl-1H-pyrazol-4-yl)sulfonyl]-piperazin-1-yl]hexyl]-2,5-dihydro-4-methyl-2,5-dioxo-1H-pyrrol-1-yl]-2-(trifluoromethyl)benzonitrile | 5 | 641 |
| 313 | 4-[2,5-Dihydro-3-methyl-4-[6-[4-[(1-methyl-1H-imidazol-4-yl)sulfonyl]piperazin-1-yl]hexyl]-2,5-dioxo-1H-pyrrol-1-yl]-2-(trifluoromethyl)-benzonitrile | 5 | 593 |
| 314 | 4-[6-[1-[4-Cyano-3-(trifluoromethyl)phenyl]-2,5-dihydro-4-methyl-2,5-dioxo-1H-pyrrol-3-yl]hexyl]-N-(1,1-dimethylethyl)piperazine-1-carboxamide | 6 | 548 |
| 315 | 4-[6-[1-[4-Cyano-3-(trifluoromethyl)phenyl]-2,5-dihydro-4-methyl-2,5-dioxo-1H-pyrrol-3-yl]hexyl]-N-phenylpiperazine-1-carboxamide | 6 | 568 |
| 316 | 4-[6-[1-[4-Cyano-3-(trifluoromethyl)phenyl]-2,5-dihydro-4-methyl-2,5-dioxo-1H-pyrrol-3-yl]hexyl]-N-(naphthalen-1-yl)piperazine-1-carboxamide | 6 | 618 |
| 317 | 4-[6-[1-[4-Cyano-3-(trifluoromethyl)phenyl]-2,5-dihydro-4-methyl-2,5-dioxo-1H-pyrrol-3-yl]hexyl]-N-(naphthalen-2-yl)piperazine-1-carboxamide | 6 | 618 |
| 318 | N-(4-Cyanophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 593 |
| 319 | 4-[6-[1-[4-Cyano-3-(trifluoromethyl)phenyl]-2,5-dihydro-4-methyl-2,5-dioxo-1H-pyrrol-3-yl]hexyl]-N-(1-methylethyl)-piperazine-1-carboxamide | 6 | 534 |
| 320 | 4-[6-[1-[4-Cyano-3-(trifluoromethyl)phenyl]-2,5-dihydro-4-methyl-2,5-dioxo-1H-pyrrol-3-yl]hexyl]-N-[3-(trifluoromethyl)phenyl]piperazine-1-carboxamide | 6 | 636 |
| 321 | 4-[6-[1-[4-Cyano-3-(trifluoromethyl)phenyl]-2,5-dihydro-4-methyl-2,5-dioxo-1H-pyrrol-3-yl]hexyl]-N-(2-fluorophenyl)-piperazine-1-carboxamide | 6 | 586 |
| 322 | N-(2-Chlorophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 602 |
| 323 | 4-[6-[1-[4-Cyano-3-(trifluoromethyl)phenyl]-2,5-dihydro-4-methyl-2,5-dioxo-1H-pyrrol-3-yl]hexyl]-N-(2-methoxy-phenyl)piperazine-1-carboxamide | 6 | 598 |
| 324 | 4-[6-[1-[4-Cyano-3-(trifluoromethyl)phenyl]-2,5-dihydro-4-methyl-2,5-dioxo-1H-pyrrol-3-yl]hexyl]-N-[2-(trifluoromethyl)phenyl]piperazine-1-carboxamide | 6 | 636 |
| 325 | 4-[6-[1-[4-Cyano-3-(trifluoromethyl)phenyl]-2,5-dihydro-4-methyl-2,5-dioxo-1H-pyrrol-3-yl]hexyl]-N-(2-methyl-phenyl)piperazine-1-carboxamide | 6 | 582 |
| 326 | 4-[6-[1-[4-Cyano-3-(trifluoromethyl)phenyl]-2,5-dihydro-4-methyl-2,5-dioxo-1H-pyrrol-3-yl]hexyl]-N-(3-fluorophenyl)-piperazine-1-carboxamide | 6 | 586 |
| 327 | N-(3-Chlorophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 602 |
| 328 | 4-[6-[1-[4-Cyano-3-(trifluoromethyl)phenyl]-2,5-dihydro-4-methyl-2,5-dioxo-1H-pyrrol-3-yl]hexyl]-N-(3-methoxy-phenyl)piperazine-1-carboxamide | 6 | 598 |
| 329 | 4-[6-[1-[4-Cyano-3-(trifluoromethyl)phenyl]-2,5-dihydro-4-methyl-2,5-dioxo-1H-pyrrol-3-yl]hexyl]-N-(3-methylphenyl)piperazine-1-carboxamide | 6 | 582 |
| 330 | 4-[6-[1-[4-Cyano-3-(trifluoromethyl)phenyl]-2,5-dihydro-4-methyl-2,5-dioxo-1H-pyrrol-3-yl]hexyl]-N-(4-fluorophenyl)-piperazine-1-carboxamide | 6 | 586 |
| 331 | N-(4-Chlorophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 602 |
| 332 | 4-[6-[1-[4-Cyano-3-(trifluoromethyl)phenyl]-2,5-dihydro-4-methyl-2,5-dioxo-1H-pyrrol-3-yl]hexyl]-N-(4-methoxy-phenyl)piperazine-1-carboxamide | 6 | 598 |
| 333 | 4-[6-[1-[4-Cyano-3-(trifluoromethyl)phenyl]-2,5-dihydro-4-methyl-2,5-dioxo-1H-pyrrol-3-yl]hexyl]-N-[4-(trifluoromethyl)phenyl]piperazine-1-carboxamide | 6 | 636 |
| 334 | 4-[6-[1-[4-Cyano-3-(trifluoromethyl)phenyl]-2,5-dihydro-4-methyl-2,5-dioxo-1H-pyrrol-3-yl]hexyl]-N-(4-methylphenyl)piperazine-1-carboxamide | 6 | 582 |
| 335 | 4-[6-[1-[4-Cyano-3-(trifluoromethyl)phenyl]-2,5-dihydro-4-methyl-2,5-dioxo-1H-pyrrol-3- | 6 | 532 |

TABLE 10-continued

Compounds of General Formula I According to the Invention, in which V = Trifluoromethylbenzonitrile, W = Maleimide, n = 6

| Example | Name | Synthesis Analogous to Example | ESI-MS |
|---|---|---|---|
|  | yl]hexyl]-N-(prop-2-enyl)-piperazine-1-carboxamide |  |  |
| 336 | 4-[6-[1-[4-Cyano-3-(trifluoromethyl)phenyl]-2,5-dihydro-4-methyl-2,5-dioxo-1H-pyrrol-3-yl]hexyl]-N-cyclohexyl-piperazine-1-carboxamide | 6 | 574 |
| 337 | 4-[4-Cyano-3-(trifluoromethyl)phenyl]-2,5-dihydro-4-methyl-2,5-dioxo-1H-pyrrol-3-yl]hexyl]-N-(phenylmethyl)-piperazine-1-carboxamide | 6 | 582 |
| 338 | N-(3-Cyanophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 593 |
| 339 | 4-[6-[1-[4-Cyano-3-(trifluoromethyl)phenyl]-2,5-dihydro-4-methyl-2,5-dioxo-1H-pyrrol-3-yl]hexyl]-N-(3,5-dimethoxy-phenyl)piperazine-1-carboxamide | 6 | 628 |
| 340 | 4-[6-[1-[4-Cyano-3-(trifluoromethyl)phenyl]-2,5-dihydro-4-methyl-2,5-dioxo-1H-pyrrol-3-yl]hexyl]-N-[3-(methylsulfanyl)phenyl]piperazine-1-carboxamide | 6 | 614 |
| 341 | 4-[6-[1-[4-Cyano-3-(trifluoromethyl)phenyl]-2,5-dihydro-4-methyl-2,5-dioxo-1H-pyrrol-3-yl]hexyl]-N-(4-phenoxy-phenyl)piperazine-1-carboxamide | 6 | 660 |
| 342 | 4-[6-[1-[4-Cyano-3-(trifluoromethyl)phenyl]-2,5-dihydro-4-methyl-2,5-dioxo-1H-pyrrol-3-yl]hexyl]-N-[4-(methylsulfanyl)phenyl]piperazine-1-carboxamide | 6 | 614 |
| 343 | 4-[6-[1-[4-Cyano-3-(trifluoromethyl)phenyl]-2,5-dihydro-4-methyl-2,5-dioxo-1H-pyrrol-3-yl]hexyl]-N-[4-(1-methylethyl)phenyl]piperazine-1-carboxamide | 6 | 610 |
| 344 | 4-[6-[1-[4-Cyano-3-(trifluoromethyl)phenyl]-2,5-dihydro-4-methyl-2,5-dioxo-1H-pyrrol-3-yl]hexyl]-N-(2-phenylethyl)-piperazine-1-carboxamide | 6 | 596 |
| 345 | N-([1,1'-Biphenyl]-2-yl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 644 |
| 346 | 4-[6-[1-[4-Cyano-3-(trifluoromethyl)phenyl]-2,5-dihydro-4-methyl-2,5-dioxo-1H-pyrrol-3-yl]hexyl]-N-[4-(phenyl-methoxy)phenyl]piperazine-1-carboxamide | 6 | 674 |
| 347 | N-(2-Cyanophenyl)-4-[6-[1-[4-cyano-3-(trifluoromethyl)-phenyl]-2,5-dihydro-4-methyl-2,5-dioxo-1H-pyrrol-3-yl]-hexyl]piperazine-1-carboxamide | 6 | 593 |
| 348 | 4-[6-[1-[4-Cyano-3-(trifluoromethyl)phenyl]-2,5-dihydro-4-methyl-2,5-dioxo-1H-pyrrol-3-yl]hexyl]-N-[2-(thien-2-yl)-ethyl]piperazine-1-carboxamide | 6 | 602 |
| 349 | (1R-trans)-4-[6-[1-[4-Cyano-3-(trifluoromethyl)-phenyl]-2,5-dihydro-4-methyl-2,5-dioxo-1H-pyrrol-3-yl]hexyl]-N-(2-phenylcyclopropyl)-piperazine-1-carboxamide | 6 | 608 |
| 350 | 4-[6-[1-[4-Cyano-3-(trifluoromethyl)phenyl]-2,5-dihydro-4-methyl-2,5-dioxo-1H-pyrrol-3-yl]hexyl]-N-(2,6-difluorophenyl)piperazine-1-carboxamide | 6 | 604 |
| 351 | 4-[6-[1-[4-Cyano-3-(trifluoromethyl)phenyl]-2,5-dihydro-4-methyl-2,5-dioxo-1H-pyrrol-3-yl]hexyl]-N-(2,6-dichlorophenyl)piperazine-1-carboxamide | 6 | 636 |
| 352 | 4-[6-[1-[4-Cyano-3-(trifluoromethyl)phenyl]-2,5-dihydro-4-methyl-2,5-dioxo-1H-pyrrol-3-yl]hexyl]-N-(2,4-dimethoxy-phenyl)piperazine-1-carboxamide | 6 | 628 |
| 353 | 4-[6-[1-[4-Cyano-3-(trifluoromethyl)phenyl]-2,5-dihydro-4-methyl-2,5-dioxo-1H-pyrrol-3-yl]hexyl]-N-(2,5-dimethoxy-phenyl)piperazine-1-carboxamide | 6 | 628 |
| 354 | 4-[6-[1-[4-Cyano-3-(trifluoromethyl)phenyl]-2,5-dihydro-4-methyl-2,5-dioxo-1H-pyrrol-3-yl]hexyl]-N-(2,6-dimethyl-phenyl)piperazine-1-carboxamide | 6 | 596 |
| 355 | 4-[6-[1-[4-Cyano-3-(trifluoromethyl)phenyl]-2,5-dihydro-4-methyl-2,5-dioxo-1H-pyrrol-3-yl]hexyl]-N-(trichloroacetyl)-piperazine-1-carboxamide | 6 | 637 |
| 356 | (S)-4-[6-[1-[4-Cyano-3-(trifluoromethyl)phenyl]-2,5-dihydro-4-methyl-2,5-dioxo-1H-pyrrol-3-yl]hexyl]-N-(1-phenylethyl)piperazine-1-carboxamide | 6 | 596 |
| 357 | (R)-4-[6-[1-[4-Cyano-3-(trifluoromethyl)phenyl]-2,5-dihydro-4-methyl-2,5-dioxo-1H-pyrrol-3-yl]hexyl]-N-[1-(naphthalen-1-yl)ethyl]piperazine-1-carboxamide | 6 | 646 |
| 358 | 4-[6-[1-[4-Cyano-3-(trifluoromethyl)phenyl]-2,5-dihydro-4-methyl-2,5-dioxo-1H-pyrrol-3-yl]hexyl]-N-(2,4,6-trichlorophenyl)piperazine-1-carboxamide | 6 | 671 |
| 359 | 4-[6-[1-[4-Cyano-3-(trifluoromethyl)phenyl]-2,5-dihydro-4-methyl-2,5-dioxo-1H-pyrrol-3-yl]hexyl]-N-[2-(1-methylethyl)phenyl]piperazine-1-carboxamide | 6 | 610 |
| 360 | 4-[6-[1-[4-Cyano-3-(trifluoromethyl)phenyl]-2,5-dihydro-4-methyl-2,5-dioxo-1H-pyrrol-3-yl]hexyl]-N-(3,5-dichlorophenyl)piperazine-1-carboxamide | 6 | 636 |
| 361 | 4-[6-[1-[4-Cyano-3-(trifluoromethyl)phenyl]-2,5-dihydro-4-methyl-2,5-dioxo-1H-pyrrol-3-yl]hexyl]-N-(2,4,6-trimethyl-phenyl)piperazine-1-carboxamide | 6 | 610 |
| 362 | 4-[6-[1-[4-Cyano-3-(trifluoromethyl)phenyl]-2,5-dihydro-4-methyl-2,5-dioxo-1H-pyrrol-3-yl]hexyl]-N-[4-[(trifluoromethyl)sulfanyl]phenyl]piperazine-1-carboxamide | 6 | 668 |
| 363 | 4-[6-[1-[4-Cyano-3-(trifluoromethyl)phenyl]-2,5-dihydro-4-methyl-2,5-dioxo-1H-pyrrol-3-yl]hexyl]-N-[(2,4-dichlorophenyl)methyl]piperazine-1-carboxamide | 6 | 651 |
| 364 | 4-[6-[1-[4-Cyano-3-(trifluoromethyl)phenyl]-2,5-dihydro-4-methyl-2,5-dioxo-1H-pyrrol-3-yl]hexyl]-N-[2-(methylsulfanyl)phenyl]piperazine-1-carboxamide | 6 | 614 |
| 365 | 4-[6-[1-[4-Cyano-3-(trifluoromethyl)phenyl]-2,5-dihydro-4-methyl-2,5-dioxo-1H-pyrrol-3-yl]hexyl]-N-(2,6-dichloropyridin-4-yl)piperazine-1-carboxamide | 6 | 637 |
| 366 | (R)-4-[6-[1-[4-Cyano-3-(trifluoromethyl)phenyl]-2,5-dihydro-4-methyl-2,5-dioxo-1H-pyrrol-3-yl]hexyl]-N-(1-phenylethyl)piperazine-1-carboxamide | 6 | 596 |
| 367 | (S)-4-[6-[1-[4-Cyano-3-(trifluoromethyl)phenyl]-2,5-dihydro-4-methyl-2,5-dioxo-1H-pyrrol-3-yl]hexyl]-N-[1-(naphthalen-1-yl)thyl]piperazine-1-carboxamide | 6 | 646 |
| 368 | 4-[6-[1-[4-Cyano-3-(trifluoromethyl)phenyl]-2,5-dihydro-4-methyl-2,5-dioxo-1H-pyrrol-3-yl]hexyl]-N-[1-methyl-1-[3-(1-methylethenyl)phenyl]-ethyl]piperazine-1-carboxamide | 6 | 650 |
| 369 | 4-[6-[1-[4-Cyano-3-(trifluoromethyl)phenyl]-2,5-dihydro-4-methyl-2,5-dioxo-1H-pyrrol-3-yl]hexyl]-N-[2-(trifluoromethoxy)phenyl]piperazine-1-carboxamide | 6 | 652 |

TABLE 10-continued

Compounds of General Formula I According to the Invention, in which V = Trifluoromethylbenzonitrile, W = Maleimide, n = 6

| Example | Name | Synthesis Analogous to Example | ESI-MS |
|---|---|---|---|
| 370 | 4-[6-[1-[4-Cyano-3-(trifluoromethyl)phenyl]-2,5-dihydro-4-methyl-2,5-dioxo-1H-pyrrol-3-yl]hexyl]-N-(tricyclo[3.3.1.1$^{3,7}$]dec-1-yl)piperazine-1-carboxamide | 6 | 626 |
| 371 | 4-[6-[1-[4-Cyano-3-(trifluoromethyl)phenyl]-2,5-dihydro-4-methyl-2,5-dioxo-1H-pyrrol-3-yl]hexyl]-N-[4-(dimethylamino)phenyl]piperazine-1-carboxamide | 6 | 611 |
| 372 | 4-[6-[1-[4-Cyano-3-(trifluoromethyl)phenyl]-2,5-dihydro-4-methyl-2,5-dioxo-1H-pyrrol-3-yl]hexyl]-N-[3-[(trifluoromethyl)sulfanyl]phenyl]piperazine-1-carboxamide | 6 | 668 |
| 373 | 4-[6-[1-[4-Cyano-3-(trifluoromethyl)phenyl]-2,5-dihydro-4-methyl-2,5-dioxo-1H-pyrrol-3-yl]hexyl]-N-[(2-methylphenyl)methyl]piperazine-1-carboxamide | 6 | 596 |
| 374 | 4-[6-[1-[4-Cyano-3-(trifluoromethyl)phenyl]-2,5-dihydro-4-methyl-2,5-dioxo-1H-pyrrol-3-yl]hexyl]-N-[(3-methylphenyl)methyl]piperazine-1-carboxamide | 6 | 596 |
| 375 | 4-[6-[1-[4-Cyano-3-(trifluoromethyl)phenyl]-2,5-dihydro-4-methyl-2,5-dioxo-1H-pyrrol-3-yl]hexyl]-N-[(4-methylphenyl)methyl]piperazine-1-carboxamide | 6 | 596 |
| 376 | 4-[6-[1-[4-Cyano-3-(trifluoromethyl)phenyl]-2,5-dihydro-4-methyl-2,5-dioxo-1H-pyrrol-3-yl]hexyl]-N-[(4-methoxyphenyl)methyl]piperazine-1-carboxamide | 6 | 612 |
| 377 | 4-[6-[1-[4-Cyano-3-(trifluoromethyl)phenyl]-2,5-dihydro-4-methyl-2,5-dioxo-1H-pyrrol-3-yl]hexyl]-N-(1,1,3,3-tetramethylbutyl)piperazine-1-carboxamide | 6 | 604 |

TABLE 11

Compounds of General Formula I According to the Invention, in which V = Trifluoromethylbenzonitrile, W = Maleimide, n = 7

| Example | Name | Synthesis Analogous to Example | ESI-MS |
|---|---|---|---|
| 378 | 4-[3-[7-(4-Acetylpiperazin-1-yl)heptyl]-2,5-dihydro-4-methyl-2,5-dioxo-1H-pyrrol-1-yl]-2-(trifluoromethyl)-benzonitrile | 9 (4) | 504 |
| 379 | 4-[2,5-Dihydro-3-methyl-2,5-dioxo-4-[7-(4-(1-oxopropyl)-piperazin-1-yl]heptyl]-1H-pyrrol-1-yl]-2-(trifluoromethyl)-benzonitrile | 9 (4) | 518 |
| 380 | 4-[3-[7-[4-(Cyclopropylcarbonyl)piperazin-1-yl]heptyl]-2,5-dihydro-4-methyl-2,5-dioxo-1H-pyrrol-1-yl]-2-(trifluoromethyl)benzonitrile | 9 (4) | 530 |
| 381 | 4-[2,5-Dihydro-3-[7-[4-(methoxyacetyl)piperazin-1-yl]-heptyl]-4-methyl-2,5-dioxo-1H-pyrrol-1-yl]-2-(trifluoromethyl)benzonitrile | 9 (4) | 534 |
| 382 | 4-[2,5-Dihydro-3-[7-[4-(3-methoxy-1-oxopropyl)piperazin-1-yl]heptyl]-4-methyl-2,5-dioxo-1H-pyrrol-1-yl]-2-(trifluoromethyl)-benzonitrile | 9 (4) | 548 |
| 383 | 4-[2,5-Dihydro-3-[7-[4-[(2-methoxyethoxy)-acetyl]piperazin-1-yl]heptyl]-4-methyl-2,5-dioxo-1H-pyrrol-1-yl]-2-(trifluoromethyl)benzonitrile | 9 (4) | 578 |
| 384 | 4-[2,5-Dihydro-3-[7-[4-[[2-(2-methoxyethoxy)-ethoxy]-acetyl]piperazin-1-yl]heptyl]-4-methyl-2,5-dioxo-1H-pyrrol-1-yl]-2-(trifluoromethyl)benzonitrile | 9 (4) | 622 |

TABLE 11-continued

Compounds of General Formula I According to the Invention, in which V = Trifluoromethylbenzonitrile, W = Maleimide, n = 7

| Example | Name | Synthesis Analogous to Example | ESI-MS |
|---|---|---|---|
| 385 | 4-[2,5-Dihydro-3-[7-[4-(2-methoxybenzoyl)-piperazin-1-yl]-heptyl]-4-methyl-2,5-dioxo-1H-pyrrol-1-yl]-2-(trifluoromethyl)benzonitrile | 9 (4) | 596 |
| 386 | 4-[2,5-Dihydro-3-methyl-4-[7-[4-(methylsulfonyl)piperazin-1-yl]heptyl]-2,5-dioxo-1H-pyrrol-1-yl]-2-(trifluoromethyl)-benzonitrile | 9 | 540 |
| 387 | 4-[3-[7-[4-(Ethylsulfonyl)piperazin-1-yl]heptyl]-2,5-dihydro-4-methyl-2,5-dioxo-1H-pyrrol-1-yl]-2-(trifluoromethyl)-benzonitrile | 9 | 554 |
| 388 | 4-[3-[7-[4-(Cyclopropylsulfonyl)piperazin-1-yl]heptyl]-2,5-dihydro-4-methyl-2,5-dioxo-1H-pyrrol-1-yl]-2-(trifluoromethyl)benzonitrile | 9 | 566 |
| 389 | 4-[2,5-Dihydro-3-[7-[4-[(2-methoxyethyl)-sulfonyl]piperazin-1-yl]heptyl]-4-methyl-2,5-dioxo-1H-pyrrol-1-yl]-2-(trifluoromethyl)-benzonitrile | 9 | 584 |
| 390 | 4-[2,5-Dihydro-3-[7-[4-[[2-(2-methoxyethoxy)-ethyl]-sulfonyl]piperazin-1-yl]heptyl]-4-methyl-2,5-dioxo-1H-pyrrol-1-yl]-2-(trifluoromethyl)-benzonitrile | 9 | 628 |
| 391 | 4-[2,5-Dihydro-3-[7-[4-[[2-[2-(2-methoxyethoxy)ethoxy]-ethyl]sulfonyl]piperazin-1-yl]heptyl]-4-methyl-2,5-dioxo-1H-pyrrol-1-yl]-2-(trifluoromethyl)benzonitrile | 9 | 672 |
| 392 | 4-[2,5-Dihydro-3-methyl-2,5-dioxo-4-[7-[4-(phenylsulfonyl)piperazin-1-yl]heptyl]-1H-pyrrol-1-yl]-2-(trifluoromethyl)benzonitrile | 9 | 602 |
| 393 | 4-[2,5-Dihydro-3-methyl-2,5-dioxo-4-[7-[4-[(phenylmethyl)-sulfonyl]piperazin-1-yl]heptyl]-1H-pyrrol-1-yl]-2-(trifluoromethyl)benzonitrile | 9 | 616 |
| 394 | 4-[2,5-Dihydro-3-methyl-4-[7-[4-[(1-methyl-1H-imidazol-4-yl)sulfonyl]piperazin-1-yl]heptyl]-2,5-dioxo-1H-pyrrol-1-yl]-2-(trifluoromethyl)benzonitrile | 9 | 606 |
| 395 | 4-[7-[1-[4-Cyano-3-(trifluoromethyl)phenyl]-2,5-dihydro-4-methyl-2,5-dioxo-1H-pyrrol-3-yl]heptyl]-N-(1-methylethyl)-piperazine-1-carboxamide | 9 (6) | 547 |
| 396 | 4-[7-[1-[4-Cyano-3-(trifluoromethyl)phenyl]-2,5-dihydro-4-methyl-2,5-dioxo-1H-pyrrol-3-yl]heptyl]-N-ethylpiperazine-1-carbothioamide | 9 (12) | 549 |
| 397 | Methyl 4-[7-[1-[4-cyano-3-(trifluoromethyl)-phenyl]-2,5-dihydro-4-methyl-2,5-dioxo-1H-pyrrol-3-yl]heptyl]-piperazine-1-carboxylate | 9 (13) | 520 |
| 398 | S-Methyl 4-[7-[1-[4-cyano-3-(trifluoromethyl)-phenyl]-2,5-dihydro-4-methyl-2,5-dioxo-1H-pyrrol-3-yl)-heptyl]piperazine-1-carbothioate | 9 (13) | 536 |
| 399 | 4-[7-[1-[4-Cyano-3-(trifluoromethyl)phenyl]-2,5-dihydro-4-methyl-2,5-dioxo-1H-pyrrol-3-yl]heptyl]-N,N-dimethylpiperazine-1-sulfonamide | 9 | 569 |

TABLE 12

Compounds of General Formula I According to the Invention, in which V = Trifluoromethylbenzonitrile, W = Maleimide, n = 8

| Example | Name | Synthesis Analogous to Example | ESI-MS |
|---|---|---|---|
| 400 | 4-[3-[8-(4-Acetylpiperazin-1-yl)octyl]-2,5-dihydro-4-methyl-2,5-dioxo-1H-pyrrol-1-yl]-2-(trifluoromethyl)benzonitrile | 9 (4) | 518 |

TABLE 12-continued

Compounds of General Formula I According to the Invention, in which V = Trifluoromethylbenzonitrile, W = Maleimide, n = 8

| Example | Name | Synthesis Analogous to Example | ESI-MS |
|---|---|---|---|
| 401 | 4-[2,5-Dihydro-3-methyl-2,5-dioxo-4-[8-(4-(1-oxopropyl)-piperazin-1-yl)octyl]-1H-pyrrol-1-yl]-2-(trifluoromethyl)-benzonitrile | 9 (4) | 532 |
| 402 | 4-[3-[8-[4-(Cyclopropylcarbonyl)piperazin-1-yl]octyl]-2,5-dihydro-4-methyl-2,5-dioxo-1H-pyrrol-1-yl]-2-(trifluoromethyl)benzonitrile | 9 (4) | 544 |
| 403 | 4-[2,5-Dihydro-3-[8-[4-(methoxyacetyl)piperazin-1-yl]-octyl]4-methyl-2,5-dioxo-1H-pyrrol-1-yl]-2-(trifluoromethyl)benzonitrile | 9 (4) | 548 |
| 404 | 4-[2,5-Dihydro-3-[8-[4-(3-methoxy-1-oxopropyl)-piperazin-1-yl]octyl]-4-methyl-2,5-dioxo-1H-pyrrol-1-yl]-2-(trifluoromethyl)benzonitrile | 9 (4) | 562 |
| 405 | 4-[2,5-Dihydro-3-[8-[4-[(2-methoxyethoxy)-acetyl]piperazin-1-yl]octyl]-4-methyl-2,5-dioxo-1H-pyrrol-1-yl]-2-(trifluoromethyl)benzonitrile | 9 (4) | 592 |
| 406 | 4-[2,5-Dihydro-3-[8-[4-[[2-(2-methoxyethoxy)-ethoxy]-acetyl]piperazin-1-yl]octyl]-4-methyl-2,5-dioxo-1H-pyrrol-1-yl]-2-(trifluoromethyl)-benzonitrile | 9 (4) | 636 |
| 407 | 4-[2,5-Dihydro-3-[8-[4-(2-methoxybenzoyl)-piperazin-1-yl]-octyl]-4-methyl-2,5-dioxo-1H-pyrrol-1-yl]-2-(trifluoromethyl)-benzonitrile | 9 (4) | 610 |
| 408 | 4-[2,5-Dihydro-3-methyl-4-[8-[4-(methyl-sulfonyl)-piperazin-1-yl]octyl]-2,5-dioxo-1H-pyrrol-1-yl]-2-(trifluoromethyl)-benzonitrile | 9 | 554 |
| 409 | 4-[3-[8-[4-(Ethylsulfonyl)piperazin-1-yl]octyl]-2,5-dihydro-4-methyl-2,5-dioxo-1H-pyrrol-1-yl]-2-(trifluoromethyl)benzonitrile | 9 | 568 |
| 410 | 4-[3-[8-[4-(Cyclopropylsulfonyl)piperazin-1-yl]octyl]-2,5-dihydro-4-methyl-2,5-dioxo-1H-pyrrol-1-yl]-2-(trifluoromethyl)benzonitrile | 9 | 580 |
| 411 | 4-[2,5-Dihydro-3-[8-[4-(2-methoxyethyl)-sulfonyl]piperazin-1-yl]octyl]-4-methyl-2,5-dioxo-1H-pyrrol-1-yl]-2-(trifluoromethyl)benzonitrile | 9 | 598 |
| 412 | 4-[2,5-Dihydro-3-[8-[4-[[2-(2-methoxyethoxy)-ethyl]sulfonyl]piperazin-1-yl]octyl]-4-methyl-2,5-dioxo-1H-pyrrol-1-yl]-2-(trifluoromethyl)-benzonitrile | 9 | 642 |
| 413 | 4-[2,5-Dihydro-3-[8-[4-[[2-[2-(2-methoxy-ethoxy)-ethoxy]-ethyl]sulfonyl]piperazin-1-yl]octyl]-4-methyl-2,5-dioxo-1H-pyrrol-1-yl]-2-(trifluoromethyl)benzonitrile | 9 | 686 |
| 414 | 4-[2,5-Dihydro-3-methyl-2,5-dioxo-4-[8-[4-(phenylsulfonyl)piperazin-1-yl]octyl]-1H-pyrrol-1-yl]-2-(trifluoromethyl)benzonitrile | 9 | 616 |
| 415 | 4-[2,5-Dihydro-3-methyl-2,5-dioxo-4-[8-[4-[(phenylmethyl)-sulfonyl]piperazin-1-yl]octyl]-1H-pyrrol-1-yl]-2-(trifluoromethyl)benzonitrile | 9 | 630 |
| 416 | 4-[2,5-Dihydro-3-methyl-4-[8-[4-[(1-methyl-1H-imidazol-4-yl)sulfonyl]piperazin-1-yl]octyl]-2,5-dioxo-1H-pyrrol-1-yl]-2-(trifluoromethyl)benzonitrile | 9 | 620 |
| 417 | 4-[8-1-[4-Cyano-3-(trifluoromethyl)phenyl]-2,5-dihydro-4-methyl-2,5-dioxo-1H-pyrrol-3-yl]octyl]-N-(1-methylethyl)-piperazine-1-carboxamide | 6 | 561 |
| 418 | 4-[8-[1-[4-Cyano-3-(trifluoromethyl)phenyl]-2,5-dihydro-4-methyl-2,5-dioxo-1H-pyrrol-3-yl]octyl]-N-ethylpiperazine-1-carbothioamide | 9 (12) | 563 |
| 419 | Methyl 4-[8-[1-[4-cyano-3-(trifluoromethyl)-phenyl]-2,5-dihydro-4-methyl-2,5-dioxo-1H-pyrrol-3-yl]octyl]piperazine-1-carboxylate | 9 (13) | 534 |
| 420 | S-Methyl 4-[8-[1-[4-cyano-3-(trifluoromethyl)-phenyl]-2,5-dihydro-4-methyl-2,5-dioxo-1H-pyrrol-3-yl]octyl]piperazine-1-carbothioate | 9 (13) | 550 |
| 421 | 4-[8-[1-[4-Cyano-3-(trifluoromethyl)phenyl]-2,5-dihydro-4-methyl-2,5-dioxo-1H-pyrrol-3-yl]octyl]-N,N-dimethylpiperazine-1-sulfonamide | 9 | 583 |

TABLE 13

Compounds of General Formula I According to the Invention, in which V = Trifluoromethylphenylacetamide, W = Maleimide, n = 6

| Example | Name | Synthesis Analogous to Example | ESI-MS |
|---|---|---|---|
| 422 | N-[4-[2,5-Dihydro-3-[6-[4-(2-methoxy-benzoyl)-piperazin-1-yl]hexyl]4-methyl-2,5-dioxo-1H-pyrrol-1-yl]-2-(trifluoromethyl)phenyl]acetamide | 4 | 615 |
| 423 | N-[4-[3-[6-[4-(Cyclobutylcarbonyl)piperazin-1-yl]hexyl]-2,5 dihydro-4-methyl-2,5-dioxo-1H-pyrrol-1-yl]-2-(trifluoromethyl)phenyl]acetamide | 4 | 563 |
| 424 | N-[4-[2,5-Dihydro-3-methyl-2,5-dioxo-4-[6-[4-[(thien-2-yl)-carbonyl]piperazin-1-yl]hexyl]-1H-pyrrol-1-yl]-2-(trifluoromethyl)phenyl]acetamide | 4 | 591 |
| 425 | N-[4-[3-[6-[4-[4-(Dimethylamino)benzoyl]-piperazin-1-yl]-hexyl]-2,5-dihydro-4-methyl-2,5-dioxo-1H-pyrrol-1-yl]-2-(trifluoromethyl)-phenyl]acetamide | 4 | 628 |
| 426 | N-[4-[3-[6-(4-Acetylpiperazin-1-yl)hexyl]-2,5-dihydro-4-methyl-2,5-dioxo-1H-pyrrol-1-yl]-2-(trifluoromethyl)phenyl]acetamide | 4 | 523 |
| 427 | N-[4-[2,5-Dihydro-3-methyl-4-[6-[4-(methylsulfonyl)-piperazin-1-yl]hexyl]-2,5-dioxo-1H-pyrrol-1-yl]-2-(trifluoromethyl)phenyl]-acetamide | 5 | 559 |
| 428 | N-[4-[3-[6-[4-[(2,1,3-Benzothiadiazol-4-yl)sulfonyl]-piperazin-1-yl]hexyl]-2,5-dihydro-4-methyl-2,5-dioxo-1H-pyrrol-1-yl]-2-(trifluoromethyl)phenyl]acetamide | 5 | 679 |
| 429 | 4-[6-[1-[4-(Acetylamino)-3-(trifluoromethyl)-phenyl]-2,5-dihydro-4-methyl-2,5-dioxo-1H-pyrrol-3-yl]hexyl]-N-(pyridin-4-yl)piperazine-1-carboxamide | 6 | 601 |

TABLE 14

Compounds of General Formula I According to the Invention, in which V = Nitrotrifluoromethylbenzene, W = Maleimide, n = 6

| Example | Name | Synthesis Analogous to Example | ESI-MS |
|---|---|---|---|
| 430 | 3-[6-[4-(Cyclobutylcarbonyl)piperazin-1-yl]hexyl]-4-methyl-1-[4-nitro-3-(trifluoromethyl)phenyl]-1H-pyrrole-2,5-dione | 4 | 551 |
| 431 | 3-[6-[4-[4-(Dimethylamino)benzoyl]piperazin-1-yl]hexyl]-4-methyl-1-[4-nitro-3-(trifluoromethyl)-phenyl]-1H-pyrrole-2,5-dione | 4 | 616 |
| 432 | 3-[6-(4-Acetylpiperazin-1-yl)hexyl]-4-methyl-1-[4-nitro-3-(trifluoromethyl)phenyl]-1H-pyrrole-2,5-dione | 4 | 511 |

TABLE 14-continued

Compounds of General Formula I According to the Invention, in which V = Nitrotrifluoromethylbenzene, W = Maleimide, n = 6

| Example | Name | Synthesis Analogous to Example | ESI-MS |
|---|---|---|---|
| 433 | 3-Methyl-4-[6-[4-(methylsufonyl)piperazin-1-yl]hexyl]-1-[4-nitro-3-(trifluoromethyl)phenyl]-1H-pyrrole-2,5-dione | 5 | 547 |
| 434 | 3-[6-[4-[(2,1,3-Benzothiadiazol-4-yl)sulfonyl]-piperazin-1-yl]hexyl]-4-methyl-1-[4-nitro-3-(trifluoromethyl)phenyl]-1H-pyrrole-2,5-dione | 5 | 667 |

TABLE 15

Compounds of General Formula I According to the Invention, in which V = Bistrifluoromethylbenzene, W = Maleimide, n = 6

| Example | Name | Synthesis Analogous to Example | ESI-MS |
|---|---|---|---|
| 435 | 1-[3,4-Bis(trifluoromethyl)phenyl]-3-[6-[4-(2-methoxy-benzoyl)piperazin-1-yl]hexyl]-4-methyl-1H-pyrrole-2,5-dione | 4 | 626 |
| 436 | 3-[6-(4-Acetylpiperazin-1-yl)hexyl)-1-[3,4-bis(trifluoromethyl)phenyl]-4-methyl-1H-pyrrole-2,5-dione | 4 | 534 |
| 437 | 1-[3,4-Bis(trifluoromethyl)phenyl]-3-[6-[4-(cyclobutyl-carbonyl)piperazin-1-yl]hexyl]-4-methyl-1H-pyrrole-2,5-dione | 4 | 574 |
| 438 | 1-[3,4-Bis(trifluoromethyl)phenyl]-3-methyl-4-[6-[4-[(thien-2-yl)carbonyl]piperazin-1-yl]hexyl]-1H-pyrrole-2,5-dione | 4 | 602 |
| 439 | 1-[3,4-Bis(trifluoromethyl)phenyl]-3-[6-[4-[4-(dimethylamino)benzoyl]piperazin-1-yl]hexyl]-4-methyl-1H-pyrrole-2,5-dione | 4 | 639 |
| 440 | 1-[3,4-Bis(trifluoromethyl)phenyl]-3-methyl-4-[6-[4-(methyl-sulfonyl)piperazin-1-yl]hexyl]-1H-pyrrole-2,5-dione | 5 | 570 |
| 441 | 3-[6-[4-[(2,1,3-Benzothiadiazol-4-yl)sulfonyl]-piperazin-1-yl]hexyl]-1-[3,4-bis(trifluoro-methyl)-phenyl]-4-methyl-1H-pyrrole-2,5-dione | 5 | 690 |

TABLE 16

Compounds of General Formula I According to the Invention, in which V = Fluorotrifluoromethylbenzene, W = Maleimide, n = 6

| Example | Name | Synthesis Analogous to Example | ESI-MS |
|---|---|---|---|
| 442 | 1-[3-Fluoro-4-(trifluoromethyl)phenyl]-3-[6-[4-(2-methoxy-benzoyl)piperazin-1-yl]hexyl]-4-methyl-1H-pyrrole-2,5-dione | 4 | 576 |
| 443 | 3-[6-[4-(Cyclobutylcarbonyl)piperazin-1-yl]hexyl]-1-[3-fluoro-4-(trifluoromethyl)phenyl]-4-methyl-1H-pyrrole-2,5-dione | 4 | 524 |
| 444 | 1-[3-Fluoro-4-(trifluoromethyl)phenyl]-3-methyl-4-[6-[4-(thien-2-yl)carbonyl]piperazin-1-yl]hexyl]-1H-pyrrole-2,5-dione | 4 | 552 |
| 445 | 3-[6-[4-[4-(Dimethylamino)benzoyl]piperazin-1-yl]hexyl]-1-[3-fluoro-4-(trifluoromethyl)phenyl]-4-methyl-1H-pyrrole-2,5-dione | 4 | 589 |
| 446 | 3-[6-[4-Acetylpiperazin-1-yl)hexyl]-1-[3-fluoro-4-(trifluoromethyl)phenyl]-4-methyl-1H-pyrrole-2,5 dione | 4 | 484 |
| 447 | 1-[3-Fluoro-4-(trifluoromethyl)phenyl]-3-methyl-4-[6-[4-(methylsulfonyl)piperazin-1-yl]hexyl]-1H-pyrrole-2,5-dione | 5 | 520 |
| 448 | 3-[6-[4-[(2,1,3-Benzothiadiazol-4-yl)sulfonyl]-piperazin-1-yl]hexyl]-1-[3-fluoro-4-(trifluoromethyl)phenyl]-4-methyl-1H-pyrrole-2,5-dione | 5 | 640 |

TABLE 17

Compounds of General Formula I According to the Invention, in which
V = Isobenzofuranone, W = Maleimide, n = 4

| Example | Name | Synthesis Analogous to Example | ESI-MS |
|---|---|---|---|
| 449 | 3-[4-(4-Acetylpiperazin-1-yl)butyl]-1-(1,3-dihydro-1-oxo-isobenzofuran-5-yl)-4-methyl-1H-pyrrole-2,5-dione | 4 | 425 |
| 450 | 1-(1,3-Dihydro-1-oxoisobenzofuran-5-yl)-3-methyl-4-[4-[4-(1-oxopropyl)piperazin-1-yl]butyl]-1H-pyrrole-2,5-dione | 4 | 440 |
| 451 | 1-(1,3-Dihydro-1-oxoisobenzofuran-5-yl)-3-[4-[4-[(2-methoxyethoxy)acctyl]-piperazin-1-yl]butyl)-4-methyl-1H-pyrrole-2,5-dione | 4 | 500 |
| 452 | 1-(1,3-Dihydro-1-oxoisobenzofuran-5-yl)-3-[4-[4-[[2-(2-methoxyethoxy)ethoxy]acetyl]piperazin-1-yl]butyl]-4-methyl-1H-pyrrole-2,5-dione | 4 | 544 |
| 453 | 1-(1,3-Dihydro-1-oxoisobenzofuran-5-yl)-3-methyl-4-[4-[4-(methylsulfonyl)piperazin-1-yl)butyl]-1H-pyrrole-2,5-dione | 5 | 462 |
| 454 | 4-[4-[1-(1,3-Dihydro-1-oxoisobenzofuran-5-yl)-2,5-dihydro-4-methyl-2,5-dioxo-1H-pyrrol-3-yl]butyl]-N-ethyl-piperazine-1-carbothioamide | 12 | 471 |
| 455 | 4-[4-[1-(1,3-Dihydro-1-oxoisobenzofuran-5-yl)-2,5-dihydro-4-methyl-2,5-dioxo-1H-pyrrol-3-yl]butyl]-N-propyl-piperazine-1-carbothioamide | 12 | 485 |
| 456 | 4-[4-[1-(1,3-Dihydro-1-oxoisobenzofuran-5-yl)-2,5-dihydro-4-methyl-2,5-dioxo-1H-pyrrol-3-yl]butyl]-N-(prop-2-enyl)piperazine-1-carbothioamide | 12 | 483 |

TABLE 18

Compounds of General Formula I According to the Invention, in which
V = Isobenzofuranone, W = Maleimide, n = 5

| Example | Name | Synthesis Analogous to Example | ESI-MS |
|---|---|---|---|
| 457 | 3-[5-(4-Acetylpiperazin-1-yl)pentyl]-1-(1,3-dihydro-1-oxo-isobenzofuran-5-yl)-4-methyl-1H-pyrrole-2,5-dione | 4 | 439 |
| 458 | 1-(1,3-Dihydro-1-oxoisobenzofuran-5-yl)-3-methyl-4-[5-[4-(1-oxopropyl)piperazin-1-yl]pentyl]-1H-pyrrole-2,5-dione | 4 | 454 |
| 459 | 1-(1,3-Dihydro-1-oxoisobenzofuran-5-yl)-3-[5-[4-[(2-methoxyethoxy)acetyl]piperazin-1-yl]pentyl]-4-methyl-1H-pyrrole-2,5-dione | 4 | 514 |
| 460 | 1-(1,3-Dihydro-1-oxoisobenzofuran-5-yl)-3-[5-[4-[[2-(2-methoxyethoxy)ethoxy]acetyl]piperazin-1-yl]pentyl]-4-methyl-1H-pyrrole-2,5-dione | 4 | 558 |
| 461 | 1-(1,3-Dihydro-1-oxoisobenzofuran-5-yl)-3-methyl-4-[5-[4-(methylsulfonyl)piperazin-1-yl]pentyl]-1H-pyrrole-2,5-dione | 5 | 476 |
| 462 | 3-[5-[4-(Cyclopropylsulfonyl)piperazin-1-yl]pentyl]-1-(1,3-dihydro-1-oxoisobenzofuran-5-yl)-4-methyl-1H-pyrrole-2,5-dione | 5 | 502 |
| 463 | 1-(1,3-Dihydro-1-oxoisobenzofuran-5-yl)-3-[5-[4-[[2-[2-(2-methoxyethoxy)ethoxy]ethyl]-sulfonyl]piperazin-1-yl]-pentyl]-4-methyl-1H-pyrrole-2,5-dione | 5 | 608 |
| 464 | 4-[5-[1-(1,3-Dihydro-1-oxoisobenzofuran-5-yl)-2,5-dihydro-4-methyl-2,5-dioxo-1H-pyrrol-3-yl]pentyl]-N-ethyl-piperazine-1-carbothioamide | 12 | 471 |
| 465 | 4-[5-[1-(1,3-Dihydro-1-oxoisobenzofuran-5-yl)-2,5-dihydro-4-methyl-2,5-dioxo-1H-pyrrol-3-yl]pentyl]-N-propylpiperazine-1-carbothioamide | 12 | 485 |
| 466 | 4-[5-[1-(1,3-Dihydro-1-oxoisobenzofuran-5-yl)-2,5-dihydro-4-methyl-2,5-dioxo-1H-pyrrol-3-yl]pentyl]-N-prop-2-enyl)piperazine-1-carbothioamide | 12 | 483 |

TABLE 19

Compounds of General Formula I According to the Invention, in which
V = Isobenzofuranone, W = Maleimide, n = 6

| Example | Name | Synthesis Analogous to Example | ESI-MS |
|---|---|---|---|
| 467 | 1-(1,3-Dihydro-1-oxoisobenzofuran-5-yl)-3-[6-[4-(2-methoxybenzoyl)piperazin-1-yl]hexyl]-4-methyl-1H-pyrrole-2,5-dione | 4 | 546 |
| 468 | 3-[6-[4-(Cyclobutylcarbonyl)piperazin-1-yl]hexyl]-1-(1,3-dihydro-1-oxoisobenzofuran-5-yl)-4-methyl-1H-pyrrole-2,5-dione | 4 | 494 |
| 469 | 1-(1,3-Dihydro-1-oxoisobenzofuran-5-yl)-3-methyl-4-[6-[4-[(thien-2-yl)carbonyl]piperazin-1-yl]hexyl]-1H-pyrrole-2,5-dione | 4 | 522 |
| 470 | 1-(1,3-Dihydro-1-oxoisobenzofuran-5-yl)-3-[6-[4-[4-(dimethylamino)benzoyl]piperazin-1-yl]hexyl]-4-methyl-1H-pyrrole-2,5-dione | 4 | 559 |
| 471 | 3-[6-(4-Acetylpiperazin-1-yl)hexyl]-1-(1,3-dihydro-1-oxoisobenzofuran-5-yl)-4-methyl-1H-pyrrole-2,5-dione | 4 | 454 |
| 472 | 4-[4-[1-(1,3-Dihydro-1-oxoisobenzofuran-5-yl)-2,5-dihydro-4-methyl-2,5-dioxo-1H-pyrrol-3-yl]hexyl]-N,N-dimethylpiperazine-1-sulfonamide | 5 | 519 |
| 473 | 1-(1,3-Dihydro-1-oxoisobenzofuran-5-yl)-3-methyl-4-[6-[4-(methylsulfonyl)piperazin-1-yl]hexyl]-1H-pyrrole-2,5-dione | 5 | 490 |
| 474 | 3-[6-[4-[(2,1,3-Benzothiadiazol-4-yl)sulfonyl]-piperazin-1-yl]hexyl]-1-(1,3-dihydro-1-oxoisobenzofuran-5-yl)-4-methyl-1H-pyrrole-2,5-dione | 5 | 610 |
| 475 | 1-(1,3-Dihydro-1-oxoisobenzofuran-5-yl)-3-[6-[4-(ethyl-sulfonyl)piperazin-1-yl]hexyl]-4-methyl-1H-pyrrole-2,5-dione | 5 | 504 |
| 476 | 4-[6-[1-(1,3-Dihydro-1-oxoisobenzofuran-5-yl)-2,5-dihydro-4-methyl-2,5-dioxo-1H-pyrrol-3-yl]hexyl]-N-ethyl-piperazine-1-carbothioamide | 12 | 499 |
| 477 | 4-[6-[1-(1,3-Dihydro-1-oxoisobenzofuran-5-yl)-2,5-dihydro-4-methyl-2,5-dioxo-1H-pyrrol-3-yl]hexyl]-N-propyl-piperazine-1-carbothioamide | 12 | 513 |
| 478 | 4-[6-[1-(1,3-Dihydro-1-oxoisobenzofuran-5-yl)-2,5-dihydro-4-methyl-2,5-dioxo-1H-pyrrol-3-yl]hexyl]-N-(prop-2-enyl)piperazine-1-carbothioamide | 12 | 511 |
| 479 | 4-[6-[1-(1,3-Dihydro-1-oxoisobenzofuran-5-yl)-2,5-dihydro-4-methyl-2,5-dioxo-1H-pyrrol-3-yl]hexyl]-N-(phenylmethyl)piperazine-1-carbothioamide | 12 | 561 |
| 480 | 4-[6-[1-(1,3-Dihydro-1-oxoisobenzofuran-5-yl)-2,5-dihydro-4-methyl-2,5-dioxo-1H-pyrrol-3-yl]hexyl]-N-[(4-methylphenyl)methyl]piperazine-1-carbothioamide | 12 | 575 |
| 481 | N-[(4-Chlorophenyl)methyl]-4-[6-[1-(1,3-dihydro-1-oxo-isobenzofuran-5-yl)-2,5-dihydro-4-methyl-2,5-dioxo-1H-pyrrol-3-yl]hexyl]piperazine-1-carbothioamide | 12 | 595 |
| 482 | 4-[6-[1-(1,3-Dihydro-1-oxoisobenzofuran-5-yl)-2,5-dihydro-4-methyl-2,5-dioxo-1H-pyrrol-3-yl]hexyl]-N-phenylpiperazine-1-carbothioamide | 12 | 547 |
| 483 | 4-[6-[1-(1,3-Dihydro-1-oxoisobenzofuran-5-yl)-2,5-dihydro-4-methyl-2,5-dioxo-1H-pyrrol-3-yl]hexyl]-N-(2,6-dimethylphenyl)piperazine-1-carbothioamide | 12 | 575 |

TABLE 20

Compounds of General Formula I According to the Invention, in which V = Methylbenzoxazinone, W = Maleimide, n = 6

| Example | Name | Synthesis Analogous to Example | ESI-MS |
|---|---|---|---|
| 484 | 3-[6-[4-(2-Methoxybenzoyl)piperazin-1-yl]hexyl]-4-methyl-1-(4-methyl-1-oxo-1H-2,3-benzoxazin-6-yl)-1H-pyrrole-2,5-dione | 4 | 573 |
| 485 | 3-[6-[4-(Cyclobutylcarbonyl)piperazin-1-yl]hexyl]-4-methyl-1-(4-methyl-1-oxo-1H-2,3-benzoxazin-6-yl)-1H-pyrrole-2,5-dione | 4 | 521 |
| 486 | 3-Methyl-1-(4-methyl-1-oxo-1H-2,3-benzoxazin-6-yl)-4-[6-[4-[(thien-2-yl)carbonyl]piperazin-1-yl]hexyl]-1H-pyrrole-2,5-dione | 4 | 549 |
| 487 | 3-[6-[4-[4-(Dimethylamino)benzoyl]piperazin-1-yl]hexyl]-4-methyl-1-(4-methyl-1-oxo-1H-2,3-benzoxazin-6-yl)-1H-pyrrole-2,5-dione | 4 | 481 |
| 488 | 3-[6-(4-Acetylpiperazin-1-yl)hexyl]-4-methyl-1-(4-methyl-1-oxo-1H-2,3-benzoxazin-6-yl)-1H-pyrrole-2,5-dione | 4 | 481 |
| 489 | 3-Methyl-1-(4-methyl-1-oxo-1H-2,3-benzoxazin-6-yl)-4-[6-[4-(methylsulfonyl)piperazin-1-yl]hexyl]-1H-pyrrole-2,5-dione | 5 | 517 |

TABLE 21

Compounds of General Formula I According to the Invention, in which V = Indanone, W = Maleimide, n = 6

| Example | Name | Synthesis Analogous to Example | ESI-MS |
|---|---|---|---|
| 490 | 1-(2,3-Dihydro-1-oxo-1H-inden-5-yl)-3-[6-[4-(2-methoxy-benzoyl)piperazin-1-yl]hexyl]-4-methyl-1H-pyrrole-2,5-dione | 4 | 544 |
| 491 | 3-[6-[4-(Cyclobutylcarbonyl)piperazin-1-yl]hexyl]-1-(2,3-dihydro-1-oxo-1H-inden-5-yl)-4-methyl-1H-pyrrole-2,5-dione | 4 | 492 |
| 492 | 1-(2,3-Dihydro-1-oxo-1H-inden-5-yl)-3-methyl-4-[6-[4-[(thien-2-yl)carbonyl]piperazin-1-yl]hexyl]-1H-pyrrole-2,5-dione | 4 | 520 |
| 493 | 1-(2,3-Dihydro-1-oxo-1H-inden-5-yl)-3-[6-[4-[4-(dimethylamino)benzoyl]piperazin-1-yl]hexyl]-4-methyl-1H-pyrrole-2,5-dione | 4 | 557 |
| 494 | 3-[6-(4-Acetylpiperazin-1-yl)hexyl]-1-(2,3-dihydro-1-oxo-1H-inden-5-yl)-4-methyl-1H-pyrrole-2,5-dione | 4 | 452 |
| 495 | 1-(2,3-Dihydro-1-oxo-1H-inden-5-yl)-3-methyl-4-[6-[4-(methylsulfonyl)piperazin-1-yl]hexyl]-1H-pyrrole-2,5-dione | 5 | 488 |
| 496 | 3-[6-[4-[(2,1,3-Benzothiadiazol-4-yl)sulfonyl]piperazin-1-yl]hexyl]-1-(2,3-dihydro-1-oxo-1H-inden-5-yl)4-methyl-1H-pyrrole-2,5-dione | 5 | 608 |

TABLE 22

Compounds of General Formula I According to the Invention, in which V = Trifluoromethylbenzonitrile, W = Thiohydantoin, n = 2

| Example | Name | Synthesis Analogous to Example | ESI-MS |
|---|---|---|---|
| 497 | 4-[3-[2-(4-Acetylpiperazin-1-yl)ethyl]-4,4-dimethyl-5-oxo-2-thioxoimidazolidin-1-yl]-2-(trifluoromethyl)benzonitrile | 15 (4) | 468 |
| 498 | 4-(4,4-Dimethyl-5-oxo-3-[2-[4-(1-oxopropyl)-piperazin-1-yl]-ethyl]-2-thioxoimidazolidin-1-yl]-2-(trifluoromethyl)-benzonitrile | 15 (4) | 482 |
| 499 | 4-[4,4-Dimethyl-3-[2-[4-(2-methyl-1-oxopropyl)-piperazin-1-yl]ethyl]-5-oxo-2-thioxoimidazolidin-1-yl]-2-(trifluoromethyl)-benzonitrile | 15 (4) | 496 |

TABLE 22-continued

Compounds of General Formula I According to the Invention, in which V = Trifluoromethylbenzonitrile, W = Thiohydantoin, n = 2

| Example | Name | Synthesis Analogous to Example | ESI-MS |
|---|---|---|---|
| 500 | 4-[4,4-Dimethyl-5-oxo-3-[2-[4-(1-oxobutyl)-piperazin-1-yl]-ethyl]-2-thioxoimidazolidin-1-yl]-2-(trifluoromethyl)-benzonitrile | 15 (4) | 496 |
| 501 | 4-[3-[2-[4-(Cyclopropylcarbonyl)piperazin-1-yl]ethyl]-4,4-dimethyl-5-oxo-2-thioxoimidazolidin-1-yl]-2-(trifluoromethyl)benzonitrile | 15 (4) | 494 |
| 502 | 4-[3-[2-[4-(Cyclobutylcarbonyl)piperazin-1-yl]ethyl]-4,4-dimethyl-5-oxo-2-thioxoimidazolidin-1-yl]-2-(trifluoromethyl)benzonitrile | 15 (4) | 508 |
| 503 | 4-[4,4-Dimethyl-5-oxo-3-[2-[4-[(thien-2-yl)acetyl]-piperazin-1-yl]ethyl]-2-thioxoimidazolidin-1-yl]-2-(trifluoromethyl)-benzonitrile | 15 (4) | 550 |
| 504 | 4-[4,4-Dimethyl-5-oxo-3-[2-[4-[(thien-2-yl)carbonyl]-piperazin-1-yl]ethyl]-2-thioxoimidazolidin-1-yl]-2-(trifluoromethyl)-benzonitrile | 15 (4) | 536 |
| 505 | 4-[4,4-Dimethyl-5-oxo-3-[2-[4-[(pyridin-4-yl)carbonyl]-piperazin-1-yl]ethyl]-2-thioxoimidazolidin-1-yl]-2-(trifluoromethyl)-benzonitrile | 15 (4) | 531 |
| 506 | 4-[4,4-Dimethyl-3-[2-[4-(methylsulfonyl)piperazin-1-yl]-ethyl]-5-oxo-2-thioxoimidazolidin-1-yl]-2-(trifluoromethyl)-benzonitrile | 15 (5) | 504 |
| 507 | 4-[3-[2-[4-(Ethylsulfonyl)piperazin-1-yl]ethyl]-4,4-dimethyl-5-oxo-2-thioxoimidazolidin-1-yl]-2-(trifluoromethyl)-benzonitrile | 15 (5) | 518 |
| 508 | 4-[4,4-Dimethyl-5-oxo-3-[2-[4-(propylsulfonyl)-piperazin-1-yl]ethyl]-2-thioxoimidazolidin-1-yl]-2-(trifluoromethyl)-benzonitrile | 15 (5) | 532 |
| 509 | 4-[4,4-Dimethyl-5-oxo-3-[2-[4-(phenylsulfonyl)-piperazin-1-yl]ethyl]-2-thioxoimidazolidin-1-yl]-2-(trifluoromethyl)-benzonitrile | 15 (5) | 566 |
| 510 | 4-[3-[2-[4-[(4-Cyanophenyl)sulfonyl]piperazin-1-yl]ethyl]-4,4-dimethyl-5-oxo-2-thioxoimidazolidin-1-yl]-2-(trifluoromethyl)benzonitrile | 15 (5) | 591 |
| 511 | 4-[2-[3-[4-Cyano-3-(trifluoromethyl)phenyl]-5,5-dimethyl-4-oxo-2-thioxoimidazolidin-1-yl]ethyl]-N-ethylpiperazine-1-carbothioamide | 15 (12) | 513 |
| 512 | 4-[2-[3-[4-Cyano-3-(trifluoromethyl)phenyl]-5,5-dimethyl-4-oxo-2-thioxoimidazolidin-1-yl]ethyl]-N-propylpiperazine-1-carbothioamide | 15 (12) | 527 |
| 513 | 4-[2-[3-[4-Cyano-3-(trifluoromethyl)phenyl]-5,5-dimethyl-4-oxo-2-thioxoimidazolidin-1-yl]ethyl]-N-(prop-2-enyl)-piperazine-1-carbothioamide | 15 (12) | 525 |
| 514 | S-Methyl 4-[2-[3-[4-cyano-3-(trifluoromethyl)-phenyl]-5,5-dimethyl-4-oxo-2-thioxoimidazolidin-1-yl]ethyl]piperazine-1-carbothioate | 15 (13) | 500 |
| 515 | S-Ethyl 4-[2-[3-[4-cyano-3-(trifluoromethyl)-phenyl]-5,5-dimethyl-4-oxo-2-thioxoimidazolidin-1-yl]ethyl]piperazine-1-carbothioate | 15 (13) | 514 |

TABLE 23

Compounds of General Formula I According to the Invention, in which V = Trifluoromethylbenzonitrile, W = Thiohydantoin, n = 3

| Example | Name | Synthesis Analogous to Example | ESI-MS |
|---|---|---|---|
| 516 | 4-[3-[3-[4-(2-Methoxybenzoyl)piperazin-1-yl]propyl]-4,4-dimethyl-5-oxo-2-thioxoimidazolidin-1-yl]-2-(trifluoromethyl)benzonitrile | 15 (4) | 574 |
| 517 | 4-[3-[3-(4-Acetylpiperazin-1-yl)propyl]-4,4-dimethyl-5-oxo-2-thioxoimidazolidin-1-yl]-2-(trifluoromethyl)benzonitrile | 15 (4) | 482 |
| 518 | 4-[4,4-Dimethyl-5-oxo-3-[3-[4-(1-oxopropyl)-piperazin-1-yl]-propyl]-2-thioxoimidazolidin-1-yl]-2-(trifluoromethyl)-benzonitrile | 15 (4) | 496 |

TABLE 23-continued

Compounds of General Formula I According to the Invention, in which
V = Trifluoromethylbenzonitrile, W = Thiohydantoin, n = 3

| Example | Name | Synthesis Analogous to Example | ESI-MS |
|---|---|---|---|
| 519 | 4-[4,4-Dimethyl-3-[3-[4-(2-methyl-1-oxopropyl)piperazin-1-yl]propyl]-5-oxo-2-thioxoimidazolidin-1-yl]-2-(trifluoromethyl)-benzonitrile | 15 (4) | 510 |
| 520 | 4-[4,4-Dimethyl-5-oxo-3-[3-[4-(1-oxobutyl)-piperazin-1-yl]-propyl]-2-thioxoimidazolidin-1-yl]-2-(trifluoromethyl)-benzonitrile | 15 (4) | 510 |
| 521 | 4-[3-[3-[4-(Cyclopropylcarbonyl)piperazin-1-yl]propyl]-4,4-dimethyl-5-oxo-2-thioxoimidazolidin-1-yl]-2-(trifluoromethyl)-benzonitrile | 15 (4) | 508 |
| 522 | 4-[3-[3-[4-(Cyclobutylcarbonyl)piperazin-1-yl]propyl]-4,4-dimethyl-5-oxo-2-thioxoimidazolidin-1-yl]-2-(trifluoromethyl)-benzonitrile | 15 (4) | 522 |
| 523 | 4-[4,4-Dimethyl-5-oxo-3-[3-[4-[(thien-2-yl)acetyl]piperazin-1-yl]propyl]-2-thioxoimidazolidin-1-yl]-2-(trifluoromethyl)-benzonitrile | 15 (4) | 564 |
| 524 | 4-[4,4-Dimethyl-5-oxo-3-[3-[4-[(thien-2-yl)carbonyl]-piperazin-1-yl]propyl]-2-thioxoimidazolidin-1-yl]-2-(trifluoromethyl)benzonitrile | 15 (4) | 550 |
| 525 | 4-[4,4-Dimethyl-5-oxo-3-[3-[4-[(pyridin-4-yl)carbonyl]-piperazin-1-yl]propyl]-2-thioxoimidazolidin-1-yl]-2-(trifluoromethyl)benzonitrile | 15 (4) | 545 |
| 526 | 4-[3-[3-[4-(3-Methoxy-1-oxopropyl)piperazin-1-yl]propyl]-4,4-dimethyl-5-oxo-2-thioxoimidazolidin-1-yl]-2-(trifluoromethyl)-benzonitrile | 15 (4) | 526 |
| 527 | 4-[3-[3-[4-[(2-Methoxyethoxy)acetyl]piperazin-1-yl]propyl]-4,4-dimethyl-5-oxo-2-thioxoimidazolidin-1-yl]-2-(trifluoromethyl)-benzonitrile | 15 (4) | 556 |
| 528 | 4-[3-[3-[4-[[2-(2-Methoxyethoxy)ethoxy]-acetyl]piperazin-1-yl]propyl]-4,4-dimethyl-5-oxo-2-thioxoimidazolidin-1-yl]-2-(trifluoromethyl)-benzonitrile | 15 (4) | 600 |
| 529 | 4-[4,4-Dimethyl-3-[3-[4-(methylsulfonyl)piperazin-1-yl]-propyl]-5-oxo-2-thioxoimidazolidin-1-yl]-2-(trifluoromethyl)-benzonitrile | 15 (5) | 518 |
| 530 | 4-[3-[3-[4-(Ethylsulfonyl)piperazin-1-yl]propyl]-4,4-dimethyl-5-oxo-2-thioxoimidazolidin-1-yl]-2-(trifluoromethyl)benzonitrile | 15 (5) | 532 |
| 531 | 4-[4,4-Dimethyl-5-oxo-3-[3-[4-propylsulfonyl)-piperazin-1-yl]propyl]-2-thioxoimidazolidin-1-yl]-2-(trifluoromethyl)-benzonitrile | 15 (5) | 546 |
| 532 | 4-[3-[3-[4-[(2-Methoxyethyl)sulfonyl]piperazin-1-yl]propyl]-4,4-dimethyl-5-oxo-2-thioxoimidazolidin-1-yl]-2-(trifluoromethyl)-benzonitrile | 15 (5) | 562 |
| 533 | 4-[4,4-Dimethyl-5-oxo-3-[3-[4-(phenylsulfonyl)-piperazin-1-yl]propyl]-2-thioxoimidazolidin-1-yl]-2-(trifluoromethyl)-benzonitrile | 15 (5) | 580 |
| 534 | 4-[3-[3-[4-[(4-Cyanophenyl)sulfonyl]piperazin-1-yl]propyl]4,4-dimethyl-5-oxo-2-thioxoimidazolidin-1-yl]-2-(trifluoromethyl)-benzonitrile | 15 (5) | 605 |
| 535 | 4-[3-[3-[4-Cyano-3-(trifluoromethyl)phenyl]-5,5-dimethyl-4-oxo-2-thioxoimidazolidin-1-yl]propyl]-N-ethylpiperazine-1-carbothioamide | 15 (12) | 527 |
| 536 | 4-[3-[3-[4-Cyano-3-(trifluoromethyl)phenyl]-5,5-dimethyl-4-oxo-2-thioxoimidazolidin-1-yl]propyl]-N-propylpiperazine-1-carbothioamide | 15 (12) | 541 |
| 537 | 4-[3-[3-[4-Cyano-3-(trifluoromethyl)phenyl]-5,5-dimethyl-4-oxo-2-thioxoimidazolidin-1-yl]propyl]N-(prop-2-enyl)-piperazine-1-carbothioamide | 15 (12) | 539 |
| 538 | S-Methyl 4-[3-[3-[4-cyano-3-(trifluoromethyl)-phenyl]-5,5-dimethyl-4-oxo-2-thioxoimidazolidin-1-yl]propyl]piperazine-1-carbothioate | 15 (13) | 514 |

TABLE 23-continued

Compounds of General Formula I According to the Invention, in which
V = Trifluoromethylbenzonitrile, W = Thiohydantoin, n = 3

| Example | Name | Synthesis Analogous to Example | ESI-MS |
|---|---|---|---|
| 539 | S-Ethyl 4-[3-[3-[4-cyano-3-(trifluoromethyl)-phenyl]-5,5-dimethyl-4-oxo-2-thioxoimidazolidin-1-yl]propyl]piperazine-1-carbothioate | 15 (13) | 528 |

TABLE 24

Compounds of General Formula I According to the Invention, in which
V = Trifluoromethylbenzonitrile, W = Thiohydantoin, n = 4

| Example | Name | Synthesis Analogous to Example | ESI-MS |
|---|---|---|---|
| 540 | 4-[3-[4-(2-Methoxybenzoyl)piperazin-1-yl]butyl]-4,4-dimethyl-5-oxo-2-thioxoimidazolidin-1-yl]-2-(trifluoromethyl)benzonitrile | 4 | 588 |
| 541 | 4-[4-[3-[4-Cyano-3-(trifluoromethyl)phenyl]-5,5-dimethyl-4-oxo-2-thioxoimidazolidin-1-yl]butyl]piperazine-1-carbonitrile | 4 | 479 |
| 542 | 4-[3-[4-(4-Acetylpiperazin-1-yl)butyl]-4,4-dimethyl-5-oxo-2-thioxoimidazolidin-1-yl]-2-(trifluoromethyl)benzonitrile | 4 | 496 |
| 543 | rel-4-[3-[(2R,5S)-4-Acetyl-2,5-dimethylpiperazin-1-yl]butyl]-4,4-dimethyl-5-oxo-2-thioxoimidazolidin-1-yl]-2-(trifluoromethyl)-benzonitrile | 4 | 524 |
| 544 | 4-[3-[4-(4-Acetylhexahydro-1H-1,4-diazepin-1-yl)butyl]-4,4-dimethyl-5-oxo-2-thioxoimidazolidin-1-yl]-2-(trifluoromethyl)benzonitrile | 4 | 510 |
| 545 | 4-[4,4-Dimethyl-5-oxo-3-[4-[4-(1-oxopropyl)piperazin-1-yl]butyl]-2-thioxoimidazolidin-1-yl]-2-(trifluoromethyl)-benzonitrile | 4 | 510 |
| 546 | 4-[4,4-Dimethyl-3-[4-[4-(2-methyl-1-oxopropyl)piperazin-1-yl]butyl]-5-oxo-2-thioxoimidazolidin-1-yl]-2-(trifluoromethyl)-benzonitrile | 4 | 524 |
| 547 | rel-4-[3-[4-[(2R,5S)-2,5-Dimethyl-4-(2-methyl-1-oxopropyl)piperazin-1-yl]butyl]-4,4-dimethyl-5-oxo-2-thioxoimidazolidin-1-yl]-2-(trifluoromethyl)-benzonitrile | 4 | 552 |
| 548 | 4-[3-[4-[4-(2-Hydroxy-2-methyl-1-oxopropyl)-piperazin-1-yl]butyl]-4,4-dimethyl-5-oxo-2-thioxoimidazolidin-1-yl]-2-(trifluormethyl)-benzonitrile | 4 | 540 |
| 549 | 4-[3-[4-[4-(2,2-Dimethyl-1-oxopropyl)piperazin-1-yl]butyl]-4,4-dimethyl-5-oxo-2-thioxoimidazolidin-1-yl]-2-(trifluoromethyl)benzonitrile | 4 | 538 |
| 550 | rel-4-[3-[4-[(2R,5S)-4-(2,2-Dimethyl-1-oxopropyl)-2,5-dimethylpiperazin-1-yl]butyl]-4,4-dimethyl-5-oxo-2-thioxoimidazolidin-1-yl]-2-(trifluoromethyl)-benzonitrile | 4 | 566 |
| 551 | 4-[3-[4-[4-(2,2-Dimethyl-1-oxopropyl)hexahydro-1H-1,4-diazepin-1-yl]butyl]-4,4-dimethyl-5-oxo-2-thioxoimidazolidin-1-yl]-2-(trifluoromethyl)-benzonitrile | 4 | 552 |
| 552 | 4-[4,4-Dimethyl-5-oxo-3-[4-[4-(1-oxobutyl)piperazin-1-yl]-butyl]-2-thioxoimidazolidin-1-yl]-2-(trifluoromethyl)-benzonitrile | 4 | 524 |
| 553 | 4-[3-[4-[4-(Cyclopropylcarbonyl)piperazin-1-yl]butyl]-4,4-dimethyl-5-oxo-2-thioxoimidazolidin-1-yl]-2-(trifluoromethyl)benzonitrile | 4 | 522 |
| 554 | rel-4-[3-[4-[(2R,5S)-4-(Cyclopropylcarbonyl)-2,5 dimethylpiperazin-1-yl]butyl]-4,4-dimethyl-5-oxo 2-thioxoimidazolidin-1-yl]-2-(trifluoromethyl) benzonitrile | 4 | 550 |

TABLE 24-continued

Compounds of General Formula I According to the Invention, in which
V = Trifluoromethylbenzonitrile, W = Thiohydantoin, n = 4

| Example | Name | Synthesis Analogous to Example | ESI-MS |
|---|---|---|---|
| 555 | 4-[3-[4-[4-(Cyclobutylcarbonyl)piperazin-1-yl]butyl]-4,4-dimethyl-5-oxo-2-thioxoimidazolidin-1-yl]-2-(trifluoromethyl)benzonitrile | 4 | 536 |
| 556 | 4-[4,4-Dimethyl-5-oxo-3-[4-[4-[(thien-2-yl)acetyl]piperazin-1-yl]butyl]-2-thioxoimidazolidin-1-yl]-2-(trifluoromethyl)-benzonitrile | 4 | 578 |
| 557 | 4-[3-[4-[4-(Methoxyacetyl)piperazin-1-yl]butyl]-4,4-dimethyl-5-oxo-2-thioxoimidazolidin-1-yl]-2-(trifluoromethyl)benzonitrile | 4 | 526 |
| 558 | 4-[3-[4-[4-(3-Methoxy-1-oxopropyl)piperazin-1-yl]butyl]-4,4-dimethyl-5-oxo-2-thioxoimidazolidin-1-yl]-2-(trifluoromethyl)benzonitrile | 4 | 540 |
| 559 | 4-[3-[4-[Hexahydro-4-(3-methoxy-1-oxopropyl)-1H-1,4-diazepin-1-yl]butyl]-4,4-dimethyl-5-oxo-2-thioxoimidazolidin-1-yl]-2-(trifluoromethyl)-benzonitrile | 4 | 554 |
| 560 | 4-[3-[4-[4-[(2-Methoxyethoxy)acetyl]piperazin-1-yl]butyl]-4,4-dimethyl-5-oxo-2-thioxoimidazolidin-1-yl]-2-(trifluoromethyl)benzonitrile | 4 | 570 |
| 561 | 4-[3-[4-[4-[[2-(2-Methoxyethoxy)ethoxy]-acetyl]piperazin-1-yl]butyl]-4,4-dimethyl-5-oxo-2-thioxoimidazolidin-1-yl]-2-(trifluoromethyl)-benzonitrile | 4 | 614 |
| 562 | 4-[4,4-Dimethyl-5-oxo-2-thioxo-3-[4-[4-(trifluoroacetyl)piperazin-1-yl]butyl]imidazolidin-1-yl]-2-(trifluoromethyl)benzonitrile | 4 | 550 |
| 563 | 4-[3-[4-[Hexahydro-4-(trifluoroacetyl)-1H-1,4-diazepin-1-yl]butyl]-4,4-dimethyl-5-oxo-2-thioxoimidazolidin-1-yl]-2-(trifluoromethyl)-benzonitrile | 4 | 564 |
| 564 | 4-[3-[4-[4-[(1,3-Dimethyl-1H-pyrazol-5-yl)carbonyl]-piperazin-1-yl]butyl]-4,4-dimethyl-5-oxo-2-thioxo-imidazolidin-1-yl]-2-(trifluoromethyl)benzonitrile | 4 | 576 |
| 565 | 4-[3-[4-[4-[(Furan-3-yl)carbonyl]piperazin-1-yl]butyl]-4A-dimethyl-5-oxo-2-thioxoimidazolidin-1-yl]-2-(trifluoromethyl)benzonitrile | 4 | 548 |
| 566 | 4-[3-[4-[4-[(2,5-Dimethylfuran-3 yl)carbonyl]piperazin-1-yl]butyl]-4,4-dimethyl-5-oxo-2-thioxoimidazolidin-1-yl]-2-(trifluoromethyl)benzonitrile | 4 | 576 |
| 567 | 4-[3-[4-[4-[(Isoxazol-5-yl)carbonyl]piperazin-1-yl]butyl]-4,4-dimethyl-5-oxo-2-thioxoimidazolidin-1-yl]-2-(trifluoromethyl)benzonitrile | 4 | 549 |
| 568 | 4-[4,4-Dimethyl-3-[4-[4-[(5-methylisoxazol-3-yl)carbonyl]piperazin-1-yl]butyl]-5-oxo-2-thioxo-imidazolidin-1-yl]-2-(trifluoromethyl)benzonitrile | 4 | 563 |
| 569 | 4-[4,4-Dimethyl-5-oxo-3-[4-[4-[(thien-3-yl)carbonyl]-piperazin-1-yl]butyl]-2-thioxoimidazolidin-1-yl]-2-(trifluoromethyl)-benzonitrile | 4 | 564 |
| 570 | 4-[4,4-Dimethyl-3-[4-[4-[(4-methyl-1,2,3-thiadiazol-4-yl)-carbonyl]piperazin-1-yl]butyl]-5-oxo-2-thioxoimidazolidin-1-yl]-2-(trifluoromethyl)-benzonitrile | 4 | 580 |
| 571 | 4-[3-[4-[4-[(Furan-2-yl)carbonyl]piperazin-1-yl]butyl]-4,4-dimethyl-5-oxo-2-thioxoimidazolidin-1-yl]-2-(trifluoromethyl)benzonitrile |  | 548 |
| 572 | 4-[3-[4-[4-[(Furan-2-yl)carbonyl]hexahydro-1H-1,4-diazepin-1-yl]butyl]-4,4-dimethyl-5-oxo-2-thioxoimidazolidin-1-yl]-2-(trifluoromethyl)-benzonitrile | 4 | 562 |
| 573 | 4-[4,4-Dimethyl-5-oxo-3-[4-[4-[(thien-2-yl)carbonyl]-piperazin-1-yl]butyl]-2-thioxoimidazolidin-1-yl]-2-(trifluoromethyl)benzonitrile | 4 | 564 |
| 574 | 4-[3-[4-[Hexahydro-4-[(thien-2-yl)carbonyl]-1H-1,4-diazepin-1-yl]butyl]-4,4-dimethyl-5-oxo-2-thioxoimidazolidin-1-yl]-2-(trifluoromethyl)-benzonitrile | 4 | 578 |

TABLE 24-continued

Compounds of General Formula I According to the Invention, in which
V = Trifluoromethylbenzonitrile, W = Thiohydantoin, n = 4

| Example | Name | Synthesis Analogous to Example | ESI-MS |
|---|---|---|---|
| 575 | 4-[4,4-Dimethyl-5-oxo-3-[4-[4-[(pyridin-4-yl)carbonyl]-piperazin-1-yl]butyl]-2-thioxoimidazolidin-1-yl]-2-(trifluoromethyl)-benzonitrile | 4 | 559 |
| 576 | 4-[4,4-Dimethyl-3-[4-[4-(methylsulfonyl)piperazin-1-yl]-butyl]-5-oxo-2-thioxoimidazolidin-1-yl]-2-(trifluoromethyl)-benzonitrile | 5 | 532 |
| 577 | rel-4-[4,4-Dimethyl-3-[4-[(2R,5S)-2,5-dimethyl-4-(methylsulfonyl)piperazin-1-yl]butyl]-5-oxo-2-thioxoimidazolidin-1-yl]-2-(trifluoromethyl)-benzonitrile | 5 | 560 |
| 578 | 4-[3-[4-[Hexahydro-4-(methylsulfonyl)-1H-1,4-diazepin-1-yl]butyl]-4,4-dimethyl-5-oxo-2-thioxoimidazolidin-1-yl]-2-(trifluoromethyl)-benzonitrile | 5 | 546 |
| 579 | 4-[3-[4-[4-(Ethylsulfonyl)piperazin-1-yl]butyl]-4,4-dimethyl]-5-oxo-2-thioxoimidazolidin-1-yl]-2-(trifluoromethyl)-benzonitrile | 5 | 546 |
| 580 | 4-[4,4-Dimethyl-5-oxo-3-[4-[4-(propylsulfonyl)-piperazin-1-yl]butyl]-2-thioxoimidazolidin-1-yl]-2-(trifluoromethyl)-benzonitrile | 5 | 560 |
| 581 | 4-[3-[4-[4-[(2-Methoxyethyl)sulfonyl]piperazin-1-yl]butyl]-4,4-dimethyl-5-oxo-2-thioxoimidazolidin-1-yl]-2-(trifluoromethyl)benzonitrile | 5 | 576 |
| 582 | 4-[4,4-Dimethyl-5-oxo-3-[4-[4-(phenylsulfonyl)-piperazin-1-yl]butyl]-2-thioxoimidazolidin-1-yl]-2-(trifluoromethyl)-benzonitrile | 5 | 594 |
| 583 | 4-[3-[4-[4-[(4-Cyanophenyl)sulfonyl]piperazin-1-yl]butyl]-4,4-dimethyl-5-oxo-2-thioxoimidazolidin-1-yl]-2-(trifluoromethyl)benzonitrile | 5 | 619 |
| 584 | 4-[4,4-Dimethyl-3-[4-[4-[(1-methyl-1H-imidazol-4-yl)-sulfonyl]piperazin-1-yl]butyl]-5-oxo-2-thioxoimidazolidin-1-yl]-2-(trifluoromethyl)-benzonitrile | 5 | 598 |
| 585 | 4-[3-[4-[4-[(3,5-Dimethylisoxazol-4-yl)sulfonyl]-piperazin-1-yl]butyl]-4,4-dimethyl-5-oxo-2-thioxoimidazolidin-1-yl]-2-(trifluoromethyl)-benzonitrile | 5 | 613 |
| 586 | 4-[4-[3-[4-Cyano-3-(trifluoromethyl)phenyl]-5,5-dimethyl-4-oxo-2-thioxoimidazolidin-1-yl]butyl]-N-ethylpiperazine-1-carbothioamide | 12 | 541 |
| 587 | 4-[4-[3-[4-Cyano-3-(trifluoromethyl)phenyl]-5,5-dimethyl-4-oxo-2-thioxoimidazolidin-1-yl]butyl]-N-propylpiperazine-1-carbothioamide | 12 | 555 |
| 588 | 4-[4-[3-[4-Cyano-3-(trifluoromethyl)phenyl]-5,5-dimethyl-4-oxo-2-thioxoimidazolidin-1-yl]butyl]-N-(prop-2-enyl)-piperazine-1-carbothioamide | 12 | 553 |
| 589 | S-Methyl 4-[4-[3-[4-cyano-3-(trifluoromethyl)-phenyl]-5,5-dimethyl-4-oxo-2-thioxoimidazolidin 1-yl]butyl]piperazine-1-carbothioate | 13 | 528 |
| 590 | S-Methyl 4-[4-[3-[4-cyano-3-(trifluoromethyl)-phenyl]-5,5-dimethyl-4-oxo-2-thioxoimidazolidin-1-yl]butyl]hexahydro-1H-1,4-diazepine-1-carbothioate | 13 | 542 |
| 591 | S-Ethyl 4-[4-[3-[4-cyano-3-(trifluoromethyl)phenyl]-5,5-dimethyl-4-oxo-2-thioxoimidazolidin-1-yl]butyl]piperazine-1-carbothioate | 13 | 542 |
| 592 | N,N-Dimethyl 4-[4-[3-[4-cyano-3-(trifluoromethyl)phenyl]-5,5-dimethyl-4-oxo-2-thioxoimidazolidin-1-yl]butyl]piperazine-1-sulfonamide | 14 | 561 |

TABLE 25

Compounds of General Formula I According to the Invention, in which
V = Trifluoromethylbenzonitrile, W = Thiohydantoin, n = 5

| Example | Name | Synthesis Analogous to Example | ESI-MS |
|---|---|---|---|
| 593 | 4-[3-[5-[4-(2-Methoxybenzoyl)piperazin-1-yl]pentyl]-4,4-dimethyl-5-oxo-2-thioxoimidazolidin-1-yl]-2-(trifluoromethyl)-benzonitrile | 4 | 602 |
| 594 | 4-[5-[3-[4-Cyano-3-(trifluoromethyl)phenyl]-5,5-dimethyl-4-oxo-2-thioxoimidazolidin-1-yl]pentyl]piperazine-1-carbonitrile | 4 | 493 |
| 595 | 4-[3-[5-(4-Acetylpiperazin-1-yl)pentyl]-4,4-dimethyl-5-oxo-2-thioxoimidazolidin-1-yl]-2-(trifluoromethyl)benzonitrile | | 510 |
| 596 | rel-4-[3-[5-[(2R,6S)-4-Acetyl-2,6-dimethylpiperazin-1-yl]pentyl]-4,4-dimethyl-5-oxo-2-thioxoimidazolidin-1-yl]-2-(trifluoromethyl)benzonitrile | 4 | 538 |
| 597 | 4-[3-[5-(4-Acetylhexahydro-1H-1,4-diazepin-1-yl)pentyl]-4,4-dimethyl-5-oxo-2-thioxoimidazolidin-1-yl]-2-(trifluoro-methyl)benzonitrile | 4 | 524 |
| 598 | 4-[4,4-Dimethyl-5-oxo-3-[5-[4-[1-oxopropyl)-piperazin-1-yl]-pentyl]-2-thioxoimidazolidin-1-yl]-2-(trifluoromethyl)-benzonitrile | 4 | 524 |
| 599 | 4-[4,4-Dimethyl-3-[5-[4-(2-methyl-1-oxopropyl)-piperazin-1-yl]pentyl]-5-oxo-2-thioxoimidazolidin-1-yl]-2-(trifluoromethyl)-benzonitrile | 4 | 538 |
| 600 | 4-[3-[5-[Hexahydro-4-(2-methyl-1-oxopropyl)-1H-1,4-diazepin-1-yl]pentyl]-4,4-dimethyl-5-oxo-2-thioxoimidazolidin-1-yl]-2-(trifluoromethyl)-benzonitrile | 4 | 552 |
| 601 | 4-[3-[5-[4-(2-Hydroxy-2-methyl-1-oxopropyl)-piperazin-1-yl]pentyl]-4,4-dimethyl-5-oxo-2-thioxoimidazolidin-1-yl]-2-(trifluoromethyl)-benzonitrile | 4 | 554 |
| 602 | 4-[3-[5-[4-(2,2-Dimethyl-1-oxopropyl)piperazin-1-yl]pentyl]-4,4-dimethyl-5-oxo-2-thioxoimidazolidin-1-yl]-2-(trifluoromethyl)-benzonitrile | 4 | 552 |
| 603 | 4-[3-[5-[4-(2,2-Dimethyl-1-oxopropyl)hexahydro-1H-1,4-diazepin-1-yl]pentyl]-4,4-dimethyl-5-oxo-2-thioxoimidazolidin-1-yl]-2-(trifluoromethyl)-benzonitrile | 4 | 566 |
| 604 | 4-[4,4-Dimethyl-5-oxo-3-[5-[4-(1-oxobutyl)-piperazin-1-yl]-pentyl)-2-thioxoimidazolidin-1-yl]-2-(trifluoromethyl)-benzonitrile | 4 | 538 |
| 605 | 4-[3-[5-[4-(Cyclopropylcarbonyl)piperazin-1-yl]pentyl]-4,4-dimethyl-5-oxo-2-thioxoimidazolidin-1-yl]-2-(trifluoromethyl)-benzonitrile | 4 | 536 |
| 606 | 4-[3-[5-[4-(Cyclobutylcarbonyl)piperazin-1-yl]pentyl]-4,4-dimethyl-5-oxo-2-thioxoimidazolidin-1-yl]-2-(trifluoromethyl)-benzonitrile | 4 | 550 |
| 607 | 4-[4,4-Dimethyl-5-oxo-3-[5-[4-[(thien-2-yl)acetyl]piperazin-1-yl]pentyl]-2-thioxoimidazolidin-1-yl]-2-(trifluoromethyl)-benzonitrile | 4 | 592 |
| 608 | 4-[3-[5-[4-(Methoxyacetyl)piperazin-1-yl]pentyl]-4,4-dimethyl-5-oxo-2-thioxoimidazolidin-1-yl]-2-(trifluoromethyl)benzonitrile | 4 | 540 |
| 609 | 4-[3-[5-[4-(3-Methoxy-1-oxopropyl)piperazin-1-yl]pentyl]4,4-dimethyl-5-oxo-2-thioxoimidazolidin-1-yl]-2-(trifluoromethyl)-benzonitrile | 4 | 554 |
| 610 | 4-[3-[5-[4-[(2-Methoxyethoxy)acetyl]piperazin-1-yl]pentyl]-4,4-dimethyl-5-oxo-2-thioxoimidazolidin-1-yl]-2-(trifluoromethyl)-benzonitrile | 4 | 584 |
| 611 | 4-[3-[5-[4-[[2-(2-Methoxyethoxy)ethoxy]-acetyl]piperazin-1-yl]pentyl]-4,4-dimethyl-5-oxo-2-thioxoimidazolidin-1-yl]-2-(trifluoromethyl)-benzonitrile | 4 | 628 |

TABLE 25-continued

Compounds of General Formula I According to the Invention, in which
V = Trifluoromethylbenzonitrile, W = Thiohydantoin, n = 5

| Example | Name | Synthesis Analogous to Example | ESI-MS |
|---|---|---|---|
| 612 | 4-[4,4-Dimethyl-5-oxo-2-thioxo-3-[5-[4-(trifluoroacetyl)piperazin-1-yl]pentyl]imidazolidin-1-yl]-2-(trifluoromethyl)benzonitrile | 4 | 564 |
| 613 | 4-[3-[5-[4-[(1,3-Dimethyl-1H-pyrazol-5-yl)carbonyl)-piperazin-1-yl]pentyl]-4,4-dimethyl-5-oxo-2-thioxo-imidazolidin-1-yl)-2-(trifluoromethyl)benzonitrile | 4 | 590 |
| 614 | 4-[3-[5-[4-[(Furan-3-yl)carbonyl]piperazin-1-yl]pentyl)-4,4-dimethyl-5-oxo-2-thioxoimidazolidin-1-yl]-2-(trifluoromethyl)-benzonitrile | 4 | 562 |
| 615 | 4-[3-[5-[4-[(Furan-3-yl)carbonyl]hexahydro-1H-1,4-diazepin-1-yl]pentyl]-4,4-dimethyl-5-oxo-2-thioxoimidazolidin-1-yl]-2-(trifluoromethyl)-benzonitrile | 4 | 576 |
| 616 | 4-[3-[5-[4-[(2,5-Dimethylfuran-3-yl)carbonyl]piperazin-1-yl]pentyl]-4,4-dimethyl-5-oxo-2-thioxoimidazolidin-1-yl)-2-(trifluoromethyl)-benzonitrile | 4 | 590 |
| 617 | 4-[3-[5-[4-[(Isoxazol-5-yl)carbonyl]piperazin-1-yl]pentyl]-4,4-dimethyl-5-oxo-2-thioxoimidazolidin-1-yl]-2-(trifluoromethyl)-benzonitrile | 4 | 563 |
| 618 | 4-[4,4-Dimethyl-3-[5-[4-[(5-methylisoxazol-3 yl)carbonyl)-piperazin-1-yl]pentyl]-5-oxo-2-thioxoimidazolidin-1-yl]-2-(trifluoromethyl)-benzonitrile | 4 | 577 |
| 619 | 4-[4,4-Dimethyl-5-oxo-3-[5-[4-[(thien-3-yl)carbonyl)-piperazin-1-yl]pentyl)-2-thioxoimidazolidin-1-yl]-2-(trifluoromethyl)-benzonitrile | 4 | 578 |
| 620 | 4-[3-[5-[Hexahydro-4-[(thien-3-yl)carbonyl]-1H-1,4-diazepin-1-yl]pentyl]4,4-dimethyl-5-oxo-2-thioxoimidazolidin-1-yl]-2-(trifluoromethyl)-benzonitrile | 4 | 592 |
| 621 | 4-[4,4-Dimethyl-3-[5-[4-[(4-methyl-1,2,3-thiadiazol-4-yl)-carbonyl)piperazin-1-yl]pentyl]-5-oxo-2-thioxoimidazolidin-1-yl]-2-(trifluoromethyl)benzonitrile | 4 | 594 |
| 622 | 4-[3-[5-[4-[(Furan-2-yl)carbonyl]hexahydro-1H-1,4-diazepin-1-yl]pentyl]-4,4-dimethyl-5-oxo-2-thioxoimidazolidin-1-yl]-2-(trifluoromethyl)-benzonitrile | 4 | 576 |
| 623 | 4-[4,4-Dimethyl-5-oxo-3-[5-[4-[(thien-2-yl)carbonyl]-piperazin-1-yl]pentyl)-2-thioxoimidazolidin-1-yl]-2-(trifluoromethyl)-benzonitrile | 4 | 578 |
| 624 | 4-[3-[5-[Hexahydro-4-[(thien-2-yl)carbonyl)-1H-1,4-diazepin-1-yl]pentyl]-4,4-dimethyl-5-oxo-2-thioxoimidazolidin-1-yl]-2-(trifluoromethyl)-benzonitrile | 4 | 592 |
| 625 | 4-[4,4-Dimethyl-5-oxo-3-[5-[4-[pyridin-4-yl)carbonyl)-piperazin-1-yl)pentyl)-2-thioxoimidazolidin-1-yl]-2-(trifluoromethyl)-benzonitrile | 4 | 573 |
| 626 | 4-[4,4-Dimethyl-3-[5-[4-(methylsulfonyl)piperazin-1-yl]-pentyl]-5-oxo-2-thioxoimidazolidin-1-yl]-2-(trifluoromethyl)-benzonitrile | 5 | 546 |
| 627 | rel-4-[3-[5-[(2R,6S)-2,6-Dimethyl-4 (methylsulfonyl)piperazin-1-yl]pentyl]-4,4-dimethyl-5-oxo-2-thioxoimidazolidin-1-yl]-2-(trifluoromethyl)benzonitrile | 5 | 574 |
| 628 | 4-[3-[5-[Hexahydro-4-(methylsulfonyl)-1H-1,4-diazepin-1-yl]pentyl]4,4-dimethyl-5-oxo-2-thioxoimidazolidin-1-yl]-2-(trifluoromethyl)-benzonitrile | 5 | 560 |
| 629 | 4-[3-[5-[4-(Ethylsulfonyl)piperazin-1-yl]pentyl]-4,4-dimethyl-5-oxo-2-thioxoimidazolidin-1-yl]-2-(trifluoromethyl)benzonitrile | 5 | 560 |
| 630 | 4-[4,4-Dimethyl-5-oxo-3-[5-[4-propylsulfonyl)-piperazin-1-yl]pentyl]-2-thioxoimidazolidin-1-yl]-2-(trifluoromethyl)-benzonitrile | 5 | 574 |

TABLE 25-continued

Compounds of General Formula I According to the Invention, in which
V = Trifluoromethylbenzonitrile, W = Thiohydantoin, n = 5

| Example | Name | Synthesis Analogous to Example | ESI-MS |
|---|---|---|---|
| 631 | 4-[4,4-Dimethyl-5-oxo-3-[5-[4-(phenylsulfonyl)-piperazin-1-yl]pentyl)-2-thioxoimidazolidin-1-yl)-2-(trifluoromethyl)-benzonitrile | 5 | 608 |
| 632 | 4-[3-[5-[4-[(4-Cyanophenyl)sulfonyl]piperazin-1-yl]pentyl]-4,4-dimethyl-5-oxo-2-thioxoimidazolidin-1-yl]-2-(trifluoromethyl)-benzonitrile | 5 | 633 |
| 633 | 4-[3-[5-[4-[(2-Methoxyethoxy)sulfonyl]piperazin-1-yl]-pentyl]-4,4-dimethyl-5-oxo-2-thioxoimidazolidin-1-yl]-2-(trifluoromethyl)-benzonitrile | 5 | 590 |
| 634 | 4-[3-[5-[4-[[2-(2-Methoxyethoxy)ethyl]-sulfonyl]piperazin-1-yl]pentyl]-4,4-dimethyl-5-oxo-2-thioxoimidazolidin-1-yl]-2-(trifluoromethyl)-benzonitrile | 5 | 634 |
| 635 | 4-[3-[5-[4-[[2-[2-(2-Methoxyethoxy)ethoxy]ethyl]sulfonyl]-piperazin-1-yl]pentyl]-4,4-dimethyl-5-oxo-2-thioxo-imidazolidin-1-yl]-2-(trifluoromethyl)benzonitrile | 5 | 678 |
| 636 | 4-[4,4-Dimethyl-3-[5-[4-[(1-methyl-1H-imidazol-4-yl)-sulfonyl]piperazin-1-yl]pentyl]-5-oxo-2-thioxoimidazolidin-1-yl]-2-(trifluoromethyl)-benzonitrile | 5 | 612 |
| 637 | 4-[3-[5-[4-[(3,5-Dimethylisoxazol-4-yl)sulfonyl]piperazin-1-yl]pentyl]-4,4-dimethyl-5-oxo-2-thioxoimidazolidin-1-yl]-2-(trifluoromethyl)benzonitrile | 5 | 627 |
| 638 | 4-[5-[3-[4-Cyano-3-(trifluoromethyl)phenyl]-5,5-dimethyl-4-oxo-2-thioxoimidazolidin-1-yl]pentyl]-N-ethylpiperazine-1-carbothioamide | 12 | 555 |
| 639 | 4-[5-[3-[4-Cyano-3-(trifluoromethyl)phenyl]-5,5-dimethyl-4-oxo-2-thioxoimidazolidin-1-yl]pentyl]-N-propylpiperazine-1-carbothioamide | 12 | 569 |
| 640 | 4-[5-[3-[4-Cyano-3-(trifluoromethyl)phenyl]-5,5-dimethyl-4-oxo-2-thioxoimidazolidin-1-yl]pentyl]-N-(prop-2-enyl)-piperazine-1-carbothioamide | 12 | 567 |
| 641 | S-Methyl 4-[5-[3-[4-cyano-3-(trifluoromethyl)-phenyl]-5,5-dimethyl-4-oxo-2-thioxoimidazolidin-1-yl]pentyl]piperazine-1-carbothioate | 13 | 542 |
| 642 | S-Methyl 4-[5-[3-[4-cyano-3-(trifluoromethyl)-phenyl]-5,5-dimethyl-4-oxo-2-thioxoimidazolidin-1-yl]pentyl]hexahydro-1H-1,4-diazepin-1-carbothioate | 13 | 556 |
| 643 | S-Ethyl 4-[5-[3-[4-cyano-3-(trifluoromethyl)-phenyl]-5,5-dimethyl-4-oxo-2-thioxoimidazolidin-1-yl]pentyl]piperazine-1-carbothioate | 13 | 556 |
| 644 | N,N-Dimethyl 4-[5-[3-[4-cyano-3-(trifluoromethyl)phenyl]-5,5-dimethyl-4-oxo-2-thioxoimidazolidin-1-yl]pentyl]piperazine-1-sulfonamide | 14 | 575 |

TABLE 26

Compounds of General Formula I According to the Invention, in which
V = Trifluoromethylbenzonitrile, W = Thiohydantoin, n = 6

| Example | Name | Synthesis Analogous to Example | ESI-MS |
|---|---|---|---|
| 645 | 4-[4,4-Dimethyl-3-[6-(4-methylpiperazin-1-yl)hexyl]-5-oxo-2-thioxoimidazolidin-1-yl]-2-(trifluoromethyl)benzonitrile | 3 | 496 |
| 646 | 4-[4,4-Dimethyl-3-[6-[4-(1-methylethyl)piperazin-1-yl]-hexyl]-5-oxo-2-thioxoimidazolidin-1-yl]-2-(trifluoromethyl)-benzonitrile | 3 | 524 |
| 647 | 4-[3-[6-[4-(2-Methoxybenzoyl)piperazin-1-yl]hexyl]-4,4-dimethyl-5-oxo-2- | 4 | 616 |

TABLE 26-continued

Compounds of General Formula I According to the Invention, in which
V = Trifluoromethylbenzonitrile, W = Thiohydantoin, n = 6

| Example | Name | Synthesis Analogous to Example | ESI-MS |
|---|---|---|---|
| | thioxoimidazolidin-1-yl]-2-(trifluoromethyl)-benzonitrile | | |
| 648 | 4-[6-[3-[4-Cyano-3-(trifluoromethyl)phenyl]-5,5-dimethyl-4-oxo-2-thioxoimidazolidin-1-yl]hexyl]piperazine-1-carbonitrile | 4 | 507 |
| 649 | 4-[3-[6-(4-Acetylpiperazin-1-yl)hexyl]-4,4-dimethyl-5-oxo-2-thioxoimidazolidin-1-yl]-2-(trifluoromethyl)benzonitrile | 4 | 524 |
| 650 | rel-4-[3-[6-[(2R,5S)-4-Acetyl-2,5-dimethyl-piperazin-1-yl]hexyl]-4,4-dimethyl-5-oxo-2-thioxoimidazolidin-1-yl]-2-(trifluoromethyl)-benzonitrile | 4 | 552 |
| 651 | rel-4-[3-[6-[(2R,6S)-4-Acetyl-2,6-dimethyl piperazin-1-yl]hexyl]-4,4-dimethyl-5-oxo-2-thioxoimidazolidin-1-yl]-2-(trifluoromethyl)-benzonitrile | 4 | 552 |
| 652 | 4-[4,4-Dimethyl-5-oxo-3-[6-[4-(1-oxopropyl)-piperazin-1-yl]-hexyl]-2-thioxoimidazolidin-1-yl]-2-(trifluoromethyl)-benzonitrile | 4 | 538 |
| 653 | 4-[4,4-Dimethyl-3-[6-[4-(2-methyl-1-oxopropyl)piperazin-1-yl]hexyl]-5-oxo-2-thioxoimidazolidin-1-yl]-2-(trifluoromethyl)-benzonitrile | 4 | 552 |
| 654 | rel-4-[3-[6-[(2R,5S)-2,5-Dimethyl-4-(2-methyl-1-oxopropyl)piperazin-1-yl]hexyl]-4,4-dimethyl-5-oxo-2-thioxoimidazolidin-1-yl]-2-(trifluoomethyl)-benzonitrile | 4 | 580 |
| 655 | 4-[3-[6-[Hexahydro-4-(2-methyl-1-oxopropyl)-1H-1,4-diazepin-1-yl]hexyl]4,4-dimethyl-5-oxo-2-thioxoimidazolidin-1-yl]-2-(trifluoromethyl)-benzonitrile | 4 | 566 |
| 656 | 4-[3-[6-[4-(2-Hydroxy-2-methyl-1-oxopropyl)-piperazin-1-yl]hexyl]-4,4-dimethyl-5-oxo-2-thioxoimidazolidin-1-yl]-2-(trifluoromethyl)-benzonitrile | 4 | 568 |
| 657 | 4-[3-[6-[4-(2,2-Dimethyl-1-oxopropyl)piperazin-1-yl]hexyl]-4,4-dimethyl-5-oxo-2-thioxoimidazolidin-1-yl]-2-(trifluoromethyl)-benzonitrile | 4 | 566 |
| 658 | rel-4-[3-[6-[(2R,5S)-4-2,2-Dimethyl-1-oxopropyl)-2,5-dimethylpiperazin-1-yl]hexyl]-4,4-dimethyl-5-oxo-2-thioxoimidazolidin-1-yl]-2-(trifluoromethyl)-benzonitrile | 4 | 594 |
| 659 | rel-4-[3-[6-[(2R,6S)4-(2,2-Dimethyl-1-oxopropyl)-2,6-dimethylpiperazin-1-yl]hexyl]-4,4-dimethyl-5-oxo-2-thioxoimidazolidin-1-yl]-2-(trifluoromethyl)-benzonitrile | 4 | 594 |
| 660 | 4-[4,4-Dimethyl-5-oxo-3-[6-[4-(1-oxobutyl)piperazin-1-yl]-hexyl]-2-thioxoimidazolidin-1-yl]-2-(trifluoromethyl)-benzonitrile | 4 | 552 |
| 661 | 4-[3-[6-[4-(Cyclopropylcarbonyl)piperazin-1-yl]hexyl]-4,4-dimethyl-5-oxo-2-thioxoimidazolidin-1-yl]-2-(trifluoromethyl)-benzonitrile | 4 | 550 |
| 662 | rel-4-[3-[6-[(2R,5S)-4-(Cyclopropylcarbonyl)-2,5-dimethylpiperazin-1-yl]hexyl]-4,4-dimethyl-5-oxo-2-thioxoimidazolidin-1-yl]-2-(trifluoromethyl)-benzonitrile | 4 | 578 |
| 663 | 4-[3-[6-[4-(Cyclobutylcarbonyl)piperazin-1-yl]hexyl]-4,4-dimethyl-5-oxo-2-thioxoimidazolidin-1-yl]-2-(trifluoromethyl)-benzonitrile | 4 | 564 |
| 664 | 4-[3-[6-[4-(Methoxyacetyl)piperazin-1-yl]hexyl]-4,4-dimethyl-5-oxo-2-thioxoimidazolidin-1-yl]-2-(trifluoromethyl)benzonitrile | 4 | 554 |
| 665 | 4-[3-[6-[4-(3-Methoxy-1-oxopropyl)piperazin-1-yl]hexyl]-4,4-dimethyl-5-oxo-2-thioxoimidazolidin-1-yl]-2-(trifluoromethyl)-benzonitrile | 4 | 568 |
| 666 | rel-4-[3-[6-[(2R,5S)-4-(3-Methoxy-1-oxopropyl)-2,5-dimethylpiperazin-1-yl]hexyl]-4,4-dimethyl-5- | 4 | 596 |

TABLE 26-continued

Compounds of General Formula I According to the Invention, in which
V = Trifluoromethylbenzonitrile, W = Thiohydantoin, n = 6

| Example | Name | Synthesis Analogous to Example | ESI-MS |
|---|---|---|---|
| | oxo-2-thioxoimidazolidin-1-yl]-2-(trifluoromethyl)-benzonitrile | | |
| 667 | 4-[3-[6-[Hexahydro-4-(3-methoxy-1-oxopropyl)-1H-1,4-diazepin-1-yl]hexyl]-4,4-dimethyl-5-oxo-2-thioxoimidazolidin-1-yl]-2-(trifluoromethyl)-benzonitrile | 4 | 582 |
| 668 | 4-[3-[6-[4-[(2-Methoxyethoxy)acetyl]piperazin-1-yl]hexyl]-4,4-dimethyl-5-oxo-2-thioxoimidazolidin-1-yl]-2-(trifluoromethyl)-benzonitrile | 4 | 598 |
| 669 | 4-[3-[6-[4-[[2-(2-Methoxyethoxy)ethoxy]-acetyl]piperazin-1-yl]hexyl]-4,4-dimethyl-5-oxo-2-thioxoimidazolidin-1-yl]-2-(trifluoromethyl)-benzonitrile | 4 | 642 |
| 670 | 4-[4,4-Dimethyl-5-oxo-2-thioxo-3-[6-[4-(trifluoroacetyl)piperazin-1-yl]hexyl]imidazolidin-1-yl]-2-(trifluoromethyl)benzonitrile | 4 | 578 |
| 671 | rel-4-[3-[6-[(2R,5S)-2,5-Dimethyl-4-(trifluoroacetyl)piperazin-1-yl]hexyl]-4,4-dimethyl-5-oxo-2-thioxoimidazolidin-1-yl]-2-(trifluoromethyl)benzonitrile | 4 | 606 |
| 672 | 4-[4,4-Dimethyl-5-oxo-3-[6-[4-[(thien-2-yl)acetyl]piperazin-1-yl]hexyl]-2-thioxoimidazolidin-1-yl]-2-(trifluoromethyl)-benzonitrile | 4 | 606 |
| 673 | rel-4-[3-[6-[(2R,5S)-4-[(Furan-3-yl)carbonyl]-2,5-dimethylpiperazin-1-yl]hexyl]-4,4-dimethyl-5-oxo-2-thioxoimidazolidin-1-yl]-2-(trifluoromethyl)-benzonitrile | 4 | 604 |
| 674 | rel-4-[3-[6-[(2R,5S)-4-[(Isoxazol-5-yl)carbonyl]-2,5-dimethylpiperazin-1-yl]hexyl]-4,4-dimethyl-5-oxo-2-thioxoimidazolidin-1-yl]-2-(trifluoromethyl)-benzonitrile | 4 | 605 |
| 675 | 4-[3-[6-[4-[(Furan-2-yl)carbonyl]piperazin-1-yl]hexyl]-4,4-dimethyl-5-oxo-2-thioxoimidazolidin-1-yl]-2-(trifluoromethyl)-benzonitrile | 4 | 576 |
| 676 | rel-4-[3-[6-[(2R,5S)-4-[(Furan-2-yl)carbonyl]-2,5-dimethylpiperazin-1 -yl]hexyl]-4,4-dimethyl-5-oxo-2-thioxoimidazolidin-1-yl]-2-(trifluoromethyl)-benzonitrile | 4 | 604 |
| 677 | 4-[3-[6-[4-[(Furan-2-yl)carbonyl]hexahydro-1H-1,4-diazepin-1-yl]hexyl]-4,4-dimethyl-5-oxo-2-thioxoimidazolidin-1-yl]-2-(trifluoromethyl)-benzonitrile | 4 | 590 |
| 678 | 4-[4,4-Dimethyl-5-oxo-3-[6-[4-[(thien-2-yl)carbonyl]-piperazin-1-yl]hexyl]-2 thioxoimidazolidin-1-yl]-2-(trifluoromethyl)-benzonitrile | 4 | 592 |
| 679 | rel-4-[3-[6-[(2R,5S)-2,5-Dimethyl-4-[(thien-2 yl)carbonyl]piperazin-1-yl]hexyl]-4,4-dimethyl-5-oxo-2-thioxoimidazolidin-1-yl]-2-(trifluoromethyl)benzonitrile | 4 | 620 |
| 680 | 4-[3-[6-[Hexahydro-4-[(thien-2-yl)carbonyl]-1H-1,4-diazepin-1-yl]hexyl]-4,4-dimethyl-5-oxo-2-thioxoimidazolidin-1-yl]-2-(trifluoromethyl)-benzonitrile | 4 | 606 |
| 681 | 4-[4,4-Dimethyl-5-oxo-3-[6-[4-[(pyridin-4-yl)carbonyl]-piperazin-1-yl]hexyl]-2-thioxoimidazolidin-1-yl]-2-(trifluoromethyl)-benzonitrile | 4 | 587 |
| 682 | 4-[4,4-Dimethyl-3-[6-[4-(methylsulfonyl)piperazin-1-yl]-hexyl]-5-oxo-2-thioxoimidazolidin-1-yl]-2-(trifluoromethyl)-benzonitrile | 5 | 560 |
| 683 | rel-4-[3-[6-[(2R,5S)-2,5-Dimethyl-4-(methylsulfonyl)piperazin-1-yl]hexyl]-4,4-dimethyl-5-oxo-2-thioxoimidazolidin-1-yl]-2-(trifluoromethyl)benzonitrile | 5 | 588 |
| 684 | rel-4-[3-[6-[(2R,6S)-2,6-Dimethyl-4-(methylsulfonyl)piperazin-1-yl]hexyl]-4,4-dimethyl-5-oxo-2-thioxoimidazolidin-1-yl]-2-(trifluoromethyl)benzonitrile | 5 | 588 |

TABLE 26-continued

Compounds of General Formula I According to the Invention, in which
V = Trifluoromethylbenzonitrile, W = Thiohydantoin, n = 6

| Example | Name | Synthesis Analogous to Example | ESI-MS |
|---|---|---|---|
| 685 | 4-[3-[6-[Hexahydro-4-(methylsulfonyl)-1H-1,4-diazepin-1-yl]hexyl]-4,4-dimethyl-5-oxo-2-thioxoimidazolidin-1-yl]-2-(trifluoromethyl)-benzonitrile | 5 | 574 |
| 686 | 4-[3-[6-[4-(Ethylsulfonyl)piperazin-1-yl]hexyl]-4,4-dimethyl-5-oxo-2-thioxoimidazolidin-1-yl]-2-(trifluoromethyl)benzonitrile | 5 | 574 |
| 687 | rel-4-[3-[6-[(2R,5S)4-(Ethylsulfonyl)-2,5-dimethylpiperazin-1-yl]hexyl]-4,4-dimethyl-5-oxo-2-thioxoimidazolidin-1-yl]-2-(trifluoromethyl)-benzonitrile | 5 | 602 |
| 688 | 4-[4,4-Dimethyl-5-oxo-3-[6-[4-propylsulfonyl)-piperazin-1-yl]hexyl]-2-thioxoimidazolidin-1-yl]-2-(trifluoromethyl)benzonitrile | 5 | 588 |
| 689 | 4-[4,4-Dimethyl-3-[6-[4-[(1-methylethyl)-sulfonyl]piperazin-1-yl]hexyl]-5-oxo-2-thioxoimidazolidin-1-yl]-2-(trifluoromethyl)-benzonitrile | 5 | 588 |
| 690 | 4-[3-[6-[4-[(2-Methoxyethyl)sulfonyl]piperazin-1-yl]hexyl]-4,4-dimethyl-5-oxo-2-thioxoimidazolidin-1-yl]-2-(trifluoromethyl)-benzonitrile | 5 | 604 |
| 691 | 4-[4,4-Dimethyl-5-oxo-3-[6-[4-(phenylsulfonyl)-piperazin-1-yl]hexyl]-2-thioxoimidazolidin-1-yl]-2-(trifluoromethyl)benzonitrile | 5 | 622 |
| 692 | 4-[3-[6-[4-[(4-Cyanophenyl)sulfonyl]piperazin-1-yl]hexyl]-4,4-dimethyl-5-oxo-2-thioxoimidazolidin-1-yl]-2-(trifluoromethyl)-benzonitrile | 5 | 647 |
| 693 | 4-[6-[3-[4-Cyano-3-(trifluoromethyl)phenyl]-5,5-dimethyl-4-oxo-2-thioxoimidazolidin-1-yl]hexyl]-N-ethylpiperazine-1-carbothioamide | 12 | 569 |
| 694 | 4-[6-[3-[4-Cyano-3-(trifluoromethyl)phenyl]-5,5-dimethyl-4-oxo-2-thioxoimidazolidin-1-yl]hexyl]-N-propylpiperazine-1-carbothioamide | 12 | 583 |
| 695 | 4-[6-[3-[4-Cyano-3-(trifluoromethyl)phenyl]-5,5-dimethyl-4-oxo-2-thioxoimidazolidin-1-yl]hexyl]-N-(prop-2-enyl)-piperazine-1-carbothioamide | 12 | 581 |
| 696 | S-Methyl 4-[6-[3-[4-cyano-3-(trifluoromethyl)-phenyl]-5,5-dimethyl-4-oxo-2-thioxoimidazolidin-1-yl]hexyl]piperazine-1-carbothioate | 13 | 556 |
| 697 | S-Methyl 4-[6-[3-[4-cyano-3-(trifluoromethyl)-phenyl]-5,5-dimethyl-4-oxo-2-thioxoimidazolidin-1-yl]hexyl]hexahydro-1H-1,4-diazepine-1-carbothioate | 13 | 570 |
| 698 | S-Ethyl 4-[6-[3-[4-cyano-3-(trifluoromethyl)-phenyl]-5,5-dimethyl-4-oxo-2-thioxoimidazolidin-1-yl]hexyl]piperazine-1-carbothioate | 13 | 570 |

TABLE 27

Compounds of General Formula I According to the Invention, in which
V = Trifluoromethylbenzonitrile, W = Thiohydantoin, n = 7

| Example | Name | Synthesis Analogous to Example | ESI-MS |
|---|---|---|---|
| 699 | 4-[4,4-Dimethyl-3-[7-(4-methylpiperazin-1-yl)heptyl]-5-oxo-2-thioxoimidazolidin-1-yl]-2-(trifluoromethyl)benzonitrile | 3 | 510 |
| 700 | 4-[7-[3-[4-Cyano-3-(trifluoromethyl)phenyl]-5,5-dimethyl-4-oxo-2-thioxoimidazolidin-1-yl]heptyl]piperazine-1-carbonitrile | 4 | 521 |
| 701 | 4-[3-[7-(4-Acetylpiperazin-1-yl)heptyl]-4,4-dimethyl-5-oxo-2-thioxoimidazolidin-1-yl]-2-(trifluoromethyl)benzonitrile | 4 | 538 |
| 702 | rel-4-[3-[7-[(2R,6S)-4-Acetyl-2,6-dimethyl-piperazin-1-yl]heptyl]-4,4-dimethyl-5-oxo-2- | 4 | 566 |

TABLE 27-continued

Compounds of General Formula I According to the Invention, in which
V = Trifluoromethylbenzonitrile, W = Thiohydantoin, n = 7

| Example | Name | Synthesis Analogous to Example | ESI-MS |
|---|---|---|---|
|  | thioxoimidazolidin-1-yl]-2-(trifluoromethyl)-benzonitrile |  |  |
| 703 | 4-[3-[7-[4-(2-Hydroxy-2-methyl-1-oxopropyl)-piperazin-1-yl]heptyl]-4,4-dimethyl-5-oxo-2-thioxoimidazolidin-1-yl]-2-(trifluoromethyl)-benzonitrile | 4 | 582 |
| 704 | 4-[3-[7-[4-(2,2-Dimethyl-1-oxopropyl)piperazin-1-yl]heptyl]-4,4-dimethyl-5-oxo-2-thioxoimidazolidin-1-yl]-2-(trifluoromethyl)-benzonitrile | 4 | 580 |
| 705 | rel-4-[3-[7-[(2R,6S)-4-(2,2-Dimethyl-1-oxopropyl)-2,6-dimethylpiperazin-1-yl]heptyl]-4,4-dimethyl-5-oxo-2-thioxoimidazolidin-1-yl]-2-(trifluoromethyl)-benzonitrile | 4 | 608 |
| 706 | 4-[3-[7-[4-(Methoxyacetyl)piperazin-1-yl]heptyl]-4,4-dimethyl-5-oxo-2-thioxoimidazolidin-1-yl]-2-(trifluoromethyl)benzonitrile | 4 | 568 |
| 707 | 4-[4,4-Dimethyl-5-oxo-2-thioxo-3-[7-[4-(trifluoroacetyl)piperazin-1-yl]heptyl]imidazolidin-1-yl]-2-(trifluoromethyl)benzonitrile | 4 | 592 |
| 708 | rel-4-[3-[7-[(2R,6S)-2,6-Dimethyl-4-(trifluoroacetyl)piperazin-1-yl]heptyl]-4,4-dimethyl-5-oxo-2-thioxoimidazolidin-1-yl]-2-(trifluoromethyl)benzonitrile | 4 | 620 |
| 709 | 4-[4,4-Dimethyl-3-[7-[4-(methylsulfonyl)piperazin-1-yl]heptyl]-5-oxo-2-thioxoimidazolidin-1-yl]-2-(trifluoromethyl)benzonitrile | 5 | 574 |
| 710 | rel-4-[3-[7-[(2R,6S)-2,6-Dimethyl-4-(methylsulfonyl)piperazin-1-yl]heptyl]-4,4-dimethyl-5-oxo-2-thioxoimidazolidin-1-yl]-2-(trifluoromethyl)benzonitrile | 5 | 602 |
| 711 | 4-[3-[7-[4-[(2-Methoxyethyl)sulfonyl]piperazin-1-yl]heptyl)-4,4-dimethyl-5-oxo-2-thioxoimidazolidin-1-yl]-2-(trifluoromethyl)-benzonitrile | 5 | 618 |

TABLE 28

Compounds of General Formula I According to the Invention, in which
V = Trifluoromethylbenzonitrile, W = Thiohydantoin, n = 8

| Example | Name | Synthesis Analogous to Example | ESI-MS |
|---|---|---|---|
| 712 | 4-[8-[3-[4-Cyano-3-(trifluoromethyl)phenyl]-5,5-dimethyl-4-oxo-2-thioxoimidazolidin-1-yl]octyl]piperazine-1-carbonitrile | 4 | 535 |
| 713 | rel-4-[3-[8-[(2R,6S)-4-Acetyl-2,6-dimethylpiperazin-1-yl]octyl]-4,4-dimethyl-5-oxo-2-thioxoimidazolidin-1-yl]-2-(trifluoromethyl)-benzonitrile | 4 | 580 |
| 714 | 4-[4,4-Dimethyl-3-[8-[4-(2-methyl-1-oxopropyl)-piperazin-1-yl]octyl]-5-oxo-2-thioxoimidazolidin-1-yl]-2-(trifluoromethyl)-benzonitrile | 4 | 580 |
| 715 | 4-[3-[8-[4-(2-Hydroxy-2-methyl-1-oxopropyl)-piperazin-1-yl]octyl]-4,4-dimethyl-5-oxo-2-thioxoimidazolidin-1-yl]-2-(trifluoromethyl)-benzonitrile | 4 | 596 |
| 716 | rel-4-[3-[8-[(2R,6S)-4-(2,2-Dimethyl-1-oxopropyl)-2,6-dimethylpiperazin-1-yl]octyl]-4,4-dimethyl-5-oxo-2-thioxoimidazolidin-1-yl]-2-(trifluormethyl)benzonitril | 4 | 622 |
| 717 | 4-[3-[8-[4-(Cyclopropylcarbonyl)piperazin-1-yl]octyl)-4,4-dimethyl-5-oxo-2-thioxoimidazolidin-1-yl]-2-(trifluoromethyl)benzonitrile | 4 | 578 |
| 718 | 4-[3-[8-[4-(Cyclobutylcarbonyl)piperazin-1-yl]octyl]-4,4-dimethyl-5-oxo-2-thioxoimidazolidin-1-yl]-2-(trifluoromethyl)benzonitrile | 4 | 592 |

TABLE 28-continued

Compounds of General Formula I According to the Invention, in which
V = Trifluoromethylbenzonitrile, W = Thiohydantoin, n = 8

| Example | Name | Synthesis Analogous to Example | ESI-MS |
|---|---|---|---|
| 719 | 4-[3-[8-[4-(Methoxyacetyl)piperazin-1-yl]octyl]-4,4-dimethyl-5-oxo-2-thioxoimidazolidin-1-yl]-2-(trifluoromethyl)benzonitrile | 4 | 582 |
| 720 | 4-[4,4-Dimethyl-5-oxo-2-thioxo-3-[8-[4-(trifluoroacetyl)piperazin-1-yl]octyl]imidazolidin-1-yl]-2-(trifluoromethyl)benzonitrile | 4 | 606 |
| 721 | 4-[4,4-Dimethyl-5-oxo-3-[8-[4-[(thien-2-yl)carbonyl]-piperazin-1-yl]octyl]-2-thioxoimidazolidin-1-yl]-2-(trifluoromethyl)-benzonitrile | 4 | 620 |
| 722 | 4-[4,4-Dimethyl-5-oxo-3-[8-[4-[(pyridin-4-yl)carbonyl]-piperazin-1-yl]octyl]-2-thioxoimidazolidin-1-yl]-2-(trifluoromethyl)-benzonitrile | 4 | 615 |
| 723 | 4-[4,4-Dimethyl-3-[8-[4-(methylsulfonyl)piperazin-1-yl]-octyl)-5-oxo-2-thioxoimidazolidin-1-yl]-2-(trifluoromethyl)-benzonitrile | 5 | 588 |
| 724 | 4-[4,4-Dimethyl-5-oxo-3-[8-[4-(propylsulfonyl)-piperazin-1-yl]octyl]-2-thioxoimidazolidin-1-yl]-2-(trifluoromethyl)benzonitrile | 5 | 616 |
| 725 | 4-[4,4-Dimethyl-3-[8-[4-[(1-methylethyl)-sulfonyl]piperazin-1-yl]octyl]-5-oxo-2-thioxoimidazolidin-1-yl]-2-(trifluoromethyl)-benzonitrile | 5 | 616 |
| 726 | 4-[3-[8-[4-[(2-Methoxyethyl)sulfonyl]piperazin-1-yl]octyl]-4,4-dimethyl-5-oxo-2-thioxoimidazolidin-1-yl]-2-(trifluoromethyl)benzonitrile | 5 | 632 |
| 727 | 4-[3-[8-[4-[(4-Cyanophenyl)sulfonyl]piperazin-1-yl]octyl]-4,4-dimethyl-5-oxo-2-thioxoimidazolidin-1-yl]-2-(trifluoromethyl)benzonitrile | 5 | 675 |
| 728 | 4-[8-[3-[4-Cyano-3-(trifluoromethyl)phenyl]-5,5-dimethyl-4-oxo-2-thioxoimidazolidin-1-yl]octyl]-N-ethylpiperazine-1-carbothioamide | 12 | 597 |
| 729 | 4-[8-[3-[4-Cyano-3-(trifluoromethyl)phenyl]-5,5-dimethyl-4-oxo-2-thioxoimidazolidin-1-yl]octyl]-N-(prop-2-enyl)-piperazine-1-carbothioamide | 12 | 609 |
| 730 | S-Methyl 4-[8-[3-[4-cyano-3-(trifluoromethyl)-phenyl]-5,5-dimethyl-4-oxo-2-thioxoimidazolidin-1-yl]octyl]piperazine-1-carbothioate | 13 | 584 |
| 731 | N,N-Dimethyl 4-[8-[3-[4-cyano-3-(trifluoromethyl)phenyl]-5,5-dimethyl-4-oxo-2-thioxoimidazolidin-1-yl]octyl)piperazine-1-sulfonamide | 14 | 617 |

TABLE 29

Compounds of General Formula I According to the Invention, in which
V = Isobenzofuranone, W = Thiohydantoin, n = 3

| Example | Name | Synthesis Analogous to Example | ESI-MS |
|---|---|---|---|
| 732 | 3-(1,3-Dihydro-1-oxoisobenzofuran-5-yl)-5,5-dimethyl-1-[3-[4-[(thien-2-yl)carbonyl]piperazin-1-yl]propyl]-2-thioxoimidazolidin-4-one | 15 (4) | 513 |
| 733 | 3-[1,3-Dihydro-1-oxoisobenzofuran-5-yl)-1-[3-[4-[4-(dimethylamino)benzoyl]piperazin-1-yl]propyl]-5,5-dimethyl-2-thioxoimidazolidin-4-one | 15 (4) | 550 |
| 734 | N-[(4-Chlorophenyl)methyl]-4-[3-[3-(1,3-dihydro-1-oxo-isobenzofuran-5-yl)-5,5-dimethyl-4-oxo-2-thioxo-imidazolidin-1-yl]propyl]piperazine-1-carbothioamide | 15 (12) | 586 |
| 735 | S-Ethyl 4-[3-[3-(1,3-dihydro-1-oxoisobenzofuran-5-yl)-5,5-dimethyl-4-oxo-2-thioxoimidazolidin-1-yl]propyl]piperazine-1-carbothioate | 15 (13) | 491 |
| 736 | 4-[3-[3-(1,3-Dihydro-1-oxoisobenzofuran-5-yl)-5,5-dimethyl-4-oxo-2-thioxoimidazolidin-1- | 15 (14) | 502 |

TABLE 29-continued

Compounds of General Formula I According to the Invention, in which V = Isobenzofuranone, W = Thiohydantoin, n = 3

| Example | Name | Synthesis Analogous to Example | ESI-MS |
|---|---|---|---|
| | yl]propyl)-N,N-diethylpiperazine-1-carboxylic acid amide | | |

TABLE 30

Compounds of General Formula I According to the Invention, in which V = Isobenzofuranone, W = Thiohydantoin, n = 4

| Example | Name | Synthesis Analogous to Example | ESI-MS |
|---|---|---|---|
| 737 | 3-(1,3-Dihydro-1-oxoisobenzofuran-5-yl)-5,5-dimethyl-1-[4-[4-[(thien-2-yl)carbonyl]piperazin-1-yl]butyl]-2-thioxo-imidazolidin-4-one | 4 | 527 |
| 738 | 3-(1,3-Dihydro-1-oxoisobenzofuran-5-yl)-1-[4-[4-(2-methoxybenzoyl)piperazin-1-yl]butyl]-5,5-dimethyl-2-thioxoimidazolidin-4-one | 4 | 551 |
| 739 | 3-(1,3-Dihydro-1-oxoisobenzofuran-5-yl)-1-[4-[4-[4-(dimethylamino)benzoyl]piperazin-1-yl]butyl]-5,5-dimethyl-2-thioxoimidazolidin-4-one | 4 | 564 |
| 740 | 1-[4-[4-[(2,1,3-Benzothiadiazol-4-yl)sulfonyl]-piperazin-1-yl]butyl]-3-(1,3-dihydro-1-oxoisobenzofuran-5-yl)-5,5-dimethyl-2-thioxoimidazolidin-4-one | 5 | 615 |
| 741 | N-(2,6-Dichloropyridin-4-yl)-4-[4-[3-(1,3-dihydro-1-oxo-isobenzofuran-5-yl)-5,5-dimethyl-4-oxo-2-thioxo-imidazolidin-1-yl]butyl]piperazine-1-carboxylic acid amide | 6 | 606 |
| 742 | S-Methyl 4-[4-[3-(1,3-dihydro-1-oxoisobenzofuran-5-yl)-5,5-dimethyl-4-oxo-2-thioxoimidazolidin-1-yl]butyl]-piperazine-1-carbothioate | 13 | 491 |
| 743 | S-Ethyl 4-[4-[3-(1,3-dihydro-1-oxoisobenzofuran-5-yl)-5,5-dimethyl-4-oxo-2-thioxoimidazolidin-1-yl]butyl]piperazine-1-carbothioate | 13 | 505 |

TABLE 31

Compounds of General Formula I According to the Invention, in which V = Isobenzofuranone, W = Thiohydantoin, n = 5

| Example | Name | Synthesis Analogous to Example | ESI-MS |
|---|---|---|---|
| 744 | 3-(1,3-Dihydro-1-oxoisobenzofuran-5-yl)-5,5-dimethyl-1-[5-[4-(2-methyl-1-oxopropyl)piperazin-1-yl]pentyl]-2-thioxoimidazolidin-4-one | 4 | 501 |
| 745 | 3-(1,3-Dihydro-1-oxoisobenzofuran-5-yl)-5,5-dimethyl-1-[5-[4-[(thien-2-yl)acetyl]piperazin-1-yl]pentyl]-2-thioxo-imidazolidin-4-one | 4 | 555 |
| 746 | 3-(1,3-Dihydro-1-oxoisobenzofuran-5-yl)-5,5-dimethyl-1-[5-[4-[(thien-2-yl)carbonyl]piperazin-1-yl]pentyl]-2-thioxo-imidazolidin-4-one | 4 | 541 |
| 747 | 3-(1,3-Dihydro-1-oxoisobenzofuran-5-yl)-1-[5-[4-ethyl-sulfonyl)piperazin-1-yl]pentyl]-5,5-dimethyl-2-thioxo-imidazolidin-4-one | 5 | 523 |
| 748 | 4-[[4-[5-[3-(1,3-Dihydro-1-oxoisobenzofuran-5-yl)-5,5-dimethyl-4-oxo-2-thioxoimidazolidin-1-yl]pentyl]piperazin-1-yl]sulfonyl]benzonitrile | 5 | 596 |
| 749 | S-Ethyl 4-[5-[3-(1,3-dihydro-1-oxoisobenzofuran-5-yl)-5,5-dimethyl-4-oxo-2-thioxoimidazolidin-1-yl]pentyl]piperazine-1-carbothioate | 13 | 519 |

TABLE 32

Compounds of General Formula I According to the Invention, in which
V = Isobenzofuranone, W = Thiohydantoin, n = 6

| Example | Name | Synthesis Analogous to Example | ESI-MS |
|---|---|---|---|
| 750 | 3-(1,3-Dihydro-1-oxoisobenzofuran-5-yl)-1-[6-[4-(2-methoxybenzoyl)piperazin-1-yl]hexyl]-5,5 dimethyl-2-thioxoimidazolidin-4-one | 4 | 579 |
| 751 | 3-(1,3-Dihydro-1-oxoisobenzofuran-5-yl)-1-[6-[4-[4-(dimethylamino)benzoyl]piperazin-1-yl]hexyl]-5,5-dimethyl-2-thioxoimidazolidin-4-one | 4 | 592 |
| 752 | 3-[[4-[6-[3-(1,3-Dihydro-1-oxoisobenzofuran-5-yl)-5,5-dimethyl-4-oxo-2-thioxoimidazolidin-1-yl]hexyl]piperazin-1-yl]carbonyl]benzonitrile | 4 | 574 |
| 753 | 1-[6-(4-Acetylpiperazin-1-yl)hexyl]-3-(1,3-dihydro-1-oxo-isobenzofuran-5-yl)-5,5-dimethyl-2-thioxoimidazolidin-4-one | 4 | 487 |
| 754 | 3-(1,3-Dihydro-1-oxoisobenzofuran-5-yl)-5,5-dimethyl-1-[6-[4-(1-oxopropyl)piperazin-1-yl]hexyl]-2-thioxoimidazolidin-4-one | 4 | 501 |
| 755 | 3-(1,3-Dihydro-1-oxoisobenzofuran-5-yl)-5,5-dimethyl-1-[6-[4-(2-methyl-1-oxopropyl)-piperazin-1-yl]hexyl]-2-thioxoimidazolidin-4-one | 4 | 515 |
| 756 | 3-(1,3-Dihydro-1-oxoisobenzofuran-5-yl)-5,5-dimethyl-1-[6-[4-(1-oxobutyl)piperazin-1-yl]hexyl]-2-thioxo-imidazolidin-4-one | 4 | 515 |
| 757 | 1-[6-[4-(Cyclopropylcarbonyl)piperazin-1-yl]hexyl]-3-(1,3-dihydro-1-oxoisobenzofuran-5-yl)-5,5-dimethyl-2-thioxoimidazolidin-4-one | 4 | 513 |
| 758 | 1-[6-[4-(Cyclobutylcarbonyl)piperazin-1-yl]hexyl]-3-(1,3-dihydro-1-oxoisobenzofuran-5-yl)-5,5-dimethyl-2-thioxo-imidazolidin-4-one | 4 | 527 |
| 759 | 3-(1,3-Dihydro-1-oxoisobenzofuran-5-yl)-5,5-dimethyl-1-[6-[4-[(pyridin-4-yl)carbonyl]piperazin-1-yl]hexyl]-2-thioxo-imidazolidin-4-one | 4 | 550 |
| 760 | 3-(1,3-Dihydro-1-oxoisobenzofuran-5-yl)-5,5-dimethyl-1-[6-[4-[(thien-2-yl)carbonyl]piperazin-1-yl]hexyl]-2-thioxo-imidazolidin-4-one | 4 | 555 |
| 761 | 3-(1,3-Dihydro-1-oxoisobenzofuran-5-yl)-5,5-dimethyl-1-[6-[4-[(thien-2-yl)acetyl]piperazin-1-yl]hexyl]-2-thioxo-imidazolidin-4-one | 4 | 569 |
| 762 | 3-(1,3-Dihydro-1-oxoisobenzofuran-5-yl)-5,5-dimethyl-1-[6-[4-(methylsulfonyl)piperazin-1-yl]hexyl]-2-thioxo-imidazolidin-4-one | 5 | 523 |
| 763 | 3-(1,3-Dihydro-1-oxoisobenzofuran-5-yl)-1-[6-[4-(ethylsulfonyl)piperazin-1-yl]hexyl]-5,5-dimethyl-2-thioxo-imidazolidin-4-one | 5 | 537 |
| 764 | 3-(1,3-Dihydro-1-oxoisobenzofuran-5-yl)-5,5-dimethyl-1-[6-[4-(propylsulfonyl)piperazin-1-yl]hexyl]-2-thioxo-imidazolidin-4-one | 5 | 551 |
| 765 | 3-(1,3-Dihydro-1-oxoisobenzofuran-5-yl)-5,5-dimethyl-1-[6-[4-(phenylsulfonyl)piperazin-1-yl]hexyl]-2-thioxo-imidazolidin-4-one | 5 | 585 |
| 766 | 4-[[4-[6-[3-(1,3-Dihydro-1-oxoisobenzofuran-5-yl)-5,5-dimethyl-4-oxo-2-thioxoimidazolidin-1-yl]hexyl]piperazin-1-yl]sulfonyl]benzonitrile | 5 | 610 |
| 767 | 1-[6-[4-[(2,1,3-Benzothiadiazol-4-yl)sulfonyl]-piperazin-1-yl]hexyl]-3-(1,3-dihydro-1-oxoisobenzofuran-5-yl)-5,5-dimethyl-2-thioxoimidazolidin-4-one | 5 | 643 |
| 768 | 4-[6-[3-(1,3-Dihydro-1-oxoisobenzofuran-5-yl)-5,5-dimethyl-4-oxo-2-thioxoimidazolidin-1-yl]hexyl]-N-[3-(methylsulfonyl)phenyl]piperazine-1-carboxylic acid amide | 6 | 610 |
| 769 | 4-[6-[3-(1,3-Dihydro-1-oxoisobenzofuran-5-yl)-5,5-dimethyl-4-oxo-2-thioxoimidazolidin-1-yl]hexyl)-N-(3-fluorophenyl)piperazine-1-carboxylic acid amide | 6 | 582 |
| 770 | 4-[6-[3-(1,3-Dihydro-1-oxoisobenzofuran-5-yl)-5,5-dimethyl-4-oxo-2-thioxoimidazolidin-1-yl]hexyl]-N-(4-fluorophenyl)piperazine-1-carboxylic acid amide | 6 | 582 |
| 771 | 4-[6-[3-(1,3-Dihydro-1-oxoisobenzofuran-5-yl)-5,5-dimethyl-4-oxo-2-thioxoimidazolidin-1-yl]hexyl]-N-ethyl-piperazine-1-carbothioamide | 12 | 532 |

TABLE 32-continued

Compounds of General Formula I According to the Invention, in which
V = Isobenzofuranone, W = Thiohydantoin, n = 6

| Example | Name | Synthesis Analogous to Example | ESI-MS |
|---|---|---|---|
| 772 | 4-[6-[3-(1,3-Dihydro-1-oxoisobenzofuran-5-yl)-5,5-dimethyl-4-oxo-2-thioxoimidazolidin-1-yl]hexyl]-N-propyl-piperazine-1-carbothioamide | 12 | 546 |
| 773 | 4-[6-[3-(1,3-Dihydro-1-oxoisobenzofuran-5-yl)-5,5-dimethyl-4-oxo-2-thioxoimidazolidin-1-yl]hexyl]-N-(prop-2-enyl)piperazine-1 carbothioamide | 12 | 544 |
| 774 | 4-[6-[3-(1,3-Dihydro-1-oxoisobenzofuran-5-yl)-5,5-dimethyl-4-oxo-2-thioxoimidazolidin-1-yl]hexyl]-N-phenyl-piperazine-1-carbothioamide | 12 | 580 |
| 775 | 4-[6-[3-(1,3-Dihydro-1-oxoisobenzofuran-5-yl)-5,5-dimethyl-4-oxo-2-thioxoimidazolidin-1-yl]hexyl]-N-(phenylmethyl)piperazine-1-carbothioamide | 12 | 594 |
| 776 | S-Methyl 4-[6-[3-(1,3-dihydro-1-oxoisobenzofuran-5-yl)-5,5-dimethyl-4-oxo-2-thioxoimidazolidin-1-yl]hexyl]-piperazine-1-carbothioate | 13 | 519 |
| 777 | S-Ethyl 4-[6-[3-(1,3-dihydro-1-oxoisobenzofuran-5-yl)-5,5-dimethyl-4-oxo-2-thioxoimidazolidin-1-yl]hexyl]piperazine-1-carbothioate | 13 | 533 |
| 778 | 4-[6-[3-(1,3-Dihydro-1-oxoisobenzofuran-5-yl)-5,5-dimethyl-4-oxo-2-thioxoimidazolidin-1-yl]hexyl]-N,N-diethylpiperazine-1-carboxylic acid amide | 14 | 544 |

TABLE 33

Compounds of General Formula I According to the Invention, in which
V = Isobenzofuranone, W = Thiohydantoin, n = 7

| Example | Name | Synthesis Analogous to Example | ESI-MS |
|---|---|---|---|
| 779 | 3-(1,3-Dihydro-1-oxoisobenzofuran-5-yl)-1-[7-[4-(2-methoxybenzoyl)piperazin-1-yl]heptyl]-5,5-dimethyl-2-thioxoimidazolidin-4-one | 4 | 593 |
| 780 | 1-[7-(4-Acetylpiperazin-1-yl)heptyl]-3-(1,3 dihydro-1-oxo-isobenzofuran-5-yl)-5,5-dimethyl-2-thioxoimidazolidin-4-one | 4 | 501 |
| 781 | 3-(1,3-Dihydro-1-oxoisobenzofuran-5-yl)-5,5-dimethyl-1-[7-[4-(1-oxopropyl)piperazin-1-yl]heptyl]-2-thioxo-imidazolidin-4-one | 4 | 515 |
| 782 | 3-(1,3-Dihydro-1-oxoisobenzofuran-5-yl)-5,5-dimethyl-1-[7-[4-(2-methyl-1-oxopropyl)piperazin-1-yl]heptyl]-2-thioxoimidazolidin-4-one | 4 | 529 |
| 783 | 3-(1,3-Dihydro-1-oxoisobenzofuran-5-yl)-5,5-dimethyl-1-[7-[4-(1-oxobutyl)piperazin-1-yl]heptyl]-2-thioxo-imidazolidin-4-one | 4 | 529 |
| 784 | 1-[7-[4-(Cyclopropylcarbonyl)piperazin-1-yl]heptyl]-3-(1,3-dihydro-1-oxoisobenzofuran-5-yl)-5,5-dimethyl-2-thioxo-imidazolidin-4-one | 4 | 527 |
| 785 | 1-(7-[4-(Cyclobutylcarbonyl)piperazin-1-yl]heptyl]-3-(1,3-dihydro-1-oxoisobenzofuran-5-yl)-5,5-dimethyl-2-thioxo-imidazolidin-4-one | 4 | 541 |
| 786 | 3-(1,3-Dihydro-1-oxoisobenzofuran-5-yl)-5,5-dimethyl-1-[7-[4-[(thien-2-yl)carbonyl]piperazin-1-yl]heptyl]-2-thioxo-imidazolidin-4-one | 4 | 569 |
| 787 | 3-(1,3-Dihydro-1-oxoisobenzofuran-5-yl)-5,5-dimethyl-1-[7-[4-[(thien-2-yl)acetyl]piperazin-1-yl]heptyl]-2-thioxo-imidazolidin-4-one | 4 | 583 |
| 788 | 3-(1,3-Dihydro-1-oxoisobenzofuran-5-yl)-5,5-dimethyl-1-[7-[4-(methylsulfonyl)piperazin-1-yl]heptyl]-2-thioxo-imidazolidin-4-one | 5 | 537 |
| 789 | 3-(1,3-Dihydro-1-oxoisobenzofuran-5-yl)-1-[7-[4-(ethyl-sulfonyl)piperazin-1-yl]heptyl]-5,5-dimethyl-2-thioxo-imidazolidin-4-one | 5 | 551 |

TABLE 33-continued

Compounds of General Formula I According to the Invention, in which
V = Isobenzofuranone, W = Thiohydantoin, n = 7

| Example | Name | Synthesis Analogous to Example | ESI-MS |
|---|---|---|---|
| 790 | 3-(1,3-Dihydro-1-oxoisobenzofuran-5-yl)-5,5-dimethyl-1-[7-[4-(propylsulfonyl)piperazin-1-yl]heptyl]-2-thioxo-imidazolidin-4-one | 5 | 565 |
| 791 | 3-(1,3-Dihydro-1-oxoisobenzofuran-5-yl)-5,5-dimethyl-1-[7-[4-(phenylsulfonyl)piperazin-1-yl]heptyl]-2-thioxo-imidazolidin-4-one | 5 | 599 |
| 792 | 4-[7-[3-(1,3-Dihydro-1-oxoisobenzofuran-5-yl)-5,5-dimethyl-4-oxo-2-thioxoimidazolidin-1-yl]heptyl]-N-ethyl-piperazine-1-carbothioamide | 12 | 546 |
| 793 | 4-[7-[3-(1,3-Dihydro-1-oxoisobenzofuran-5-yl)-5,5-dimethyl-4-oxo-2-thioxoimidazolidin-1-yl]heptyl]-N-propyl-piperazine-1-carbothioamide | 12 | 560 |
| 794 | 4-[7-[3-(1,3-Dihydro-1-oxoisobenzofuran-5-yl)-5,5-dimethyl-4-oxo-2-thioxoimidazolidin-1-yl]heptyl]-N-prop-2-enyl)piperazine-1-carbothioamide | 12 | 558 |
| 795 | S-Methyl 4-[7-[3-(1,3-dihydro-1-oxoisobenzofuran-5-yl)-5,5-dimethyl-4-oxo-2-thioxoimidazolidin-1-yl]heptyl]-piperazine-1-carbothioate | 13 | 533 |
| 796 | S-Ethyl 4-[7-[3-(1,3-dihydro-1-oxoisobenzofuran-5-yl)-5,5-dimethyl-4-oxo-2-thioxoimidazolidin-1-yl]heptyl]piperazine-1-carbothioate | 13 | 547 |

TABLE 34

Compounds of General Formula I According to the Invention, in which
V = Isobenzofuranone, W = Thiohydantoin, n = 8

| Example | Name | Synthesis Analogous to Example | ESI-MS |
|---|---|---|---|
| 797 | 3-(1,3-Dihydro-1-oxoisobenzofuran-5-yl)-1-[8-[4-(2-methoxybenzoyl)piperazin-1-yl]octyl]-5,5-dimethyl-2-thioxoimidazolidin-4-one | 4 | 607 |
| 798 | 3-(1,3-Dihydro-1-oxoisobenzofuran-5-yl)-1-[8-[4-[4-(dimethylamino)benzoyl]piperazin-1-yl]octyl]-5,5-dimethyl-2-thioxoimidazolidin-4-one | 4 | 620 |
| 799 | 1-[8-(4-Acetylpiperazin-1-yl)octyl]-3-(1,3-dihydro-1-oxo-isobenzofuran-5-yl)-5,5-dimethyl-2-thioxoimidazolidin-4-one | 4 | 515 |
| 800 | 3-(1,3-Dihydro-1-oxoisobenzofuran-5-yl)-5,5-dimethyl-1-[8-[4-(1-oxopropyl)piperazin-1-yl]octyl]-2-thioxo-imidazolidin-4-one | 4 | 529 |
| 801 | 1-[8-[4-(Cyclopropylcarbonyl)piperazin-1-yl]octyl]-3-(1,3-dihydro-1-oxoisobenzofuran-5-yl)-5,5-dimethyl-2-thioxo-imidazolidin-4-one | 4 | 541 |
| 802 | 1-[8-[4-(Cyclobutylcarbonyl)piperazin-1-yl]octyl]-3-(1,3-dihydro-1-oxoisobenzofuran-5-yl)-5,5-dimethyl-2-thioxo-imidazolidin-4-one | 4 | 555 |
| 803 | 3-(1,3-Dihydro-1-oxoisobenzofuran-5-yl)-5,5-dimethyl-1-[8-[4-[(thien-2-yl)carbonyl]piperazin-1-yl]octyl]-2-thioxo-imidazolidin-4-one | 4 | 583 |
| 804 | 3-(1,3-Dihydro-1-oxoisobenzofuran-5-yl)-5,5-dimethyl-1-[8-[4-[(thien-2-yl)acetyl]piperazin-1-yl]octyl]-2-thioxo-imidazolidin-4-one | 4 | 597 |
| 805 | 3-(1,3-Dihydro-1-oxoisobenzofuran-5-yl)-5,5-dimethyl-1-[8-[4-[(pyridin-4-yl)carbonyl]piperazin-1-yl]octyl]-2-thioxo-imidazolidin-4-one | 4 | 578 |
| 806 | 3-(1,3-Dihydro-1-oxoisobenzofuran-5-yl)-5,5-dimethyl-1-[8-[4-(methylsulfonyl)piperazin-1-yl]octyl]-2-thioxo-imidazolidin-4-one | 5 | 551 |
| 807 | 3-(1,3-Dihydro-1-oxoisobenzofuran-5-yl)-1-[8-[4-(ethylsulfonyl)piperazin-1-yl]octyl]-5,5-dimethyl-2-thioxo-imidazolidin-4-one | 5 | 565 |
| 808 | 3-(1,3-Dihydro-1-oxoisobenzofuran-5-yl)-5,5-dimethyl-1-[8-[4-(propylsulfonyl)piperazin-1-yl]octyl]-2-thioxo-imidazolidin-4-one | 5 | 579 |

TABLE 34-continued

Compounds of General Formula I According to the Invention, in which
V = Isobenzofuranone, W = Thiohydantoin, n = 8

| Example | Name | Synthesis Analogous to Example | ESI-MS |
|---|---|---|---|
| 809 | 3-(1,3-Dihydro-1-oxoisobenzofuran-5-yl)-5,5-dimethyl-2-thioxo-1-[8-[4-[(2,2,2-trifluoroethyl)-sulfonyl]piperazin-1-yl]-octyl]imidazolidin-4-one | 5 | 619 |
| 810 | 3-(1,3-Dihydro-1-oxoisobenzofuran-5-yl)-5,5-dimethyl-1-[8-[4-(phenylsulfonyl)piperazin-1-yl]octyl]-2-thioxo-imidazolidin-4-one | 5 | 613 |
| 811 | 4-[8-[3-(1,3-Dihydro-1-oxoisobenzofuran-5-yl)-5,5-dimethyl-4-oxo-2-thioxoimidazolidin-1-yl]octyl]-N-[3-(methylsulfanyl)phenyl]piperazine-1-carboxylic acid amide | 6 | 638 |
| 812 | 4-[8-[3-(1,3-Dihydro-1-oxoisobenzofuran-5-yl)-5,5-dimethyl-4-oxo-2-thioxoimidazolidin-1-yl]octyl]-N-(3-fluorophenyl)piperazine-1-carboxylic acid amide | 6 | 610 |
| 813 | 4-[8-[3-(1,3-Dihydro-1-oxoisobenzofuran-5-yl)-5,5-dimethyl-4-oxo-2-thioxoimidazolidin-1-yl]octyl)-N-ethylpiperazine-1-carbothioamide | 12 | 560 |
| 814 | 4-[8-[3-(1,3-Dihydro-1-oxoisobenzofuran-5-yl)-5,5-dimethyl-4-oxo-2-thioxoimidazolidin-1-yl]octyl]-N-propylpiperazine-1-carbothioamide | 12 | 574 |
| 815 | 4-[8-[3-(1,3-Dihydro-1-oxoisobenzofuran-5-yl)-5,5-dimethyl-4-oxo-2-thioxoimidazolidin-1-yl]octyl]-N-(prop-2-enyl)piperazine-1-carbothioamide | 12 | 572 |
| 816 | 4-[8-[3-(1,3-Dihydro-1-oxoisobenzofuran-5-yl)-5,5-dimethyl-4-oxo-2-thioxoimidazolidin-1-yl]octyl]-N-(phenylmethyl)piperazine-1-carbothioamide | 12 | 622 |
| 817 | 4-[8-[3-(1,3-Dihydro-1-oxoisoberzofuran-5-yl)-5,5-dimethyl-4-oxo-2-thioxoimidazolidin-1-yl]octyl]-N-(phenyl-piperazine-1-carbothioamide | 12 | 608 |
| 818 | S-Methyl 4-[8-[3-(1,3-dihydro-1-oxoisobenzofuran-5-yl)-5,5-dimethyl-4-oxo-2-thioxoimidazolidin-1-yl]octyl]-piperazine-1-carbothioate | 13 | 547 |
| 819 | S-Ethyl 4-[8-[3-(1,3-dihydro-1-oxoisobenzofuran-5-yl)-5,5-dimethyl-4-oxo-2-thioxoimidazolidin-1-yl]octyl]piperazine-1-carbothioate | 13 | 561 |
| 820 | 4-[8-[3-(1,3-Dihydro-1-oxoisobenzofuran-5-yl)-5,5-dimethyl-4-oxo-2-thioxoimidazolidin-1-yl]octyl]-N,N-diethylpiperazine-1-carboxylic acid amide | 14 | 572 |

TABLE 35

Compounds of General Formula I According to the Invention, in which
V = Methylbenzoxazinone, W = Thiohydantoin, n = 5

| Example | Name | Synthesis Analogous to Example | ESI-MS |
|---|---|---|---|
| 821 | 6-[4,4-Dimethyl-5-oxo-3-[5-[4-(methylsulfonyl)-piperazin-1-yl]pentyl]-2-thioxoimidazolidin-1-yl]-4-methyl-1H-2,3-benzoxazin-1-one | 5 | 536 |

TABLE 36

Compounds of General Formula I According to the Invention, in which
V = Methylbenzoxazinone, W = Thiohydantoin, n = 6

| Example | Name | Synthesis Analogous to Example | ESI-MS |
|---|---|---|---|
| 822 | 6-[4,4-Dimethyl-5-oxo-3-[6-[4-(methylsulfonyl)-piperazin-1-yl]hexyl]-2-thioxoimidazolidin-1-yl]-4-methyl-1H-2,3-benzoxazin-1-one | 5 | 550 |

TABLE 37

Compounds of General Formula I According to the Invention, in which V = Indanone, W = Thiohydantoin, n = 6

| Example | Name | Synthesis Analogous to Example | ESI-MS |
|---|---|---|---|
| 823 | 1-[6-(4-Acetylpiperazin-1-yl)hexyl]-3-(2,3-dihydro-1-oxo-1H-inden-5-yl)-5,5-dimethyl-2-thioxoimidazolidin-4-one | 4 | 485 |
| 824 | 3-(2,3-Dihydro-1-oxo-1H-inden-5-yl)-5,5-dimethyl-1-[6-[4-(2-methyl-1-oxopropyl)piperazin-1-yl]hexyl]-2-thioxoimidazolidin-4-one | 4 | 513 |
| 825 | 3-(2,3-Dihydro-1-oxo-1H-inden-5-yl)-5,5-dimethyl-1-[6-[4-[(thien-2-yl)carbonyl]piperazin-1-yl]hexyl]-2-thioxoimidazolidin-4-one | 4 | 553 |
| 826 | 3-(2,3-Dihydro-1-oxo-1H-inden-5-yl)-5,5-dimethyl-1-[6-[4-[(pyridin-4-yl)carbonyl]piperazin-1-yl]hexyl]-2-thioxoimidazolidin-4-one | 4 | 548 |
| 827 | 3-(2,3-Dihydro-1-oxo-1H-inden-5-yl)-5,5-dimethyl-1-[6-[4-(methylsulfonyl)piperazin-1-yl]hexyl]-2-thioxoimidazolidin-4-one | 5 | 521 |
| 828 | 3-(2,3-Dihydro-1-oxo-1H-inden-5-yl)-5,5-dimethyl-1-[6-[4-(propylsulfonyl)piperazin-1-yl]hexyl]-2-thioxoimidazolidin-4-one | 5 | 549 |
| 829 | 4-[6-[3-(2,3-Dihydro-1-oxo-1H-inden-5-yl)-5,5-dimethyl-4-oxo-2-thioxoimidazolidin-1-yl]hexyl]-N-ethylpiperazine-1-carbothioamide | 12 | 530 |
| 830 | S-Methyl 4-[6-[3-(2,3-dihydro-1-oxo-1H-inden-5-yl)-5,5-dimethyl-4-oxo-2-thioxoimidazolidin-1-yl]hexyl]piperazine-1-carbothioate | 13 | 517 |

The entries disclosures of all applications, patents and publications, cited herein and of corresponding Germany Application No. 101 59 035.0, filed Nov. 23, 2001, and Germany Application No. 102 38 742.7 of Aug. 19, 2002, and U.S. Provisional Application Serial No. 406,650, filed Aug. 29, 2002 and U.S. Provisional Application No. 60/383,785, filed May 30, 2002 are incorporated by references herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula I, in which

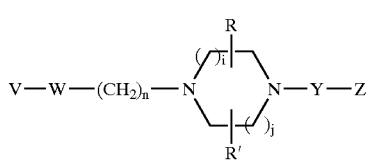

I

V stands for a substituted, aromatic radical of formula II,

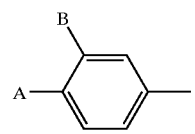

II in which
A stands for an acetyl group, an acetylamino group, a cyano group, a nitro group, a trifluoromethyl group, or a halogen,
B stands for a hydrogen atom, a halogen or a trifluoromethyl group, or
A and B together stand for a cyclic group of formula III or IV that is bonded to the aromatic ring, whereby E stands for a methylene group or an oxygen atom,

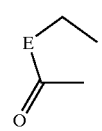

III

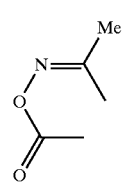

IV

W stands for a group of formula V,

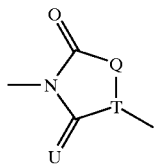

in which
T is carbon or nitrogen,
if T is carbon, a double bond is present between Q and T, and Q means a group =C(CH$_3$)— and U means oxygen, and n is one of the integral values 1, 2, 3, 4, 5, 6, 7, or 8, or
if T is nitrogen, a single bond is present between Q and T, and Q means a group —(CH$_3$)$_2$— and U means sulfur, and n is one of the integral values 2, 3, 4, 5, 6, 7, or 8,
i and j, independently of one another, stand for the values 1 and 2, whereby i+j is 2 or 3,
R and R', independently of one another, are a hydrogen atom or a methyl group,
Y stands for a bond between the heterocyclic nitrogen and Z, for a carbonyl group —C(O)—, for a sulfonyl group —S(O)$_2$—, for an iminocarbonyl group —C(O)N(Z')—, for an iminosulfonyl group —S(O)$_2$N(Z')—, for an imino(thioxomethyl) group —C(S)N(Z')—, for an oxycarbonylimino(thioxomethyl) group —C(S)N(Z')C(O)O—, for an oxycarbonyl group —C(O)O—, or for a sulfanylcarbonyl group —C(O)S—, and
Z and Z', independently of one another, stand for a hydrogen atom, a branched or unbranched C$_1$–C$_8$-alkyl group, a C$_3$–C$_6$-cycloalkyl group that is optionally substituted with a phenyl radical, a (C$_3$–C$_6$-cycloalkyl)-C$_1$–C$_4$-alkylene group, a branched or unbranched C$_2$–C$_5$-alkenyl group, a C$_3$–C$_5$-alkynyl group, a C$_1$–C$_4$-alkoxy group, a cyano group, a phenylsulfanyl group, a hydroxy-C$_1$–C$_4$-alkylene group, a (2-methoxyethoxy)methyl group, a [2-(2-methoxyethoxy)ethoxy]methyl group, a 2-(2-methoxyethoxy)ethyl group, a 2-[2-(2-methoxyethoxy)ethoxy]ethyl group, a C$_1$–C$_4$-alkoxy-C$_1$–C$_4$-alkylene group, a C$_1$–C$_4$-alkoxycarbonyl-C$_1$–C$_4$-alkylene group, an adamantyl group, a trichloroacetyl group; an aryl, heteroaryl, heterocyclyl, aryl-C$_1$–C$_4$-alkylene, heteroaryl-C$_1$–C$_4$-alkylene, aryloxy-C$_1$–C$_4$-alkylene, heteroaryloxy-C$_1$–C$_4$-alkylene, or aryl-C$_1$–C$_4$-alkylenoxy-C$_1$–C$_4$-alkylene group that is unsubstituted or that is substituted with up to three branched or unbranched C$_1$–C$_4$-alkyl, C$_2$–C$_6$-alkenyl, C$_3$–C$_6$-cycloalkyl, phenyl, cyano, halogen, methoxy, ethoxy, phenoxy, benzyloxy, methylsulfanyl, ethylsulfanyl, benzylsulfanyl, phenylsulfanyl, dimethylamino, acetylamino, trifluoromethyl, trifluoromethoxy, trifluoromethylsulfanyl, acetyl, (1-iminoethyl) or nitro groups, or a radical of formula C$_p$F$_q$H$_r$ with p=1, 2, 3, 4, q>1 and q+r=2p+1,
or a pharmacologically compatible salt thereof.

2. A compound of formula I according to claim 1, wherein i=j=1.

3. A compound of formula I according to claim 1, wherein R and R' mean H.

4. A compound of formula I according to claim 1, wherein T=carbon.

5. A compound of formula I according to claim 1, wherein T=nitrogen.

6. A compound of formula I according to claim 4, wherein
i=j=1,
n=1, 2, 3, 4, 5, 6, 7 or 8,
R and R' are hydrogen,
A stands for an acetyl group, an acetylamino group, a cyano group, a nitro group, a trifluoromethyl group or a halogen, and
B stands for a hydrogen atom, a halogen or a trifluoromethyl group, or
A and B together stand for a cyclic group of formula III or IV that is bonded to the aromatic ring, whereby E stands for a methylene group or an oxygen atom

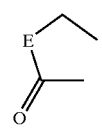

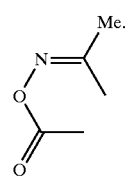

7. A compound of formula I according to claim 5, wherein
i=j=1,
n=2, 3, 4, 5, 6, 7 or 8,
R and R' are hydrogen,
A stands for an acetyl group, an acetylamino group, a cyano group, a nitro group, a trifluoromethyl group or a halogen, and
B stands for a hydrogen atom, a halogen or a trifluoromethyl group, or
A and B together stand for a cyclic group of formula III or IV that is bonded to the aromatic ring, whereby E stands for a methylene group or an oxygen atom

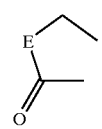

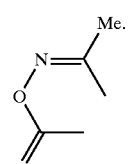

8. A compound according to claim 1, selected from the group consisting of:
1,1-Dimethylethyl 4-[5-[1-[4-cyano-3-(trifluoromethyl)phenyl]-2,5-dihydro-4-methyl-2,5-dioxo-1H-pyrrol-3-yl]pentyl]piperazine-1-carboxylate;
4-[2,5-Dihydro-3-methyl-4-[5-[4-[2-(methylsulfanyl)phenyl]piperazin-1-yl]pentyl]-2,5-dioxo-1H-pyrrol-1-yl]-2-(trifluoromethyl)benzonitrile;
4-[3-[5-[4-(4-Cyanobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-[4-[(3-Fluorophenyl)sulfonyl]piperazin-1-yl]pentyl]-2,5-dihydro-4-methyl-2,5-dioxo-1H-pyrrol-1-yl]-2-(trifluoromethyl)benzonitrile;

4-[5-[1-[4-Cyano-3-(trifluoromethyl)phenyl]-2,5-dihydro-4-methyl-2,5-dioxo-1H-pyrrol-3-yl]pentyl]-N-[4-(dimethylamino)phenyl]piperazine-1-carboxamide;

4-[2,5-Dihydro-3-methyl-4-[3-[4-(1-methylethylsulfonyl)piperazin-1-yl]propyl]-2,5-dioxo-1H-pyrrol-1-yl]-2-(trifluoromethyl)benzonitrile;

4-[2,5-Dihydro-3-methyl-4-[[4-(1-methylethylsulfonyl)piperazin-1-yl]methyl]-2,5-dioxo-1H-pyrrol-1-yl]-2-(trifluoromethyl)benzonitrile;

4-[2,5-Dihydro-3-methyl-4-[7-[4-(1-methylethylsulfonyl)piperazin-1-yl]heptyl]-2,5-dioxo-1H-pyrrol-1-yl]-2-(trifluoromethyl)benzonitrile;

1,1-Dimethylethyl 4-[5-[3-(1,3-dihydro-1-oxoisobenzofuran-5-yl)-5,5-dimethyl-4-oxo-2-thioxoimidazolidin-1-yl]pentyl]piperazine-1-carboxylate;

4-[5-[3-(1,3-Dihydro-1-oxoisobenzofuran-5-yl)-5,5-dimethyl-4-oxo-2-thioxoimidazolidin-1-yl]pentyl]-N-ethylpiperazine-1-carbothioamide;

S-Methyl 4-[5-[3-(1,3-dihydro-1-oxoisobenzofuran-5-yl)-5,5-dimethyl-4-oxo-2-thioxoimidazolidin-1-yl]pentyl]piperazine-1-carbothioate;

4-[5-[3-(1,3-Dihydro-1-oxoisobenzofuran-5-yl)-5,5-dimethyl-4-oxo-2-thioxoimidazolidin-1-yl]pentyl]-N,N-diethylpiperazine-1-carboxamide;

4-[3-[2-[4-(2-Methoxybenzoyl)piperazin-1-yl]ethyl]-4,4-dimethyl-5-oxo-2-thioxoimidazolidin-1-yl]-2-(trifluoromethyl)benzonitrile;

4-[3-[(4-Acetylpiperazin-1-yl)methyl]-2,5-dihydro-4-methyl-2,5-dioxo-1H-pyrrol-1-yl]-2-(trifluoromethyl)benzonitrile;

4-[2,5-Dihydro-3-[[4-(methoxyacetyl)piperazin-1-yl]methyl]-4-methyl-2,5-dioxo-1H-pyrrol-1-yl]-2-(trifluoromethyl)benzonitrile;

4-[2,5-Dihydro-3-[4-[[(2-methoxyethoxy)acetyl]piperazin-1-yl]methyl]-4-methyl-2,5-dioxo-1H-pyrrol-1-yl]-2-(trifluoromethyl)benzonitrile;

4-[2,5-Dihydro-3-[[4-[[2-(2-methoxyethoxy)ethoxy]acetyl]piperazin-1-yl]methyl]-4-methyl-2,5-dioxo-1H-pyrrol-1-yl]-2-(trifluoromethyl)benzonitrile;

4-[2,5-Dihydro-3-[[4-(2-methoxybenzoyl)piperazin-1-yl]methyl]-4-methyl-2,5-dioxo-1H-pyrrol-1-yl]-2-(trifluoromethyl)benzonitrile;

4-[2,5-Dihydro-3-methyl-4-[[4-(methylsulfonyl)piperazin-1-yl]methyl]-2,5-dioxo-1H-pyrrol-1-yl]-2-(trifluoromethyl)benzonitrile;

4-[3-[[4-(Ethylsulfonyl)piperazin-1-yl]methyl]-2,5-dihydro-4-methyl-2,5-dioxo-1H-pyrrol-1-yl]-2-(trifluoromethyl)benzonitrile;

4-[2,5-Dihydro-3-[[4-(2-methoxyethyl)sulfonyl]-piperazin-1-yl]methyl]-4-methyl-2,5-dioxo-1H-pyrrol-1-yl]-2-(trifluoromethyl)benzonitrile;

4-[2,5-Dihydro-3-[[4-[[2-(2-methoxyethoxy)ethyl]sulfonyl]piperazin-1-yl]methyl]-4-methyl-2,5-dioxo-1H-pyrrol-1-yl]-2-(trifluoromethyl)benzonitrile;

4-[2,5-Dihydro-3-methyl-2,5-dioxo-4-[[4-(phenylsulfonyl)piperazin-1-yl]methyl]-1H-pyrrol-1-yl]-2-(trifluoromethyl)benzonitrile;

4-[3-[2-(4-Acetylpiperazin-1-yl)ethyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[2-(4-(1-oxopropyl)piperazin-1-yl)ethyl]-1H-pyrrol-1-yl]-2-(trifluoromethyl)benzonitrile;

4-[3-[2-[4-(Cyclopropylcarbonyl)piperazin-1-yl]ethyl]-2,5-dihydro-4-methyl-2,5-dioxo-1H-pyrrol-1-yl]-2-(trifluoromethyl)benzonitrile;

4-[2,5-Dihydro-3-[2-[4-(methoxyacetyl)piperazin-1-yl]ethyl]-4-methyl-2,5-dioxo-1H-pyrrol-1-yl]-2-(trifluoromethyl)benzonitrile;

4-[2,5-Dihydro-3-[2-[4-(3-methoxy-1-oxopropyl)piperazin-1-yl]ethyl]-4-methyl-2,5-dioxo-1H-pyrrol-1-yl]-2-(trifluoromethyl)benzonitrile;

4-[2,5-Dihydro-3-[2-[4-[(2-methoxyethoxy)acetyl]piperazin-1-yl]ethyl]-4-methyl-2,5-dioxo-1H-pyrrol-1-yl]-2-(trifluoromethyl)benzonitrile;

4-[2,5-Dihydro-3-[2-[4-[[2-(2-methoxyethoxy)ethoxy]acetyl]piperazin-1-yl]ethyl]-4-methyl-2,5-dioxo-1H-pyrrol-1-yl]-2-(trifluoromethyl)benzonitrile;

4-[2,5-Dihydro-3-[2-[4-(2-methoxybenzoyl)piperazin-1-yl]ethyl]-4-methyl-2,5-dioxo-1H-pyrrol-1-yl]-2-(trifluoromethyl)benzonitrile;

4-[2,5-Dihydro-3-methyl-4-[2-[4-(methylsulfonyl)piperazin-1-yl]ethyl]-2,5-dioxo-1H-pyrrol-1-yl]-2-(trifluoromethyl)benzonitrile;

4-[3-[2-[4-(Ethylsulfonyl)piperazin-1-yl]ethyl]-2,5-dihydro-4-methyl-2,5-dioxo-1H-pyrrol-1-yl]-2-(trifluoromethyl)benzonitrile;

4-[3-[2-[4-(Cyclopropylsulfonyl)piperazin-1-yl]ethyl]-2,5-dihydro-4-methyl-2,5-dioxo-1H-pyrrol-1-yl]-2-(trifluoromethyl)benzonitrile;

4-[2,5-Dihydro-3-[2-[4-(2-methoxyethyl)sulfonyl]piperazin-1-yl]ethyl]-4-methyl-2,5-dioxo-1H-pyrrol-1-yl]-2-(trifluoromethyl)benzonitrile;

4-[2,5-Dihydro-3-[2-[4-[[2-(2-methoxyethoxy)ethyl]sulfonyl]piperazin-1-yl]ethyl]-4-methyl-2,5-dioxo-1H-pyrrol-1-yl]-2-(trifluoromethyl)benzonitrile;

4-[2,5-Dihydro-3-[2-[4-[[2-[2-(2-methoxyethoxy)ethoxy]ethyl]sulfonyl]-piperazin-1-yl]ethyl]-4-methyl-2,5-dioxo-1H-pyrrol-1-yl]-2-(trifluoromethyl)benzonitrile;

4-[2,5-Dihydro-3-methyl-2,5-dioxo-4-[2-[4-(phenylsulfonyl)piperazin-1-yl]ethyl]-1H-pyrrol-1-yl]-2-(trifluoromethyl)benzonitrile;

4-[2,5-Dihydro-3-methyl-2,5-dioxo-4-[2-[4-[(phenylmethyl)sulfonyl]piperazin-1-yl]ethyl]-1H-pyrrol-1-yl]-2-(trifluoromethyl)benzonitrile;

4-[2,5-Dihydro-3-methyl-4-[2-[4-[(1-methyl-1H-imidazol-4-yl)sulfonyl]piperazin-1-yl]ethyl]-2,5-dioxo-1H-pyrrol-1-yl]-2-(trifluoromethyl)benzonitrile;

4-[2-[1-[4-Cyano-3-(trifluoromethyl)phenyl]-2,5-dihydro-4-methyl-2,5-dioxo-1H-pyrrol-3-yl]ethyl]-N-(1-methylethyl)piperazine-1-carboxamide;

4-[2-[1-[4-Cyano-3-(trifluoromethyl)phenyl]-2,5-dihydro-4-methyl-2,5-dioxo-1H-pyrrol-3-yl]ethyl]-N-ethylpiperazine-1-carbothioamide;

Methyl 4-[2-[1-[4-cyano-3-(trifluoromethyl)phenyl]-2,5-dihydro-4-methyl-2,5-dioxo-1H-pyrrol-3-yl]ethyl]piperazine-1-carboxylate;

S-Methyl 4-[2-[1-[4-cyano-3-(trifluoromethyl)phenyl]-2,5-dihydro-4-methyl-2,5-dioxo-1H-pyrrol-3-yl]ethyl]piperazine-1-carbothioate;

4-[2-[1-[4-Cyano-3-(trifluoromethyl)phenyl]-2,5-dihydro-4-methyl-2,5-dioxo-1H-pyrrol-3-yl]ethyl]-N,N-dimethylpiperazine-1-sulfonamide;

4-[3-[3-(4-Acetylpiperazin-1-yl)propyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[3-(4-(1-oxopropyl)piperazin-1-yl)propyl]-1H-pyrrol-1-yl]-2-(trifluoromethyl)benzonitrile;

4-[3-[3-[4-(Cyclopropylcarbonyl)piperazin-1-yl]propyl]-2,5-dihydro-4-methyl-2,5-dioxo-1H-pyrrol-1-yl]-2-(trifluoromethyl)benzonitrile;

4-[2,5-Dihydro-3-[3-[4-(methoxyacetyl)piperazin-1-yl]propyl]-4-methyl-2,5-dioxo-1H-pyrrol-1-yl]-2-(trifluoromethyl)benzonitrile;

4-[2,5-Dihydro-3-[3-[4-(3-methoxy-1-oxopropyl)piperazin-1-yl]propyl]-4-methyl-2,5-dioxo-1H-pyrrol-1-yl]-2-(trifluoromethyl)benzonitrile;

4-[2,5-Dihydro-3-[3-[4-[(2-methoxyethoxy)acetyl]piperazin-1-yl]propyl]-4-methyl-2,5-dioxo-1H-pyrrol-1-yl]-2-(trifluoromethyl)benzonitrile;

4-[2,5-Dihydro-3-[3-[4-[[2-(2-methoxyethoxy)ethoxy]acetyl]piperazin-1-yl]propyl]-4-methyl-2,5-dioxo-1H-pyrrol-1-yl]-2-(trifluoromethyl)benzonitrile;

4-[2,5-Dihydro-3-[3-[4-(2-methoxybenzoyl)piperazin-1-yl]propyl]-4-methyl-2,5-dioxo-1H-pyrrol-1-yl]-2-(trifluoromethyl)benzonitrile;

4-[2,5-Dihydro-3-methyl-4-[3-[4-(methylsulfonyl)piperazin-1-yl]propyl]-2,5-dioxo-1H-pyrrol-1-yl]-2-(trifluoromethyl)benzonitrile;

4-[3-[3-[4-(Ethylsulfonyl)piperazin-1-yl]propyl]-2,5-dihydro-4-methyl-2,5-dioxo-1H-pyrrol-1-yl]-2-(trifluoromethyl)benzonitrile;

4-[3-[3-[4-(Cyclopropylsulfonyl)piperazin-1-yl]propyl]-2,5-dihydro-4-methyl-2,5-dioxo-1H-pyrrol-1-yl]-2-(trifluoromethyl)benzonitrile;

4-[2,5-Dihydro-3-[3-[4-(2-methoxyethyl)sulfonyl]piperazin-1-yl]propyl]-4-methyl-2,5-dioxo-1H-pyrrol-1-yl]-2-(trifluoromethyl)benzonitrile;

4-[2,5-Dihydro-3-[3-[4-[[2-(2-methoxyethoxy)ethyl]sulfonyl]piperazin-1-yl]propyl]-4-methyl-2,5-dioxo-1H-pyrrol-1-yl]-2-(trifluoromethyl)benzonitrile;

4-[2,5-Dihydro-3-[3-[4-[[2-[2-(2-methoxyethoxy)ethoxy]ethyl]-sulfonyl]piperazin-1-yl]propyl]-4-methyl-2,5-dioxo-1H-pyrrol-1-yl]-2-(trifluoromethyl)benzonitrile;

4-[2,5-Dihydro-3-methyl-2,5-dioxo-4-[3-[4-(phenyl-sulfonyl)piperazin-1-yl]propyl-1H-pyrrol-1-yl]-2-(trifluoromethyl)benzonitrile;

4-[2,5-Dihydro-3-methyl-2,5-dioxo-4-[3-[4-[(phenylmethyl)sulfonyl]piperazin-1-yl]propyl]-1H-pyrrol-1-yl]-2-(trifluoromethyl)benzonitrile;

4-[2,5-Dihydro-3-methyl-4-[3-[4-[(1-methyl-1H-imidazol-4-yl)sulfonyl]-piperazin-1-yl]propyl]-2,5-dioxo-1H-pyrrol-1-yl]-2-(trifluoromethyl)benzonitrile;

4-[3-[1-[4-Cyano-3-(trifluoromethyl)phenyl]-2,5-dihydro-4-methyl-2,5-dioxo-1H-pyrrol-3-yl]propyl]-N-(1-methylethyl)-piperazine-1-carboxamide;

4-[3-[1-[4-Cyano-3-(trifluoromethyl)phenyl]-2,5-dihydro-4-methyl-2,5-dioxo-1H-pyrrol-3-yl]propyl]-N-ethylpiperazine-1-carbothioamide;

Methyl 4-[3-[1-[4-cyano-3-(trifluoromethyl)phenyl]-2,5-dihydro-4-methyl-2,5-dioxo-1H-pyrrol-3-yl]propyl]piperazine-1-carboxylate;

S-Methyl 4-[3-[1-[4-cyano-3-(trifluoromethyl)phenyl]-2,5-dihydro-4-methyl-2,5-dioxo-1H-pyrrol-3-yl]propyl]piperazine-1-carbothioate;

4-[3-[1-[4-Cyano-3-(trifluoromethyl)phenyl]-2,5-dihydro-4-methyl-2,5-dioxo-1H-pyrrol-3-yl]propyl]-N,N-dimethylpiperazine-1-sulfonamide;

1,1-Dimethylethyl-4-[4-[1-[4-cyano-3-(trifluoromethyl)phenyl]-2,5-dihydro-4-methyl-2,5-dioxo-1H-pyrrol-3-yl]butyl]piperazine-1-carboxylate;

4-[2,5-Dihydro-3-methyl-4-[4-[4-[2-(methylsulfanyl)phenyl]piperazin-1-yl]butyl]-2,5-dioxo-1H-pyrrol-1-yl]-2-(trifluoromethyl)benzonitrile;

4-[3-[4-[4-(3,5-Dichloropyridin-4-yl)piperazin-1-yl]butyl]-2,5-dihydro-4-methyl-dioxo-1H-pyrrol-1-yl]-2-(trifluoromethyl)benzonitrile;

4-[3-[4-[4-(Cyclopentylacetyl)piperazin-1-yl]butyl]-2,5-dihydro-4-methyl-2,5-dioxo-1H-pyrrol-1-yl]-2-(trifluoromethyl)benzonitrile;

4-[3-[4-[4-(2,6-Difluorobenzoyl)piperazin-1-yl]butyl]-2,5-dihydro-4-methyl-2,5-dioxo-1H-pyrrol-1-yl]-2-(trifluoromethyl)benzonitrile;

4-[3-[4-[4-(2,6-Dichlorobenzoyl)piperazin-1-yl]butyl]-2,5-dihydro-4-methyl-2,5-dioxo-1H-pyrrol-1-yl]-2-(trifluoromethyl)benzonitrile;

4-[3-[4-(4-(3-Fluorobenzoyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-[4-[4-(3-methoxybenzoyl)piperazin-1-yl]butyl]-4-methyl-2,5-dioxo-1H-pyrrol-1-yl]-2-(trifluoromethyl)benzonitrile;

4-[2,5-Dihydro-3-methyl-4-[4-[4-(3-methylbenzoyl)piperazin-1-yl]butyl]-2,5-dioxo-1H-pyrrol-1-yl]-2-(trifluoromethyl)benzonitrile;

4-[3-[4-[4-(4-Fluorobenzoyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl[4-[4-[(naphthalen-1-yl)carbonyl]piperazin-1-yl]butyl]-2,5-dioxo-1H-pyrrol-1-yl]-2-(trifluoromethyl)benzonitrile;

4-[2,5-Dihydro-3-methyl-4-[4-[4-[(naphthalen-2-yl)-carbonyl]piperazin-1-yl]butyl]-2,5-dioxo-1H-pyrrol-1-yl]-2-(trifluoromethyl)benzonitrile;

4-[3-[4-[4-(3-Cyanobenzoyl)piperazin-1-yl]butyl]-2,5-dihydro-4-methyl-2,5-dioxo-1H-pyrrol-1-yl]-2-(trifluoromethyl)benzonitrile;

4-[3-[4-[4-(Cyclohexylcarbonyl)piperazin-1-yl]butyl]-2,5-dihydro-4-methyl-2,5-dioxo-1H-pyrrol-1-yl]-2-(trifluoromethyl)benzonitrile;

4-[3-[4-[4-[(Furan-2-yl)carbonyl]piperazin-1-yl]butyl]-2,5-dihydro-4-methyl-2,5-dioxo-1H-pyrrol-1-yl]-2-(trifluoromethyl)benzonitrile;

4-[3-[4-[4-(Cyclopentylcarbonyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-4-[4-[4-[(5-methylisoxazol-3-yl)carbonyl]piperazin-1-yl]butyl]-2,5-dioxo-1H-pyrrol-1-yl]-2-(trifluoromethyl)benzonitrile;

4-[2,5-Dihydro-3-methyl-2,5-dioxo-4-[4-[4-(phenylacetyl)piperazin-1-yl]butyl]-1H-pyrrol-1-yl]-2-(trifluoromethyl)benzonitrile;

4-[2,5-Dihydro-3-[4-[4-(2-methoxybenzoyl)piperazin-1-yl]butyl]-4-methyl-2,5-dioxo-1H-pyrrol-1-yl]-2-(trifluoromethyl)benzonitrile;

4-[2,5-Dihydro-3-[4-[4-(methoxyacetyl)piperazin-1-yl]butyl]-4-methyl-2,5-dioxo-1H-pyrrol-1-yl]-2-(trifluoromethyl)benzonitrile;

4-[3-[4-[4-(2-Chlorobenzoyl)piperazin-1-yl]butyl]-2,5-dihydro-4-methyl-2,5-dioxo-1H-pyrrol-1-yl]-2-(trifluoromethyl)benzonitrile;

4-[3-[4-[4-(2-Fluorobenzoyl)piperazin-1-yl]butyl]-2,5-dihydro-4-methyl-2,5-dioxo-1H-pyrrol-1-yl]-2-(trifluoromethyl)benzonitrile;

4-[3-[4-(4-Benzoylpiperazin-1-yl)butyl]-2,5-dihydro-4-methyl-2,5-dioxo-1H-pyrrol-1-yl]-2-(trifluoromethyl)benzonitrile;

4-[3-[4-[4-(Cyclobutylcarbonyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[4-[4-[(pyridin-3-yl)carbonyl]piperazin-1-yl]butyl]-1H-pyrrol-1-yl]-2-(trifluoromethyl)benzonitrile;

4-[2,5-Dihydro-3-methyl-2,5-dioxo-4-[4-[4-[(pyridin-4-yl)carbonyl]piperazin-1-yl]butyl]-1H-pyrrol-1-yl]-2-(trifluoromethyl)benzonitrile;

4-[3-[4-[4-[4-(Dimethylamino)benzoyl]piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[4-[4-[(phenylsulfanyl)acetyl]piperazin-1-yl]butyl]-1H-pyrrol-1-yl]-2-(trifluoromethyl)benzonitrile;

4-[2,5-Dihydro-3-methyl-2,5-dioxo-4-[4-[4-(phenoxyacetyl)piperazin-1-yl]butyl]-1H-pyrrol-1-yl)-2-(trifluoromethyl)benzonitrile;

4-[2,5-Dihydro-3-methyl-2,5-dioxo-4-[4-[4-[(thien-2-yl)carbonyl]piperazin-1-yl]butyl]-1H-pyrrol-1-yl]-2-(trifluoromethyl)benzonitrile;

4-[2,5-Dihydro-3-methyl-2,5-dioxo-4-[4-[4-(3-phenyl-1-oxopropyl)piperazin-1-yl]butyl]-1H-pyrrol-1-yl]-2-(trifluoromethyl)benzonitrile;

4-[3-[4-[4-[(1,3-Benzodioxol-5-yl)carbonyl]piperazin-1-yl]butyl]-2,5-dihydro-4-methyl-2,5-dioxo-1H-pyrrol-1-yl]-2-(trifluoromethyl)benzonitrile;

4-[2,5-Dihydro-3-[4-[4-[(4-methoxyphenyl)acetyl]piperazin-1-yl]butyl]-4-methyl-2,5-dioxo-1H-pyrrol-1-yl]-2-(trifluoromethyl)benzonitrile;

4-[2,5-Dihydro-3-methyl-4-[4-[4-(2-methylbenzoyl)piperazin-1-yl]butyl]-2,5-dioxo-1H-pyrrol-1-yl]-2-(trifluoromethyl)benzonitrile;

4-[3-[4-[4-(4-Chlorobenzoyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[4-[4-[(thien-2-yl)acetyl]piperazin-1-yl]butyl]-1H-pyrrol-1-yl]-2-(trifluoromethyl)benzonitrile;

4-[3-[4-[4-(3-Chlorobenzoyl)piperazin-1-yl]butyl]-2,5-dihydro-4-methyl-2,5-dioxo-1H-pyrrol-1-yl]-2-(trifluoromethyl)benzonitrile;

4-[3-[4-[4-(4-Cyanobenzoyl)piperazin-1-yl]butyl]-2,5-dihydro-4-methyl-2,5-dioxo-1H-pyrrol-1-yl]-2-(trifluoromethyl)benzonitrile;

4-[2,5-Dihydro-3-[4-[4-(3-methoxy-1-oxopropyl)piperazin-1-yl]butyl]-4-methyl-2,5-dioxo-1H-pyrrol-1-yl]-2-(trifluoromethyl)benzonitrile;

4-[2,5-Dihydro-3-[4-[4-[(2-methoxyethoxy)acetyl]piperazin-1-yl]butyl]-4-methyl-2,5-dioxo-1H-pyrrol-1-yl]-2-(trifluoromethyl)benzonitrile;

4-[2,5-Dihydro-3-[4-[4-[[2-(2-methoxyethoxy)ethoxy]acetyl]piperazin-1-yl]butyl]-4-methyl-2,5-dioxo-1H-pyrrol-1-yl]-2-(trifluoromethyl)benzonitrile;

4-[4-[4-[4-(Cyclopropylsulfonyl)piperazin-1-yl]butyl]-2,5-dihydro-3-methyl-2,5-dioxo-1H-pyrrol-1-yl]-2-(trifluoromethyl)benzonitrile;

4-[2,5-Dihydro-3-[4-[4-[(2-methoxyethyl)sulfonyl]piperazin-1-yl]butyl]-4-methyl-2,5-dioxo-1H-pyrrol-1-yl]-2-(trifluoromethyl)benzonitrile;

4-[2,5-Dihydro-3-[4-[4-[[2-(2-methoxyethoxy)ethyl]sulfonyl]piperazin-1-yl]butyl]-4-methyl-2,5-dioxo-1H-pyrrol-1-yl]-2-(trifluoromethyl)benzonitrile;

4-[2,5-Dihydro-3-[4-[4-[[2-[2-(2-methoxyethoxy)ethoxy]-ethyl]sulfonyl]piperazin-1-yl]butyl]-4-methyl-2,5-dioxo-1H-pyrrol-1-yl]-2-(trifluoromethyl)benzonitrile;

4-[1-[4-Cyano-3-(trifluoromethyl)phenyl]-2,5-dihydro-4-methyl-2,5-dioxo-1H-pyrrol-3-yl]butyl]-N,N-dimethylpiperazine-1-sulfonamide;

4-[2,5-Dihydro-3-methyl-2,5-dioxo-4-[4-[4-(phenylsulfonyl)piperazin-1-yl]butyl]-1H-pyrrol-1-yl]-2-(trifluoromethyl)benzonitrile;

4-[2,5-Dihydro-3-methyl-4-[4-[4-(methylsulfonyl)piperazin-1-yl]butyl]-2,5-dioxo-1H-pyrrol-1-yl]-2-(trifluoromethyl)benzonitrile;

4-[2,5-Dihydro-3-methyl-4-[4-[4-[(4-methylphenyl)sulfonyl]piperazin-1-yl]butyl]-2,5-dioxo-1H-pyrrol-1-yl]-2-(trifluoromethyl)benzonitrile;

N-[4-[[4-[4-[1-[4-Cyano-3-(trifluoromethyl)phenyl]-2,5-dihydro-4-methyl-2,5-dioxo-1H-pyrrol-3-yl]butyl]piperazin-1-y]sulfonyl]phenyl]acetamide;

4-[3-[4-[4-[(4-Chlorophenyl)sulfonyl]piperazin-1-yl]butyl]-2,5-dihydro-4-methyl-2,5-dioxo-1H-pyrrol-1-yl]-2-(trifluoromethyl)benzonitrile;

4-[3-[4-[4-[(4-Cyanophenyl)sulfonyl]piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-4-[4-[4-[(naphthalen-2-yl)sulfonyl]piperazin-1-yl]butyl]-2,5-dioxo-1H-pyrrol-1-yl]-2-(trifluoromethyl)benzonitrile;

4-[3-[4-[4-[(Quinolin-8-yl)sulfonyl]piperazin-1-yl]butyl]-2,5-dihydro-4-methyl-2,5-dioxo-1H-pyrrol-1-yl]-2-(trifluoromethyl)benzonitrile;

4-[3-[4-[4-[(2-Cyanophenyl)sulfonyl]piperazin-1-yl]butyl]-2,5-dihydro-4-methyl-2,5-dioxo-1H-pyrrol-1-yl]-2-(trifluoromethyl)benzonitrile;

4-(3-[4-[4-[(3-Cyanophenyl)sulfonyl]piperazin-1-yl]butyl]-2,5-dihydro-4-methyl-2,5-dioxo-1H-pyrrol-1-yl]-2-(trifluoromethyl)benzonitrile;

4-[3-[4-[4-[(3,5-Dimethylisoxazol-4-yl)sulfonyl]piperazin-1-yl]butyl]-2,5-dihydro-4-methyl-2,5-dioxo-1H-pyrrol-1-yl]-2-(trifluoromethyl)benzonitrile;

4-[3-[4-[4-[(5-Chloro-1,3-dimethyl-1H-pyrazol-4-yl)sulfonyl]piperazin-1-yl]butyl]-2,5-dihydro-4-methyl-2,5-dioxo-1H-pyrrol-1-yl]-2-(trifluoromethyl)benzonitrile;

4-[2,5-Dihydro-3-methyl-4-[4-[4-[(1-methyl-1H-imidazol-4-yl)sulfonyl]-piperazin-1-yl]butyl]-2,5-dioxo-1H-pyrrol-1-yl]-2-(trifluoromethyl)benzonitrile;

4-[3-[4-[4-(Butylsulfonyl)piperazin-1-yl]butyl]-2,5-dihydro-4-methyl-2,5-dioxo-1H-pyrrol-1-yl]-2-(trifluoromethyl)benzonitrile;

4-[4-[1-[4-Cyano-3-(trifluoromethyl)phenyl]-2,5-dihydro-4-methyl-2,5-dioxo-1H-pyrrol-3-yl]butyl]-N-phenylpiperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-(naphthalen-1-yl)piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-naphthalen-2-yl)piperazine-1-carboxamide;

N-(2-Chlorophenyl)-4-[4-[1-[4-cyano-3-(trifluoromethyl)phenyl]-2,5-dihydro-4-methyl-2,5-dioxo-1H-pyrrol-3-yl]butyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-[2-(trifluoromethyl)phenyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-(3-methoxyphenyl)piperazine-1-carboxamide;

N-(4-Chlorophenyl)-4-[4-[1-[4-cyano-3-(trifluoromethyl)phenyl]-2,5-dihydro-4-methyl-2,5-dioxo-1H-pyrrol-3-yl]butyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-(4-phenoxyphenyl)piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-[4-(methylsulfanyl)phenyl]piperazine-1-carboxamide;

N-[(1,1'-Biphenyl)-2-yl)-4-[1-[4-cyano-3-(trifluoromethyl)phenyl]-2,5-dihydro-4-methyl-2,5-dioxo-1H-pyrrol-3-yl]butyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-(2,5-dimethoxyphenyl)piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-[2-(1-methylethyl)phenyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-(2,4,6-trimethylphenyl)piperazine-1-carboxamide;

(R)-4-[4-[1-[4-Cyano-3-(trifluoromethyl)phenyl]-2,5-dihydro-4-methyl-2,5-dioxo-1H-pyrrol-3-yl]butyl]-N-(1-phenylethyl)piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-[2-(1,1-dimethylethyl)phenyl]piperazine-1-carboxamide;

4-[4-[1-[4-Cyano-3-(trifluoromethyl)phenyl]-2,5-dihydro-4-methyl-2,5-dioxo-1H-pyrrol-3-yl]butyl]-N-hexylpiperazine-1-carboxamide;

4-[2,5-Dihydro-3-methyl-2,5-dioxo-4-[5-[4-(pyrazin-2-yl)piperazin-1-yl]pentyl]-1H-pyrrol-1-yl]-2-(trifluoromethyl)benzonitrile;

4-[3-[5-[4-(2,4-Difluorophenyl)piperazin-1-yl]pentyl]-2,5-dihydro-4-methyl-2,5-dioxo-1H-pyrrol-1-yl]-2-(trifluoromethyl)benzonitrile;

4-[3-[5-[4-[(Furan-2-yl)carbonyl]piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-4-[5-[4-[(5-methylisoxazol-3-yl)carbonyl]piperazin-1-yl]pentyl]-2,5-dioxo-1H-pyrrol-1-yl]-2-(trifluoromethyl)benzonitrile;

4-[2,5-Dihydro-3-methyl-2,5-dioxo-4-[5-[4-(phenylacetyl)piperazin-1-yl]pentyl]-1H-pyrrol-1-yl]-2-(trifluoromethyl)benzonitrile;

4-[2,5-Dihydro-3-[5-[4-(4-methoxybenzoyl)piperazin-1-yl]pentyl]-4-methyl-2,5-dioxo-1H-pyrrol-1-yl]-2-(trifluoromethyl)benzonitrile;

4-[2,5-Dihydro-3-[5-[4-(2-methoxybenzoyl)piperazin-1-yl]pentyl]-4-methyl-2,5-dioxo-1H-pyrrol-1-yl]-2-(trifluoromethyl)benzonitrile;

4-[2,5-Dihydro-3-[5-[4-(methoxyacetyl)piperazin-1-yl]pentyl]-4-methyl-2,5-dioxo-1H-pyrrol-1-yl]-2-(trifluoromethyl)benzonitrile;

4-[3-[5-[4-(2-Chlorobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(2-Fluorobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-(4-Benzoylpiperazin-1-yl)pentyl]-2,5-dihydro-4-methyl-2,5-dioxo-1H-pyrrol-1-yl]-2-(trifluoromethyl)benzonitrile;

4-[3-[5-[4-(Cyclobutylcarbonyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(3,4-Dimethoxybenzoyl)piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[(pyridin-3-yl)carbonyl]piperazin-1-yl]pentyl]-1H-pyrrol-1-yl]-2-(trifluoromethyl)benzonitrile;

4-[3-[5-[4-(Cyclopropylcarbonyl)piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[(pyridin-4-yl)carbonyl]piperazin-1-yl]pentyl]-1H-pyrrol-1-yl]-2-(trifluoromethyl)benzonitrile;

4-[3-[5-[4-[4-(Dimethylamino)benzoyl]piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[(phenylsulfanyl)acetyl]piperazin-1-yl]pentyl]-1H-pyrrol-1-yl]-2-(trifluoromethyl)benzonitrile;

4-[2,5-Dihydro-3-methyl-2,5-dioxo-4-[5-[4-(phenoxyacetyl)piperazin-1-yl]pentyl]-1H-pyrrol-1-yl]-2-(trifluoromethyl)benzonitrile;

4-[2,5-Dihydro-3-methyl-2,5-dioxo-4-[5-[4-[(thien-2-yl)carbonyl]piperazin-1-yl]pentyl]-1H-pyrrol-1-yl]-2-(trifluoromethyl)benzonitrile;

4-[2,5-Dihydro-3-methyl-2,5-dioxo-4-[5-[4-(3-phenyl-1-oxopropyl)piperazin-1-yl]pentyl]-1H-pyrrol-1-yl]-2-(trifluoromethyl)benzonitrile;

4-[3-[5-[4-[(1,3-Benzodioxol-5-yl)carbonyl]piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-[5-[4-[(4-methoxyphenyl)acetyl]piperazin-1-yl]pentyl]-4-methyl-2,5-dioxo-1H-pyrrol-1-yl]-2-(trifluoromethyl)benzonitrile;

4-[2,5-Dihydro-3-methyl-4-[5-[4-(2-methylbenzoyl)piperazin-1-yl]pentyl]-2,5-dioxo-1H-pyrrol-1-yl]-2-(trifluoromethyl)benzonitrile;

4-[2,5-Dihydro-3-methyl-2,5-dioxo-4-[5-[4-[(thien-2-yl)acetyl]piperazin-1-yl]pentyl]-1H-pyrrol-1-yl]-2-(trifluoromethyl)benzonitrile;

4-[3-[5-[4-[(4-Chlorophenoxy)acetyl]piperazin-1-yl]pentyl]-2,5-dihydro-4-methyl-2,5-dioxo-1H-pyrrol-1-yl]-2-(trifluoromethyl)benzonitrile;

4-[3-[5-[4-(3-Cyclopentyl-1-oxopropyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(3-Chlorobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(3,3-Dimethyl-1-oxobutyl)piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-4-[5-[4-(3-methyl-1-oxobutyl)piperazin-1-yl]pentyl]-2,5-dioxo-1H-pyrrol-1-yl)-2-(trifluoromethyl)benzonitrile;

4-[2,5-Dihydro-4-methyl-2,5-dioxo-3-[5-[4-[(phenylmethoxy)acetyl]piperazin-1-yl]pentyl]-1H-pyrrol-1-yl]-2-(trifluoromethyl)benzonitrile;

4-[3-[5-[4-(Cyclopentylacetyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(2,6-Difluorobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(2,6-Dichlorobenzoyl)piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[2-(trifluoromethyl)benzoyl]piperazin-1-yl]pentyl]-1H-pyrrol-1-yl]-2-(trifluoromethyl)benzonitrile;

4-[3-[5-[4-(3-Fluorobenzoyl)piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[3-(trifloromethyl)benzoyl]piperazin-1-yl]pentyl]-1H-pyrrol-1-yl]-2-(trifluoromethyl)benzonitrile;

4-[2,5-Dihydro-3-methyl-4-[5-[4-(4-methylbenzoyl)piperazin-1-yl]pentyl]-2,5-dioxo-1H-pyrrol-1-yl]-2-(trifluoromethyl)benzonitrile;

4-[2,5-Dihydro-3-methyl-4-[5-[4-[(naphthalen-1-yl)carbonyl]piperazin-1-yl]pentyl]-2,5-dioxo-1H-pyrrol-1-yl]-2-(trifluoromethyl)benzonitrile;

4-[2,5-Dihydro-3-methyl-4-[5-[4-[(naphthalen-2-yl)carbonyl]piperazin-1-yl]pentyl]-2,5-dioxo-1H-pyrrol-1-yl]-2-(trifluoromethyl)benzonitrile;

4-[3-[5-[4-(3-Cyanobenzoyl)piperazin-1-yl]pentyl]-2,5-dihydro-4-methyl-2,5-dioxo-1H-pyrrol-1-yl]-2-(trifluoromethyl)benzonitrile;

4-[3-[5-[4-(Cyclohexylcarbonyl)piperazin-1-yl]pentyl]-2,5-dihydro-4-methyl-2,5-dioxo-1H-pyrrol-1-yl]-2-(trifluoromethyl)benzonitrile;

4-[3-[5-(4-Acetylpiperazin-1-yl)pentyl]-2,5-dihydro-4-methyl-2,5-dioxo-1H-pyrrol-1-yl]-2-(trifluoromethyl)benzonitrile;

4-[2,5-Dihydro-3-[5-[4-(3-methoxy-1-oxopropyl)piperazin-1-yl]pentyl]-4-methyl-2,5-dioxo-1H-pyrrol-1-yl]-2-(trifluoromethyl)benzonitrile;

4-[2,5-Dihydro-3-[5-[4-[(2-methoxyethoxy)acetyl]piperazin-1-yl]pentyl]-4-methyl-2,5-dioxo-1H-pyrrol-1-yl]-2-(trifluoromethyl)benzonitrile;

4-[2,5-Dihydro-3-[5-(4-[[2-(2-methoxyethoxy)ethoxy]acetyl]piperazin-1-yl]pentyl]-4-methyl-2,5-dioxo-1H-pyrrol-1-yl]-2-(trifluoromethyl)benzonitrile;

4-[4-[5-[4-(Cyclopropylsulfonyl)piperazin-1-yl]pentyl]-2,5-dihydro-3-methyl-2,5-dioxo-1H-pyrrol-1-yl]-2-(trifluoromethyl)benzonitrile;

4-[2,5-Dihydro-3-[5-[4-(2-methoxyethyl)sulfonyl]piperazin-1-yl]pentyl]-4-methyl-2,5-dioxo-1H-pyrrol-1-yl]-2-(trifluoromethyl)benzonitrile;

4-[2,5-Dihydro-3-[5-[4-[[2-(2-methoxyethoxy)ethyl]sulfonyl]piperazin-1-yl]pentyl]-4-methyl-2,5-dioxo-1H-pyrrol-1-yl]-2-(trifluoromethyl)benzonitrile;

4-[2,5-Dihydro-3-[5-[4-[[2-[2-(2-methoxyethoxy)ethoxy]-ethyl]sulfonyl]piperazin-1-yl]pentyl]-4-methyl-2,5-dioxo-1H-pyrrol-1-yl]-2-(trifluoromethyl)benzonitrile;

4-[5-[1-[4-Cyano-3-(trifluoromethyl)phenyl]-2,5-dihydro-4-methyl-2,5-dioxo-1H-pyrrol-3-yl]pentyl]-N,N-dimethylpiperazine-1-sulfonamide;

4-[2,5-Dihydro-3-methyl-2,5-dioxo-4-[5-[4-[(1-methylethyl)sulfonyl]piperazin-1-yl]pentyl]-1H-pyrrol-1-yl]-2-(trifluoromethyl)benzonitrile;

4-[2,5-Dihydro-3-methyl-2,5-dioxo-4-[5-[4-(phenylsulfonyl)piperazin-1-yl]pentyl]-1H-pyrrol-1-yl]-2-(trifluoromethyl)benzonitrile;

4-[2,5-Dihydro-3-methyl-4-[5-[4-(methylsulfonyl)piperazin-1-yl]pentyl]-2,5-dioxo-1H-pyrrol-1-yl]-2-(trifluoromethyl)benzonitrile;

4-[3-[5-[4-[(4-Chlorophenyl)sulfonyl]piperazin-1-yl]pentyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[5-[4-[(phenylmethyl)sulfonyl]piperazin-1-yl]pentyl]-1H-pyrrol-1-yl]-2-(trifluoromethyl)benzonitrile;

4-[3-[5-[4-[(4-Cyanophenyl)sulfonyl]piperazin-1-yl]pentyl]-2,5-dihydro-4-methyl-2,5-dioxo-1H-pyrrol-1-yl]-2-(trifluoromethyl)benzonitrile;

4-[4-[5-[4-[(Quinolin-8-yl)sulfonyl]piperazin-1-yl]pentyl]-2,5-dihydro-3-methyl-2,5-dioxo-1H-pyrrol-1-yl]-2-(trifluoromethyl)benzonitrile;

4-[3-[5-[4-[(2-Fluorophenyl)sulfonyl]piperazin-1-yl]pentyl]-2,5-dihydro-4-methyl-2,5-dioxo-1H-pyrrol-1-yl]-2-(trifluoromethyl)benzonitrile;

4-[3-[5-[4-[(2,5-Dimethoxyphenyl)sulfonyl]piperazin-1-yl]pentyl]-2,5-dihydro-4-methyl-2,5-dioxo-1H-pyrrol-1-yl]-2-(trifluoromethyl)benzonitrile;

4-[3-[5-[4-[(3-Cyanophenyl)sulfonyl]piperazin-1-yl]pentyl]-2,5-dihydro-4-methyl-2,5-dioxo-1H-pyrrol-1-yl]-2-(trifluoromethyl)benzonitrile;

4-[3-[5-[4-[(2,1,3-Benzothiadiazol-4-yl)sulfonyl]piperazin-1-yl]pentyl]-2,5-dihydro-4-methyl-2,5-dioxo-1H-pyrrol-1-yl]-2-(trifluoromethyl)benzonitrile;

4-[5-[1-[4-Cyano-3-(trifluoromethyl)phenyl]-2,5-dihydro-4-methyl-2,5-dioxo-1H-pyrrol-3-yl]pentyl]-N-(1,1-dimethylethyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(naphthalen-1-yl)piperazine-1-carboxamide;

N-(4-Cyanophenyl)-4-[5-[1-[4-cyano-3-(trifluoromethyl)phenyl]-2,5-dihydro-4-methyl-2,5-dioxo-1H-pyrrol-3-yl]pentyl]piperazine-1-carboxamide;

N-(2-Chlorophenyl)-4-[5-[1-[4-cyano-3-(trifluoromethyl)phenyl]-2,5-dihydro-4-methyl-2,5-dioxo-1H-pyrrol-3-yl]pentyl]piperazine-1-carboxamide;

4-[5-[1-[4Cyano-3-(trifluoromethyl)phenyl]-2,5-dihydro-4-methyl-2,5-dioxo-1H-pyrrol-3-yl]pentyl]-N-[2-(trifluoromethyl)phenyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(2-methylphenyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(3-methylphenyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(4-fluorophenyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(4-methoxyphenyl)piperazine-1-carboxamide;

N-(3-Cyanophenyl)-4-[5-[1-[4-cyano-3-(trifluoromethyl)phenyl]-2,5-dihydro-4-methyl-2,5-dioxo-1H-pyrrol-3-yl]pentyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(3,5-dimethoxyphenyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(2-phenylethyl)piperazine-1-carboxamide;

N-([1,1'-Biphenyl]-2-yl)-4-[5-[1-[4-cyano-3-(trifluoromethyl)phenyl]-2,5-dihydro-4-methyl-2,5-dioxo-1H-pyrrol-3-yl]pentyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-[2-(1-methylethyl)phenyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(2,6-dichloropyridin-4-yl)piperazine-1-carboxamide;

(R)-4-[5-[1-[4-Cyano-3-(trifluoromethyl)phenyl]-2,5-dihydro-4-methyl-2,5-dioxo-1H-pyrrol-3-yl]pentyl]-N-(1-phenylethyl)piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-[3-[(trifluoromethyl)sulfanyl]phenyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-[(3-methylphenyl)methyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-[(4-methoxyphenyl)methyl]piperazine-1-carboxamide;

4-[5-[1-[4-Cyano-3-(trifluoromethyl)phenyl]-2,5-dihydro-4-methyl-2,5-dioxo-1H-pyrrol-3-yl]pentyl]-N-(1,1,3,3-tetramethylbutyl)piperazine-1-carboxamide;

1,1-Dimethylethyl 4-[6-[1-[4-cyano-3-(trifluoromethyl)phenyl]-2,5-dihydro-4-methyl-2,5-dioxo-1H-pyrrol-3-yl]hexyl]piperazine-1-carboxylate;

4-[2,5-Dihydro-3-methyl-4-[6-(4-methylpiperazin-1-yl)hexyl]-2,5-dioxo-1H-pyrrol-2-yl]-2-(trifluoromethyl)benzonitrile;

Ethyl 4-[6-[1-[4-cyano-3-(trifluoromethyl)phenyl]-2,5-dihydro-4-methyl-2,5-dioxo-1H-pyrrol-3-yl]hexyl]piperazine-1-carboxylate;

4-[2,5-Dihydro-3-methyl-2,5-dioxo-4-[6-[4-(pyridin-2-yl)piperazin-1-yl]hexyl]-1H-pyrrol-1-yl]-2-(trifluoromethyl)benzonitrile;

(Phenylmethyl) 4-[6-[1-[4-cyano-3-(trifluoromethyl)phenyl]-2,5-dihydro-4-methyl-2,5-dioxo-1H-pyrrol-3-yl]hexyl]piperazine-1-carboxylate;

4-[2,5-Dihydro-3-methyl-2,5-dioxo-4-[6-[4-(pyrimidin-2-yl)piperazin-1-yl]hexyl]-1H-pyrrol-1-yl]-2-(trifluoromethyl)benzonitrile;

4-[2,5-Dihydro-3-[6-[4-(2-methoxyphenyl)piperazin-1-yl]hexyl]-4-methyl-2,5-dioxo-1H-pyrrol-1-yl]-2-(trifluoromethyl)benzonitrile;

4-[2,5-Dihydro-3-methyl-4-[6-[4-(2-nitrophenyl)piperazin-1-yl]hexyl]-2,5-dioxo-1H-pyrrol-1-yl]-2-(trifluoromethyl)benzonitrile;

4-[2,5-Dihydro-3-methyl-2,5-dioxo-4-[6-[4-pyrazin-2-yl)piperazin-1-yl]hexyl]-1H-pyrrol-1-yl]-2-(trifluoromethyl)benzonitrile;

4-[2,5-Dihydro-3-methyl-4-[6-[4-[2-(methylsulfanyl)phenyl]piperazin-1-yl]hexyl]-2,5-dioxo-1H-pyrrol-1-yl]-2-(trifluoromethyl)benzonitrile;

4-[2,5-Dihydro-3-methyl-2,5-dioxo-4-[6-[4-[3-(trifluoromethyl)pyridin-2-yl]piperazin-1-yl]hexyl]-1H-pyrrol-1-yl]-2-(trifluoromethyl)benzonitrile;

4-[2,5-Dihydro-3-[6-[4-(2-methoxyethyl)piperazin-1-yl]hexyl]-4-methyl-2,5-dioxo-1H-pyrrol-1-yl]-2-(trifluoromethyl)benzonitrile;

4-[3-[6-[4-(3,5-Dichloropyridin-4-yl)piperazin-1-yl]hexyl]-2,5-dihydro-4-methyl-2,5-dioxo-1H-pyrrol-1-yl]-2-(trifluoromethyl)benzonitrile;

4-[3-[6-(4-Acetylpiperazin-1-yl)hexyl]-2,5-dihydro-4-methyl-2,5-dioxo-1H-pyrrol-1-yl]-2-(trifluoromethyl)benzonitrile;

4-[3-[6-[4-[(Furan-2-yl)carbonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[(tetrahydrofuran-2-yl)carbonyl]piperazin-1-yl]hexyl]-1H-pyrrol-1-yl]-2-(trifluoromethyl)benzonitrile;

4-[3-[6-[4-(Cyclopentylcarbonyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-4-[6-[4-[(5-methylisoxazol-3-yl)carbonyl]piperazin-1-yl]hexyl]-2,5-dioxo-1H-pyrrol-1-yl]-2-(trifluoromethyl)benzonitrile;

4-[2,5-Dihydro-3-methyl-2,5-dioxo-4-[6-[4-(phenylacetyl)piperazin-1-yl]hexyl]-1H-pyrrol-1-yl]-2-(trifluoromethyl)benzonitrile;

4-[2,5-Dihydro-3-[6-[4-(4-methoxybenzoyl)piperazin-1-yl]hexyl]-4-methyl-2,5-dioxo-1H-pyrrol-1-yl]-2-(trifluoromethyl)benzonitrile;

4-[2,5-Dihydro-3-[6-[4-(2-methoxybenzoyl)piperazin-1-yl]hexyl]-4-methyl-2,5-dioxo-1H-pyrrol-1-yl]-2-(trifluoromethyl)benzonitrile;

4-[2,5-Dihydro-3-[6-[4-(methoxyacetyl)piperazin-1-yl]hexyl]-4-methyl-2,5-dioxo-1H-pyrrol-1-yl]-2-(trifluoromethyl)benzonitrile;

4-[3-[6-[4-(2-Chlorobenzoyl)piperazin-1-yl]hexyl]-2,5-dihydro-4-methyl-2,5-dioxo-1H-pyrrol-1-yl]-2-(trifluoromethyl)benzonitrile;

4-[3-[6-[4-(2-Fluorobenzoyl)piperazin-1-yl]hexyl]-2,5-dihydro-4-methyl-2,5-dioxo-1H-pyrrol-1-yl]-2-(trifluoromethyl)benzonitrile;

4-[3-[6-(4-Benzoylpiperazin-1-yl)hexyl]-2,5-dihydro-4-methyl-2,5-dioxo-1H-pyrrol-1-yl]-2-(trifluoromethyl)benzonitrile;

4-[3-[6-[4-(Cyclobutylcarbonyl)piperazin-1-yl]hexyl]-2,5-dihydromethyl-2,5-dioxo-1H-pyrrol-1-yl]-2-(trifluoromethyl)benzonitrile;

4-[3-[6-[4-(3,4-Dimethoxybenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[(phenylsulfanyl)acetyl]piperazin-1-yl]hexyl]-1H-pyrrol-1-yl]-2-(trifluoromethyl)benzonitrile;

4-[2,5-Dihydro-3-methyl-2,5-dioxo-4-[6-[4-(phenoxyacetyl)piperazin-1-yl]hexyl]-1H-pyrrol-1-yl]-2-(trifluoromethyl)benzonitrile;

4-[2,5-Dihydro-3-methyl-2,5-dioxo-4-[6-[4-[(thien-2-yl)carbonyl]piperazin-1-yl]hexyl]-1H-pyrrol-1-yl]-2-(trifluoromethyl)benzonitrile;

4-[2,5-Dihydro-3-methyl-2,5-dioxo-4-[6-[4-(3-phenyl-1-oxopropyl)piperazin-1-yl]hexyl]-1H-pyrrol-1-yl]-2-(trifluoromethyl)benzonitrile;

4-[3-[6-[4-[(1,3-Benzodioxol-5-yl)carbonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-[6-[4-[(4-methoxyphenyl)acetyl]piperazin-1-yl]hexyl]-4-methyl-2,5-dioxo-1H-pyrrol-1-yl]-2-(trifluoromethyl)benzonitrile;

4-[2,5-Dihydro-3-methyl-4-[6-[4-(2-methylbenzoyl)piperazin-1-yl]hexyl]-2,5-dioxo-1H-pyrrol-1-yl]-2-(trifluoromethyl)benzonitrile;

4-[3-[6-[4-(4-Chlorobenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[(thien-2-yl)acetyl]piperazin-1-yl]hexyl]-1H-pyrrol-1-yl]-2-(trifluoromethyl)benzonitrile;

4-[3-[6-[4-[(4 Chlorophenoxy)acetyl]piperazin-1-yl]hexyl]-2,5-dihydro-4-methyl-2,5-dioxo-1H-pyrrol-1-yl]-2-(trifluoromethyl)benzonitrile;

4-[3-[6-[4-(3-Cyclopentyl-1-oxopropyl)piperazin-1-yl]hexyl]-2,5-dihydro-4-methyl-2,5-dioxo-1H-pyrrol-1-yl]-2-(trifluoromethyl)benzonitrile;

4-[3-[6-[4-(3-Chlorobenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[4-trifluoromethyl)benzoyl]piperazin-1-yl]hexyl]-1H-pyrrol-1-yl]-2-(trifluoromethyl)benzonitrile;

4-[3-[6-[4-(4-cyanobenzoyl)piperazin-1-yl]hexyl]-2,5-dihydro-4-methyl-2,5-dioxo-1H-pyrrol-1-yl]-2-(trifluoromethyl)benzonitrile;

4-[3-[6-[4-(3,3-Dimethyl-1-oxobutyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-4-[6-[4-(3-methyl-1-oxobutyl)piperazin-1-yl]hexyl]-2,5-dioxo-1H-pyrrol-1-yl]-2-(trifluoromethyl)benzonitrile;

4-[2,5-Dihydro-3-methyl-2,5-dioxo-4-[6-[4-[(phenylmethoxy)acetyl]piperazin-1-yl]hexyl]-1H-pyrrol-1-yl]-2-(trifluoromethyl)benzonitrile;

4-[3-[6-[4-(Cyclopentylacetyl)piperazin-1-yl]hexyl-2,5-dihydro-4-methyl-2,5-dioxo-1H-pyrrol-1-yl]-2-(trifluoromethyl)benzonitrile;

4-[3-[6-[4-(2,6-Difluorobenzoyl)piperazin-1-yl]hexyl]-2,5-dihydro-4-methyl-2,5-dioxo-1H-pyrrol-1-yl]-2-(trifluoromethyl)benzonitrile;

4-[3-[6-[4-(2,6-Dichlorobenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[2-(trifluoromethyl)benzoyl]piperazin-1-yl]hexyl]-1H-pyrrol-1-yl]-2-(trifluoromethyl)benzonitrile;

4-[3-[6-[4-(3-Fluorobenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-[6-[4-(3-methoxybenzoyl)piperazin-1-yl]hexyl]-4-methyl-2,5-dioxo-1H-pyrrol-1-yl]-2-(trifluoromethyl)benzonitrile;

4-[2,5-Dihydro-3-methyl-2,5-dioxo-4-[6-[4-[3-(trifuoromethyl)benzoyl]piperazin-1-yl]hexyl]-1H-pyrrol-1-yl]-2-(trifluoromethyl)benzonitrile; 4-[2,5-Dihydro-3-methyl-4-[6-[4-(3-methylbenzoyl)piperazin-1-yl]hexyl]-2,5-dioxo-1H-pyrrol-1-yl]-2-(trifluoromethyl)benzonitrile;

4-[3-[6-[4-(4-Fluorobenzoyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-4-[6-[4-(4-methylbenzoyl)piperazin-1-yl]hexyl]-2,5-dioxo-1H-pyrrol-1-yl]-2-(trifluoromethyl)benzonitrile;

4-[2,5-Dihydro-3-methyl-4-[6-[4-[(naphthalen-1-yl)carbonyl]piperazin-1-yl]hexyl]-2,5-dioxo-1H-pyrrol-1-yl]-2-(trifluoromethyl)benzonitrile;

4-[2,5-Dihydro-3-methyl-4-[6-[4-[(naphthalen-2-yl)carbonyl]piperazin-1-yl]hexyl]-2,5-dioxo-1H-pyrrol-1-yl]-2-(trifluoromethyl)benzonitrile;

4-[3-[6-[4-(3-Cyanobenzoyl)piperazin-1-yl]hexyl]-2,5-dihydro-4-methyl-2,5-dioxo-1H-pyrrol-1-yl]-2-(trifluoromethyl)benzonitrile;

4-[3-[6-[4-(Cyclohexylcarbonyl)piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-[6-[4-(3-methoxy-1-oxopropyl)piperazin-1-yl]hexyl]-4-methyl-2,5-dioxo-1H-pyrrol-1-yl]-2-(trifluoromethyl)benzonitrile;

4-[2,5-Dihydro-3-[6-[4-[(2-methoxyethoxy)acetyl]piperazin-1-yl]hexyl]-4-methyl-2,5-dioxo-1H-pyrrol-1-yl]-2-(trifluoromethyl)benzonitrile;

4-[2,5-Dihydro-3-[6-[4-[[2-(2-methoxyethoxy)ethoxy]acetyl]piperazin-1-yl]hexyl]-4-methyl-2,5-dioxo-1H-pyrrol-1-yl]-2-(trifluoromethyl)benzonitrile;

4-[4-[6-[4-(Cyclopropylsulfonyl)piperazin-1-yl]hexyl]-2,5-dihydro-3-methyl-2,5-dioxo-1H-pyrrol-1-yl]-2-(trifluoromethyl)benzonitrile;

4-[2,5-Dihydro-3-[6-[4-(2-methoxyethyl)sulfonyl]piperazin-1-yl]hexyl]-4-methyl-2,5-dioxo-1H-pyrrol-1-yl]-2-(trifluoromethyl)benzonitrile;

4-[2,5-Dihydro-3-[6-[4-[[2-(2-methoxyethoxy)ethyl]sulfonyl]piperazin-1-yl]hexyl]-4-methyl-2,5-dioxo-1H-pyrrol-1-yl]-2-(trifluoromethyl)benzonitrile;

4-[2,5-Dihydro-3-[6-[4-[[2-[2-(2-methoxyethoxy)ethoxy]ethyl]sulfonyl]-piperazin-1-yl]hexyl]-4-methyl-2,5-dioxo-1H-pyrrol-1-yl]-2-(trifluoromethyl)-benzonitrile;

4-[6-[1-[4-Cyano-3-(trifluoromethyl)phenyl]-2,5-dihydro-4-methyl-2,5-dioxo-1H-pyrrol-3-yl]hexyl]-N,N-dimethylpiperazine-1-sulfonamide;

4-[3-[6-[4-[[4-(1,1-Dimethylethyl)phenoxy]acetyl]-piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-(phenylsulfonyl)piperazin-1-yl]hexyl]-1H-pyrrol-1-yl]-2-(trifluoromethyl)benzonitrile;

4-[2,5-Dihydro-3-methyl-4-[6-[4-(methylsulfonyl)piperazin-1-yl]hexyl]-2,5-dihydro-1H-pyrrol-1-yl]-2-(trifluoromethyl)benzonitrile;

4-[2,5-Dihydro-3-methyl-4-[6-[4-[(4-methylphenyl)-sulfonylpiperazin-1-yl]hexyl]-2,5-dioxo-1H-pyrrol-1-yl]-2-(trifluoromethyl)benzonitrile;

N-[4-[[4-[6-[1-[4-Cyano-3-(trifluoromethyl)phenyl]-2,5-dihydro-4-methyl-2,5-dioxo-1H-pyrrol-3-yl]hexyl]piperazin-1-yl]sulfonyl]phenyl]acetamide;

4-[2,5-Dihydro-3-methyl-2,5-dioxo-4-[6-[4-[(phenylmethyl)sulfonyl]piperazin-1-yl]hexyl]-1H-pyrrol-1-yl]-2-(trifluoromethyl)benzonitrile;

4-[3-[6-[4-[(4-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl[6-[4-[(naphthalen-2-yl)sulfonyl]piperazin-1-yl]hexyl]-2,5-dioxo-1H-pyrrol-1-yl]-2-(trifluoromethyl)benzonitrile;

4-[3-[6-[4-[[5-(Dimethylamino)naphthalen-1-yl]sulfonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[6-[4-[(thien-2-yl)sulfonyl]piperazin-1-yl]hexyl]-1H-pyrrol-1-yl]-2-(trifluoromethyl)benzonitrile;

4-[3-[6-[4-[(Quinolin-8-yl)sulfonyl]piperazin-1-yl]hexyl]-2,5-dihydro-4-methyl-2,5-dioxo-1H-pyrrol-1-yl]-2-(trifluoromethyl)benzonitrile;

4-[3-[6-[4-[(2-Fluorophenyl)sulfonyl]piperazin-1-yl]hexyl]-2,5-dihydro-4-methyl-2,5-dioxo-1H-pyrrrol-1-yl]-2-(trifluoromethyl)benzonitrile;

4-[3-[6-[4-[(2-Chlorophenyl)sulfonyl]piperazin-1-yl]hexyl]-2,5-dihydro-4-methyl-2,5-dioxo-1H-pyrrol-1-yl]-2-(trifluoromethyl)benzonitrile;

4-[3-[6-[4-[(2-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile;

4-[3-[6-[4-[(3-Cyanophenyl)sulfonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-4-[6-[4-[[5-[2-methyl-5-(trifluoromethyl)-2H-pyrazol-3-yl]thien-2-yl]sulfonyl]piperazin-1-yl]hexyl]-2,5-dioxo-1H-pyrrol-1-yl]-2-(trifluoromethyl)benzonitrile;

4-[2,5-Dihydro-3-methyl-2,5-dioxo-4-[6-[4-[[1,2,3,4-tetrahydro-2-(trifluoroacetyl)isoquinolin-7-yl]sulfonyl]piperazin-1-yl]hexyl]-1H-pyrrol-1-yl]-2-(trifluoromethyl)benzonitrile;

4-[3-[6-[4-[(3,5-Dimethylisoxazol-4-yl)sulfonyl]piperazin-1-yl]hexyl]-2,5-dihydro-4-methyl-2,5-dioxo-1H-pyrrol-1-yl]-2-(trifluoromethyl)benzonitrile;

4-[3-[6-[4-[(5-Chloro-1,3-dimethyl-1H-pyrazol-4-yl)sulfonyl]piperazin-1-yl]hexyl]-2,5-dihydro-4-methyl-2,5-dioxo-1H-pyrrol-1-yl]-2-(trifluoromethyl)benzonitrile;

4-[2,5-Dihydro-3-methyl-4-[6-[4-[(1-methyl-1H-imidazol-4-yl)sulfonyl]-piperazin-1-yl]hexyl]-2,5-dioxo-1H-pyrrol-1-yl]-2-(trifluoromethyl)benzonitrile;

4-[6-(1-[4-Cyano-3-(trifluoromethyl)phenyl]-2,5-dihydro-4-methyl-2,5-dioxo-1H-pyrrol-3-yl]hexyl]-N-(1,1-dimethylethyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-phenylpiperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(naphthalen-1-yl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(naphthalen-2-yl)piperazine-1-carboxamide;

N-(4-Cyanophenyl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(1-methylethyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[3-(trifluoromethyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2-fluorophenyl)piperazine-1-carboxamide;

N-(2-Chlorophenyl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2-methoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[2-(trifluoromethyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2-methylphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(3-fluorophenyl)piperazine-1-carboxamide;

N-(3-Chlorophenyl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-1-pyrrol-3-yl]hexyl]-N-(3-methoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(3-methylphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(4-fluorophenyl)piperazine-1-carboxamide;

N-(4-Chlorophenyl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(4-methoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[4-(trifluoromethyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(4-methylphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(prop-2-enyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-cyclohexylpiperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(phenylmethyl)piperazine-1-carboxamide;

N-(3-Cyanophenyl)-4-[6-[1-[4-cyano-3-(trifluoromethyl) phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(3,5-dimethoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[3-(methylsulfanyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(4-phenoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[4-(methylsulfanyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[4-(1-methylethyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2-phenylethyl)piperazine-1-carboxamide;

N-([1,1'-Biphenyl]-2-yl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[4-(phenylmethoxy)phenyl]piperazine-1-carboxamide;

N-(2-Cyanophenyl)-4-[6-[1-[4-cyano-3-(trifluoromethyl)phenyl]-2,5-dihydro-4-methyl-2,5-dioxo-1H-pyrrol-3-yl]hexyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[2-(thien-2-yl)ethyl]piperazine-1-carboxamide;

(1R-trans)-4-[6-[1-[4-Cyano-3-(trifluoromethyl)phenyl]-2,5-dihydro-4-methyl-2,5-dioxo-1H-pyrrol-3-yl]hexyl]-N-(2-phenylcyclopropyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,6-difluorophenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,6-dichlorophenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,4-dimethoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,5-dimethoxyphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,6-dimethylphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(trichloroacetyl)piperazine-1-carboxamide;

(S)-4-[6-[1-[4-Cyano-3-(trifluoromethyl)phenyl]-2,5-dihydro-4-methyl-2,5-dioxo-1H-pyrrol-3-yl]hexyl]-N-(1-phenylethyl)piperazine-1-carboxamide;

(R)-4-[6-[1-[4-Cyano-3-(trifluoromethyl)phenyl]-2,5-dihydro-4-methyl-2,5-dioxo-1H-pyrrol-3-yl]hexyl]-N-[1-(naphthalen-1-yl)ethyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,4,6-trichlorophenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[2-(1-methylethyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(3,5-dichlorophenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,4,6-trimethylphenyl)piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[4-[(trifluoromethyl)sulfanyl]phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[(2,4-dichlorophenyl)methyl]piperazine-1-carboxamide;

4-[6-[1-[4-Cyano-3-(trifluoromethyl)phenyl)-2,5-dihydro-4-methyl-2,5-dioxo-1H-pyrrol-3-yl]hexyl]-N-[2-(methylsulfanyl)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(2,6-dichloropyridin-4-yl)piperazine-1-carboxamide;

(R)-4-[6-[1-[4-Cyano-3-(trifluoromethyl)phenyl]-2,5-dihydro-4-methyl-2,5-dioxo-1H-pyrrol-3-yl]hexyl]-N-(1-phenylethyl)piperazine-1-carboxamide;

(S)-4-[6-[1-[4-Cyano-3-(trifluoromethyl)phenyl]-2,5-dihydro-4-methyl-2,5-dioxo-1H-pyrrol-3-yl]hexyl]-N-[1-(naphthalen-1-yl)ethyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[1-methyl-1-[3-(1-methylethenyl)phenyl]ethyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[2-(trifluoromethoxy)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-tricyclo[3.3.1.1$^{3,7}$]dec-1-yl)piperazine-1-carboxamide;

4-[6-[1-[4-Cyano-3-(trifluoromethyl)phenyl]-2,5-dihydro-4-methyl-2,5-dioxo-1H-pyrrol-3-yl)hexyl]-N-[4-(dimethylamino)phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[3-[(trifluoromethyl)sulfanyl]phenyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[(2-methylphenyl)methyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[(3-methylphenyl)methyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[(4-methylphenyl)methyl]piperazine-1-carboxamide;

4-[6-[1-[4-Cyano-3-(trifluoromethyl)phenyl]-2,5-dihydro-4-methyl-2,5-dioxo-1H-pyrrol-3-yl]hexyl]-N-[(4-methoxyphenyl)methyl]piperazine 1-carboxamide;

4-[6-[1-[4-Cyano-3-(trifluoromethyl)phenyl]-2,5-dihydro-4-methyl-2,5-dioxo-1H-pyrrol-3-yl]hexyl]-N-(1,1,3,3-tetramethylbutyl)piperazine-1-carboxamide;

4-[3-[7-(4-Acetylpiperazin-1-yl)heptyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[7-(4-(1-oxopropyl)piperazin-1-yl)heptyl]-1H-pyrrol-1-yl]-2-(trifluoromethyl)benzonitrile;

4-[3-[7-[4-(Cyclopropylcarbonyl)piperazin-1-yl]heptyl]-2,5-dihydro-4-methyl-2,5-dioxo-1H-pyrrol-1-yl]-2-(trifluoromethyl)benzonitrile;

4-[2,5-Dihydro-3-[7-[4-(methoxyacetyl)piperazin-1-yl]heptyl]-4-methyl-2,5-dioxo-1H-pyrrol-1-yl]-2-(trifluoromethyl)benzonitrile;

4-[2,5-Dihydro-3-[7-[4-(3-methoxy-1-oxopropyl)piperazin-1-yl]heptyl]-4-methyl-2,5-dioxo-1H-pyrrol-1-yl]-2-(trifluoromethyl)benzonitrile;

4-[2,5-Dihydro-3-[7-[4-[(2-methoxyethoxy)acetyl]piperazin-1-yl]heptyl]-4-methyl-2,5-dioxo-1H-pyrrol-1-yl]-2-(trifluoromethyl)benzonitrile;

4-[2,5-Dihydro-3-[7-[4-[[2-(2-methoxyethoxy)ethoxy]acetyl]piperazin-1-yl]heptyl]-4-methyl-2,5-dioxo-1H-pyrrol-1-yl]-2-(trifluoromethyl)benzonitrile;

4-[2,5-Dihydro-3-[7-[4-(2-methoxybenzoyl)piperazin-1-yl]heptyl]-4-methyl-2,5-dioxo-1H-pyrrol-1-yl]-2-(trifluoromethyl)benzonitrile;

4-[2,5-Dihydro-3-methyl-4-[7-[4-(methylsulfonyl)piperazin-1-yl]heptyl]-2,5-dioxo-1H-pyrrol-1-yl]-2-(trifluoromethyl)benzonitrile;

4-[3-[7-[4-(Ethylsulfonyl)piperazin-1-yl]heptyl]-2,5-dihydro-4-methyl-2,5-dioxo-1H-pyrrol-1-yl]-2-(trifluoromethyl)benzonitrile;

4-[3-[7-[4-(Cyclopropylsulfonyl)piperazin-1-yl]heptyl]-2,5-dihydro-4-methyl-2,5-dioxo-1H-pyrrol-1-yl]-2-(trifluoromethyl)benzonitrile;

4-[2,5-Dihydro-3-[7-[4-(2-methoxyethyl)sulfonyl]piperazin-1-yl]heptyl]-4-methyl-2,5-dioxo-1H-pyrrol-1-yl]-2-(trifluoromethyl)benzonitrile;

4-[2,5-Dihydro-3-[7-(4-[[2-(2-methoxyethoxy)ethyl]sulfonyl]piperazin-1-yl]heptyl]-4-methyl-2,5-dioxo-1H-pyrrol-1-yl]-2-(trifluoromethyl)benzonitrile;

4-[2,5-Dihydro-3-[7-[4-[(2-(2-(2-methoxyethoxy)ethoxy]ethyl]sulfonyl]-piperazin-1-yl]heptyl]-4-methyl-2,5-dioxo-1H-pyrrol-1-yl]-2-(trifluoromethyl)benzonitrile;

4-[2,5-Dihydro-3-methyl-2,5-dioxo-4-[7-[4-(phenylsulfonyl)piperazin-1-yl]heptyl]-1H-pyrrol-1-yl]-2-(trifluoromethyl)benzonitrile;

4-[2,5-Dihydro-3-methyl-2,5-dioxo-4-[7-[4-[(phenylmethyl)sulfonyl]piperazin-1-yl]heptyl]-1H-pyrrol-1-yl]-2-(trifluoromethyl)benzonitrile;

4-[2,5-Dihydro-3-methyl-4-[7-[4-[(1-methyl-1H-imidazol-4-yl)sulfonyl]-piperazin-1-yl]heptyl]-2,5-dioxo-1H-pyrrol-1-yl]-2-(trifluoromethyl)benzonitrile;

4-[7-[1-[4-Cyano-3-(trifluoromethyl)phenyl]-2,5-dihydro-4-methyl-2,5-dioxo-1H-pyrrol-3-yl]heptyl]-N-(1-methylethyl)piperazine-1-carboxamide;

4-[7-[1-[4-Cyano-3-(trifluoromethyl)phenyl]-2,5-dihydro-4-methyl-2,5-dioxo-1H-pyrrol-3-yl]heptyl]-N-ethylpiperazine-1-carbothioamide;

Methyl 4-[7-[1-[4-cyano-3-(trifluoromethyl)phenyl]-2,5-dihydro-4-methyl-2,5-dioxo-1H-pyrrol-3-yl]heptyl] piperazine-1-carboxylate;

S-Methyl 4-[7-[1-[4-cyano-3-(trifluoromethyl)phenyl]-2,5-dihydro-4-methyl-2,5-dioxo-1H-pyrrol-3-yl]heptyl] piperazine-1-carbothioate;

4-[7-[1-[4-Cyano-3-(trifluoromethyl)phenyl]-2,5-dihydro-4-methyl-2,5-dioxo-1H-pyrrol-3-yl]heptyl]-N,N-dimethylpiperazine-1-sulfonamide;

4-[3-[8-(4-Acetylpiperazin-1-yl)octyl]-2,5-dihydro-4-methyl-2,5-dioxo-1H-pyrrol-1-yl]-2-(trifluoromethyl)benzonitrile;

4-[2,5-Dihydro-3-methyl-2,5-dioxo-4-[8-(4-(1-oxopropyl)piperazin-1-yl)octyl]-1H-pyrrol-1-yl]-2-(trifluoromethyl)benzonitrile;

4-[3-[8-[4-(Cyclopropylcarbonyl)piperazin-1-yl]octyl]-2,5-dihydro-4-methyl-2,5-dioxo-1H-pyrrol-1-yl]-2-(trifluoromethyl)benzonitrile;

4-[2,5-Dihydro-3-[8-[4-(methoxyacetyl)piperazin-1-yl]octyl]-4-methyl-2,5-dioxo-1H-pyrrol-1-yl]-2-(trifluoromethyl)benzonitrile;

4-[2,5-Dihydro-3-[8-[4-(3-methoxy-1-oxopropyl)piperazin-1-yl]octyl]-4-methyl-2,5-dioxo-1H-pyrrol-1-yl]-2-(trifluoromethyl)benzonitrile;

4-[2,5-Dihydro-3-[8-[4-[(2-methoxyethoxy)acetyl]piperazin-1-yl]octyl]-4-methyl-2,5-dioxo-1H-pyrrol-1-yl]-2-(trifluoromethyl)benzonitrile;

4-[2,5-Dihydro-3-[8-[4-[[2-(2-methoxyethoxy)ethoxy]acetyl]piperazin-1-yl]octyl]-4-methyl-2,5-dioxo-1H-pyrrol-1-yl]-2-(trifluoromethyl)benzonitrile;

4-[2,5-Dihydro-3-[8-[4-(2-methoxybenzoyl)piperazin-1-yl]octyl]-4-methyl-2,5-dioxo-1H-pyrrol-1-yl]-2-(trifluoromethyl)benzonitrile;

4-[2,5-Dihydro-3-methyl-4-[8-[4-(methylsulfonyl)piperazin-1-yl]octyl]-2,5-dioxo-1H-pyrrol-1-yl]-2-(trifluoromethyl)benzonitrile;

4-[3-[8-[4-(Ethylsulfonyl)piperazin-1-yl]octyl]-2,5-dihydro-4-methyl-2,5-dioxo-1H-pyrrol-1-yl]-2-(trifluoromethyl)benzonitrile;

4-[3-[8-[4-(Cyclopropylsulfonyl)piperazin-1-yl]octyl]-2,5-dihydro-4-methyl-2,5-dioxo-1H-pyrrol-1-yl]-2-(trifluoromethyl)benzonitrile;

4-[2,5-Dihydro-3-[8-[4-(2-methoxyethyl)sulfonyl]piperazin-1-yl]octyl]-4-methyl-2,5-dioxo-1H-pyrrol-1-yl]-2-(trifluoromethyl)benzonitrile;

4-[2,5-Dihydro-3-[8-[4-[[2-(2-methoxyethoxy)ethyl]sulfonyl]piperazin-1-yl]octyl]-4-methyl-2,5-dioxo-1H-pyrrol-1-yl]-2-(trifluoromethyl)benzonitrile;

4-[2,5-Dihydro-3-[8-[4-[[2-[2-(2-methoxyethoxy)ethoxy]-ethyl]sulfonyl]piperazin-1-yl]octyl]-4-methyl-2,5-dioxo-1H-pyrrol-1-yl]-2-(trifluoromethyl)benzonitrile;

4-[2,5-Dihydro-3-methyl-2,5-dioxo-4-[8-[4-(phenylsulfonyl)piperazin-1-yl]octyl-1H-pyrrol-1-yl]-2-(trifluoromethyl)benzonitrile;

4-[2,5-Dihydro-3-methyl-2,5-dioxo-4-[8-[4-[(phenylmethyl)sulfonyl]piperazin-1-yl]octyl]-1H-pyrrol-1-yl]-2-(trifluoromethyl)benzonitrile;

4-[2,5-Dihydro-3-methyl-4-[8-[4-[(1-methyl-1H-imidazol-4-yl)sulfonyl]-piperazin-1-yl]octyl]-2,5-dioxo-1H-pyrrol-1-yl]-2-(trifluoromethyl)benzonitrile;

4-[8-[1-[4-Cyano-3-(trifluoromethyl)phenyl]-2,5-dihydro-4-methyl-2,5-dioxo-1H-pyrrol-3-yl]octyl]-N-(1-methylethyl)piperazine-1-carboxamide;

4-[8-[1-[4-Cyano-3-(trifluoromethyl)phenyl]-2,5-dihydro-4-methyl-2,5-dioxo-1H-pyrrol-3-yl]octyl]-N-ethylpiperazine-1-carbothioamide;

Methyl 4-[8-[1-[4-cyano-3-(trifluoromethyl)phenyl]-2,5-dihydro-4-methyl-2,5-dioxo-1H-pyrrol-3-yl]octyl] piperazine-1-carboxylate;

S-Methyl 4-[8-[1-[4-cyano-3-(trifluoromethyl)phenyl]-2,5-dihydro-4-methyl-2,5-dioxo-1H-pyrrol-3-yl]octyl] piperazine-1-carbothioate;

4-[8-[1-[4-Cyano-3-(trifluoromethyl)phenyl]-2,5-dihydro-4-methyl-2,5-dioxo-1H-pyrrol-3-yl]octyl]-N,N-dimethylpiperazine-1-sulfonamide;

N-[4-[2,5-Dihydro-3-[6-[4-(2-methoxybenzoyl)piperazin-1-yl]hexyl]-4-methyl-2,5-dioxo-1H-pyrrol-1-yl]-2-(trifluoromethyl)phenyl]acetamide;

N-[4-[3-[6-[4-(Cyclobutylcarbonyl)piperazin-1-yl]hexyl]-2,5-dihydro-4-methyl-2,5-dioxo-1H-pyrrol-1-yl]-2-(trifluoromethyl)phenyl]acetamide;

N-[4-[2,5-Dihydro-3-methyl-2,51dioxo[6-[4-[(thien-2-yl)-carbonyl]piperazin-1-yl]hexyl]-1H-pyrrol-1-yl]-2-(trifluoromethyl)phenyl]acetamide;

N-[4-[3-[6-[4-(Dimethylamino)benzoyl]piperazin-1-yl]hexyl]-2,5-dihydro-4-methyl-2,5-dioxo-1H-pyrrol-1-yl]-2-(trifluoromethyl)phenyl]acetamide;

N-[4-[3-[6-(4-Acetylpiperazin-1-yl)hexyl]-2,5-dihydro-4-methyl-2,5-dioxo-1H-pyrrol-1-yl]-2-(trifluoromethyl)phenyl]acetamide;

N-[4-[2,5-Dihydro-3-methyl[6-[4-(methylsulfonyl)piperazin-1-yl]hexyl]-2,5-dioxo-1H-pyrrol-1-yl]-2-(trifluoromethyl)phenyl]acetamide;

N-[4-[3-[6-[4-[(2,1,3-Benzothiadiazol-4-yl)sulfonyl]piperazin-1-yl]hexyl]-2,5-dihydro-4-methyl-2,5-dioxo-1H-pyrrol-1-yl]-2-(trifluoromethyl)phenyl]acetamide;

4-[6-[1-[4-(ACETYLAMINO)-3-(TRIFLUOROMETHYL)PHENYL]-2,5-DIHYDRO-4-METHYL-2,5-DIOXO-1H-PYRROL-3-YL]HEXYL]-N-(PYRIDIN-4-YL)PIPERAZINE-1-CARBOXAMIDE;

3-[6-[4-(Cyclobutylcarbonyl)piperazin-1-yl]hexyl]-4-methyl-1-[4-nitro-3-(trifluoromethyl)phenyl]-1H-pyrrole-2,5-dione;

3-[6-[4-[4-(Dimethylamino)benzoyl]piperazin-1-yl]hexyl]-4-methyl-1-[4-nitro-3-(trifluoromethyl)phenyl]-1H-pyrrole-2,5-dione;

3-[6-(4-Acetylpiperazin-1-yl)hexyl]-4-methyl-1-[4-nitro-3-(trifluoromethyl)-phenyl]-1H-pyrrole-2,5-dione;

3-Methyl-4-[6-[4-(methylsufonyl)piperazin-1-yl]hexyl]-1-[4-nitro-3-(trifluoromethyl)phenyl]-1H-pyrrole-2,5-dione;

3-[6-[4-[(2,1,3-Benzothiadiazol-4-yl)sulfonyl]piperazin-1-yl]hexyl]-4-methyl-1-[4-nitro-3-(trifluoromethyl)phenyl]-1H-pyrrole-2,5-dione;

1-[3,4-Bis(trifluoromethyl)phenyl]-3-[6-[4-(2-methoxybenzoyl)piperazin-1-yl]hexyl]-4-methyl-1H-pyrrole-2,5-dione;

3-[6-(4-Acetylpiperazin-1-yl)hexyl]-1-[3,4-bis(trifluoromethyl)phenyl]-4-methyl-1H-pyrrole-2,5-dione;

1-[3,4-Bis(trifluoromethyl)phenyl]-3-[6-[4-(cyclobutylcarbonyl)piperazin-1-yl]hexyl]-4-methyl-1H-pyrrole-2,5-dione;

1-[3,4-Bis(trifluoromethyl)phenyl]-3-methyl-4-[6-[4-[(thien-2-yl)carbonyl]-piperazin-1-yl]hexyl]-1H-pyrrole-2,5-dione;

1-[3,4-Bis(trifluoromethyl)phenyl]-3-[6-[4-[4-(dimethylamino)benzoyl]piperazin-1-yl]hexyl]-4-methyl-1H-pyrrole-2,5-dione;

1-[3,4-Bis(trifluoromethyl)phenyl]-3-methyl-4-[6-[4-(methylsulfonyl)piperazin-1-yl]hexyl]-1H-pyrrole-2,5-dione;

3-[6-[4-[(2,1,3-Benzothiadiazol-4-yl)sulfonyl]piperazin-1-yl]hexyl]-1-[3,4-bis(trifluoromethyl)phenyl]-4-methyl-1H-pyrrole-2,5-dione;

-[3-Fluoro-4-(trifluoromethyl)phenyl]-3-[6-[4-(2-methoxybenzoyl)piperazin-1-yl]hexyl]-4-methyl-1H-pyrrole-2,5-dione;

3-[6-[4-(Cyclobutylcarbonyl)piperazin-1-yl]hexyl]-1-[3-fluoro-4-(trifluoromethyl)phenyl]-4-methyl-1H-pyrrole-2,5-dione;

1-[3-Fluoro-4-(trifluoromethyl)phenyl]-3-methyl-4-[6-[4-(thien-2-yl)carbonyl]piperazin-1-yl]hexyl]-1H-pyrrole-2,5-dione;

3-[6-[4-[4-(Dimethylamino)benzoyl]piperazin-1-yl]hexyl-]-1-[3-fluoro-4-(trifluoromethyl)phenyl]-4-methyl-1H-pyrrole-2,5-dione;

3-[6-[4-Acetylpiperazin-1-yl)hexyl]-1-[3-fluoro-4-(trifluoromethyl)phenyl]-4-methyl-1H-pyrrole-2,5-dione;

1-[3-Fluoro-4-(trifluoromethyl)phenyl]-3-methyl-4-[6-[4-(methylsulfonyl)-piperazin-1-yl]hexyl]-1H-pyrrole-2,5-dione;

3-[6-[4-[(2,1,3-Benzothiadiazol-4-yl)sulfonyl]piperazin-1-yl]hexyl]-1-[3-fluoro-(trifluoromethyl)phenyl]-4-methyl-1H-pyrrole-2,5-dione;

3-[4-(4-Acetylpiperazin-1-yl)butyl]-1-(1,3-dihydro-1-oxoisobenzofuran-5-yl)-4-methyl-1H-pyrrole-2,5-dione;

1-(1,3-Dihydro-1-oxoisobenzofuran-5-yl)-3-methyl-4-[4-[4-(1-oxopropyl)-piperazin-1-yl]butyl]-1H-pyrrole-2,5-dione;

1-(1,3-Dihydro-1-oxoisobenzofuran-5-yl)-3-[4-[4-[(2-methoxyethoxy)acetyl]piperazin-1-yl]butyl]-4-methyl-1H-pyrrole-2,5-dione;

1-(1,3-Dihydro-1-oxoisobenzofuran-5-yl)-3-[4-[4-[[2-(2-methoxyethoxy)ethoxy]acetyl]piperazin-1-yl]butyl]-4-methyl-1H-pyrrole-2,5-dione;

1-(1,3-Dihydro-1-oxoisobenzofuran-5-yl)-3-methyl-4-[4-[4-(methylsulfonyl)piperazin-1-yl]butyl]-1H-pyrrole-2,5-dione;

4-[4-[1-(1,3-Dihydro-1-oxoisobenzofuran-5-yl)-2,5-dihydro-4-methyl-2,5-dioxo-1H-pyrrol-3-yl]butyl]-N-ethylpiperazine-1-carbothioamide;

4-[4-[1-(1,3-Dihydro-1-oxoisobenzofuran-5-yl)-2,5-dihydro-4-methyl-2,5-dioxo-1H-pyrrol-3-yl]butyl]-N-propylpiperazine-1-carbothioamide;

4-[4-[1-(1,3-Dihydro-1-oxoisobenzofuran-5-yl)-2,5-dihydro-4-methyl-2,5-dioxo-1H-pyrrol-3-yl]butyl]-N-(prop-2-enyl)piperazine-1-carbothioamide;

3-[5-(4-Acetylpiperazin-1-yl)pentyl]-1-(1,3-dihydro-1-oxoisobenzofuran-5-yl)-4-methyl-1H-pyrrole-2,5-dione;

1-(1,3-Dihydro-1-oxoisobenzofuran-5-yl)-3-methyl-4-[5-[4-(1-oxopropyl)-piperazin-1-yl]pentyl]-1H-pyrrole-2,5-dione;

1-(1,3-Dihydro-1-oxoisobenzofuran-5-yl)-3-[5-[4-[(2-methoxyethoxy)acetyl]piperazin-1-yl]pentyl]-4-methyl-1H-pyrrole-2,5-dione;

1-(1,3-Dihydro-1-oxoisobenzofuran-5-yl)-3-[5-[4-[[2-(2-methoxyethoxy)ethoxy]acetyl]piperazin-1-yl]pentyl]-4-methyl-1H-pyrrole-2,5-dione;

1-(1,3-Dihydro-1-oxoisobenzofuran-5-yl)-3-methyl-4-[5-[4-(methylsulfonyl)piperazin-1-yl]pentyl]-1H-pyrrole-2,5-dione;

3-[5-[4-(Cyclopropylsulfonyl)piperazin-1-yl]pentyl]-1-(1,3-dihydro-1-oxoisobenzofuran-5-yl)-4-methyl-1H-pyrrole-2,5-dione;

1-(1,3-Dihydro-1-oxoisobenzofuran-5-yl)-3-[5-[4-[[2-[2-(2-methoxyethoxy)ethoxy]ethyl]sulfonyl]piperazin-1-yl]pentyl]-4-methyl-1H-pyrrole-2,5-dione;

4-[5-[1-(1,3-Dihydro-1-oxoisobenzofuran-5-yl)-2,5-dihydro-4-methyl-2,5-dioxo-1H-pyrrol-3-yl]pentyl]-N-ethylpiperazine-1-carbothioamide;

4-[5-[1-(1,3-Dihydro-1-oxoisobenzofuran-5-yl)-2,5-dihydro-4-methyl-2,5-dioxo-1H-pyrrol-3-yl]pentyl]-N-propylpiperazine-1-carbothioamide;

4-[5-[1-(1,3-Dihydro-1-oxoisobenzofuran-5-yl)-2,5-dihydro-4-methyl-2,5-dioxo-1H-pyrrol-3-yl]pentyl]-N-(prop-2-enyl)piperazine-1-carbothioamide;

1-(1,3-Dihydro-1-oxoisobenzofuran-5-yl)-3-[6-[4-(2-methoxybenzoyl)piperazin-1-yl]hexyl]-4-methyl-1H-pyrrole-2,5-dione;

3-[6-[4-(Cyclobutylcarbonyl)piperazin-1-yl]hexyl]-1-(1,3-dihydro-1-oxoisobenzofuran-5-yl)-4-methyl-1H-pyrrole-2,5-dione;

1-(1,3-Dihydro-1-oxoisobenzofuran-5-yl)-3-methyl-4-[6-[4-[(thien-2-yl)carbonyl]piperazin-1-yl]hexyl]-1H-pyrrole-2,5-dione;

1-(1,3-Dihydro-1-oxoisobenzofuran-5-yl)-3-[6-[4-[4-(dimethylamino)benzoyl]piperazin-1-yl]hexyl]-4-methyl-1H-pyrrole-2,5-dione;

3-[6-(4-Acetylpiperazin-1-yl)hexyl]-1-(1,3-dihydro-1-oxoisobenzofuran-5-yl)-4-methyl-1H-pyrrole-2,5-dione;

4-[4-[1-(1,3-Dihydro-1-oxoisobenzofuran-5-yl)-2,5-dihydro-4-methyl-2,5-dioxo-1H-pyrrol-3-yl]hexyl]-N,N-dimethylpiperazine-1-sulfonamide;

1-(1,3-Dihydro-1-oxoisobenzofuran-5-yl)-3-methyl-4-[6-[4-(methylsulfonyl)piperazin-1-yl]hexyl]-1H-pyrrole-2,5-dione;

3-[6-[4-[(2,1,3-Benzothiadiazolyl)sulfonyl]piperazin-1-yl]hexyl]-1-(1,3-dihydro-1-oxoisobenzofuran-5-yl)-4-methyl-1H-pyrrole-2,5-dione;

1-(1,3-Dihydro-1-oxoisobenzofuran-5-yl)-3-[6-[4-(ethylsulfonyl)piperazin-1-yl]hexyl]-4-methyl-1H-pyrrole-2,5-dione;

4-[6-[1-(1,3-Dihydro-1-oxoisobenzofuran-5-yl)-2,5-dihydro-4-methyl-2,5-dioxo-1H-pyrrol-3-yl]hexyl]-N-ethylpiperazine-1-carbothioamide;

4-[6-[1-(1,3-Dihydro-1-oxoisobenzofuran-5-yl)-2,5-dihydro-4-methyl-2,5-dioxo-1H-pyrrol-3-yl]hexyl]-N-propylpiperazine-1-carbothioamide;

4-[6-[1-(1,3-Dihydro-1-oxoisobenzofuran-5-yl)-2,5-dihydro-4-methyl-2,5-dioxo-1H-pyrrol-3-yl]hexyl]-N-(prop-2-enyl)piperazine-1-carbothioamide;

4-[6-[1-(1,3-Dihydro-1-oxoisobenzofuran-5-yl)-2,5-dihydro-4-methyl-2,5-dioxo-1H-pyrrol-3-yl]hexyl]-N-(phenylmethyl)piperazine-1-carbothioamide;

4-[6-[1-(1,3-Dihydro-1-oxoisobenzofuran-5-yl)-2,5-dihydro-4-methyl-2,5-dioxo-1H-pyrrol-3-yl]hexyl]-N-[(4-methylphenyl)methyl]piperazine-1-carbothioamide;

N-[(4-Chlorophenyl)methyl]-4-[6-[1-(1,3-dihydro-1-oxoisobenzofuran-5-yl)-2,5-dihydro-4-methyl-2,5-dioxo-1H-pyrrol-3-yl]hexyl]piperazine-1-carbothioamide;

4-[6-[1-(1,3-Dihydro-1,1-oxoisobenzofuran-5-yl)-2,5-dihydro-4-methyl-2,5-dioxo-1H-pyrrol-3-yl]hexyl]-N-phenylpiperazine-1-carbothioamide;

4-[6-[1-(1,3-Dihydro-1-oxoisobenzofuran-5-yl)-2,5-dihydromethyl-2,5-dioxo-1H-pyrrol-3-yl]hexyl]-N-(2,6-dimethylphenyl)piperazine-1-carbothioamide;

3-[6-[4-(2-Methoxybenzoyl)piperazin-1-yl]hexyl]-4-methyl-1-(4-methyl-1-oxo-1H-2,3-benzoxazin-6-yl)-1H-pyrrole-2,5-dione;

3-[6-[4-(Cyclobutylcarbonyl)piperazin-1-yl]hexyl]-4-methyl-1-(4-methyl-1-oxo-1H-2,3-benzoxazin-6-yl)-1H-pyrrole-2,5-dione;

3-Methyl-1-(4-methyl-1-oxo-1H-2,3-benzoxazin-6-yl)-4-[6-[4-[(thien-2-yl)carbonyl]piperazin-1-yl]hexyl]-1H-pyrrole-2,5-dione;

3-[6-[4-[4-(Dimethylamino)benzoyl]piperazin-1-yl]hexyl]-4-methyl-1-(4-methyl-1-oxo-1H-2,3-benzoxazin-6-yl)-1H-pyrrole-2,5-dione;

3-(6-(4-Acetylpiperazin-1-yl)hexyl]-4-methyl-1-(4-methyl-1-oxo-1H-2,3-benzoxazin-6-yl)-1H-pyrrole-2,5-dione;

3-Methyl-1-(4-methyl-1-oxo-1H-2,3-benzoxazin-6-yl)-4-[6-[4-(methylsulfonyl)piperazin-1-yl]hexyl]-1H-pyrrole-2,5-dione;

1-(2,3-Dihydro-1-oxo-1H-inden-5-yl)-3-[6-[4-(2-methoxybenzoyl)piperazin-1-yl]hexyl]-4-methyl-1H-pyrrole-2,5-dione;

3-[6-[4-(Cyclobutylcarbonyl)piperazin-1-yl]hexyl]-1-(2,3-dihydro-1-oxo-1H-inden-5-yl)-4-methyl-1H-pyrrole-2,5-dione;

1-(2,3-Dihydro-1-oxo-1H-inden-5-yl)-3-methyl-4-[6-[4-[(thien-2-yl)carbonyl]piperazin-1-yl]hexyl]-1H-pyrrole-2,5-dione;

1-(2,3-Dihydro-1-oxo-1H-inden-5-yl)-3-[6-[4-[4-(dimethylamino)benzoyl]-piperazin-1-yl]hexyl]-4-methyl-1H-pyrrole-2,5-dione;

3-[6-(4-Acetylpiperazin-1-yl)hexyl]-1-(2,3-dihydro-1-oxo-1H-inden-5-yl)-4-methyl-1H-pyrrole-2,5-dione;

1-(2,3-Dihydro-1-oxo-1H-inden-5-yl)-3-methyl-4-[6-[4-(methylsulfonyl)-piperazin-1-yl]hexyl]-1H-pyrrole-2,5-dione;

3-[6-[4-[(2,1,3-Benzothiadiazol-4-yl)sulfonyl]piperazin-1-yl]hexyl]-1-(2,3-dihydro-1-oxo-1H-inden-5-yl)-4-methyl-1H-pyrrole-2,5-dione;

4-[3-[2-(4-Acetylpiperazin-1-yl)ethyl]-4,4-dimethyl-5-oxo-2-thioxoimidazolidin-1-yl]-2-(trifluoromethyl)benzonitrile;

4-[4,4-Dimethyl-5-oxo-3-[2-[4-(1-oxopropyl)piperazin-1-yl]ethyl]-2-thioxoimidazolidin-1-yl]-2-(trifluoromethyl)benzonitrile;

4-[4,4-Dimethyl-3-[2-[4-(2-methyl-1-oxopropyl)piperazin-1-yl]ethyl]-5-oxo-2-thioxoimidazolidin-1-yl]-2-(trifluoromethyl)benzonitrile;

4-[4,4-Dimethyl-5-oxo-3-[2-[4-(1-oxobutyl)piperazin-1-yl]ethyl]-2-thioxoimidazolidin-1-yl]-2-(trifluoromethyl)benzonitrile;

4-[3-[2-[4-(Cyclopropylcarbonyl)piperazin-1-yl]ethyl]-4,4-dimethyl-5-oxo-2-thioxoimidazolidin-1-yl]-2-(trifluoromethyl)benzonitrile;

4-[3-[2-[4-(Cyclobutylcarbonyl)piperazin-1-yl]ethyl]-4,4-dimethyl-5-oxo-2-thioxoimidazolidin-1-yl]-2-(trifluoromethyl)benzonitrile;

4-[4,4-Dimethyl-5-oxo-3-[2-[4-[(thien-2-yl)acetyl]piperazin-1-yl]ethyl]-2-thioxoimidazolidin-1-yl]-2-(trifluoromethyl)benzonitrile;

4-[4,4-Dimethyl-5-oxo-3-[2-[4-[(thien-2-yl)carbonyl]piperazin-1-yl]ethyl]-2-thioxoimidazolidin-1-yl]-2-(trifluoromethyl)benzonitrile;

4-[4,4-Dimethyl-5-oxo-3-[2-[4-[(pyridin-4-yl)carbonyl]piperazin-1-yl]ethyl]-2-thioxoimidazolidin-1-yl]-2-(trifluoromethyl)benzonitrile;

4-[4,4-Dimethyl-3-[2-[4-(methylsulfonyl)piperazin-1-yl]ethyl]-5-oxo-2-thioxoimidazolidin-1-yl]-2-(trifluoromethyl)benzonitrile;

4-[3-[2-[4-(Ethylsulfonyl)piperazin-1-yl]ethyl]-4,4-dimethyl-5-oxo-2-thioxoimidazolidin-1-yl]-2-(trifluoromethyl)benzonitrile;

4-[4,4-Dimethyl-5-oxo-3-[2-[4-(propylsulfonyl)piperazin-1-yl]ethyl]-2-thioxoimidazolidin-1-yl]-2-(trifluoromethyl)benzonitrile;

4-[4,4-Dimethyl-5-oxo-3-[2-[4-(phenylsulfonyl)piperazin-1-yl]ethyl]-2-thioxoimidazolidin-1-yl]-2-(trifluoromethyl)benzonitrile;

4-[3-[2-[4-[(4-Cyanophenyl)sulfonyl]piperazin-1-yl]ethyl]-4,4-dimethyl-5-oxo-2-thioxoimidazolidin-1-yl]-2-(trifluoromethyl)benzonitrile;

4-[2-[3-[4-Cyano-3-(trifluoromethyl)phenyl]-5,5-dimethyl-4-oxo-2-thioxoimidazolidin-1-yl]ethyl]-N-ethylpiperazine-1-carbothioamide;

4-[2-[3-[4-Cyano-3-(trifluoromethyl)phenyl]-5,5-dimethyl-4-oxo-2-thioxoimidazolidin-1-yl]ethyl]-N-propylpiperazine-1-carbothioamide;

4-[2-[3-[4-Cyano-3-(trifluoromethyl)phenyl]-5,5-dimethyl-4-oxo-2-thioxoimidazolidin-1-yl]ethyl]-N-(prop-2-enyl)piperazine-1-carbothioamide;

S-Methyl 4-[2-[3-[4-cyano-3-(trifluoromethyl)phenyl]-5,5-dimethyl-4-oxo-2-thioxoimidazolidin-1-yl]ethyl]piperazine-1-carbothioate;

S-ETHYL 4-[2-[3-[4-CYANO-3-(TRIFLUOROMETHYL)PHENYL]-5,5-DIMETHYL-4-OXO-2-THIOXOIMIDAZOLIDIN-1-YL]ETHYL]PIPERAZINE-1-CARBOTHIOATE;

4-[3-[3-[4-(2-Methoxybenzoyl)piperazin-1-yl]propyl]-4,4-dimethyl-5-oxo-2-thioxoimidazolidin-1-yl]-2-(trifluoromethyl)benzonitrile;

4-[3-[3-(4-Acetylpiperazin-1-yl)propyl]-4,4-dimethyl-5-oxo-2-thioxoimidazolidin-1-yl]-2-(trifluoromethyl)benzonitrile;

4-[4,4-Dimethyl-5-oxo-3-[3-[4-(1-oxopropyl)piperazin-1-yl]-propyl]-2-thioxoimidazolidin-1-yl]-2-(trifluoromethyl)benzonitrile;

4-[4,4-Dimethyl-3-[3-[4-(2-methyl-1-oxopropyl)piperazin-1-yl]propyl]-5-oxo-2-thioxoimidazolidin-1-yl]-2-(trifluoromethyl)benzonitrile;

4-[4,4-Dimethyl-5-oxo-3-[3-[4-(1-oxobutyl)piperazin-1-yl]propyl]-2-thioxoimidazolidin-1-yl]-2-(trifluoromethyl)benzonitrile;

4-[3-[3-[4(Cyclopropylcarbonyl)piperazin-1-yl]propyl]-4,4-dimethyl-5-oxo-2-thioxoimidazolidin-1-yl]-2-(trifluoromethyl)benzonitrile;

4-[3-[3-[4-(Cyclobutylcarbonyl)piperazin-1-yl]propyl]-4,4-dimethyl-5-oxo-2-thioxoimidazolidin-1-yl]-2-(trifluoromethyl)benzonitrile;

4-[4,4-Dimethyl-5-oxo-3-[3-[4-[(thien-2-yl)acetyl]piperazin-1-yl]propyl]-2-thioxoimidazolidin-1-yl]-2-(trifluoromethyl)benzonitrile;

4-[4,4-Dimethyl-5-oxo-3-[3-[4-[(thien-2-yl)carbonyl]piperazin-1-yl]propyl]-2-thioxoimidazolidin-1-yl]-2-(trifluoromethyl)benzonitrile;

4-[4,4-Dimethyl-5-oxo-3-[3-[4-[(pyridin-4-yl)carbonyl]piperazin-1-yl]propyl]-2-thioxoimidazolidin-1-yl]-2-(trifluoromethyl)benzonitrile;

4-[3-[3-[4-(3-Methoxy-1-oxopropyl)piperazin-1-yl]propyl]-4,4-dimethyl-5-oxo-2-thioxoimidazolidin-1-yl]-2-(trifluoromethyl)benzonitrile;

4-[3-[3-[4-[(2-Methoxyethoxy)acetyl]piperazin-1-yl]propyl]-4,4-dimethyl-5-oxo-2-thioxoimidazolidin-1-yl]-2-(trifluoromethyl)benzonitrile;

4-[3-[3-[4-[[2-(2-Methoxyethoxy)ethoxy]acetyl]piperazin-1-yl]propyl]-4,4-dimethyl-5-oxo-2-thioxoimidazolidin-1-yl]-2-(trifluoromethyl)benzonitrile;

4-[4,4-Dimethyl-3-[3-[4-(methylsulfonyl)piperazin-1-yl]propyl]-5-oxo-2-thioxoimidazolidin-1-yl]-2-(trifluoromethyl)benzonitrile;

4-[3-[3-[4-(Ethylsulfonyl)piperazin-1-yl]propyl]-4,4-dimethyl-5-oxo-2-thioxoimidazolidin-1-yl]-2-(trifluoromethyl)benzonitrile;

4-[4,4-Dimethyl-5-oxo-3-[3-[4-(propylsulfonyl)piperazin-1-yl]propyl]-2-thioxoimidazolidin-1-yl]-2-(trifluoromethyl)benzonitrile;

4-[4,4-Dimethyl-5-oxo-3-[3-[4-(phenylsulfonyl)piperazin-1-yl]propyl]-2-thioxoimidazolidin-1-yl)]-2-(trifluoromethyl)benzonitrile;

4-[3-[3-[4-[(4-Cyanophenyl)sulfonyl]piperazin-1-yl]propyl]-4,4-dimethyl-5-oxo-2-thioxoimidazolidin-1-yl]-2-(trifluoromethyl)benzonitrile;

4-[3-[3-[4-Cyano-3-(trifluoromethyl)phenyl]-5,5-dimethyl-4-oxo-2-thioxoimidazolidin-1-yl]propyl]-N-ethylpiperazine-1-carbothioamide;

4-[3-[3-[4-Cyano-3-(trifluoromethyl)phenyl]-5,5-dimethyl-4-oxo-2-thioxoimidazolidin-1-yl]propyl]-N-propylpiperazine-1-carbothioamide;

4-[3-[3-[4-Cyano-3-(trifluoromethyl)phenyl]-5,5-dimethyl-4-oxo-2-thioxoimidazolidin-1-yl]propyl]-N-(prop-2-enyl)piperazine-1-carbothioamide;

S-Methyl 4-[3-[3-[4-cyano-3-(trifluoromethyl)phenyl]-5,5-dimethyl-4-oxo-2-thioxoimidazolidin-1-yl]propyl]piperazine-1-carbothioate;

S-Ethyl 4-[3-[3-[4-cyano-3-(trifluoromethyl)phenyl]-5,5-dimethyl-4-oxo-2-thioxoimidazolidin-1-yl]propyl]piperazine-1-carbothioate;

4-[3-[4-[4-(2-Methoxybenzoyl)piperazin-1-yl]butyl]-4,4-dimethyl-5-oxo-2-thioxoimidazolidin-1-yl]-2-(trifluoromethyl)benzonitrile;

4-[3-[4-(4-Acetylpiperazin-1-yl)butyl]-4,4-dimethyl-5-oxo-2-thioxoimidazolidin-1-yl]-2-(trifluoromethyl)benzonitrile;

4-[4,4-Dimethyl-5-oxo-3-[4-[4-(1-oxopropyl)piperazin-1-yl]butyl]-2-thioxoimidazolidin-1-yl]-2-(trifluoromethyl)benzonitrile;

4-[4,4-Dimethyl-3-[4-[4-(2-methyl-1-oxopropyl)piperazin-1-yl]butyl]-5-oxo-2-thioxoimidazolidin-1-yl]-2-(trifluoromethyl)benzonitrile;

4-[4,4-Dimethyl-5-oxo-3-[4-[4-(1-oxobutyl)piperazin-1-yl]butyl]-2-thioxoimidazolidin-1-yl]-2-(trifluoromethyl)benzonitrile;

4-[3-[4-[4-(Cyclopropylcarbonyl)piperazin-1-yl]butyl]-4,4-dimethyl-5-oxo-2-thioxoimidazolidin-1-yl]-2-(trifluoromethyl)benzonitrile;

4-[3-[4-[4-(Cyclobutylcarbonyl)piperazin-1-yl]butyl]-4,4-dimethyl-5-oxo-2-thioxoimidazolidin-1-yl]-2-(trifluoromethyl)benzonitrile;

4-[4,4-Dimethyl-5-oxo-3-[4-[4-[(thien-2-yl)acetyl]piperazin-1-yl]butyl]-2-thioxoimidazolidin-1-yl]-2-(trifluoromethyl)benzonitrile;

4-[3-[4-[4-(3-Methoxy-1-oxopropyl)piperazin-1-yl]butyl]-4,4-dimethyl-5-oxo-2-thioxoimidazolidin-1-yl]-2-(trifluoromethyl)benzonitrile;

4-[3-[4-[4-[(2-Methoxyethoxy)acetyl]piperazin-1-yl]
butyl]-4,4-dimethyl-5-thioxoimidazolidin-1-yl]-2-
(trifluoromethyl)benzonitrile;

4-[3-[4-[4-[[2-(2-Methoxyethoxy)ethoxy]acetyl]
piperazin-1-yl]butyl]-4,4-dimethyl-5-oxo-2-
thioxoimidazolidin-1-yl]-2-(trifluoromethyl)
benzonitrile;

4-[3-[4-[4-[(1,3-Dimethyl-1H-pyrazol-5-yl)carbonyl]
piperazin-1-yl]butyl]-4,4-dimethyl-5-oxo-2-
thioxoimidazolidin-1-yl]-2-(trifluoromethyl)
benzonitrile;

4-[3-[4-[4-[(Furan-3-yl)carbonyl]piperazin-1-yl]butyl]-4,
4-dimethyl-5-oxo-2-thioxoimidazolidin-1-yl]-2-
(trifluoromethyl)benzonitrile;

4-[3-[4-[4-[(2,5-Dimethylfuran-3-yl)carbonyl]piperazin-
1-yl]butyl]-4,4-dimethyl-5-oxo-2-thioxoimidazolidin-
1-yl]-2-(trifluoromethyl)benzonitrile;

4-[3-[4-[4-[(Isoxazol-5-yl)carbonyl]piperazin-1-yl]
butyl]-4,4-dimethyl-5-oxo-2-thioxoimidazolidin-1-yl]-
2-(trifluoromethyl)benzonitrile;

4-[4,4-Dimethyl-3-[4-[4-[(S-methylisoxazol-3-yl)
carbonyl]piperazin-1-yl]butyl]-5-oxo-2-
thioxoimidazolidin-1-yl]-2-(trifluoromethyl)
benzonitrile;

4-[4,4-Dimethyl-5-oxo-3-[4-[4-[(thien-3-yl)carbonyl]
piperazin-1-yl]butyl]-2-thioxoimidazolidin-1-yl]-2-
(trifluoromethyl)benzonitrile;

4-[4,4-Dimethyl-3-[4-[4-[(4-methyl-1,2,3-thiadiazol-4-
yl)carbonyl]piperazin-1-yl]butyl]-5-oxo-2-
thioxoimidazolidin-1-yl]-2-(trifluoromethyl)
benzonitrile;

4-[3-[4-[4-[(Furan-2-yl)carbonyl]piperazin-1-yl]butyl]-4,
4-dimethyl-5-oxo-2-thioxoimidazolidin-1-yl]-2-
(trifluoromethyl)benzonitrile;

4-[4,4-Dimethyl-5-oxo-3-[4-[4-[(thien-2-yl)carbonyl]
piperazin-1-yl]butyl]-2-thioxoimidazolidin-1-yl]-2-
(trifluoromethyl)benzonitrile;

4-[4,4-Dimethyl-5-oxo-3-[4-[4-[(pyridin-4-yl)carbonyl]
piperazin-1-yl]butyl]-2-thioxoimidazolidin-1-yl]-2-
(trifluoromethyl)benzonitrile;

4-[4,4-Dimethyl-3-[4-[4-(methylsulfonyl)piperazin-1-yl]
butyl]-5-oxo-2-thioxoimidazolidin-1-yl]-2-
(trifluoromethyl)benzonitrile;

4-[3-[4-[4-(ethylsulfonyl)piperazin-1-yl]butyl]-4,4-
dimethyl-5-oxo-2-thioxoimidazolidin-1-yl]-2-
(trifluoromethyl)benzonitrile;

4-[4,4-Dimethyl-5-oxo-3-[4-[4-(propylsulfonyl)
piperazin-1-yl]butyl]-2-thioxoimidazolidin-1-yl]-2-
(trifluoromethyl)benzonitrile;

4-[4,4-Dimethyl-5-oxo-3-[4-[4-(phenylsulfonyl)
piperazin-1-yl]butyl]-2-thioxoimidazolidin-1-yl]-2-
(trifluoromethyl)benzonitrile;

4-[3-[4-[4-[(4-Cyanophenyl)sulfonyl]piperazin-1-yl]
butyl]-4,4-dimethyl-5-oxo-2-thioxoimidazolidin-1-yl]-
2-(trifluoromethyl)benzonitrile;

4-[4,4-Dimethyl-3-[4-[4-[(1-methyl-1H-imidazol-4-yl)
sulfonyl]piperazin-1-yl]butyl]-5-oxo-2-
thioxoimidazolidin-1-yl]-2-(trifluoromethyl)
benzonitrile;

4-[3-[4-[4-[(3,5-Dimethylisoxazol-4-yl)sulfonyl]
piperazin-1-yl]butyl]-4,4-dimethyl-5-oxo-2-
thioxoimidazolidin-1-yl]-2-(trifluoromethyl)
benzonitrile;

4-[4-[3-[4-Cyano-3-(trifluoromethyl)phenyl]-5,5-
dimethyl-4-oxo-2-thioxoimidazolidin-1-yl]butyl]-N-
ethylpiperazine-1-carbothioamide;

4-[4-[3-[4-Cyano-3-(trifluoromethyl)phenyl]-5,5-
dimethyl-4-oxo-2-thioxoimidazolidin-1-yl]butyl]-N-
propylpiperazine-1-carbothioamide;

4-[4-[3-[4-Cyano-3-(trifluoromethyl)phenyl]-5,5-
dimethyl-4-oxo-2-thioxoimidazolidin-1-yl]butyl]-N-
(prop-2-enyl)piperazine-1-carbothioamide;

S-Methyl 4-[4-[3-[4-cyano-3-(trifluoromethyl)phenyl]-5,
5-dimethyl-4-oxo-2-thioxoimidazolidin-1-yl]butyl]
piperazine-1-carbothioate;

S-Ethyl 4-[4-[3-[4-cyano-3-(trifluoromethyl)phenyl]-5,5-
dimethyl-4-oxo-2-thioxoimidazolidin-1-yl]butyl]
piperazine-1-carbothioate;

4-[3-[5-(4-Acetylpiperazin-1-yl)pentyl]-4,4-dimethyl-5-
oxo-2-thioxoimidazolidin-1-yl]-2-(trifluoromethyl)
benzonitrile;

4-[4,4-Dimethyl-5-oxo-3-[5-[4-[1-oxopropyl)piperazin-
1-yl]pentyl]-2-thioxoimidazolidin-1-yl]-2-
(trifluoromethyl)benzonitrile;

4-[4,4-Dimethyl-3-[5-[4-(2-methyl-1-oxopropyl)
piperazin-1-yl]pentyl]-2-thioxoimidazolidin-1-yl]-2-
(trifluoromethyl)benzonitrile;

4-[4,4-Dimethyl-5-oxo-3-[5-[4-(1-oxobutyl)piperazin-1-
yl]pentyl]-2-thioxoimidazolidin-1-yl]-2-
(trifluoromethyl)benzonitrile;

4-[3-[5-[4-(Cyclopropylcarbonyl)piperazin-1-yl]pentyl]-
4,4-dimethyl-5-oxo-2-thioxoimidazolidin-1-yl]-2-
(trifluoromethyl)benzonitrile;

4-[3-[5-[4-(Cyclobutylcarbonyl)piperazin-1-yl]pentyl]-4,
4-dimethyl-5-oxo-2-thioxoimidazolidin-1-yl]-2-
(trifluoromethyl)benzonitrile;

4-[4,4-Dimethyl-5-oxo-3-[5-[4-[(thien-2-yl)acetyl]
piperazin-1-yl]pentyl]-2-thioxoimidazolidin-1-yl]-2-
(trifluoromethyl)benzonitrile;

4-[3-[5-[4-(3-Methoxy-1-oxopropyl)piperazin-1-yl]
pentyl]-4,4-dimethyl-5-oxo-2-thioxoimidazolidin-1-
yl]-2-(trifluoromethyl)benzonitrile;

4-[3-[5-[4-[(2-Methoxyethoxy)acetyl]piperazin-1-yl]
pentyl]-4,4-dimethyl-5-oxo-2-thioxoimidazolidin-1-
yl]-2-(trifluoromethyl)benzonitrile;

4-[3-[5-[4-[[2-(2-Methoxyethoxy)ethoxy]acetyl]
piperazin-1-yl]pentyl]-4,4-dimethyl-5-oxo-2-
thioxoimidazolidin-1-yl]-2-(trifluorometbyl)
benzonitrile;

4-[3-[5-[4-[(1,3-Dimethyl-1H-pyrazol-5-yl)carbonyl]
piperazin-1-yl]pentyl]-4,4-dimethyl-5-oxo-2-
thioxoimidazolidin-1-yl]-2-(trifluoromethyl)
benzonitrile;

4-[3-[5-[4-[(Furan-3-yl)carbonyl]piperazin-1-yl]pentyl]-
4,4-dimethyl-5-thioxoimidazolidin-1-yl]-2-
(trifluoromethyl)benzonitrile;

4-[3-[5-[4-[(2,5-Dimethylfuran-3-yl)carbonyl]piperazin-
1-yl]pentyl]-4,4-dimethyl-5-oxo-2-
thioxoimidazolidin-1-yl]-2-(trifluoromethyl)
benzonitrile;

4-[3-[5-[4-[(Isoxazol-5-yl)carbonyl]piperazin-1-yl]
pentyl]-4,4-dimethyl-5-thioxoimidazolidin-1-yl]-2-
(trifluoromethyl)benzonitrile;

4-[4,4-Dimethyl-3-[5-[4-[(5-methylisoxazol-3-yl)
carbonyl]piperazin-1-yl]pentyl]-5-oxo-2-
thioxoimidazolidin-1-yl]-2-(trifluoromethyl)
benzonitrile;

4-[4,4-Dimethyl-5-oxo-3-[5-[4-[(thien-3-yl)carbonyl]
piperazin-1-yl]pentyl]-2-thioxoimidazolidin-1-yl]-2-
(trifluoromethyl)benzonitrile;

4-[4,4-Dimethyl-3-[5-[4-[(4-methyl-1,2,3-thiadiazol-4-yl)carbonyl]piperazin-1-yl]pentyl]-5-oxo-2-thioxoimidazolidin-1-yl]-2-(trifluoromethyl)benzonitrile;

4-[4,4-Dimethyl-5-oxo-3-[5-[4-[(thien-2-yl)carbonyl]piperazin-1-yl]pentyl]-2-thioxoimidazolidin-1-yl]-2-(trifluoromethyl)benzonitrile;

4-[4,4-Dimethyl-5-oxo-3-[5-[4-[(pyridin-4-yl)carbonyl]piperazin-1-yl]pentyl]-2-thioxoimidazolidin-1-yl]-2-(trifluoromethyl)benzonitrile;

4-[4,4-Dimethyl-3-[5-[4-(methylsulfonyl)piperazin-1-yl]pentyl]-5-oxo-2-thioxoimidazolidin-1-yl]-2-(trifluoromethyl)benzonitrile;

4-[3-[5-[4-(Ethylsulfonyl)piperazin-1-yl]pentyl]-4,4-dimethyl-5-oxo-2-thioxoimidazolidin-1-yl]-2-(trifluoromethyl)benzonitrile;

4-[4,4-Dimethyl-5-oxo-3-[5-[4-(propylsulfonyl)piperazin-1-yl]pentyl]-2-thioxoimidazolidin-1-yl]-2-(trifluoromethyl)benzonitrile;

4-[4,4-Dimethyl-5-oxo-3-[5-[4-(phenylsulfonyl)piperazin-1-yl]pentyl]-2-thioxoimidazolidin-1-yl]-2-(trifluoromethyl)benzonitrile;

4-[3-[5-[4-[(4-Cyanophenyl)sulfonyl]piperazin-1-yl]pentyl]-4,4-dimethyl-5-oxo-2-thioxoimidazolidin-1-yl]-2-(trifluoromethyl)benzonitrile;

4-[3-[5-[4-[(2-Methoxyethyl)sulfonyl]piperazin-1-yl]pentyl]-4,4-dimethyl-5-oxo-2-thioxoimidazolidin-1-yl]-2-(trifluoromethyl)benzonitrile;

4-[3-[5-[4-[[2-(2-Methoxyethoxy)ethyl]sulfonyl]piperazin-1-yl]pentyl]-4,4-dimethyl-5-oxo-2-thioxoimidazolidin-1-yl]-2-(trifluoromethyl)benzonitrile;

4-[3-[5-[4-[[2-[2-(2-Methoxyethoxy)ethoxy]ethyl]sulfonyl]piperazin-1-yl]pentyl]-4,4-dimethyl-5-oxo-2-thioxoimidazolidin-1-yl]-2-(trifluoromethyl)benzonitrile;

4-[4,4-Dimethyl-3-[5-[4-[(1-methyl-1H-imidazol-4-yl)sulfonyl]piperazin-1-yl]pentyl]-5-oxo-2-thioxoimidazolidin-1-yl]-2-(trifluoromethyl)benzonitrile;

4-[3-[5-[4-[(3,5-Dimethylisoxazol-4-yl)sulfonyl]piperazin-1-yl]pentyl]-4,4-dimethyl-5-oxo-2-thioxoimidazolidin-1-yl]-2-(trifluoromethyl)benzonitrile;

4-[5-[3-[4-Cyano-3-(trifluoromethyl)phenyl]-5,5-dimethyl-4-oxo-2-thioxoimidazolidin-1-yl]pentyl]-N-ethylpiperazine-1-carbothioamide;

4-[5-[3-[4-Cyano-3-(trifluoromethyl)phenyl]-5,5-dimethyl-4-oxo-2-thioxoimidazolidin-1-yl]pentyl]-N-propylpiperazine-1-carbothioamide;

4-[5-[3-[4-Cyano-3-(trifluoromethyl)phenyl]-5,5-dimethyl-4-oxo-2-thioxoimidazolidin-1-yl]pentyl]-N-(prop-2-enyl)piperazine-1-carbothioamide;

S-Methyl 4-[5-[3-[4-cyano-3-(trifluoromethyl)phenyl]-5,5-dimethyl-4-oxo-2-thioxoimidazolidin-1-yl]pentyl]piperazine-1-carbothioate;

S-ETHYL 4-[5-[3-[4-CYANO-3-(TRIFLUOROMETHYL)PHENYL]-5,5-DIMETHYL-4-OXO-2-THIOXOIMIDAZOLIDIN-1-YL]PENTYL]PIPERAZINE-1-CARBOTHIOATE;

4-[4,4-Dimethyl-3-[6-(4-methylpiperazin-1-yl)hexyl]-5-oxo-2-thioxoimidazolidin-1-yl]-2-(trifluoromethyl)benzonitrile;

4-[4,4-Dimethyl-3-[6-[4-(1-methylethyl)piperazin-1-yl]hexyl]-5-oxo-2-thioxoimidazolidin-1-yl]-2-(trifluoromethyl)benzonitrile;

4-[3-[6-[4-(2-Methoxybenzoyl)piperazin-1-yl]hexyl]-4,4-dimethyl-5-oxo-2-thioxoimidazolidin-1-yl]-2-(trifluoromethyl)benzonitrile;

4-[3-[6-(4-Acetylpiperazin-1-yl)hexyl]-4,4-dimethyl-5-oxo-2-thioxoimidazolidin-1-yl]-2-(trifluoromethyl)benzonitrile;

4-[4,4-Dimethyl-5-oxo-3-[6-[4-(1-oxopropyl)piperazin-1-yl]hexyl]-2-thioxoimidazolidin-1-yl]-2-(trifluoromethyl)benzonitrile;

4-[4,4-Dimethyl-3-[6-[4-(2-methyl-1-oxopropyl)piperazin-1-yl]hexyl]-5-oxo-2-thioxoimidazolidin-1-yl]-2-(trifluoromethyl)benzonitrile;

4-[4,4-Dimethyl-5-oxo-3-[6-[4-(1-oxobutyl)piperazin-1-yl]hexyl]-2-thioxoimidazolidin-1-yl]-2-(trifluoromethyl)benzonitrile;

4-[3-[6-[4-(Cyclopropylcarbonyl)piperazin-1-yl]hexyl]-4,4-dimethyl-5-oxo-2-thioxoimidazolidin-1-yl]-2-(trifluoromethyl)benzonitrile;

4-[3-[6-[4-(Cyclobutylcarbonyl)piperazin-1-yl]hexyl]-4,4-dimethyl-5-oxo-2-thioxoimidazolidin-1-yl]-2-(trifluoromethyl)benzonitrile;

4-[3-[6-[4-(3-Methoxy-1-oxopropyl)piperazin-1-yl]hexyl]-4,4-dimethyl-5-oxo-2-thioxoimidazolidin-1-yl]-2-(trifluoromethyl)benzonitrile;

4-[3-[6-[4-[(2-Methoxyethoxy)acetyl]piperazin-1-yl]hexyl]-4,4-dimethyl-5-oxo-2-thioxoimidazolidin-1-yl]-2-(trifluoromethyl)benzonitrile;

4-[3-[6-[4-[[2-(2-Methoxyethoxy)ethoxy]acetyl]piperazin-1-yl]hexyl]-4,4-dimethyl-5-oxo-2-thioxoimidazolidin-1-yl]-2-(trifluoromethyl)benzonitrile;

4-[4,4-Dimethyl-5-oxo-3-[6-[4-[(thien-2-yl)acetyl]piperazin-1-yl]hexyl]-2-thioxoimidazolidin-1-yl]-2-(trifluoromethyl)benzonitrile;

4-[3-[6-[4-[(Furan-2-yl)carbonyl]piperazin-1-yl]hexyl]-4,4-dimethyl-5-oxo-2-thioxoimidazolidin-1-yl]-2-(trifluoromethyl)benzonitrile;

4-[4,4-Dimethyl-5-oxo-3-[6-[4-[(thien-2-yl)carbonyl]piperazin-1-yl]hexyl]-2-thioxoimidazolidin-1-yl]-2-(trifluoromethyl)benzonitrile;

4-[4,4-Dimethyl-5-oxo-3-[6-[4-[(pyridin-4-yl)carbonyl]piperazin-1-yl]hexyl]-2-thioxoimidazolidin-1-yl]-2-(trifluoromethyl)benzonitrile;

4-[4,4-Dimethyl-3-[6-[4-(methylsulfonyl)piperazin-1-yl]hexyl]-5-oxo-2-thioxoimidazolidin-1-yl]-2-(trifluoromethyl)benzonitrile;

4-[3-[6-[4-(Ethylsulfonyl)piperazin-1-yl]hexyl]-4,4-dimethyl-5-oxo-2-thioxoimidazolidin-1-yl]-2-(trifluoromethyl)benzonitrile;

4-[4,4-Dimethyl-5-oxo-3-[6-[4-(propylsulfonyl)piperazin-1-yl]hexyl]-2-thioxoimidazolidin-1-yl]-2-(trifluoromethyl)benzonitrile;

4-[4,4-Dimethyl-5-oxo-3-[6-[4-(phenylsulfonyl)piperazin-1-yl]hexyl]-2-thioxoimidazolidin-1-yl]-2-(trifluoromethyl)benzonitrile;

4-[3-[6-[4-[(4-Cyanophenyl)sulfonyl]piperazin-1-yl]hexyl]-4,4-dimethyl-5-oxo-2-thioxoimidazolidin-1-yl]-2-(trifluoromethyl)benzonitrile;

4-[6-[3-[4-Cyano-3-(trifluoromethyl)phenyl]-5,5-dimethyl-4-oxo-2-thioxoimidazolidin-1-yl]hexyl]-N-ethylpiperazine-1-carbothioamide;

4-[6-[3-[4-Cyano-3-(trifluoromethyl)phenyl]-5,5-dimethyl-4-oxo-2-thioxoimidazolidin-1-yl]hexyl]-N-propylpiperazine-1-carbothioamide;

4-[6-[3-[4-Cyano-3-(trifluoromethyl)phenyl]-5,5-dimethyl-4-oxo-2-thioxoimidazolidin-1-yl]hexyl]-N-(prop-2-enyl)piperazine-1-carbothioamide;

S-Methyl 4-[6-[3-[4-cyano-3-(trifluoromethyl)phenyl]-5,5-dimethyl-4-oxo-2-thioxoimidazolidin-1-yl]hexyl]piperazine-1-carbothioate;

S-ETHYL 4-[6-[3-[4-CYANO-3-(TRIFLUOROMETHYL)PHENYL]-5,5-DIMETHYL4-OXO-2-THIOXOIMIDAZOLIDIN-1-YL]HEXYL]PIPERAZINE-1-CARBOTHIOATE;

4-[4,4-Dimethyl-3-[7-(4-methylpiperazin-1-yl)heptyl]-5-oxo-2-thioxoimidazolidin-1-yl]-2-(trifluoromethyl)benzonitrile;

4-[3-[7-(4-Acetylpiperazin-1-yl)heptyl]-4,4-dimethyl-5-oxo-2-thioxoimidazolidin-1-yl]-2-(trifluoromethyl)benzonitrile;

4-[4,4-Dimethyl-3-[7-[4-(methylsulfonyl)piperazin-1-yl]heptyl]-5-oxo-2-thioxoimidazolidin-1-yl]-2-(trifluoromethyl)benzonitrile;

4-[4,4-Dimethyl-3-[8-[4-(2-methyl-1-oxopropyl)piperazin-1-yl]octyl]-5-oxo-2-thioxoimidazolidin-1-yl]-2-(trifluoromethyl)benzonitrile;

4-[3-[8-[4-(Cyclopropylcarbonyl)piperazin-1-yl]octyl]-4,4-dimethyl-5-oxo-2-thioxoimidazolidin-1-yl]-2-(trifluoromethyl)benzonitrile;

4-[3-[8-[4-(Cyclobutylcarbonyl)piperazin-1-yl]octyl]-4,4-dimethyl-5-oxo-2-thioxoimidazolidin-1-yl]-2-(trifluoromethyl)benzonitrile;

4-[4,4-Dimethyl-5-oxo-3-[8-[4-[(thien-2-yl)carbonyl]piperazin-1-yl]octyl]-2-thioxoimidazolidin-1-yl]-2-(trifluoromethyl)benzonitrile;

4-[4,4-Dimethyl-5-oxo-3-[8-[4-[(pyridin-4-yl)carbonyl]piperazin-1-yl]octyl]-2-thioxoimidazolidin-1-yl]-2-(trifluoromethyl)benzonitrile;

4-[4,4-Dimethyl-3-[8-[4-(methylsulfonyl)piperazin-1-yl]octyl]-5-oxo-2-thioxoimidazolidin-1-yl]-2-(trifluoromethyl)benzonitrile;

4-[4,4-Dimethyl-5-oxo-3-[8-[4-(propylsulfonyl)piperazin-1-yl]octyl]-2-thioxoimidazolidin-1-yl]-2-(trifluoromethyl)benzonitrile;

4-[4,4-Dimethyl-3-[8-[4-[(1-methylethyl)sulfonyl]piperazin-1-yl]octyl]-5-oxo-2-thioxoimidazolidin-1-yl]-2-(trifluoromethyl)benzonitrile;

4-[3-[8-[4-[(2-Methoxyethyl)sulfonyl]piperazin-1-yl]octyl]-4,4-dimethyl-5-oxo-2-thioxoimidazolidin-1-yl]-2-(trifluoromethyl)benzonitrile;

4-[3-[8-[4-[(4-Cyanophenyl)sulfonyl]piperazin-1-yl]octyl]-4,4-dimethyl-5-oxo-2-thioxoimidazolidin-1-yl]-2-(trifluoromethyl)benzonitrile;

4-[8-[3-[4-Cyano-3-(trifluoromethyl)phenyl]-5,5-dimethyl-4-oxo-2-thioxoimidazolidin-1-yl]octyl]-N-ethylpiperazine-1-carbothioamide;

4-[8-[3-[4-Cyano-3-(trifluoromethyl)phenyl]-5,5-dimethyl-4-oxo-2-thioxoimidazolidin-1-yl]octyl]-N-(prop-2-enyl)piperazine-1-carbothioamide;

S-METHYL 4-[8-[3-[4-CYANO-3-(TRIFLUOROMETHYL)PHENYL]-5,5-DIMETHYL-4-OXO-2-THIOXOIMIDAZOLIDIN-1-YL]OCTYL]PIPERAZINE-1-CARBOTHIOATE;

3-(1,3-Dihydro-1-oxoisobenzofuran-5-yl)-5,5-dimethyl-1-[3-[4-[(thien-2-yl)carbonyl]piperazin-1-yl]propyl]-2-thioxoimidazolidin-4-one;

3-[1,3-Dihydro-1-oxoisobenzofuran-5-yl]-1-[3-[4-[4-(dimethylamino)benzoyl]piperazin-1-yl]propyl]-5,5-dimethyl-2-thioxoimidazolidin-4-one;

N-[(4-Chlorophenyl)methyl]-4-[3-[3-(1,3-dihydro-1-oxoisobenzofuran-5-yl)-5,5-dimethyl-4-oxo-2-thioxoimidazolidin-1-yl]propyl]piperazine-1-carbothioamide;

S-Ethyl 4-[3-[3-(1,3-dihydro-1-oxoisobenzofuran-5-yl)-5,5-dimethyl-4-oxo-2-thioxoimidazolidin-1-yl]propyl]piperazine-1-carbothioate;

4-[3-[3-(1,3-Dihydro-1-oxoisobenzofuran-5-yl)-5,5-dimethyl-4-oxo-2-thioxoimidazolidin-1-yl]propyl]-N,N-diethylpiperazine-1-carboxylic acid amide;

3-(1,3-Dihydro-1-oxoisobenzofuran-5-yl)-5,5-dimethyl-1-[4-[4-[(thien-2-yl)carbonyl]piperazin-1-yl]butyl]-2-thioxoimidazolidin-4-one;

3-(1,3-Dihydro-1-oxoisobenzofuran-5-yl)-1-[4-[4-(2-methoxybenzoyl)piperazin-1-yl]butyl]-5,5-dimethyl-2-thioxoimidazolidin-4-one;

3-(1,3-Dihydro-1-oxoisobenzofuran-5-yl)-1-[4-[4-[4-(dimethylamino)benzoyl]piperazin-1-yl]butyl]-5,5-dimethyl-2-thioxoimidazolidin-4-one;

1-[4-[4-[2,1,3-Benzothiadiazol-4-yl)sulfonyl]piperazin-1-yl]butyl]-3-(1,3-dihydro-1-oxoisobenzofuran-5-yl)-5,5-dimethyl-2-thioxoimidazolidin-4-one;

N-(2,6-Dichloropyridin-4-yl)-4-[3-[3-(1,3-dihydro-1-oxoisobenzofuran-5-yl)-5,5-dimethyl-4-oxo-2-thioxoimidazolidin-1-yl]butyl]piperazine-1-carboxylic acid amide;

S-Methyl 4-[4-[3-(1,3-dihydro-1-oxoisobenzofuran-5-yl)-5,5-dimethyl-4-oxo-2-thioxoimidazolidin-1-yl]butyl]piperazine-1-carbothioate;

S-Ethyl 4-[4-[3-(1,3-dihydro-1-oxoisobenzofuran-5-yl)-5,5-dimethyl-4-oxo-2-thioxoimidazolidin-1-yl]butyl]piperazine-1-carbothioate;

3-(1,3-Dihydro-1-oxoisobenzofuran-5-yl)-5,5-dimethyl-1-[5-[4-(2-methyl-1-oxopropyl)piperazin-1-yl]pentyl]-2-thioxoimidazolidin-4-one;

3-(1,3-Dihydro-1-oxoisobenzofuran-5-yl)-5,5-dimethyl-1-[5-[4-[(thien-2-yl)acetyl]piperazin-1-yl]pentyl]-2-thioxoimidazolidin-4-one;

3-(1,3-Dihydro-1-oxoisobenzofuran-5-yl)-5,5-dimethyl-1-[5-[4-[(thien-2-yl)carbonyl]piperazin-1-yl]pentyl]-2-thioxoimidazolidin-4-one;

3-(1,3-Dihydro-1-oxoisobenzofuran-5-yl)-1-[5-[4-ethylsulfonyl)piperazin-1-yl]pentyl]-5,5-dimethyl-2-thioxoimidazolidin-4-one;

4-[[4-[5-[3-(1,3-Dihydro-1-oxoisobenzofuran-5-yl)-5,5-dimethyl-4-oxo-2-thioxoimidazolidin-1-yl]pentyl]piperazin-1-yl]sulfonyl]benzonitrile;

S-Ethyl 4-[5-[3-(1,3-dihydro-1-oxoisobenzofuran-5-yl)-5,5-dimethyl-4-oxo-2-thioxoimidazolidin-1-yl]pentyl]piperazine-1-carbothioate;

3-(1,3-Dihydro-1-oxoisobenzofuran-5-yl)-1-[6-[4-(2-methoxybenzoyl)piperazin-1-yl]hexyl]-5,5-dimethyl-2-thioxoimidazolidin-4-one;

3-(1,3-Dihydro-1-oxoisobenzofuran-5-yl)-1-[6-[4-[4-(dimethylamino)benzoyl]piperazin-1-yl]hexyl]-5,5-dimethyl-2-thioxoimidazolidin-4-one;

3-[[4-[6-[3-(1,3-Dihydro-1-oxoisobenzofuran-5-yl)-5,5-dimethyl-4-oxo-2-thioxoimidazolidin-1-yl]hexyl]piperazin-1-yl]carbonyl]benzonitrile;

1-[6-(4-Acetylpiperazin-1-yl)hexyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[6-[4-(1-oxopropyl)piperazin-1-yl]hexyl]-2-thioxoimidazolidin-4-one;

3-(1,3-Dihydro-1-oxoisobenzofuran-5-yl)-5,5-dimethyl-1-[6-[4-(2-methyl-1-oxopropyl)piperazin-1-yl]hexyl]-2-thioxoimidazolidin-4-one;

3-(1,3-Dihydro-1-oxoisobenzofuran-5-yl)-5,5-dimethyl-1-[6-[4-(1-oxobutyl)piperazin-1-yl]hexyl]-2-thioxoimidazolidin-4-one;

1-[6-[4-(Cyclopropylcarbonyl)piperazin-1-yl]hexyl]-3-(1,3-dihydro-1-oxoisobenzofuran-5-yl)-5,5-dimethyl-2-thioxoimidazolidin-4-one;

1-[6-[4-(Cyclobutylcarbonyl)piperazin-1-yl]hexyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[6-[4-[(pyridin-4-yl)carbonyl]piperazin-1-yl]hexyl]-2-thioxoimidazolidin-4-one;

3-(1,3-Dihydro-1-oxoisobenzofuran-5-yl)-5,5-dimethyl-1-[6-[4-[(thien-2-yl)carbonyl]piperazin-1-yl]hexyl]-2-thioxoimidazolidin-4-one;

3-(1,3-Dihydro-1-oxoisobenzofuran-5-yl)-5,5-dimethyl-1-[6-[4-[(thien-2-yl)acetyl]piperazin-1-yl]hexyl]-2-thioxoimidazolidin-4-one;

3-(1,3-Dihydro-1-oxoisobenzofuran-5-yl)-5,5-dimethyl-1-[6-[4-(methylsulfonyl)piperazin-1-yl]hexyl]-2-thioxoimidazolidin-4-one;

3-(1,3-Dihydro-1-oxoisobenzofuran-5-yl)-1-[6-[4-(ethylsulfonyl)piperazin-1-yl]hexyl]-5,5-dimethyl-2-thioxoimidazolidin-4-one;

3-(1,3-Dihydro-1-oxoisobenzofuran-5-yl)-5,5-dimethyl-1-[6-[4-(propylsulfonyl)piperazin-1-yl]hexyl]-2-thioxoimidazolidin-4-one;

3-(1,3-Dihydro-1-oxoisobenzofuran-5-yl)-5,5-dimethyl-1-[6-[4-(phenylsulfonyl)piperazin-1-yl]hexyl]-2-thioxoimidazolidin-4-one;

4-[[4-[6-[3-(1,3-Dihydro-1-oxoisobenzofuran-5-yl)-5,5-dimethyl-4-oxo-2-thioxoimidazolidin-1-yl]hexyl]piperazin-1-yl]sulfonyl]benzonitrile;

1-[6-[4-[(2,1,3-Benzothiadiazol-4-yl)sulfonyl]piperazin-1-yl]hexyl]-3-(1,3-dihydro-1-oxoisobenzofuran-5-yl)-5,5-dimethyl-2-thioxoimidazolidin-4-one;

4-[6-[3-(1,3-Dihydro-1-oxoisobenzofuran-5-yl)-5,5-dimethyl-4-oxo-2-thioxoimidazolidin-1-yl]hexyl]-N-[3-(methylsulfanyl)phenyl]piperazine-1-carboxylic acid amide;

4-[6-[3-(1,3-Dihydro-1-oxoisobenzofuran-5-yl)-5,5-dimethyl-4-oxo-2-thioxoimidazolidin-1-yl]hexyl]-N-(3-fluorophenyl)piperazine-1-carboxylic acid amide;

4-[6-[3-(1,3-Dihydro-1-oxoisobenzofuran-5-yl)-5,5-dimethyl-4-oxo-2-thioxoimidazolidin-1-yl]hexyl]-N-(4-fluorophenyl)piperazine-1-carboxylic acid amide;

4-[6-[3-(1,3-Dihydro-1-oxoisobenzofuran-5-yl)-5,5-dimethyl-4-oxo-2-thioxoimidazolidin-1-yl]hexyl]-N-ethylpiperazine-1-carbothioamide;

4-[6-[3-(1,3-Dihydro-1-oxoisobenzofuran-5-yl)-5,5-dimethyl-4-oxo-2-thioxoimidazolidin-1-yl]hexyl]-N-propylpiperazine-1-carbothioamide;

4-[6-[3-(1,3-Dihydro-1-oxoisobenzofuran-5-yl)-5,5-dimethyl-4-oxo-2-thioxoimidazolidin-1-yl]hexyl]-N-(prop-2-enyl)piperazine-1-carbothioamide;

4-[6-[3-(1,3-Dihydro-1-oxoisobenzofuran-5-yl)-5,5-dimethyl-4-oxo-2-thioxoimidazolidin-1-yl]hexyl]-N-phenylpiperazine-1-carbothioamide;

4-[6-[3-(1,3-Dihydro-1-oxoisobenzofuran-5-yl)-5,5-dimethyl-4-oxo-2-thioxoimidazolidin-1-yl]hexyl]-N-(phenylmethyl)piperazine-1-carbothioamide;

S-Methyl 4-[6-[3-(1,3-dihydro-1-oxoisobenzofuran-5-yl)-5,5-dimethyl-4-oxo-2-thioxoimidazolidin-1-yl]hexyl]piperazine-1-carbothioate;

S-Ethyl 4-[6-[3-(1,3-dihydro-1-oxoisobenzofuran-5-yl)-5,5-dimethyl-4-oxo-2-thioxoimidazolidin-1-yl]hexyl]piperazine-1-carbothioate;

4-[6-[3-(1,3-DIHYDRO-1-OXOISOBENZOFURAN-5-YL)-5,5-DIMETHYL-4-OXO-2-THIOXOIMIDAZOLIDIN-1-YL)HEXYL]-N,N-DIETHYLPIPERAZINE-1-CARBOXYLIC ACID AMIDE;

3-(1,3-Dihydro-1-oxoisobenzofuran-5-yl)-1-[7-[4-(2-methoxybenzoyl)piperazin-1-yl]heptyl]-5,5-dimethyl-2-thioxoimidazolidin-4-one;

1-[7-(4-Acetylpiperazin-1-yl)heptyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[7-[4-(1-oxopropyl)piperazin-1-yl]heptyl]-2-thioxoimidazolidin-4-one;

3-(1,3-Dihydro-1-oxoisobenzofuran-5-yl)-5,5-dimethyl-1-[7-[4-(2-methyl-1-oxopropyl)piperazin-1-yl]heptyl]-2-thioxoimidazolidin-4-one;

3-(1,3-Dihydro-1-oxoisobenzofuran-5-yl)-5,5-dimethyl-1-[7-[4-(1-oxobutyl)piperazin-1-yl]heptyl]-2-thioxoimidazolidin-4-one;

1-[7-[4-(Cyclopropylcarbonyl)piperazin-1-yl]heptyl]-3-(1,3-dihydro-1-oxoisobenzofuran-5-yl)-5,5-dimethyl-2-thioxoimidazolidin-4-one;

1-[7-[4-(Cyclobutylcarbonyl)piperazin-1-yl]heptyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[7-[4-[(thien-2-yl)carbonyl]piperazin-1-yl]heptyl]-2-thioxoimidazolidin-4-one;

3-(1,3-Dihydro-1-oxoisobenzofuran-5-yl)-5,5-dimethyl-1-[7-[4-[(thien-2-yl)acetyl]piperazin-1-yl]heptyl]-2-thioxoimidazolidin-4-one;

3-(1,3-Dihydro-1-oxoisobenzofuran-5-yl)-5,5-dimethyl-1-[7-[4-(methylsulfonyl)piperazin-1-yl]heptyl]-2-thioxoimidazolidin-4-one;

3-(1,3-Dihydro-1-oxoisobenzofuran-5-yl)-1-[7-[4-(ethylsulfonyl)piperazin-1-yl]heptyl]-5,5-dimethyl-2-thioxoimidazolidin-4-one;

3-(1,3-Dihydro-1-oxoisobenzofuran-5-yl)-5,5-dimethyl-1-[7-[4-(propylsulfonyl)piperazin-1-yl]heptyl]-2-thioxoimidazolidin-4-one;

3-(1,3-Dihydro-1-oxoisobenzofuran-5-yl)-5,5-dimethyl-1-[7-[4-(phenylsulfonyl)piperazin-1-yl]heptyl]-2-thioxoimidazolidin-4-one;

4-[7-[3-(1,3-Dihydro-1-oxoisobenzofuran-5-yl)-5,5-dimethyl-4-oxo-2-thioxoimidazolidin-1-yl]heptyl]-N-ethylpiperazine-1-carbothioamide;

4-[7-[3-(1,3-Dihydro-1-oxoisobenzofuran-5-yl)-5,5-dimethyl-4-oxo-2-thioxoimidazolidin-1-yl]heptyl]-N-propylpiperazine-1-carbothioamide;

4-[7-[3-(1,3-Dihydro-1-oxoisobenzofuran-5-yl)-5,5-dimethyl-4-oxo-2-thioxoimidazolidin-1-yl]heptyl]-N-(prop-2-enyl)piperazine-1-carbothioamide;

S-Methyl 4-[7-[3-(1,3-dihydro-1-oxoisobenzofuran-5-yl)-5,5-dimethyl-4-oxo-2-thioxoimidazolidin-1-yl]heptyl]piperazine-1-carbothioate;

S-Ethyl 4-[7-[3-(1,3-dihydro-1-oxoisobenzofuran-5-yl)-5,5-dimethyl-4-oxo-2-thioxoimidazolidin-1-yl]heptyl]piperazine-1-carbothioate;

3-(1,3-Dihydro-1-oxoisobenzofuran-5-yl)-1-[8-[4-(2-methoxybenzoyl)piperazin-1-yl]octyl]-5,5-dimethyl-2-thioxoimidazolidin-4-one;

3-(1,3-Dihydro-1-oxoisobenzofuran-5-yl)-1-[8-[4-[4-(dimethylamino)benzoyl]piperazin-1-yl]octyl]-5,5-dimethyl-2-thioxoimidazolidin-4-one;

1-[8-(4-Acetylpiperazin-1-yl)octyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[8-[4-(1-oxopropyl)piperazin-1-yl]octyl]-2-thioxoimidazolidin-4-one;

1-[8-[4-(Cyclopropylcarbonyl)piperazin-1-yl]octyl]-3-(1,3-dihydro-1-oxoisobenzofuran-5-yl)-5,5-dimethyl-2-thioxoimidazolidin-4-one;

1-[8-[4-(Cyclobutylcarbonyl)piperazin-1-yl]octyl]-3-(1,3-dihydro-1-oxoisobenzofuran-5-yl)-5,5-dimethyl-2-thioxoimidazolidin-4-one;

3-(1,3-Dihydro-1-oxoisobenzofuran-5-yl)-5,5-dimethyl-1-[8-[4-[(thien-2-yl)carbonyl]piperazin-1-yl]octyl]-2-thioxoimidazolidin-4-one;

3-(1,3-Dihydro-1-oxoisobenzofuran-5-yl)-5,5-dimethyl-1-[8-[4-[(thien-2-yl)acetyl]piperazin-1-yl]octyl]-2-thioxoimidazolidin-4-one;

3-(1,3-Dihydro-1-oxoisobenzofuran-5-yl)-5,5-dimethyl-1-[8-[4-[(pyridin-4-yl)carbonyl]piperazin-1-yl]octyl]-2-thioxoimidazolidin-4-one;

3-(1,3-Dihydro-1-oxoisobenzofuran-5-yl)-5,5-dimethyl-1-[8-[4-(methylsulfonyl)piperazin-1-yl]octyl]-2-thioxoimidazolidin-4-one;

3-(1,3-Dihydro-1-oxoisobenzofuran-5-yl)-1-[8-[4-(ethylsulfonyl)piperazin-1-yl]octyl]-5,5-dimethyl-2-thioxoimidazolidin-4-one;

3-(1,3-Dihydro-1-oxoisobenzofuran-5-yl)-5,5-dimethyl-1-[8-[4-(propylsulfonyl)piperazin-1-yl]octyl]-2-thioxoimidazolidin-4-one;

3-(1,3-Dihydro-1-oxoisobenzofuran-5-yl)-5,5-dimethyl-2-thioxo-1-[8-[4-[(2,2,2-trifluoroethyl)sulfonyl]piperazin-1-yl]octyl]imidazolidin-4-one;

3-(1,3-Dihydro-1-oxoisobenzofuran-5-yl)-5,5-dimethyl-1-[8-[4-(phenylsulfonyl)piperazin-1-yl]octyl]-2-thioxoimidazolidin-4-one;

4-[8-[3-(1,3-Dihydro-1-oxoisobenzofuran-5-yl)-5,5-dimethyl-4-oxo-2-thioxoimidazolidin-1-yl]octyl]-N-[3-(methylsulfanyl)phenyl]piperazine-1-carboxylic acid amide;

4-[8-[3-(1,3-Dihydro-1-oxoisobenzofuran-5-yl)-5,5-dimethyl-4-oxo-2-thioxoimidazolidin-1-yl]octyl]-N-(3-fluorophenyl)piperazine-1-carboxylic acid amide;

4-[8-[3-(1,3-Dihydro-1-oxoisobenzofuran-5-yl)-5,5-dimethyl-4-oxo-2-thioxoimidazolidin-1-yl]octyl]-N-ethylpiperazine-1-carbothioamide;

4-[8-[3-(1,3-Dihydro-1-oxoisobenzofuran-5-yl)-5,5-dimethyl-4-oxo-2-thioxoimidazolidin-1-yl]octyl]-N-propylpiperazine-1-carbothioamide;

4-[8-[3-(1,3-Dihydro-1-oxoisobenzofuran-5-yl)-5,5-dimethyl-4-oxo-2-thioxoimidazolidin-1-yl]octyl]-N-(prop-2-enyl)piperazine-1-carbothioamide;

4-[8-[3-(1,3-Dihydro-1-oxoisobenzofuran-5-yl)-5,5-dimethyl-4-oxo-2-thioxoimidazolidin-1-yl]octyl]-N-(phenylmethyl)piperazine-1-carbothioamide;

4-[8-[3-(1,3-Dihydro-1-oxoisobenzofuran-5-yl)-5,5-dimethyl-4-oxo-2-thioxoimidazolidin-1-yl]octyl]-N-phenyl-piperazine-1-carbothioamide;

S-Methyl 4-[8-[3-(1,3-dihydro-1-oxoisobenzofuran-5-yl)-5,5-dimethyl-4-oxo-2-thioxoimidazolidin-1-yl]octyl]piperazine-1-carbothioate;

S-Ethyl 4-[8-[3-(1,3-dihydro-1-oxoisobenzofuran-5-yl)-5,5-dimethyl-4-oxo-2-thioxoimidazolidin-1-yl]octyl]piperazine-1-carbothioate;

4-[8-[3-(1,3-Dihydro-1-oxoisobenzofuran-5-yl)-5,5-dimethyl-4-oxo-2-thioxoimidazolidin-1-yl]octyl]-N,N-diethylpiperazine-1-carboxylic acid amide;

6-[4,4-Dimethyl-5-oxo-3-[5-[4-(methylsulfonyl)piperazin-1-yl]pentyl]-2-thioxoimidazolidin-1-yl]-4-methyl-1H-2,3-benzoxazin-1-one;

6-[4,4-Dimethyl-5-oxo-3-[6-[4-(methylsulfonyl)piperazin-1-yl]hexyl]-2-thioxoimidazolidin-1-yl]-4-methyl-1H-2,3-benzoxazin-1-one;

1-[6-(4-Acetylpiperazin-1-yl)hexyl]-3-(2,3-dihydro-1-oxo-1H-inden-5-yl)-5,5-dimethyl-2-thioxoimidazolidin-4-one;

3-(2,3-Dihydro-1-oxo-1H-inden-5-yl)-5,5-dimethyl-1-[6-[4-(2-methyl-1-oxopropyl)piperazin-1-yl]hexyl]-2-thioxoimidazolidin-4-one;

3-(2,3-Dihydro-1-oxo-1H-inden-5-yl)-5,5-dimethyl-1-[6-[4-[(thien-2-yl)carbonyl]piperazin-1-yl]hexyl]-2-thioxoimidazolidin-4-one;

3-(2,3-Dihydro-1-oxo-1H-inden-5-yl)-5,5-dimethyl-1-[6-[4-[(pyridin-4-yl)carbonyl]piperazin-1-yl]hexyl]-2-thioxoimidazolidin-4-one;

3-(2,3-Dihydro-1-oxo-1H-inden-5-yl)-5,5-dimethyl-1-[6-[4-(methylsulfonyl)piperazin-1-yl]hexyl]-2-thioxoimidazolidin-4-one;

3-(2,3-Dihydro-1-oxo-1H-inden-5-yl)-5,5-dimethyl-1-[6-[4-(propylsulfonyl)piperazin-1-yl]hexyl]-2-thioxoimidazolidin-4-one;

4-[6-[3-(2,3-Dihydro-1-oxo-1H-inden-5-yl)-5,5-dimethyl-4-oxo-2-thioxoimidazolidin-1-yl]hexyl]-N-ethylpiperazine-1-carbothioamide; and S-Methyl 4-[6-[3-(2,3-dihydro-1-oxo-1H-inden-5-yl)-5,5-dimethyl-4-oxo-2-thioxoimidazolidin-1-yl]hexyl]piperazine-1-carbothioate.

9. A compound according to claim 1, selected from the group consisting of:

4-[3-[3-[4-[(2-Methoxyethyl)sulfonyl]piperazin-1-yl]propyl]-4,4-dimethyl-5-oxo-2-thioxoimidazolidin-1-yl]-2-(trifluoromethyl)benzonitrile;

4-[4-[3-[4-Cyano-3-(trifluoromethyl)phenyl]-5,5-dimethyl-4-oxo-2-thioxoimidazolidin-1-yl]butyl]piperazine-1-carbonitrile;

rel-4-[3-[4-[(2R,5S)-4-Acetyl-2,5-dimethylpiperazin-1-yl]butyl]-4,4-dimethyl-5-oxo-2-thioxoimidazolidin-1-yl]-2-(trifluoromethyl)benzonitrile;

4-[3-[4-(4-Acetylhexahydro-1H-1,4-diazepin-1-yl)butyl]-4,4-dimethyl-5-oxo-2-thioxoimidazolidin-1-yl]-2-(trifluoromethyl)benzonitrile;

rel-4-[3-[4-[(2R,5S)-2,5-Dimethyl-4-(2-methyl-1-oxopropyl)piperazin-1-yl]butyl]-4,4-dimethyl-5-oxo-2-thioxoimidazolidin-1-yl]-2-(trifluoromethyl)benzonitrile;

4-[3-[4-[4-(2-Hydroxy-2-methyl-1-oxopropyl)piperazin-1-yl]butyl]-4,4-dimethyl-5-oxo-2-thioxoimidazolidin-1-yl]-2-(trifluoromethyl)benzonitrile;

4-[3-[4-[4-(2,2-Dimethyl-1-oxopropyl)piperazin-1-yl]butyl]-4,4-dimethyl-5-oxo-2-thioxoimidazolidin-1-yl]-2-(trifluoromethyl)benzonitrile;

rel-4-[3-[4-[(2R,5S)-4-(2,2-Dimethyl-1-oxopropyl)-2,5-dimethylpiperazin-1-yl]butyl]-4,4-dimethyl-5-oxo-2-thioxoimidazolidin-1-yl]-2-(trifluoromethyl)benzonitrile;

4-[3-[4-[4-(2,2-Dimethyl-1-oxopropyl)hexahydro-1H-1,4-diazepin-1-yl]butyl]-4,4-dimethyl-5-oxo-2-thioxoimidazolidin-1-yl]-2-(trifluoromethyl)benzonitrile;

rel-4-[3-[4-[(2R,5S)-4-(Cyclopropylcarbonyl)-2,5-dimethylpiperazin-1-yl]butyl]-4,4-dimethyl-5-oxo-2-thioxoimidazolidin-1-yl]-2-(trifluoromethyl)benzonitrile;

4-[3-[4-[4-(Methoxyacetyl)piperazin-1-yl]butyl]-4,4-dimethyl-5-oxo-2-thioxoimidazolidin-1-yl]-2-(trifluoromethyl)benzonitrile;

4-[3-[4-[Hexahydro-4-(3-methoxy-1-oxopropyl)-1H-1,4-diazepin-1-yl]butyl]-4,4-dimethyl-5-oxo-2-thioxoimidazolidin-1-yl]-2-(trifluoromethyl)benzonitrile;

4-[4,4-Dimethyl-5-oxo-2-thioxo-3-[4-[4-(trifluoroacetyl)piperazine-1-butyl]imidazolidin-1-yl]-2-(trifluoromethyl)benzonitrile;

4-[3-[4-[Hexahydro-4-(trifluoroacetyl)-1H-1,4-diazepin-1-yl]butyl]-4,4-dimethyl-5-oxo-2-thioxoimidazolidin-1-yl]-2-(trifluoromethyl)benzonitrile;

4-[3-[4-[4-[(Furan-2-yl)carbonyl]hexahydro-1H-1,4-diazepin-1-yl]butyl]-4,4-dimethyl-5-oxo-2-thioxoimidazolidin-1-yl]-2-(trifluoromethyl)benzonitrile;

4-[3-[4-[Hexahydro-4-[(thien-2-yl)carbonyl]-1H-1,4-diazepin-1-yl]butyl]-4,4-dimethyl-5-oxo-2-thioxoimidazolidin-1-yl]-2-(trifluoromethyl)benzonitrile;

rel-4-[4,4-Dimethyl-3-[4-[(2R,5S)-2,5-dimethyl-4-(methylsulfonyl)piperazin-1-yl]butyl]-5-oxo-2-thioxoimidazolidin-1-yl]-2-(trifluoromethyl)benzonitrile;

4-[3-[4-[Hexahydro-4-(methylsulfonyl)-1H-1,4-diazepin-1-yl]butyl]-4,4-dimethyl-5-oxo-2-thioxoimidazolidin-1-yl]-2-(trifluoromethyl)benzonitrile;

4-[3-[4-[4-[(2-Methoxyethyl)sulfonyl]piperazin-1-yl]butyl]-4,4-dimethyl-5-oxo-2-thioxoimidazolidin-1-yl)-2-(trifluoromethyl)benzonitrile;

S-Methyl 4-[4-[3-[4-cyano-3-(trifluoromethyl)phenyl]-5,5-dimethyl-4-oxo-2-thioxoimidazolidin-1-yl]butyl]hexahydro-1H-1,4-diazepine-1-carbothioate;

N,N-Dimethyl 4-[4-[3-[4-cyano-3-(trifluoromethyl)phenyl]-5,5-dimethyl-4-oxo-2-thioxoimidazolidin-1-yl]butyl]piperazine-1-sulfonamide;

4-[3-[5-[4-(2-Methoxybenzoyl)piperazin-1-yl]pentyl]-4,4-dimethyl-5-oxo-2-thioxoimidazolidin-1-yl]-2-(trifluoromethyl)benzonitrile;

4-[5-[3-[4-Cyano-3-(trifluoromethyl)phenyl]-5,5-dimethyl-4-oxo-2-thioxoimidazolidin-1-yl]pentyl]piperazine-1-carbonitrile;

rel-4-[3-[5-[(2R,6S)-4-Acetyl-2,6dimethylpiperazin-1-yl]pentyl]-4,4-dimethyl-5-oxo-2-thioxoimidazolidin-1-yl]-2-(trifluoromethyl)benzonitrile;

4-[3-[5-(4-Acetylhexahydro-1H-1,4-diazepin-1-yl)pentyl]-4,4-dimethyl-5-oxo-2-thioxoimidazolidin-1-yl]-2-(trifluoromethyl)benzonitrile;

4-[3-[5-[Hexahydro-4-(2-methyl-1-oxopropyl)-1H-1,4-diazepin-1-yl]pentyl]-4,4-dimethyl-5-oxo-2-thioxoimidazolidin-1-yl]-2-(trifluoromethyl)benzonitrile;

4-[3-[5-[4-(2-Hydroxy-2-methyl-1-oxopropyl)piperazin-1-yl]pentyl]-4,4-dimethyl-5-oxo-2-thioxoimidazolidin-1-yl]-2-(trifluoromethyl)benzonitrile;

4-[3-[5-[4-(2,2-Dimethyl-1-oxopropyl)piperazin-1-yl]pentyl]-4,4-dimethyl-5-oxo-2-thioxoimidazolidin-1-yl]-2-(trifluoromethyl)benzonitrile;

4-[3-[5-[4-(2,2-Dimethyl-1-oxopropyl)hexahydro-1H-1,4-diazepin-1-yl]pentyl]-4,4-dimethyl-5-oxo-2-thioxoimidazolidin-1-yl]-2-(trifluoromethyl)benzonitrile;

4-[3-[5-[4-(Methoxyacetyl)piperazin-1-yl]pentyl]-4,4-dimethyl-5-oxo-2-thioxoimidazolidin-1-yl]-2-(trifluoromethyl)benzonitrile;

4-[4,4-Dimethyl-5-oxo-2-thioxo-3-[5-[4-(trifluoroacetyl)piperazin-1-yl]pentyl]imidazolidin-1-yl]-2-(trifluoromethyl)benzonitrile;

4-[3-[5-[4-[(Furan-3-yl)carbonyl]hexahydro-1H-1,4-diazepin-1-yl]pentyl]-4,4-dimethyl-5-oxo-2-thioxoimidazolidin-1-yl]-2-(trifluoromethyl)benzonitrile;

4-[3-[5-[Hexahydro-4-[(thien-3-yl)carbonyl]-1H-1,4-diazepin-1-yl]pentyl]-4,4-dimethyl-5-oxo-2-thioxoimidazolidin-1-yl]-2-(trifluoromethyl)benzonitrile;

4-[3-[5-[4-[(Furan-2-yl)carbonyl]hexahydro-1H-1,4-diazepin-1-yl]pentyl]-4,4-dimethyl-5-oxo-2-thioxoimidazolidin-1-yl]-2-(trifluoromethyl)benzonitrile;

4-[3-[5-[Hexahydro-4-[(thien-2-yl)carbonyl]-1H-1,4-diazepin-1-yl]pentyl]-4,4-dimethyl-5-oxo-2-thioxoimidazolidin-1-yl]-2-(trifluoromethyl)benzonitrile;

rel-4-[3-[5-[(2R,6S)-2,6-Dimethyl-4-(methylsulfonyl)piperazin-1-yl]pentyl]-4,4-dimethyl-5-oxo-2-thioxoimidazolidin-1-yl]-2-(trifluoromethyl)benzonitrile;

4-[3-[5-[Hexahydro-4-(methylsulfonyl)-1H-1,4-diazepin-1-yl]pentyl]-4,4-dimethyl-5-oxo-2-thioxoimidazolidin-1-yl]-2-(trifluoromethyl)benzonitrile;

S-Methyl 4-[5-[3-[4-cyano-3-(trifluoromethyl)phenyl]-5,5-dimethyl-4-oxo-2-thioxoimidazolidin-1-yl]pentyl]hexahydro-1H-1,4-diazepine-1-carbothioate;

N,N-Dimethyl 4-[5-[3-[4-cyano-3-(trifluoromethyl)phenyl]-5,5-dimethyl-4-oxo-2-thioxoimidazolidin-1-yl]pentyl]piperazine-1-sulfonamide;

4-[6-[3-[4-Cyano-3-(trifluoromethyl)phenyl]-5,5-dimethyl-4-oxo-2-thioxoimidazolidin-1-yl]hexyl]piperazine-1-carbonitrile;

rel-4-[3-[6-[(2R,5S)-4-Acetyl-2,5-dimethylpiperazin-1-yl]hexyl]-4,4-dimethyl-2-thioxoimidazolidin-1-yl]-2-(trifluoromethyl)benzonitrile;

rel-4-[3-[6-[(2R,6S)-4-Acetyl-2,6-dimethylpiperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-2,5-Dimethyl-4-(2-methyl-1-oxopropyl)piperazin-1-yl]hexyl]-4,4-dimethyl-5-oxo-2-thioxoimidazolidin-1-yl]-2-(trifluoromethyl)benzonitrile;

4-[3-[6-[Hexahydro-4-(2-methyl-1-oxopropyl)-1H-1,4-diazepin-1-yl]hexyl]-4,4-dimethyl-5-oxo-2-thioxoimidazolidin-1-yl]-2-(trifluoromethyl)benzonitrile;

4-[3-[6-[4-(2-Hydroxy-2-methyl-1-oxopropyl)piperazin-1-yl]hexyl]-4,4-dimethyl-5-oxo-2-thioxoimidazolidin-1-yl]-2-(trifluoromethyl)benzonitrile;

4-[3-[6-[4-(2,2-Dimethyl-1-oxopropyl)piperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-(2,2-Dimethyl-1-oxopropyl)-2,5-dimethylpiperazin-1-yl]hexyl]-4,4-dimethyl-5-oxo-2-thioxoimidazolidin-1-yl]-2-(trifluoromethyl)benzonitrile;

rel-4-[3-[6-[(2R,6S)-4-(2,2-Dimethyl-1-oxopropyl)-2,6-dimethylpiperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-(Cyclopropylcarbonyl)-2,5-dimethylpiperazin-1-yl]hexyl]-4,4-dimethyl-5-oxo-2-thioxoimidazolidin-1-yl]-2-(trifluoromethyl)benzonitrile;

4-[3-[6-[4-(Methoxyacetyl)piperazin-1-yl]hexyl]-4,4-dimethyl-5-oxo-2-thioxoimidazolidin-1-yl]-2-(trifluoromethyl)benzonitrile;

rel-4-[3-[6-[(2R,5S)4-(3-Methoxy-1-oxopropyl)-2,5-dimethylpiperazin-1-yl]hexyl]-4,4-dimethyl-5-oxo-2-thioxoimidazolidin-1-yl]-2-(trifluoromethyl)benzonitrile;

4-[3-[6-[Hexahydro-4-(3-methoxy-1-oxopropyl)-1H-1,4-diazepin-1-yl]hexyl]-4,4-dimethyl-5-oxo-2-thioxoimidazolidin-1-yl]-2-(trifluoromethyl)benzonitrile;

4-[4,4-Dimethyl-5-oxo-2-thioxo-3-[6-[4-(trifluoroacetyl)piperazin-1-yl]hexyl]imidazolidin-1-yl]-2-(trifluoromethyl)benzonitrile;

rel-4-[3-[6-[(2R,5S)-2,5-Dimethyl-4trifluoroacetyl)piperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-[(Furan-3-yl)carbonyl]-2,5-dimethylpiperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-[(Isoxazol-5-yl)carbonyl]-2,5-dimethylpiperazin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-[(Furan-2-yl)carbonyl]-2,5-dimethylpiperazin-1-yl]hexyl]-4,4-dimethyl-5-oxo-2-thioxoimidazolidin-1-yl]-2-(trifluoromethyl)benzonitrile;

4-[3-[6-[4-[(Furan-2-yl)carbonyl]hexahydro-1H-1,4-diazepin-1-yl]hexyl]-4,4-dimethyl-5-oxo-2-thioxoimidazolidin-1-yl]-2-(trifluoromethyl)benzonitrile;

rel-4-[3-[6-[(2R,5S)-2,5-Dimethyl-4-[(thien-2-yl)carbonyl]piperazin-1-yl]hexyl]-4,4-dimethyl-5-oxo-2-thioxoimidazolidin-1-yl]-2-(trifluoromethyl)benzonitrile;

4-[3-[6-[Hexahydro-4-[(thien-2-yl)carbonyl]-1H-1,4-diazepin-1-yl]hexyl]-4,4-dimethyl-5-oxo-2-thioxoimidazolidin-1-yl]-2-(trifluoromethyl)benzonitrile;

rel4-[3-[6-[(2R,5S)-2,5-Dimethyl-4-(methylsulfonyl)piperazin-1-yl]hexyl]-4,4-dimethyl-5-oxo-2-thioxoimidazolidin-1-yl]-2-(trifluoromethyl)benzonitrile;

rel-4-[3-[6-[(2R,6S)-2,6-Dimethyl-4-(methylsulfonyl)piperazin-1-yl]hexyl]-4,4-dimethyl-5-oxo-2-thioxoimidazolidin-1-yl]-2-(trifluoromethyl)benzonitrile;

4-[3-[6-[Hexahydro-4-methylsulfonyl)-1H-1,4-diazepin-1-yl]hexyl]-4,4-dimethyl-5-oxo-2-thioxoimidazolidin-1-yl]-2-(trifluoromethyl)benzonitrile;

rel-4-[3-[6-[(2R,5S)-4-(Ethylsulfonyl)-2,5-dimethylpiperazin-1-yl]hexyl]-4,4-dimethyl-5-oxo-2-thioxoimidazolidin-1-yl]-2-(trifluoromethyl)benzonitrile;

4-[4,4-Dimethyl-3-[6-[4-[(1-methylethyl)sulfonyl]piperazin-1-yl]hexyl]-5-oxo-2-thioxoimidazolidin-1-yl]-2-(trifluoromethyl)benzonitrile;

4-[3-[6-[4-[(2-Methoxyethyl)sulfonyl]piperazin-1-yl]hexyl]-4,4-dimethyl-5-oxo-2-thioxoimidazolidin-1-yl]-2-(trifluoromethyl)benzonitrile;

S-Methyl 4-[6-[3-[4-cyano-3-(trifluoromethyl)phenyl]-5,5-dimethyl-4-oxo-2-thioxoimidazolidin-1-yl]hexyl]hexahydro-1H-1,4-diazepine-1-carbothioate;

4-[7-[3-[4-Cyano-3-(trifluoromethyl)phenyl]-5,5-dimethyl-4-oxo-2-thioxoimidazolidin-1-yl]heptyl]piperazine-1-carbonitrile;

rel-4-[3-[7-[(2R,6S)-4-Acetyl-2,6-dimethylpiperazin-1-yl]heptyl]-4,4-dimethyl-2-thioxoimidazolidin-1-yl]-2-(trifluoromethyl)benzonitrile;

4-[3-[7-[4-(2-Hydroxy-2-methyl-1-oxopropyl)piperazin-1-yl]heptyl]-4,4-dimethyl-5-oxo-2-thioxoimidazolidin-1-yl]-2-(trifluoromethyl)benzonitrile;

4-[3-[7-[4-(2,2-Dimethyl-1-oxopropyl)piperazin-1-yl]heptyl]-4,4-dimethyl-5-oxo-2-thioxoimidazolidin-1-yl]-2-(trifluoromethyl)benzonitrile;

rel-4-[3-[7-[(2R,6S)-4-(2,2-Dimethyl-1-oxopropyl)-2,6-dimethylpiperazin-1-yl]heptyl]-4,4-dimethyl-5-oxo-2-thioxoimidazolidin-1-yl]-2-(trifluoromethyl)benzonitrile;

4-[3-[7-[4-(Methoxyacetyl)piperazin-1-yl]heptyl]-4,4-dimethyl-5-oxo-2-thioxoimidazolidin-1-yl]-2-(trifluoromethyl)benzonitrile;

4-[4,4-Dimethyl-5-oxo-2-thioxo-3-[7-[4-(trifluoroacetyl)piperazin-1-yl]heptyl]imidazolidin-1-yl]-2-(trifluoromethyl)benzonitrile;

rel-4-[3-[7-[(2R,6S)-2,6-Dimethyl-4-(trifluoroacetyl)piperazin-1-yl]heptyl]-4,4-dimethyl-5-oxo-2-thioxoimidazolidin-1-yl]-2-(trifluoromethyl)benzonitrile;

rel-4-[3-[7-[(2R,6S)-2,6-Dimethyl-4-(methylsulfonyl)piperazin-1-yl]heptyl]-4,4-dimethyl-5-oxo-2-thioxoimidazolidin-1-yl]-2-(trifluoromethyl)benzonitrile;

4-[3-[7-(4-[(2-Methoxyethyl)sulfonyl]piperazin-1-yl]heptyl]-4,4-dimethyl-5-oxo-2-thioxoimidazolidin-1-yl]-2-(trifluoromethyl)benzonitrile;

4-[8-[3-[4-Cyano-3-(trifluoromethyl)phenyl]-5,5-dimethyl-4-oxo-2-thioxoimidazolidin-1-yl]octyl]piperazine-1-carbonitrile;

rel-4-[3-[8-[(2R,6S)-4-Acetyl-2,6-dimethylpiperazin-1-yl]octyl]-4,4-dimethyl-5-oxo-2-thioxoimidazolidin-1-yl]-2-(trifluoromethyl)benzonitrile;

4-[3-[8-[4-(2-Hydroxy-2-methyl-1-oxopropyl)piperazin-1-yl]octyl]-4,4-dimethyl-5-oxo-2-thioxoimidazolidin-1-yl]-2-(trifluoromethyl)benzonitrile;

rel-4-[3-[8-[(2R,6S)-4-(2,2-Dimethyl-1-oxopropyl)-2,6-dimethylpiperazin-1-yl]hexyl]-4,4-dimethyl-5-oxo-2-thioxoimidazolidin-1-yl]-2-(trifluoromethyl)benzonitrile;

4-[3-[8-[4-(Methoxyacetyl)piperazin-1-yl]octyl]-4,4-dimethyl-5-oxo-2-thioxoimidazolidin-1-yl]-2-(trifluoromethyl)benzonitrile;

4-[4,4-Dimethyl-5-oxo-2-thioxo-3-[8-[4-(trifluoroacetyl)piperazin-1-yl]octyl]imidazolidin-1-yl]-2-(trifluoromethyl)benzonitrile;

4-[3-[8-[4-(Methoxyacetyl)piperazin-1-yl]octyl]-4,4-dimethyl-5-oxo-2-thioxoimidazolidin-1-yl]-2-(trifluoromethyl)benzonitrile;

4-[4,4-Dimethyl-5-oxo-2-thioxo-3-[8-[4-(trifluoroacetyl)piperazin-1-yl]octyl]imidazolidin-1-yl]-2-(trifluoromethyl)benzonitrile and N,N-Dimethyl 4-[8-[3-[4-cyano-3-(trifluoromethyl)phenyl]-5,5-dimethyl-4-oxo-2-thioxoimidazolidin-1-yl]octyl]piperazine-1-sulfonamide.

10. Process for the production of a compound of formula I according to claim 1, which comprises:

either reacting a compound of formula VIII

V—W—(CH$_2$)$_n$—N(piperazine with R, R', i, j)—NH        VIII in which V, W, n, i, j, R and R' have the meaning indicated with one of the reagents

Z—N=O,

Z—N=S,

Z—COCl,

Z—SO$_2$Cl,

ZO—COCl,

ZS—COCl,

ZZ'N—COCl, in which Z and Z' have the meaning indicated, in the presence of a base, or reacting a compound of the formula VII V—W—(CH$_2$)$_n$—I        VII with a product of the formula VI HN(piperazine with R, R', i, j)—N—Y—Z        VI in which i, j, Y, Z, R and R' have the meaning indicated, in the presence of a base and optionally then converting the resulting product into a pharmacologically compatible salt.

11. An intermediate of the formula VIII:

V—W—(CH$_2$)$_n$—N(piperazine with R, R', i, j)—NH        VIII in which

V stands for a substituted aromatic radical of formula II, (benzene with A, B substituents)        II in which A stands for an acetyl group, an acetylamino group, a cyano group, a nitro group, a trifluoromethyl group or a halogen B stands for a hydrogen atom, a halogen or a trifluoromethyl group, or A and B together stand for a cyclic group of formula II or IV that is bonded to the aromatic ring, whereby E stands for a methylene group or an oxygen atom, (cyclic structure with E and O)        III (structure with Me, N, O)        IV W stands for a group of formula V, (imidazolidine-type ring with Q, T, U)        V in which T stands for carbon, and a double bond is present between Q and T, and Q means a group =C(CH$_3$)— and U means oxygen, n is one of the integral values 1, 2, 3, 4, 5, 6, 7, or 8, i and j, independently of one another, are 1 or 2, whereby i+j is 2 or 3, and R and R', independently of one another, are a hydrogen atom or a methyl group.

12. An intermediate of the formula VIII:

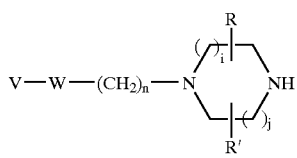

VIII in which

V stands for a substituted aromatic radical of formula II,

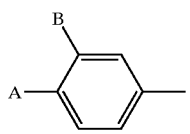

II in which

A and B together stand for a cyclic group of formula III or IV that is bonded to the aromatic ring, whereby E stands for a methylene group or an oxygen atom,

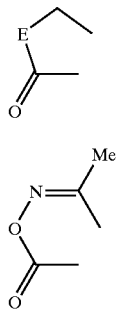

III

IV

W stands for a group of formula V,

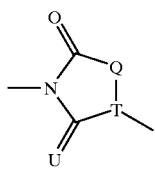

V in which

T stands for nitrogen, and a single bond is present between Q and T, and Q means a group —C(CH$_3$)$_2$— and U means sulfur, n is one of the integral values 2, 3, 4, 5, 6, 7, or 8, i and j, independently of one another, are 1 or 2, whereby i+j is 2 or 3, R and R', independently of one another, are a hydrogen atom or a methyl group.

13. An intermediate of formula VII:

V—W—(CH$_2$)$_n$—I

VII in which

V stands for a substituted aromatic radical of formula II,

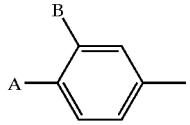

II in which

A stands for an acetyl group, an acetylamino group, a cyano group, a nitro group, a trifluoromethyl group or a halogen, B stands for a hydrogen atom, a halogen or a trifluoromethyl group, or A and B together stand for a cyclic group of formula III or IV that is bonded to the aromatic ring, whereby E stands for a methylene group or an oxygen atom,

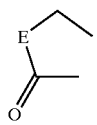

III

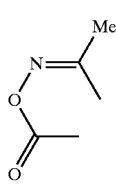

IV

W stands for a group of formula V,

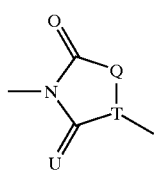

V in which

T stands for carbon, and a double bond is present between Q and T, and Q means a group =C(CH$_3$)— and U means oxygen, n is one of the integral values 1, 2, 3, 4, 5, 6, 7, or 8.

14. An intermediate of formula VII:

V—W—(CH$_2$)$_n$—I

VII in which

V stands for a substituted aromatic radical of formula II,

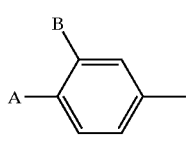

II in which

A and B together stand for a cyclic group of formula III or IV that is bonded to the aromatic ring, whereby E stands for a methylene group or an oxygen atom,

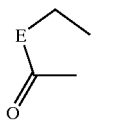

III

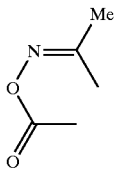

IV

W stands for a group of formula V.

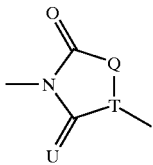

V in which

T stands for nitrogen, and a single bond is present between Q and T, and Q means a group —C(CH)$_2$— and U means sulfur, and n is one of the integral values 2, 3, 4, 5, 6, 7, or 8.

15. A pharmaceutical composition which comprises at least one compound of formula I according to claim 1, together with at least one pharmaceutically compatible adjuvant or vehicle.

16. A compound of claim 1, wherein halogen, in each occurrence, is fluorine or chlorine.

17. A compound of claim 1, wherein:

aryl in each occurrence is phenyl, naphthalen-1-yl, naphthalen-2-yl, [1,1'-biphenyl]-2-yl, [1,1'-biphenyl]-3-yl or [1,1'-biphenyl]-4-yl, heteroaryl, in each occurrence, is pyridinyl, pyrimidinyl, quinolinyl, isoquinolinyl, benzofuranyl, benzothienyl, 1,3-benzodioxolyl, 2,1,3-benzothiadiazolyl, indolyl, furanyl, thienyl, oxazolyl, isoxazolyl, thiazolyl, pyrrolyl, pyrazolyl or imidazolyl, and heterocyclyl, in each occurrence, is piperidinyl, morpholinyl, thiomorpholinyl, piperazinyl, tetrahydrofuranyl, tetrahydrothienyl, imidazolidinyl or pyrrolidinyl group.

18. A method for preparing a pharmaceutical composition which comprises combining at least one compound of formula I according to claim 1, with at least one pharmaceutically compatible adjuvant or vehicle.

19. A method for treating prostate cancer which comprises administering a compound of claim 1 to a patient in need thereof.

20. A method for treating benign prostate hyperplasia, andogenetic alopecia, hirsutism or androgen-dependent acne which comprises administering a compound of claim 1 to a patient in need thereof.

* * * * *